US008317776B2

(12) United States Patent
Ferren et al.

(10) Patent No.: US 8,317,776 B2
(45) Date of Patent: Nov. 27, 2012

(54) CIRCULATORY MONITORING SYSTEMS AND METHODS

(75) Inventors: Bran Ferren, Beverly Hills, CA (US); Jeffrey John Hagen, Plymouth, MN (US); Roderick A. Hyde, Redmond, WA (US); Muriel Y. Ishikawa, Livermore, CA (US); Eric C. Leuthardt, St. Louis, MO (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1085 days.

(21) Appl. No.: 12/154,162

(22) Filed: May 19, 2008

(65) Prior Publication Data
US 2009/0157058 A1    Jun. 18, 2009

Related U.S. Application Data

(63) Continuation-in-part of application No. 12/004,107, filed on Dec. 18, 2007.

(51) Int. Cl.
*A61K 9/22* (2006.01)
(52) U.S. Cl. .................. 604/891.1; 604/65; 604/266
(58) Field of Classification Search ............ 604/65, 604/66, 67, 266, 891.1
See application file for complete search history.

(56) References Cited

U.S. PATENT DOCUMENTS

| | | |
|---|---|---|
| 3,409,008 A | 11/1966 | Mortensen et al. |
| 3,673,189 A | 6/1972 | Curran et al. |
| 4,039,665 A | 8/1977 | Foley |
| 4,138,156 A | 2/1979 | Bonner |
| 4,303,984 A | 12/1981 | Houvig |
| 4,312,358 A | 1/1982 | Barney |
| 4,379,461 A | 4/1983 | Nilsson et al. |
| 4,536,274 A | 8/1985 | Papadakis et al. |
| 4,569,355 A | 2/1986 | Bitterly |
| 4,629,336 A | 12/1986 | Ishizaka |
| 4,649,933 A | 3/1987 | Jackson |
| 4,689,041 A | 8/1987 | Corday et al. |

(Continued)

FOREIGN PATENT DOCUMENTS
JP            7059754 A    3/1995
(Continued)

OTHER PUBLICATIONS

Brill, S. et al.; "Bier's Block: 100 Years Old and Still Going Strong"; Acta Anaesthesiologica Scandinavica; 2004; pp. 117-122; vol. 48; Acta Anaesthesiol Scand.

(Continued)

*Primary Examiner* — Bhisma Mehta

(57) ABSTRACT

Systems and methods are described for obtaining and acting upon information indicative of circulatory health and related phenomena in human beings or other subjects. Some involve implementing or deploying therapeutic administration systems, for example, for obtaining one or more indications of a lytic material in a vicinity of one or more body lumens and accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens.

31 Claims, 94 Drawing Sheets

U.S. PATENT DOCUMENTS

| | | |
|---|---|---|
| 4,804,054 A | 2/1989 | Howson et al. |
| 4,819,658 A | 4/1989 | Kolodner |
| 4,820,261 A | 4/1989 | Schmoll et al. |
| 4,860,751 A | 8/1989 | Callaghan |
| 4,981,596 A | 1/1991 | Shiino et al. |
| 5,012,411 A | 4/1991 | Policastro et al. |
| 5,036,462 A | 7/1991 | Kaufman et al. |
| 5,153,827 A | 10/1992 | Coutré et al. |
| 5,178,153 A | 1/1993 | Einzig |
| 5,188,106 A | 2/1993 | Nappholz et al. |
| 5,201,318 A | 4/1993 | Rava et al. |
| 5,242,382 A | 9/1993 | Gorsuch et al. |
| 5,243,998 A | 9/1993 | Silverman et al. |
| 5,256,538 A | 10/1993 | Aiken et al. |
| 5,262,669 A | 11/1993 | Wakatabe et al. |
| 5,282,467 A | 2/1994 | Piantadosi et al. |
| 5,305,745 A | 4/1994 | Zacouto |
| 5,335,313 A | 8/1994 | Douglas |
| 5,348,002 A | 9/1994 | Caro |
| 5,348,015 A | 9/1994 | Moehring et al. |
| 5,360,005 A | 11/1994 | Wilk |
| 5,429,137 A | 7/1995 | Phelps et al. |
| 5,438,983 A | 8/1995 | Falcone |
| 5,441,051 A | 8/1995 | Hileman et al. |
| 5,443,440 A | 8/1995 | Tumey et al. |
| 5,445,616 A | 8/1995 | Kratoska et al. |
| 5,474,574 A | 12/1995 | Payne et al. |
| 5,497,787 A | 3/1996 | Nemesdy et al. |
| 5,508,203 A | 4/1996 | Fuller et al. |
| 5,524,636 A | 6/1996 | Sarvazyan et al. |
| 5,546,955 A | 8/1996 | Wilk |
| 5,558,638 A | 9/1996 | Evers et al. |
| 5,576,952 A | 11/1996 | Stutman et al. |
| 5,593,431 A | 1/1997 | Sheldon |
| 5,601,811 A | 2/1997 | Gallagher et al. |
| 5,620,475 A | 4/1997 | Magnusson |
| 5,628,322 A | 5/1997 | Mine |
| 5,662,109 A | 9/1997 | Hutson |
| 5,671,750 A | 9/1997 | Shinoda |
| 5,699,934 A | 12/1997 | Kolcun et al. |
| 5,713,858 A | 2/1998 | Heruth et al. |
| 5,718,247 A | 2/1998 | Frankel |
| 5,722,972 A | 3/1998 | Power et al. |
| 5,724,983 A | 3/1998 | Selker et al. |
| 5,725,492 A | 3/1998 | Igo et al. |
| 5,740,540 A | 4/1998 | Emmermann |
| 5,755,571 A | 5/1998 | Companion |
| 5,755,741 A | 5/1998 | Vogel |
| 5,769,801 A | 6/1998 | Tumey et al. |
| 5,793,969 A | 8/1998 | Kamentsky et al. |
| 5,795,327 A | 8/1998 | Wilson et al. |
| 5,807,261 A | 9/1998 | Benaron et al. |
| 5,832,182 A | 11/1998 | Zhang et al. |
| 5,833,603 A | 11/1998 | Kovacs et al. |
| 5,840,049 A | 11/1998 | Tumey et al. |
| 5,857,998 A | 1/1999 | Barry |
| 5,879,292 A | 3/1999 | Sternberg et al. |
| 5,886,142 A | 3/1999 | Thakur et al. |
| 5,892,570 A | 4/1999 | Stevens |
| 5,911,689 A | 6/1999 | Smith et al. |
| 5,925,016 A | 7/1999 | Chornenky et al. |
| 5,931,797 A | 8/1999 | Tumey et al. |
| 5,935,075 A | 8/1999 | Casscells et al. |
| 5,941,829 A | 8/1999 | Saltzstein et al. |
| 5,942,986 A | 8/1999 | Shabot et al. |
| 5,960,797 A | 10/1999 | Kramer et al. |
| 5,963,997 A | 10/1999 | Hagopian |
| 5,967,986 A | 10/1999 | Cimochowski et al. |
| 5,978,693 A | 11/1999 | Hamilton et al. |
| 5,983,429 A | 11/1999 | Stacy et al. |
| 5,987,345 A | 11/1999 | Engelmann et al. |
| 5,989,194 A | 11/1999 | Davenport et al. |
| 5,989,245 A | 11/1999 | Prescott |
| 5,991,654 A | 11/1999 | Tumey et al. |
| 5,991,694 A | 11/1999 | Gudat et al. |
| 5,993,400 A | 11/1999 | Rincoe et al. |
| 5,997,472 A | 12/1999 | Bonnell et al. |
| 5,999,836 A | 12/1999 | Nelson et al. |
| 5,999,842 A | 12/1999 | Harrison et al. |
| 6,014,346 A | 1/2000 | Malone |
| 6,014,626 A | 1/2000 | Cohen |
| 6,015,387 A | 1/2000 | Schwartz et al. |
| 6,019,729 A | 2/2000 | Itoigawa et al. |
| 6,023,637 A | 2/2000 | Liu et al. |
| 6,025,128 A | 2/2000 | Veltri et al. |
| 6,033,364 A | 3/2000 | Ohman et al. |
| 6,034,526 A | 3/2000 | Montant et al. |
| 6,035,230 A | 3/2000 | Kang et al. |
| 6,047,201 A | 4/2000 | Jackson, III |
| 6,047,203 A | 4/2000 | Sackner et al. |
| 6,056,692 A | 5/2000 | Schwartz |
| 6,063,044 A | 5/2000 | Leonard et al. |
| 6,064,770 A | 5/2000 | Scarth et al. |
| 6,069,696 A | 5/2000 | McQueen et al. |
| 6,071,956 A | 6/2000 | Slepian et al. |
| 6,075,755 A | 6/2000 | Zarchan |
| 6,077,256 A | 6/2000 | Mann |
| 6,081,741 A | 6/2000 | Hollis |
| 6,084,174 A | 7/2000 | Hedengren et al. |
| 6,086,247 A | 7/2000 | von Hollen |
| 6,098,908 A | 8/2000 | Ng |
| 6,117,077 A | 9/2000 | Del Mar et al. |
| 6,117,087 A | 9/2000 | Kamm et al. |
| 6,121,002 A | 9/2000 | Robins |
| 6,124,597 A | 9/2000 | Shehada et al. |
| 6,126,614 A | 10/2000 | Jenkins et al. |
| 6,133,837 A | 10/2000 | Riley |
| 6,137,527 A | 10/2000 | Abdel-Malek et al. |
| 6,139,495 A | 10/2000 | De La Huerga |
| 6,139,499 A | 10/2000 | Wilk |
| 6,146,358 A | 11/2000 | Rowe |
| 6,149,674 A | 11/2000 | Borders |
| 6,152,881 A | 11/2000 | Raines et al. |
| 6,161,041 A | 12/2000 | Stoop et al. |
| 6,165,151 A | 12/2000 | Weiner |
| 6,165,787 A | 12/2000 | Crabtree et al. |
| 6,168,563 B1 | 1/2001 | Brown |
| 6,170,997 B1 | 1/2001 | Glew et al. |
| 6,177,873 B1 | 1/2001 | Cragun |
| 6,179,786 B1 | 1/2001 | Young |
| 6,179,793 B1 | 1/2001 | Rothman et al. |
| 6,186,962 B1 | 2/2001 | Lloyd et al. |
| 6,190,313 B1 | 2/2001 | Hinkle |
| 6,192,143 B1 | 2/2001 | Souluer |
| 6,193,669 B1 | 2/2001 | Degany et al. |
| 6,195,571 B1 | 2/2001 | Osuge |
| 6,196,973 B1 | 3/2001 | Lazenby et al. |
| 6,197,345 B1 | 3/2001 | Porter |
| 6,200,270 B1 | 3/2001 | Biehl et al. |
| 6,206,835 B1 | 3/2001 | Spillman, Jr. et al. |
| 6,210,301 B1 | 4/2001 | Abraham-Fuchs et al. |
| 6,216,066 B1 | 4/2001 | Goebel et al. |
| 6,217,554 B1 | 4/2001 | Green |
| 6,217,846 B1 | 4/2001 | Stuttle |
| 6,219,929 B1 | 4/2001 | Tasker et al. |
| 6,228,034 B1 | 5/2001 | Voss et al. |
| 6,228,049 B1 | 5/2001 | Schroeder et al. |
| 6,231,591 B1 | 5/2001 | Desai |
| 6,233,479 B1 | 5/2001 | Haddad et al. |
| 6,233,487 B1 | 5/2001 | Mika et al. |
| 6,238,349 B1 | 5/2001 | Hickey |
| 6,238,354 B1 | 5/2001 | Alvarez |
| 6,240,582 B1 | 6/2001 | Reinke |
| 6,241,661 B1 | 6/2001 | Schluess et al. |
| 6,246,992 B1 | 6/2001 | Brown |
| 6,258,046 B1 | 7/2001 | Kimball et al. |
| 6,263,243 B1 | 7/2001 | Lang |
| 6,267,728 B1 | 7/2001 | Hayden |
| 6,268,161 B1 | 7/2001 | Han et al. |
| 6,269,376 B1 | 7/2001 | Dhillon et al. |
| 6,270,463 B1 | 8/2001 | Morris, Sr. et al. |
| 6,271,618 B1 | 8/2001 | Hoffmann et al. |
| 6,271,766 B1 | 8/2001 | Didden et al. |
| 6,272,367 B1 | 8/2001 | Chance |
| 6,275,733 B1 | 8/2001 | Park et al. |
| 6,277,071 B1 | 8/2001 | Hennessy et al. |
| 6,280,390 B1 | 8/2001 | Akselrod et al. |

| | | |
|---|---|---|
| 6,282,441 B1 | 8/2001 | Raymond et al. |
| 6,282,448 B1 | 8/2001 | Katz et al. |
| 6,283,951 B1 | 9/2001 | Flaherty et al. |
| 6,287,608 B1 | 9/2001 | Levin et al. |
| 6,299,347 B1 | 10/2001 | Pompei |
| 6,300,085 B1 | 10/2001 | Alkon |
| 6,304,775 B1 | 10/2001 | Iasemidis et al. |
| 6,305,377 B1 | 10/2001 | Portwood et al. |
| 6,312,378 B1 | 11/2001 | Bardy |
| 6,317,731 B1 | 11/2001 | Luciano |
| 6,322,548 B1 | 11/2001 | Payne et al. |
| 6,332,502 B1 | 12/2001 | Mills et al. |
| 6,336,900 B1 | 1/2002 | Alleckson et al. |
| 6,336,903 B1 | 1/2002 | Bardy |
| 6,338,719 B1 | 1/2002 | Drzewiecki et al. |
| 6,340,928 B1 | 1/2002 | McCurdy |
| 6,352,502 B1 | 3/2002 | Chaiken et al. |
| 6,354,999 B1 | 3/2002 | Dgany et al. |
| 6,355,000 B1 | 3/2002 | Ogura |
| 6,358,201 B1 | 3/2002 | Childre et al. |
| 6,361,495 B1 | 3/2002 | Grolman |
| 6,363,270 B1 | 3/2002 | Colla et al. |
| 6,377,834 B1 | 4/2002 | Zhou et al. |
| 6,382,568 B1 | 5/2002 | Snell |
| 6,383,136 B1 | 5/2002 | Jordan |
| 6,383,137 B1 | 5/2002 | Berry |
| 6,384,627 B1 | 5/2002 | Fross et al. |
| 6,385,332 B1 | 5/2002 | Zahalka et al. |
| 6,387,048 B1 | 5/2002 | Schulman et al. |
| 6,387,059 B1 | 5/2002 | Marchitto et al. |
| 6,393,315 B1 | 5/2002 | Aprahamian et al. |
| 6,402,371 B2 | 6/2002 | Pompei et al. |
| 6,409,662 B1 | 6/2002 | Lloyd et al. |
| 6,413,223 B1 | 7/2002 | Yang et al. |
| 6,413,233 B1 | 7/2002 | Sites et al. |
| 6,416,471 B1 | 7/2002 | Kumar et al. |
| 6,425,875 B1 | 7/2002 | Reifman et al. |
| 6,430,430 B1 | 8/2002 | Gosche |
| 6,438,216 B1 | 8/2002 | Aktas |
| 6,440,067 B1 | 8/2002 | DeLuca et al. |
| 6,440,084 B1 | 8/2002 | Gentempo et al. |
| 6,440,090 B1 | 8/2002 | Schallhorn |
| 6,442,241 B1 | 8/2002 | Tsumpes |
| 6,442,421 B1 | 8/2002 | Le Van Quyen et al. |
| 6,445,183 B1 | 9/2002 | Shimizu et al. |
| 6,445,945 B1 | 9/2002 | Arsenault |
| 6,447,455 B2 | 9/2002 | Bang et al. |
| 6,447,460 B1 | 9/2002 | Zheng et al. |
| 6,450,027 B1 | 9/2002 | Hogfors et al. |
| 6,454,705 B1 | 9/2002 | Cosentino et al. |
| 6,454,718 B1 | 9/2002 | Clift |
| 6,455,243 B1 | 9/2002 | Jeejeebhoy |
| 6,458,150 B1 | 10/2002 | Evans et al. |
| 6,459,929 B1 | 10/2002 | Hopper et al. |
| 6,461,303 B2 | 10/2002 | Angelsen |
| 6,463,310 B1 | 10/2002 | Swedlow et al. |
| 6,464,646 B1 | 10/2002 | Shalom et al. |
| 6,468,242 B1 | 10/2002 | Wilson et al. |
| 6,473,708 B1 | 10/2002 | Watkins et al. |
| 6,475,155 B2 | 11/2002 | Ogura et al. |
| 6,475,159 B1 | 11/2002 | Casscells et al. |
| 6,475,170 B1 | 11/2002 | Doron et al. |
| 6,478,737 B2 | 11/2002 | Bardy |
| 6,478,757 B1 | 11/2002 | Barak |
| 6,482,197 B2 | 11/2002 | Finch et al. |
| 6,484,047 B1 | 11/2002 | Vilsmeier |
| 6,485,416 B1 | 11/2002 | Platt et al. |
| 6,487,507 B1 | 11/2002 | Mansfield et al. |
| 6,490,490 B1 | 12/2002 | Uchikubo et al. |
| 6,497,222 B2 | 12/2002 | Bolz et al. |
| 6,501,849 B1 | 12/2002 | Gupta et al. |
| 6,505,196 B2 | 1/2003 | Drucker et al. |
| 6,506,437 B1 | 1/2003 | Harish et al. |
| 6,507,663 B2 | 1/2003 | Souluer |
| 6,507,747 B1 | 1/2003 | Gowda et al. |
| 6,507,754 B2 | 1/2003 | Le Van Quyen et al. |
| 6,509,747 B2 | 1/2003 | Nagai et al. |
| 6,511,477 B2 | 1/2003 | Altman et al. |
| 6,513,026 B1 | 1/2003 | Horvitz et al. |
| 6,514,195 B1 | 2/2003 | Ferek-Petric |
| 6,514,226 B1 | 2/2003 | Levin et al. |
| 6,518,016 B1 | 2/2003 | Bertina et al. |
| 6,520,919 B1 | 2/2003 | Nunome et al. |
| 6,525,712 B1 | 2/2003 | Held |
| 6,529,757 B1 | 3/2003 | Patel et al. |
| 6,529,759 B1 | 3/2003 | Tucker et al. |
| 6,533,724 B2 | 3/2003 | McNair |
| 6,536,949 B1 | 3/2003 | Heuser |
| 6,537,228 B1 | 3/2003 | Lambert |
| 6,539,302 B1 | 3/2003 | Bender et al. |
| 6,540,668 B1 | 4/2003 | Schulz et al. |
| 6,542,767 B1 | 4/2003 | McNichols et al. |
| 6,544,186 B1 | 4/2003 | Shelby et al. |
| 6,544,202 B2 | 4/2003 | McEwen et al. |
| 6,545,603 B1 | 4/2003 | Launay et al. |
| 6,547,736 B1 | 4/2003 | Moehring et al. |
| 6,547,746 B1 | 4/2003 | Marino |
| 6,547,749 B2 | 4/2003 | Hansen |
| 6,551,306 B1 | 4/2003 | Carriazo |
| 6,552,531 B1 | 4/2003 | Fey et al. |
| 6,554,819 B2 | 4/2003 | Reich |
| 6,559,769 B2 | 5/2003 | Anthony et al. |
| 6,560,804 B2 | 5/2003 | Wise et al. |
| 6,561,996 B1 | 5/2003 | Gorsuch |
| 6,567,705 B1 | 5/2003 | Stokes et al. |
| 6,569,095 B2 | 5/2003 | Eggers |
| 6,573,063 B2 | 6/2003 | Hochman |
| 6,577,901 B2 | 6/2003 | Thompson |
| 6,580,016 B2 | 6/2003 | Teirstein et al. |
| 6,580,994 B2 | 6/2003 | Katayama et al. |
| 6,582,379 B1 | 6/2003 | Stisen |
| 6,583,411 B1 | 6/2003 | Altmann et al. |
| 6,584,345 B2 | 6/2003 | Govari |
| 6,584,628 B1 | 7/2003 | Kummer et al. |
| 6,584,931 B1 | 7/2003 | Kall et al. |
| 6,585,328 B1 | 7/2003 | Oexman et al. |
| 6,585,763 B1 | 7/2003 | Keilman et al. |
| 6,591,182 B1 | 7/2003 | Cece et al. |
| 6,592,567 B1 | 7/2003 | Levin et al. |
| 6,594,518 B1 | 7/2003 | Benaron et al. |
| 6,597,940 B2 | 7/2003 | Bishop et al. |
| 6,597,948 B1 | 7/2003 | Rockwell et al. |
| 6,600,425 B1 | 7/2003 | Parsadayan |
| 6,600,949 B1 | 7/2003 | Turcott |
| 6,604,650 B2 | 8/2003 | Sagar |
| 6,606,579 B1 | 8/2003 | Gu |
| 6,610,024 B1 | 8/2003 | Benatti |
| 6,611,846 B1 | 8/2003 | Stoodley |
| 6,612,982 B1 | 9/2003 | Ouchi |
| 6,615,071 B1 | 9/2003 | Casscells, III et al. |
| 6,616,606 B1 | 9/2003 | Petersen et al. |
| 6,616,611 B1 | 9/2003 | Moehring |
| 6,616,613 B1 | 9/2003 | Goodman |
| 6,620,115 B2 | 9/2003 | Sarvazyan et al. |
| 6,620,146 B2 | 9/2003 | Gibbs |
| 6,621,506 B1 | 9/2003 | Burbidge |
| 6,621,918 B1 | 9/2003 | Hu et al. |
| 6,625,252 B2 | 9/2003 | Mirabella |
| 6,626,840 B2 | 9/2003 | Drzewiecki et al. |
| 6,629,937 B2 | 10/2003 | Watrous |
| 6,631,287 B2 | 10/2003 | Newman et al. |
| 6,635,017 B1 | 10/2003 | Moehring et al. |
| 6,635,027 B1 | 10/2003 | Cragg et al. |
| 6,635,049 B1 | 10/2003 | Robinson et al. |
| 6,636,621 B2 | 10/2003 | Thebaud |
| 6,636,755 B2 | 10/2003 | Toida |
| 6,638,218 B2 | 10/2003 | Bulat |
| 6,643,646 B2 | 11/2003 | Su et al. |
| 6,645,165 B2 | 11/2003 | Waldridge et al. |
| 6,645,192 B2 | 11/2003 | Kenison et al. |
| 6,646,556 B1 | 11/2003 | Smith et al. |
| 6,647,093 B2 | 11/2003 | Schmitz et al. |
| 6,652,465 B2 | 11/2003 | Ogura |
| 6,658,292 B2 | 12/2003 | Kroll et al. |
| 6,659,327 B2 | 12/2003 | Heck et al. |
| 6,660,028 B2 | 12/2003 | Magers et al. |
| 6,663,242 B1 | 12/2003 | Davenport |
| 6,668,188 B2 | 12/2003 | Sun et al. |

| Patent | Date | Inventor |
|---|---|---|
| 6,671,529 B2 | 12/2003 | Claure et al. |
| 6,671,540 B1 | 12/2003 | Hochman |
| 6,671,541 B2 | 12/2003 | Bishop et al. |
| 6,671,547 B2 | 12/2003 | Lyster et al. |
| 6,672,307 B2 | 1/2004 | McDonald et al. |
| 6,673,561 B1 | 1/2004 | Morris |
| 6,675,040 B1 | 1/2004 | Cosman |
| 6,676,608 B1 | 1/2004 | Keren |
| 6,679,830 B2 | 1/2004 | Kolarovic et al. |
| 6,682,483 B1 | 1/2004 | Abend et al. |
| 6,682,490 B2 | 1/2004 | Roy et al. |
| 6,685,303 B1 | 2/2004 | Trauernicht et al. |
| 6,687,230 B1 | 2/2004 | Furutono et al. |
| 6,687,544 B1 | 2/2004 | Levine et al. |
| 6,689,069 B2 | 2/2004 | Bratteli et al. |
| 6,689,612 B2 | 2/2004 | Samsoondar |
| 6,689,974 B2 | 2/2004 | Guillot et al. |
| 6,690,267 B2 | 2/2004 | Linden et al. |
| 6,691,979 B2 | 2/2004 | Parsons et al. |
| 6,694,176 B1 | 2/2004 | Tsujita et al. |
| 6,694,177 B2 | 2/2004 | Eggers et al. |
| 6,699,231 B1 | 3/2004 | Sterman et al. |
| 6,706,001 B2 | 3/2004 | Fresco |
| 6,709,444 B1 | 3/2004 | Makower |
| 6,711,436 B1 | 3/2004 | Duhaylongsod |
| 6,715,402 B2 | 4/2004 | Pfaff et al. |
| 6,717,337 B2 | 4/2004 | Howarth et al. |
| 6,720,712 B2 | 4/2004 | Scott et al. |
| 6,720,875 B2 | 4/2004 | Philippe |
| 6,721,980 B1 | 4/2004 | Price et al. |
| 6,731,976 B2 | 5/2004 | Penn et al. |
| 6,732,884 B2 | 5/2004 | Topliffe et al. |
| 6,733,447 B2 | 5/2004 | Lai et al. |
| 6,733,461 B2 | 5/2004 | Bratteli |
| 6,735,331 B1 | 5/2004 | Binnun et al. |
| 6,736,790 B2 | 5/2004 | Barbut et al. |
| 6,738,655 B1 | 5/2004 | Sen et al. |
| 6,738,769 B2 | 5/2004 | Sharp |
| 6,740,042 B1 | 5/2004 | Lerner et al. |
| 6,740,045 B2 | 5/2004 | Amano |
| 6,740,076 B2 | 5/2004 | Hoben et al. |
| 6,748,929 B2 | 6/2004 | Przymusinski et al. |
| 6,749,619 B2 | 6/2004 | Ouriel et al. |
| 6,751,255 B1 | 6/2004 | Reuven et al. |
| 6,752,771 B2 | 6/2004 | Rothman et al. |
| 6,755,783 B2 | 6/2004 | Cosentino et al. |
| 6,757,412 B1 | 6/2004 | Parsons et al. |
| 6,763,261 B2 | 7/2004 | Casscells, III et al. |
| 6,763,262 B2 | 7/2004 | Hohla et al. |
| 6,770,045 B2 | 8/2004 | Naft et al. |
| 6,773,404 B2 | 8/2004 | Poezevera et al. |
| 6,776,756 B2 | 8/2004 | Feldon et al. |
| 6,783,492 B2 | 8/2004 | Dominguez et al. |
| 6,785,358 B2 | 8/2004 | Johnson et al. |
| 6,786,879 B1 | 9/2004 | Bolam et al. |
| 6,790,204 B2 | 9/2004 | Zadno-Azizi et al. |
| 6,791,460 B2 | 9/2004 | Dixon et al. |
| 6,793,625 B2 | 9/2004 | Cavallaro et al. |
| 6,798,226 B2 | 9/2004 | Altmann et al. |
| 6,801,137 B2 | 10/2004 | Eggers |
| 6,802,811 B1 | 10/2004 | Slepian |
| 6,804,654 B2 | 10/2004 | Kobylevsky et al. |
| 6,809,653 B1 | 10/2004 | Mann et al. |
| 6,810,876 B2 | 11/2004 | Berthon-Jones |
| 6,813,009 B2 | 11/2004 | Riordan et al. |
| 6,816,743 B2 | 11/2004 | Moreno et al. |
| 6,816,744 B2 | 11/2004 | Garfield et al. |
| 6,822,564 B2 | 11/2004 | Al-Ali |
| 6,822,571 B2 | 11/2004 | Conway |
| 6,824,512 B2 | 11/2004 | Warkentin et al. |
| 6,826,578 B2 | 11/2004 | Brackett et al. |
| 6,830,549 B2 | 12/2004 | Bui et al. |
| 6,830,577 B2 | 12/2004 | Nash et al. |
| 6,834,306 B1 | 12/2004 | Tsimelzon |
| 6,835,351 B2 | 12/2004 | Huber et al. |
| 6,835,553 B2 | 12/2004 | Han et al. |
| 6,836,528 B2 | 12/2004 | Reddy et al. |
| 6,837,351 B2 | 1/2005 | Showalter et al. |
| 6,839,455 B2 | 1/2005 | Kaufman |
| 6,840,117 B2 | 1/2005 | Hubbard, Jr. |
| 6,843,772 B2 | 1/2005 | Nunome et al. |
| 6,843,774 B2 | 1/2005 | Foust et al. |
| 6,845,146 B2 | 1/2005 | Rick et al. |
| 6,847,841 B1 | 1/2005 | El Hatw |
| 6,847,913 B2 | 1/2005 | Wigley et al. |
| 6,852,132 B1 | 2/2005 | Houser et al. |
| 6,854,459 B1 | 2/2005 | Cox |
| 6,856,831 B2 | 2/2005 | Griffin et al. |
| 6,871,214 B2 | 3/2005 | Parsons et al. |
| 6,878,111 B2 | 4/2005 | Kenknight et al. |
| 6,878,117 B1 | 4/2005 | Watrous |
| 6,878,518 B2 | 4/2005 | Whitehead |
| 6,880,387 B2 | 4/2005 | Kessler et al. |
| 6,881,192 B1 | 4/2005 | Park |
| 6,885,882 B2 | 4/2005 | Cote et al. |
| 6,886,002 B2 | 4/2005 | Horvitz |
| 6,886,200 B2 | 5/2005 | Blyshak et al. |
| 6,887,201 B2 | 5/2005 | Bardy |
| 6,892,405 B1 | 5/2005 | Dimitriu et al. |
| 6,893,089 B2 | 5/2005 | McMillen et al. |
| 6,893,396 B2 | 5/2005 | Schulze et al. |
| 6,895,265 B2 | 5/2005 | Silver |
| 6,898,457 B1 | 5/2005 | Kraus et al. |
| 6,898,585 B2 | 5/2005 | Benson et al. |
| 6,902,576 B2 | 6/2005 | Drasler et al. |
| 6,905,505 B2 | 6/2005 | Nash et al. |
| 6,907,375 B2 | 6/2005 | Guggari et al. |
| 6,908,431 B2 | 6/2005 | Bardy |
| 6,908,437 B2 | 6/2005 | Bardy |
| 6,916,424 B2 | 7/2005 | Collins et al. |
| 6,921,365 B2 | 7/2005 | Lee |
| 6,922,592 B2 | 7/2005 | Thompson et al. |
| 6,923,771 B2 | 8/2005 | Ogura et al. |
| 6,925,621 B2 | 8/2005 | Mielke et al. |
| 6,926,668 B2 | 8/2005 | Bardy |
| 6,929,922 B1 | 8/2005 | Connor et al. |
| 6,932,091 B2 | 8/2005 | Frazier et al. |
| 6,934,579 B2 | 8/2005 | Mantzardis et al. |
| 6,936,025 B1 | 8/2005 | Evans et al. |
| 6,939,304 B2 | 9/2005 | Schnall et al. |
| 6,939,322 B2 | 9/2005 | Crank et al. |
| 6,942,616 B2 | 9/2005 | Kerr, III |
| 6,942,626 B2 | 9/2005 | Salisbury et al. |
| 6,943,574 B2 | 9/2005 | Altmann et al. |
| 6,944,497 B2 | 9/2005 | Stypulkowski |
| 6,945,944 B2 | 9/2005 | Kuiper et al. |
| 6,947,780 B2 | 9/2005 | Scharf |
| 6,947,781 B2 | 9/2005 | Asada et al. |
| 6,949,075 B2 | 9/2005 | Hatlesad et al. |
| 6,950,692 B2 | 9/2005 | Gelikonov et al. |
| 6,950,693 B1 | 9/2005 | Wehberg |
| 6,953,666 B2 | 10/2005 | Kinkade, Jr. et al. |
| 6,955,113 B2 | 10/2005 | Demers |
| 6,959,211 B2 | 10/2005 | Rule et al. |
| 6,961,327 B2 | 11/2005 | Niu |
| 6,961,971 B2 | 11/2005 | Schneider et al. |
| 6,963,772 B2 | 11/2005 | Bloom et al. |
| 6,966,557 B2 | 11/2005 | Kirk et al. |
| 6,966,650 B2 | 11/2005 | Hu et al. |
| 6,968,294 B2 | 11/2005 | Gutta et al. |
| 6,968,375 B1 | 11/2005 | Brown |
| 6,969,345 B2 | 11/2005 | Jassawalla et al. |
| 6,969,355 B2 | 11/2005 | Narimatsu |
| 6,970,737 B1 | 11/2005 | Brodnick et al. |
| 6,970,847 B1 | 11/2005 | Melen et al. |
| 6,972,122 B2 | 12/2005 | Haroon et al. |
| 6,974,463 B2 | 12/2005 | Magers et al. |
| 6,974,567 B2 | 12/2005 | Edwards et al. |
| 6,975,232 B1 | 12/2005 | McKenna |
| 6,975,898 B2 | 12/2005 | Seibel |
| 6,978,169 B1 | 12/2005 | Guerra |
| 6,978,182 B2 | 12/2005 | Mazar et al. |
| 6,979,293 B2 | 12/2005 | Hansmann et al. |
| 6,979,296 B2 | 12/2005 | Hansmann et al. |
| 6,980,851 B2 | 12/2005 | Zhu et al. |
| 6,980,852 B2 | 12/2005 | Jersey-Willuhn et al. |
| 6,983,178 B2 | 1/2006 | Fine et al. |
| 6,984,207 B1 | 1/2006 | Sullivan et al. |

| | | |
|---|---|---|
| 6,984,373 B2 | 1/2006 | Wescott et al. |
| 6,988,088 B1 | 1/2006 | Miikkulainen et al. |
| 6,988,499 B2 | 1/2006 | Holt et al. |
| 6,990,365 B1 | 1/2006 | Parker et al. |
| 6,990,371 B2 | 1/2006 | Powers et al. |
| 6,990,455 B2 | 1/2006 | Vozick et al. |
| 6,990,980 B2 | 1/2006 | Richey, II |
| 6,993,167 B1 | 1/2006 | Skladnev et al. |
| 6,993,380 B1 | 1/2006 | Modarres |
| 6,993,382 B2 | 1/2006 | Casscells et al. |
| 6,996,427 B2 | 2/2006 | Ali et al. |
| 6,999,812 B2 | 2/2006 | Kawada et al. |
| 7,001,338 B2 | 2/2006 | Hayek et al. |
| 7,003,340 B2 | 2/2006 | Say et al. |
| 7,003,525 B1 | 2/2006 | Horvitz et al. |
| 7,004,907 B2 | 2/2006 | Banet et al. |
| 7,004,911 B1 | 2/2006 | Tu et al. |
| 7,006,676 B1 | 2/2006 | Zeylikovich et al. |
| 7,006,858 B2 | 2/2006 | Silver et al. |
| 7,006,861 B2 | 2/2006 | Flock et al. |
| 7,011,633 B2 | 3/2006 | Strandberg |
| 7,011,645 B2 | 3/2006 | McGuckin, Jr. et al. |
| 7,014,861 B2 | 3/2006 | Roorda et al. |
| 7,016,021 B2 | 3/2006 | Nakajima et al. |
| 7,016,467 B2 | 3/2006 | Brooks |
| 7,016,601 B1 | 3/2006 | Yoneya et al. |
| 7,020,666 B2 | 3/2006 | Doise et al. |
| 7,024,234 B2 | 4/2006 | Margulies et al. |
| 7,025,778 B2 | 4/2006 | Hayashi et al. |
| 7,027,871 B2 | 4/2006 | Burnes et al. |
| 7,029,447 B2 | 4/2006 | Rantala |
| 7,030,764 B2 | 4/2006 | Smith et al. |
| 7,033,776 B2 | 4/2006 | Toombs |
| 7,035,684 B2 | 4/2006 | Lee |
| 7,037,256 B2 | 5/2006 | Osbon et al. |
| 7,037,273 B2 | 5/2006 | Zhu et al. |
| 7,038,595 B2 | 5/2006 | Seely |
| 7,039,698 B2 | 5/2006 | Slemmer et al. |
| 7,041,079 B2 | 5/2006 | Yozu et al. |
| 7,043,288 B2 | 5/2006 | Davis, III et al. |
| 7,047,083 B2 | 5/2006 | Gunderson et al. |
| 7,047,149 B1 | 5/2006 | Maki et al. |
| 7,051,738 B2 | 5/2006 | Oron et al. |
| 7,052,427 B2 | 5/2006 | Kapaan et al. |
| 7,052,474 B2 | 5/2006 | Castell et al. |
| 7,058,450 B2 | 6/2006 | Struble et al. |
| 7,062,528 B2 | 6/2006 | Deguchi |
| 7,065,465 B2 | 6/2006 | Chen et al. |
| 7,066,873 B2 | 6/2006 | Hughett et al. |
| 7,069,086 B2 | 6/2006 | Von Arx |
| 7,072,711 B2 | 7/2006 | Girouard et al. |
| 7,074,188 B2 | 7/2006 | Nair et al. |
| 7,074,426 B2 | 7/2006 | Kochinke |
| 7,076,436 B1 | 7/2006 | Ross, Jr. et al. |
| 7,077,809 B2 | 7/2006 | Wu et al. |
| 7,079,035 B2 | 7/2006 | Bock et al. |
| 7,087,395 B1 | 8/2006 | Garrity et al. |
| 7,087,903 B2 | 8/2006 | Balan et al. |
| 7,088,993 B2 | 8/2006 | Dumont et al. |
| 7,092,970 B2 | 8/2006 | Shiibashi et al. |
| 7,097,625 B2 | 8/2006 | Steinberg |
| 7,098,673 B1 | 8/2006 | Launay et al. |
| 7,098,678 B2 | 8/2006 | Altmann et al. |
| 7,100,491 B2 | 9/2006 | Yatsko et al. |
| 7,104,955 B2 | 9/2006 | Bardy |
| 7,107,096 B2 | 9/2006 | Fischell et al. |
| 7,108,686 B2 | 9/2006 | Burke et al. |
| 7,110,806 B2 | 9/2006 | Prince |
| 7,112,318 B2 | 9/2006 | Madar et al. |
| 7,113,819 B2 | 9/2006 | Hamilton et al. |
| 7,115,097 B2 | 10/2006 | Johnson |
| 7,116,655 B2 | 10/2006 | Yegoshin |
| 7,116,825 B2 | 10/2006 | Lee et al. |
| 7,117,036 B2 | 10/2006 | Florio |
| 7,117,037 B2 | 10/2006 | Hiebert et al. |
| 7,122,005 B2 | 10/2006 | Shusterman |
| 7,122,019 B1 | 10/2006 | Kesten et al. |
| 7,123,950 B2 | 10/2006 | Mannheimer |
| 7,124,837 B2 | 10/2006 | Martin et al. |
| 7,127,370 B2 | 10/2006 | Kelly, Jr. et al. |
| 7,128,713 B2 | 10/2006 | Moehring et al. |
| 7,130,396 B2 | 10/2006 | Rogers et al. |
| 7,133,661 B2 | 11/2006 | Hatae et al. |
| 7,134,157 B2 | 11/2006 | Koch |
| 7,135,007 B2 | 11/2006 | Scott et al. |
| 7,135,032 B2 | 11/2006 | Akerfeldt |
| 7,136,357 B2 | 11/2006 | Soumiya et al. |
| 7,136,704 B2 | 11/2006 | Schulman |
| 7,138,902 B2 | 11/2006 | Menard |
| 7,142,632 B2 | 11/2006 | Atzinger et al. |
| 7,143,222 B2 | 11/2006 | Fisher et al. |
| 7,144,099 B2 | 12/2006 | Cabal et al. |
| 7,146,664 B1 | 12/2006 | Grosvenor |
| 7,147,600 B2 | 12/2006 | Bardy |
| 7,149,645 B2 | 12/2006 | Mangrulkar et al. |
| 7,151,957 B2 | 12/2006 | Beker et al. |
| 7,155,273 B2 | 12/2006 | Taylor |
| 7,155,281 B1 | 12/2006 | Fayram |
| 7,155,729 B1 | 12/2006 | Andrew et al. |
| 7,158,692 B2 | 1/2007 | Chalana et al. |
| 7,158,861 B2 | 1/2007 | Wang et al. |
| 7,162,061 B1 | 1/2007 | Takeo |
| 7,162,062 B2 | 1/2007 | Breitenstein et al. |
| 7,162,068 B2 | 1/2007 | Akagi |
| 7,163,520 B2 | 1/2007 | Bernard et al. |
| 7,164,941 B2 | 1/2007 | Misczynski et al. |
| 7,164,948 B2 | 1/2007 | Struble et al. |
| 7,167,734 B2 | 1/2007 | Khalil et al. |
| 7,171,251 B2 | 1/2007 | Sarussi et al. |
| 7,171,680 B2 | 1/2007 | Lange |
| 7,172,493 B2 | 2/2007 | Novak et al. |
| 7,174,005 B1 | 2/2007 | Rodkey et al. |
| 7,177,699 B2 | 2/2007 | Fabian et al. |
| 7,179,251 B2 | 2/2007 | Palasis |
| 7,180,415 B2 | 2/2007 | Bankert et al. |
| 7,180,983 B2 | 2/2007 | Uchida et al. |
| 7,181,054 B2 | 2/2007 | Zaleski |
| 7,183,057 B2 | 2/2007 | Benson |
| 7,184,580 B2 | 2/2007 | Hamid |
| 7,184,820 B2 | 2/2007 | Jersey-Willuhn et al. |
| 7,187,960 B2 | 3/2007 | Abreu |
| 7,189,204 B2 | 3/2007 | Ni et al. |
| 7,190,987 B2 | 3/2007 | Lindekugel et al. |
| 7,190,996 B2 | 3/2007 | Jarverud |
| 7,191,018 B2 | 3/2007 | Gielen et al. |
| 7,192,726 B1 | 3/2007 | Carr, Jr. et al. |
| 7,195,598 B2 | 3/2007 | Fuchs et al. |
| 7,195,640 B2 | 3/2007 | Falotico et al. |
| 7,196,620 B2 | 3/2007 | Nanba |
| 7,198,603 B2 | 4/2007 | Penner et al. |
| 7,199,494 B2 | 4/2007 | Rapp et al. |
| 7,200,431 B2 | 4/2007 | Franco et al. |
| 7,200,682 B2 | 4/2007 | Miyazaki et al. |
| 7,202,844 B2 | 4/2007 | Nakamigawa |
| 7,203,294 B2 | 4/2007 | Carnazza et al. |
| 7,205,991 B2 | 4/2007 | Fitzmaurice et al. |
| 7,207,939 B2 | 4/2007 | Husher |
| 7,208,983 B2 | 4/2007 | Imaizumi et al. |
| 7,209,671 B1 | 4/2007 | Hayee et al. |
| 7,209,955 B1 | 4/2007 | Major et al. |
| 7,211,048 B1 | 5/2007 | Najafi et al. |
| 7,211,063 B2 | 5/2007 | Tom |
| 7,212,111 B2 | 5/2007 | Tupler et al. |
| 7,213,009 B2 | 5/2007 | Pestotnik |
| 7,214,094 B2 | 5/2007 | Kaminski et al. |
| 7,214,191 B2 | 5/2007 | Stringer et al. |
| 7,214,193 B2 | 5/2007 | Freund et al. |
| 7,214,194 B2 | 5/2007 | Klyukin |
| 7,214,195 B2 | 5/2007 | Mitra |
| 7,214,202 B1 | 5/2007 | Vogel et al. |
| 7,216,263 B2 | 5/2007 | Takaoka et al. |
| 7,217,735 B1 | 5/2007 | Au et al. |
| 7,218,966 B2 | 5/2007 | Haefner |
| 7,224,281 B2 | 5/2007 | Santoso et al. |
| 7,225,005 B2 | 5/2007 | Kaufman et al. |
| 7,225,013 B2 | 5/2007 | Geva et al. |
| 7,226,415 B2 | 6/2007 | Haddad et al. |
| 7,226,419 B2 | 6/2007 | Lane et al. |

| | | | | | | |
|---|---|---|---|---|---|---|
| 7,226,422 | B2 | 6/2007 | Hatlestsad et al. | 7,306,565 B2 | 12/2007 | Fraden et al. |
| 7,226,426 | B2 | 6/2007 | Thomson | 7,306,953 B2 | 12/2007 | Probert et al. |
| 7,228,315 | B2 | 6/2007 | Finitzo et al. | 7,308,246 B2 | 12/2007 | Yamazaki et al. |
| 7,231,258 | B2 | 6/2007 | Moore et al. | 7,308,292 B2 | 12/2007 | Colvin et al. |
| 7,232,158 | B2 | 6/2007 | Wilkendorf | 7,308,309 B1 | 12/2007 | Koh |
| 7,232,415 | B2 | 6/2007 | Steinberg | 7,308,492 B2 | 12/2007 | Konopka et al. |
| 7,233,781 | B2 | 6/2007 | Hunter et al. | 7,310,564 B2 | 12/2007 | Leyerer et al. |
| 7,234,359 | B2 | 6/2007 | Hirose et al. | 7,310,607 B2 | 12/2007 | Brandt et al. |
| 7,236,815 | B2 | 6/2007 | Richards-Kortum et al. | 7,310,615 B2 | 12/2007 | Lewis |
| 7,238,158 | B2 | 7/2007 | Abend | 7,311,665 B2 | 12/2007 | Hawthorne et al. |
| 7,241,273 | B2 | 7/2007 | Maguire et al. | 7,311,727 B2 | 12/2007 | Mazumder et al. |
| 7,242,807 | B2 | 7/2007 | Waupotitsch et al. | 7,312,619 B2 | 12/2007 | Altmann et al. |
| 7,244,122 | B2 | 7/2007 | Jung et al. | 7,313,529 B2 | 12/2007 | Thompson |
| 7,248,733 | B2 | 7/2007 | Ohta | 7,314,478 B2 | 1/2008 | Hui |
| 7,248,916 | B2 | 7/2007 | Bardy | 7,315,825 B2 | 1/2008 | Rosenfeld et al. |
| 7,248,917 | B2 | 7/2007 | den Boer | 7,317,821 B2 | 1/2008 | Chen et al. |
| 7,248,921 | B2 | 7/2007 | Palreddy et al. | 7,318,004 B2 | 1/2008 | Butterfield |
| 7,250,855 | B2 | 7/2007 | Suenbuel et al. | 7,318,804 B2 | 1/2008 | Weitzel et al. |
| 7,252,637 | B2 | 8/2007 | Ebner et al. | 7,319,386 B2 | 1/2008 | Collins, Jr. et al. |
| 7,252,640 | B2 | 8/2007 | Ni et al. | 7,319,400 B2 | 1/2008 | Smith et al. |
| 7,254,425 | B2 | 8/2007 | Lowery et al. | 7,319,899 B2 | 1/2008 | Keizer |
| 7,254,430 | B2 | 8/2007 | Cho et al. | 7,320,030 B2 | 1/2008 | Brown |
| 7,254,432 | B2 | 8/2007 | Fine | 7,321,862 B2 | 1/2008 | Rosenfeld et al. |
| 7,257,531 | B2 | 8/2007 | Holub | 7,324,661 B2 | 1/2008 | Kemp et al. |
| 7,258,666 | B2 | 8/2007 | Brown | 7,325,054 B2 | 1/2008 | Ishimoto |
| 7,258,670 | B2 | 8/2007 | Bardy | 7,325,297 B2 | 2/2008 | Xia |
| 7,260,064 | B2 | 8/2007 | Basu et al. | 7,327,637 B2 | 2/2008 | Chambers et al. |
| 7,260,440 | B2 | 8/2007 | Selim et al. | 7,327,861 B2 | 2/2008 | Choshi et al. |
| 7,261,690 | B2 | 8/2007 | Teller et al. | 7,328,472 B2 | 2/2008 | Chaffee |
| 7,261,735 | B2 | 8/2007 | Lianos et al. | 7,329,236 B2 | 2/2008 | Kesten et al. |
| 7,263,073 | B2 | 8/2007 | Petite et al. | 7,329,266 B2 | 2/2008 | Royse et al. |
| 7,263,688 | B2 | 8/2007 | Pitzel et al. | 7,330,127 B2 | 2/2008 | Price et al. |
| 7,264,591 | B2 | 9/2007 | Brown | 7,331,667 B2 | 2/2008 | Grotehusmann et al. |
| 7,265,676 | B2 | 9/2007 | Gordon et al. | 7,331,928 B2 | 2/2008 | Seki et al. |
| 7,269,476 | B2 | 9/2007 | Ratnakar | 7,332,743 B2 | 2/2008 | Yang et al. |
| 7,269,483 | B2 | 9/2007 | Schubert et al. | 7,333,002 B2 | 2/2008 | Bixler et al. |
| 7,269,484 | B2 | 9/2007 | Hein | 7,333,014 B2 | 2/2008 | Agrawal et al. |
| 7,269,718 | B2 | 9/2007 | Alexander, III et al. | 7,333,844 B2 | 2/2008 | Jones et al. |
| 7,270,374 | B2 | 9/2007 | Moriggi | 7,336,018 B2 | 2/2008 | Augesky |
| 7,272,435 | B2 | 9/2007 | Rowlandson | 7,336,166 B2 | 2/2008 | Akamatsu |
| 7,273,053 | B2 | 9/2007 | Zocca et al. | 7,336,187 B2 | 2/2008 | Hubbard, Jr. et al. |
| 7,275,829 | B2 | 10/2007 | Sugiura et al. | 7,336,202 B2 | 2/2008 | Kawai et al. |
| 7,275,867 | B2 | 10/2007 | Lee | 7,336,804 B2 | 2/2008 | Steffin |
| 7,276,031 | B2 | 10/2007 | Norman et al. | 7,337,677 B2 | 3/2008 | Mizohata |
| 7,277,747 | B2 | 10/2007 | Cazares et al. | 7,337,680 B2 | 3/2008 | Kantro |
| 7,277,903 | B2 | 10/2007 | Petrocelli | 7,338,443 B1 | 3/2008 | Tucker |
| 7,278,179 | B2 | 10/2007 | Schneider | 7,338,482 B2 | 3/2008 | Lockwood et al. |
| 7,280,858 | B2 | 10/2007 | Al-Ali et al. | 7,339,299 B2 | 3/2008 | Sesita et al. |
| 7,280,992 | B2 | 10/2007 | Nitz | 7,339,587 B2 | 3/2008 | Kropfeld |
| 7,283,153 | B2 | 10/2007 | Provost et al. | 7,340,077 B2 | 3/2008 | Gokturk et al. |
| 7,284,061 | B2 | 10/2007 | Matsubayashi et al. | 7,340,240 B2 | 3/2008 | McDonald |
| 7,285,090 | B2 | 10/2007 | Stivoric et al. | 7,340,293 B2 | 3/2008 | McQuilkin |
| 7,286,648 | B1 | 10/2007 | Chang et al. | 7,340,337 B2 | 3/2008 | Katrak |
| 7,286,872 | B2 | 10/2007 | Kramer et al. | 7,340,687 B2 | 3/2008 | Sekiguchi et al. |
| 7,286,877 | B2 | 10/2007 | Daum | 7,340,951 B2 | 3/2008 | Nyce et al. |
| 7,289,029 | B2 | 10/2007 | Medema et al. | 7,343,305 B2 | 3/2008 | Benn et al. |
| 7,289,253 | B2 | 10/2007 | Thomas | 7,344,518 B2 | 3/2008 | McGuckin, Jr. et al. |
| 7,289,883 | B2 | 10/2007 | Wang et al. | 7,346,203 B2 | 3/2008 | Turek et al. |
| 7,289,927 | B2 | 10/2007 | Bedard et al. | 7,346,205 B2 | 3/2008 | Walker, Jr. |
| 7,291,111 | B2 | 11/2007 | Shertukde et al. | 7,359,747 B2 | 4/2008 | Iwanczyk et al. |
| 7,291,497 | B2 | 11/2007 | Holmes et al. | 7,369,892 B2 | 5/2008 | Ferek-Petric |
| 7,292,719 | B2 | 11/2007 | Arnon | 7,374,540 B2 | 5/2008 | Schnall |
| 7,294,108 | B1 | 11/2007 | Bornzin et al. | 7,389,142 B2 | 6/2008 | Holmström |
| 7,296,042 | B2 | 11/2007 | Edwards et al. | 7,531,133 B2 | 5/2009 | Hole et al. |
| 7,296,238 | B1 | 11/2007 | Zurawski | 7,603,166 B2 | 10/2009 | Casscells, III et al. |
| 7,297,108 | B2 | 11/2007 | Iliff | 7,623,908 B2 | 11/2009 | Boppart et al. |
| 7,297,154 | B2 | 11/2007 | Tu et al. | 7,664,548 B2 | 2/2010 | Amurthur et al. |
| 7,297,280 | B2 | 11/2007 | Krivitski et al. | 7,666,151 B2 | 2/2010 | Sullivan et al. |
| 7,297,475 | B2 | 11/2007 | Koiwai et al. | 7,729,747 B2 | 6/2010 | Stranc et al. |
| 7,299,085 | B2 | 11/2007 | Bergelson et al. | 7,740,612 B2 | 6/2010 | Hochman |
| 7,299,157 | B2 | 11/2007 | Malik | 7,780,623 B2 | 8/2010 | Soltanpour |
| 7,300,453 | B2 | 11/2007 | Yon | 7,785,258 B2 | 8/2010 | Braig et al. |
| 7,300,662 | B2 | 11/2007 | Falotico et al. | 7,789,830 B2 | 9/2010 | Ishida et al. |
| 7,300,754 | B2 | 11/2007 | Abi Fadel et al. | 7,828,739 B2 | 11/2010 | Arnold |
| 7,301,256 | B2 | 11/2007 | Marzahn | 7,833,239 B2 | 11/2010 | Nash |
| 7,303,555 | B2 | 12/2007 | Makin et al. | 7,894,874 B2 | 2/2011 | Lynch et al. |
| 7,303,575 | B2 | 12/2007 | Ogle | 7,931,600 B2 | 4/2011 | Hatlestad et al. |
| 7,304,580 | B2 | 12/2007 | Sullivan et al. | 8,005,686 B2 | 8/2011 | Smith |
| 7,305,262 | B2 | 12/2007 | Brodnick et al. | 2001/0000262 A1 | 4/2001 | McEwen et al. |

| | | |
|---|---|---|
| 2001/0031920 A1 | 10/2001 | Kaufman et al. |
| 2001/0044588 A1 | 11/2001 | Mault |
| 2001/0047137 A1 | 11/2001 | Moreno et al. |
| 2002/0016535 A1 | 2/2002 | Martin et al. |
| 2002/0042583 A1 | 4/2002 | Barak et al. |
| 2002/0099286 A1 | 7/2002 | Sandler et al. |
| 2002/0107504 A1 | 8/2002 | Gordon |
| 2002/0128545 A1 | 9/2002 | Steuer et al. |
| 2003/0026798 A1 | 2/2003 | Zimmerman et al. |
| 2003/0050542 A1 | 3/2003 | Reihl et al. |
| 2003/0065536 A1 | 4/2003 | Hansen et al. |
| 2003/0069481 A1 | 4/2003 | Hervy et al. |
| 2003/0139778 A1* | 7/2003 | Fischell et al. .................. 607/3 |
| 2003/0143158 A1 | 7/2003 | Wescott et al. |
| 2003/0149997 A1 | 8/2003 | Hageman |
| 2003/0195401 A1 | 10/2003 | Tian et al. |
| 2003/0208116 A1 | 11/2003 | Liang et al. |
| 2003/0229691 A1 | 12/2003 | Ishimoto |
| 2004/0019278 A1 | 1/2004 | Abend |
| 2004/0024298 A1 | 2/2004 | Marshik-Geurts et al. |
| 2004/0030578 A1 | 2/2004 | Cross et al. |
| 2004/0034284 A1 | 2/2004 | Aversano et al. |
| 2004/0039268 A1 | 2/2004 | Barbour et al. |
| 2004/0073146 A1 | 4/2004 | Weintraub et al. |
| 2004/0091933 A1 | 5/2004 | Stoughton et al. |
| 2004/0122354 A1 | 6/2004 | Semba |
| 2004/0133081 A1 | 7/2004 | Teller et al. |
| 2004/0138562 A1 | 7/2004 | Makower et al. |
| 2004/0143401 A1 | 7/2004 | Elling |
| 2004/0147837 A1 | 7/2004 | Macaulay et al. |
| 2004/0176668 A1 | 9/2004 | Goldstein |
| 2004/0186383 A1 | 9/2004 | Rava et al. |
| 2004/0208343 A1 | 10/2004 | Golden et al. |
| 2004/0210208 A1 | 10/2004 | Paul et al. |
| 2004/0219608 A1 | 11/2004 | Der-Balian |
| 2004/0236225 A1 | 11/2004 | Murphy et al. |
| 2004/0249293 A1 | 12/2004 | Sandler et al. |
| 2004/0260346 A1* | 12/2004 | Overall et al. .................. 607/4 |
| 2004/0265393 A1 | 12/2004 | Unger et al. |
| 2005/0004461 A1 | 1/2005 | Abend |
| 2005/0027184 A1 | 2/2005 | Saldivar et al. |
| 2005/0033154 A1 | 2/2005 | deCharms |
| 2005/0034485 A1 | 2/2005 | Klefstad-Sillonville et al. |
| 2005/0075531 A1 | 4/2005 | Loeb et al. |
| 2005/0085769 A1 | 4/2005 | MacMahon et al. |
| 2005/0090736 A1 | 4/2005 | Sommer |
| 2005/0090748 A1 | 4/2005 | Makower et al. |
| 2005/0096528 A1 | 5/2005 | Fritz et al. |
| 2005/0124969 A1 | 6/2005 | Fitzgerald et al. |
| 2005/0129731 A1 | 6/2005 | Horres et al. |
| 2005/0142210 A1 | 6/2005 | Porter |
| 2005/0148899 A1 | 7/2005 | Walker et al. |
| 2005/0148953 A1 | 7/2005 | Fulton, III |
| 2005/0159690 A1 | 7/2005 | Barak et al. |
| 2005/0175665 A1 | 8/2005 | Hunter et al. |
| 2005/0176678 A1 | 8/2005 | Horres et al. |
| 2005/0186245 A1 | 8/2005 | Hunter et al. |
| 2005/0222526 A1 | 10/2005 | Perry et al. |
| 2005/0234393 A1 | 10/2005 | Wood, Jr. |
| 2005/0234398 A1 | 10/2005 | Wood, Jr. |
| 2005/0234399 A1 | 10/2005 | Wood, Jr. |
| 2005/0234440 A1 | 10/2005 | Wood, Jr. |
| 2005/0261726 A1 | 11/2005 | Pile-Spellman |
| 2005/0287134 A1 | 12/2005 | Klein |
| 2006/0010012 A1 | 1/2006 | Franzblau et al. |
| 2006/0047301 A1 | 3/2006 | Ogle |
| 2006/0069425 A1 | 3/2006 | Hillis et al. |
| 2006/0074362 A1 | 4/2006 | Rousso et al. |
| 2006/0079784 A1 | 4/2006 | Shifrin |
| 2006/0089556 A1 | 4/2006 | Bambot et al. |
| 2006/0100530 A1 | 5/2006 | Kliot et al. |
| 2006/0124140 A1 | 6/2006 | Forsell |
| 2006/0127246 A1 | 6/2006 | Forsell |
| 2006/0135940 A1 | 6/2006 | Joshi |
| 2006/0142783 A1 | 6/2006 | Lewis et al. |
| 2006/0149313 A1 | 7/2006 | Arguello et al. |
| 2006/0181791 A1 | 8/2006 | Van Beck et al. |
| 2006/0184280 A1 | 8/2006 | Oddsson et al. |
| 2006/0224225 A1 | 10/2006 | Ransbury et al. |
| 2006/0241521 A1 | 10/2006 | Cohen |
| 2006/0253301 A1 | 11/2006 | Simms et al. |
| 2006/0290516 A1 | 12/2006 | Muehlsteff et al. |
| 2006/0293572 A1 | 12/2006 | Bulat |
| 2007/0010719 A1 | 1/2007 | Huster et al. |
| 2007/0010868 A1 | 1/2007 | Ferren et al. |
| 2007/0016079 A1 | 1/2007 | Freeman et al. |
| 2007/0021458 A1 | 1/2007 | Ishikawa et al. |
| 2007/0021774 A1 | 1/2007 | Hogendijk |
| 2007/0038042 A1 | 2/2007 | Freeman et al. |
| 2007/0043308 A1 | 2/2007 | Lee |
| 2007/0054266 A1 | 3/2007 | Sato et al. |
| 2007/0060811 A1 | 3/2007 | Roberts |
| 2007/0066929 A1 | 3/2007 | Ferren et al. |
| 2007/0078500 A1 | 4/2007 | Ryan et al. |
| 2007/0083090 A1 | 4/2007 | Sterling et al. |
| 2007/0088334 A1 | 4/2007 | Hillis et al. |
| 2007/0129639 A1 | 6/2007 | Zhang et al. |
| 2007/0142905 A1 | 6/2007 | Hezi-Yamit et al. |
| 2007/0156211 A1 | 7/2007 | Ferren et al. |
| 2007/0166707 A1 | 7/2007 | Schadt et al. |
| 2007/0167836 A1 | 7/2007 | Scepanovic et al. |
| 2007/0168024 A1 | 7/2007 | Khairkhahan |
| 2007/0185470 A1 | 8/2007 | Steinbach et al. |
| 2007/0207131 A1 | 9/2007 | Boss et al. |
| 2007/0213600 A1 | 9/2007 | John et al. |
| 2007/0213613 A1 | 9/2007 | Ishida et al. |
| 2007/0232930 A1 | 10/2007 | Freeman et al. |
| 2007/0232940 A1 | 10/2007 | Fine et al. |
| 2007/0232958 A1 | 10/2007 | Donofrio et al. |
| 2007/0233019 A1 | 10/2007 | Forsell |
| 2007/0255199 A1 | 11/2007 | Dewey |
| 2008/0004550 A1 | 1/2008 | Einav et al. |
| 2008/0044072 A1 | 2/2008 | Kiraly et al. |
| 2008/0058758 A1 | 3/2008 | Ranchod et al. |
| 2008/0071185 A1 | 3/2008 | Beck et al. |
| 2008/0077019 A1 | 3/2008 | Xiao et al. |
| 2008/0132976 A1 | 6/2008 | Kane et al. |
| 2008/0146970 A1 | 6/2008 | Litman et al. |
| 2008/0161698 A1 | 7/2008 | Sum et al. |
| 2008/0208011 A1 | 8/2008 | Shuler |
| 2008/0221457 A1 | 9/2008 | Zeng et al. |
| 2008/0242952 A1 | 10/2008 | Jung et al. |
| 2008/0262344 A1 | 10/2008 | Brummett |
| 2008/0275393 A1 | 11/2008 | Bonnette et al. |
| 2008/0294019 A1 | 11/2008 | Tran |
| 2008/0300493 A1 | 12/2008 | Gatto et al. |
| 2008/0320098 A1 | 12/2008 | Jung et al. |
| 2009/0012382 A1 | 1/2009 | Dutta et al. |
| 2009/0048577 A1 | 2/2009 | Gillies et al. |
| 2009/0063518 A1 | 3/2009 | Jung et al. |
| 2009/0198129 A1 | 8/2009 | Varghese et al. |
| 2009/0227997 A1 | 9/2009 | Wang et al. |
| 2009/0234672 A1 | 9/2009 | Dicks et al. |
| 2009/0287093 A1 | 11/2009 | Ferren et al. |
| 2009/0287101 A1 | 11/2009 | Ferren et al. |
| 2009/0306484 A1 | 12/2009 | Kurtz et al. |
| 2009/0324608 A1 | 12/2009 | Meyers et al. |
| 2010/0016733 A1 | 1/2010 | Smith et al. |
| 2010/0063365 A1 | 3/2010 | Pisani et al. |
| 2010/0234714 A1 | 9/2010 | Mercier et al. |
| 2010/0268112 A1 | 10/2010 | Short et al. |
| 2011/0068928 A1 | 3/2011 | Riley et al. |
| 2011/0087113 A1 | 4/2011 | Mack et al. |
| 2011/0098546 A1 | 4/2011 | Farazi et al. |
| 2011/0112416 A1 | 5/2011 | Myr |
| 2011/0160549 A1 | 6/2011 | Saroka et al. |
| 2011/0201955 A1 | 8/2011 | Hatlestad et al. |
| 2011/0257577 A1 | 10/2011 | Lane et al. |

FOREIGN PATENT DOCUMENTS

| | | |
|---|---|---|
| WO | WO 94/14487 | 7/1994 |
| WO | WO 2005/046482 A1 | 5/2005 |
| WO | WO 2006/109072 A2 | 10/2006 |
| WO | WO 2007/067952 A2 | 6/2007 |
| WO | WO 2007/093804 A2 | 8/2007 |

OTHER PUBLICATIONS

Brown, Eli M. et al.; "A Case Report: Prolongad Intravenous Regional Anestesia"; Anestesia and Analgesia Current Researches; May-Jun. 1966; pp. 319-321; vol. 45; located at: http://www.anesth-analg.org/cgi/reprint/45/3/319.

Butty, V.D. et al.; "Residence Times and Basins of Attraction for a Realistic Right Internal Carotid Artery With Two Aneurysms"; Biorheology; 2002; pp. 387-393; vol. 39; IOS Press.

Caceres-Loriga, Fidel Manuel et al.; "Thrombolytic Treatment as First Option in Recurrent Tricuspid Prosthetic Valve Thrombosis and Ebstein's Anomaly"; J. Pharm. Pharmaceut Sci; 2005; pp. 332-334; located at: www.cspsCanada.org.

Das, Moloy et al.; "Is Thrombolysis or Surgery the Best Option for Actue Prosthetic Valve Thrombosis?"; Interactive CardioVascular and Thoracic Surgery; 2007; pp. 806-812; vol. 6; located at: www.icvts.ctsnetjournals.org.

"Exmocare: Answers to Frequently Asked Questions"; Exmocare; printed on Mar. 18, 2008; pp. 1-4; located at: http://www.exmocare.com/faq.

"Exmocare: BT2"; Exmocare; printed on Mar. 18, 2008; pp. 1-5; located at: http://www.exmocare.com/bt2/.

Kasai, Chihiro et al.; "Real-Time Two-Dimensional Blood Flow Imaging Using an Autocorrelation Technique"; IEEE Transactions on Sonics Ultrasonics; May 1985; pp. 458-464; vol. SU-32, No. 3; IEEE.

Mabee, John et al.; "Basic Investigations: Bier Block Exsanguination: A Volumetric Comparison and Venous Pressure Study"; Academic Emergency Medicine; Feb. 2000; pp. 105-113; vol. 7, No. 2; located at: http://vvww.ncbi.nlm.nih.gov/pubmed/10691067.

Moradkhan, Raman et al.; "Metabolic Forearm Vasodilation is Enhanced Following Bier Block with Phentolamine"; Am J Physiol Heart Circ Physiol; Aug. 3, 2007; pp. H2289-H2295; vol. 293; located at: http://ajpheart.physiology.org/cgi/content/abstract/293/4/H2289 (only abstract provided).

"Phase 1 of the BT2 is Now Complete"; Exmocare—Phase I of the BT2 vital signs wristwatch complete; printed on 5/12/08; pp. 1-9; located at: http://www.exmocare.com/index.html.

"Prioritizing Interventions to Improve Rates of Thrombolysis for Ischemic Stroke"; Neurology: California Acute Stroke Pilot Registry Investigators; 2005; pp. 654-659; vol. 64; located at: www.neurology.org.

Roscitano, Antonino et al; "Case Report: Acute Dysfunction from Thrombosis of a Mechanical Mitral Valve Prosthesis"; Braz J Cardiovasc Surg; 2005; pp. 88-90; vol. 20, No. 1; Dept. of Cardiac Surgery, St. Andrea Hospital, "La Sapienza" University, Rome, Italy.

Spanner, K.; "Survey of the Various Operating Principles of Ultrasonic Piezomotors"; Actuator 2006; pp. 1-8; located at; http://www.pi-usa.us/technotes/Actuator2006_SurveryoftheVariousOperatingPrinciplesofUltrasonicPiezomotors_c.pdf.

Taskaynatan, Mehmet Ali et al.; "Bier Block With Methylprednisolone and Lidocaine in CRPS Type I: A Randomized, Double-Blinded, Placebo-Controlled Study"; Regional Anesthesia and Pain Medicine; Sep.-Oct. 2004; pp. 408-412; vol. 29, No. 5; American Society of Regional Anesthesia and Pain Medicine.

Watrous, Raymond L. et al.; "Computer-Assisted Detection of Systolic Murmurs Associated with Hypertrophic Cardiomyopathy"; Tex Heart Inst J; 2004; pp. 368-375; vol. 31, No. 4.

Edwards, David et al.; "99mTc-NC100668, an Agent for Imaging Venous Thromboembolism: The Effect of Anticoagulant or Thrombolytic Therapy on the Upake and Retuntion of Radioactivity in Blood Clots in Vivio"; Nuclear Medicine Communications; dated 2007; pp. 55-62; vol. 28; Lippincott Williams & Wilkins.

Gatto, Rodolfo et al.; "Optical Microprobe for Blood Clot Detection"; Biomedical Optics, Technical Digest; dated Mar. 19, 2006; pp. 1-3; located at: http://www.opticsinfobase.org/abstract.cfm?URI=BIO-2006-ME47.

Gatto, Rodolfo et al.; "Optical Probe for Blood Clot Detection"; Journal of Applied Spectroscopy; dated 2007; pp. 1-19; located at; http://rodolfogatto.com/papers/Gatto_2007_Optical%20Probe_AS.pdf.

Greco, Frank A.; "Reflectance Spectroscopy of Clotting Blood: A Description of the Time-Dependent Behavior"; Arch Pathol Lab Med; Dated Feb. 2004; pp. 173-180; vol. 128.

He, Hongying et al.; "Computed Tomography Evaluation of Right Heart Dysfunction in Patients with Acute Pulmonary Embolism"; J. Comput Assist. Tomogr.; dated Mar./Apr. 2006; pp. 262-266; vol. 30, No. 2; Lippincott Williams & Wilkins.

Hart, James et al.; "P.O. Pro Wireless Reflectance Pulse Oximeter: Design 1"; dated Nov. 10, 2004; pp. 1-30; located at: www.bme.uconn.edu/sendes/Spring05/Team3/papers/design2.doc.

Hintz, Susan R. et al.; "Bedside Imaging of Intracranial Hemorrhage in the Neonate Using Light: Comparison with Ultrasound, Computed Tomography, and Magnetic Resonance Imagine"; Pediatric Research; dated May 1999; pp. 737-738; vol. 45; International Pediatrics Research Foundation, Inc.

Hunter, James B. et al.; "Methods of Anaesthesia Used for Reduction of Colles' Fractures"; BMJ; dated Nov. 25, 1989; pp. 1316-1317; vol. 299, No. 6711; located at; http://ukpmc.ac.uk/articlerender.cgi?artid=932375.

ISSYS: Integrated Sensing Systems—Press Release: ISSYS Receives Phase II SBIR Grant from NSF for Development of WaferScale, Mermetric, Hybrid Integration of MEMS and Electronics; dated Oct. 2, 2007; pp. 1-2.

ISSYS: Integrated Sensing Systems—Press Release: ISSY Receives Patent for Fuel & Fluid Quality Sensor; dated Sep. 18, 2007; pp. 1-2.

ISSYS: Integrated Sensing Systems—Press Release: ISSY Receives Patent for Fuel Cell Sensor; dated Aug. 21, 2007; pp. 1-2.

ISSYS: Integrated Sensing Systems—Press Release: NSF Awards a Phase I SBIR to ISSYS Inc. for Investigating Two-Phase Microfluidic Behavior and Nanoliter Bubble Dection; dated Jul. 17, 2007; pp. 1-2.

ISSYS: Integrated Sensing Systems—Press Release: ISSYS Inc. Awarded a Patent for Wireless, Batteryless, Implantable Sensors; dated Jul. 5, 2007; p. 1.

ISSYS: Integrated Sensing Systems—Press Release: ISSY to Present Fuel Cell Sensor Poster at the "SME Tomorrow's Energy . . . Today 2006" Conference; dated Oct. 3, 2006; pp. 1-2.

ISSYS: Integrated Sensing Systems—Press Release: ISSY Will Exhibit at the Medical Design & Manufacturing Exposition and Conference; dated Sep. 26, 2006; pp. 1-2.

ISSYS: Integrated Sensing Systems—Press Release: ISSYS Methanol Concentration Sensor to be Featured at the JAIMA Exposition; dated Aug. 29, 2006; pp. 1-2.

ISSYS: Integrated Sensing Systems—Press Release: ISSYS Awarded New Patent for a Resonant Tube Viscosity Sensing Device; dated Jun. 21, 2006; pp. 1-2.

Kim, Tae Min et al.; "Clinical Predictors of Recurrent Venous Thromboembolism: A Single Institute Experience in Korea"; Thrombosis Research; dated 2008; pp. 1-7; Elsevier Ltd.

Morris, Timothy A. et al.; "Improved Imaging of Deep Venous Thrombi During Anticoagulation Using Radiolabelled Anti-D-Dimer Antibodies"; Nuclear Medicine Communications; dated 2004; pp. 917-922; vol. 25; Lippincott Williams & Wilkins.

Parker, Martyn J.; "We Need Look Critically at Evidence for Universal Use"; BMJ; dated May 24, 2008; pp. 1145-1148; vol. 336; located at:http://www.bmj.com/cgi/content/short/336/7654/1148.

Rossow, Molly J. et al.; "Blood Flow Measurements and Clot Detection with Near-Infrared Spectroscopy"; Optics InfoBase—Conference Paper: Biomedical Topical Meeting, Ft. Lauderdale, FL; dated Mar. 19, 2006; pp. 1-3; OSA/BOSD, AOIMP, TLA.

Roumen-Klappe, E.M.; "Multilayer Compression Bandaging in the Acute Phase of Deep-Vein Thrombosis Has no. Effect on the Development of the Post-Thrombotic Syndrome"; J. Thromb Thrombolysis; dated 2008; pp. 1-5; Springer.

So-Ling, Carmen et al.; "A Multi-Layered Reflection Model of Natural Human Skin"; CGI: Computer Graphics International; dated 2001; p. 0249; (only abstract provided).

Stone, Michael J. et al.; "Pulsed-High Intensity Focused Ultrasound Enhanced tPA Mediated Thrombolysis in a Novel in Vivo Clot Model, A Pilot Study"; Thromb Res.; dated 2007; pp. 193-202; vol. 121, No. 2; NIH Public Access Author Manuscript.

Vidal Melo, Marcos F. et al.; "Changes in Regional Ventilation Afer Autologus Blood Clot Pulmonary Embolism"; Anesthesiology; dated Sep. 2002; pp. 671-681; vol. 97, No. 3; American Society of Anesthesiologists, Inc.

Walsh, Fergus; "Scanner Spots Deadly Blood Clots"; BBC News; dated Apr. 13, 2007; pp. 1-3; located at http://new.bbc.co.uk/2/hi/health/6541279.stm.

Wieringa F.P. et al.; "Remote Non-Invasive Stereoscopic Imaging of Blood Vessels: First In-Vivo Results of a New Multispectral Contrast Enhancement Technology"; Annals of Biomedical Engineering; dated Dec. 2006; pp. 1870-1878; vol. 34, No. 12; Biomedical Engineering Society.

Xie, Hua et al.; "Staging Deep Venous Thrombosis Using Ultrasound Elasticity Imaging: Animal Model"; Ultrasound in Med. & Biol.; dated 2004; pp. 1385-1396; vol. 30, No. 10; World Federation for Ultrasound in Medicine & Biology.

Zhang, Quan et al.; "Study of Near Infrared Technology for Intracranial Hematoma Detection"; Journal of Biomedical Optics; dated Apr. 2000; pp. 206-213; vol. 5, No. 2.

Dieter, Robert S. et al.; "Prosthetic Heart Valve Thrombosis: An Overview"; Wisconsin Medical Journal; Bearing a date of 2002; pp. 67-68; vol. 101, No. 7.

Landry, Anthony et al.; "Theoretical and experimental quantification of carotid plaque volume measurements made by three-dimensional ultrasound using test phantoms"; Medical Physics; bearing a date of Oct. 2002; pp. 2319-2327; vol. 29, No. 10; American Association Physical Medicine.

MacKinnon, Andrew D. et al.; "Long-Term Ambulatory Monitoring for Cerebral Emboli Using Transcranial Doppler Ultrasound"; STROKE; Journal of the American Heart Association; originally published Dec. 18, 2003; pp. 73-78; American Heart Association.

Weil, M. H.; "Defining Hemodynamic Instability"; Update in Intensive Care and Emergency Medicine; 2005 ; pp. 9-17, (2 p. abstract printed on Aug. 16, 2011) ; vol. 42, part 2; (abstract located at: http://www.springerlink.com/content/1h3g72p32621125j/ ).

Carter, J. Stein; "Circulatory System"; bearing a date of Nov. 13, 2006; pp. 1-5; http://biology.clc.uc.edu/courses/bio105/circulat.htm.

Thefreedictionary.com; "Tonometer"; bearing a date of 2012, printed on Jun. 13, 2012; pp. 1-4; Farlex, Inc.; http://medical-dictionary.thefreedictionary.com/tonometer.

Baumgartner et al.; "Factors Controlling Thrombus Formation on Arterial Lesions"; Annals New York Academy of Sciences; Oct. 1985; pp. 162-177; vol. 454; Issue 1.

Smith et al.; "A Comparison of Four Methods for Distinguishing Doppler Signals From Gaseous and Particulate Emboli"; Journal of the American Heart Association; Jun. 1998; pp. 1133-1138; vol. 29; No. 6; American Heart Association; Dallas, TX.

* cited by examiner

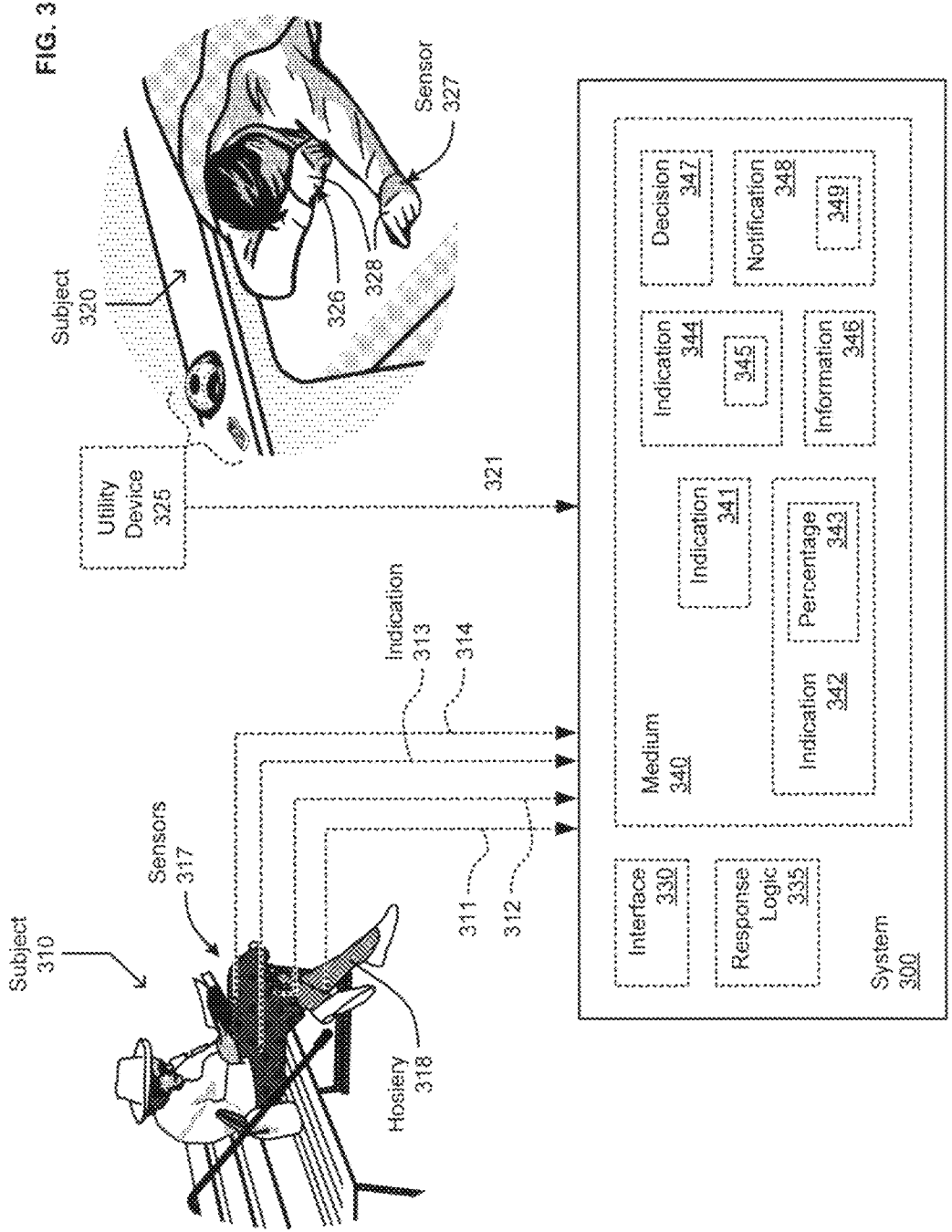

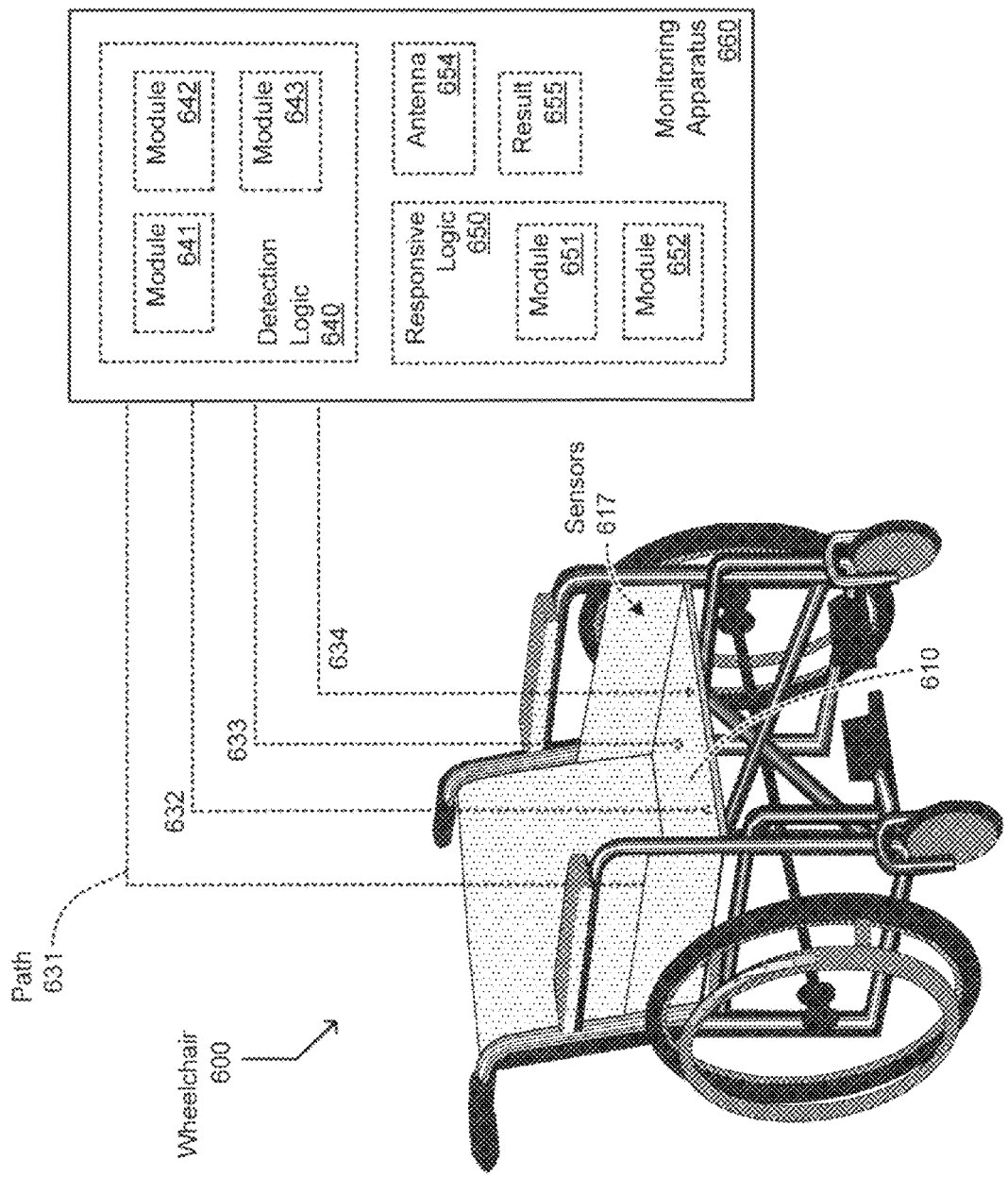

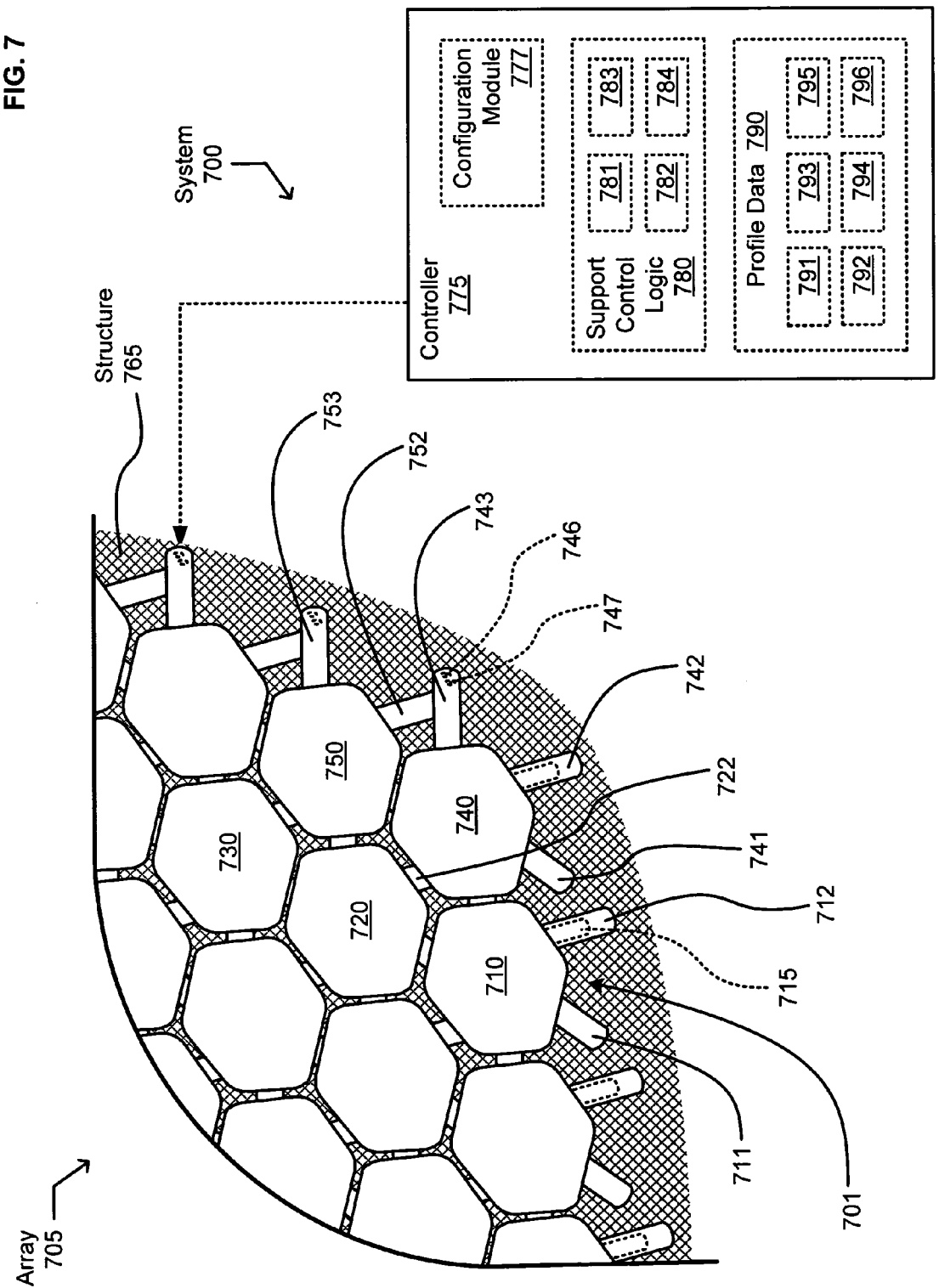

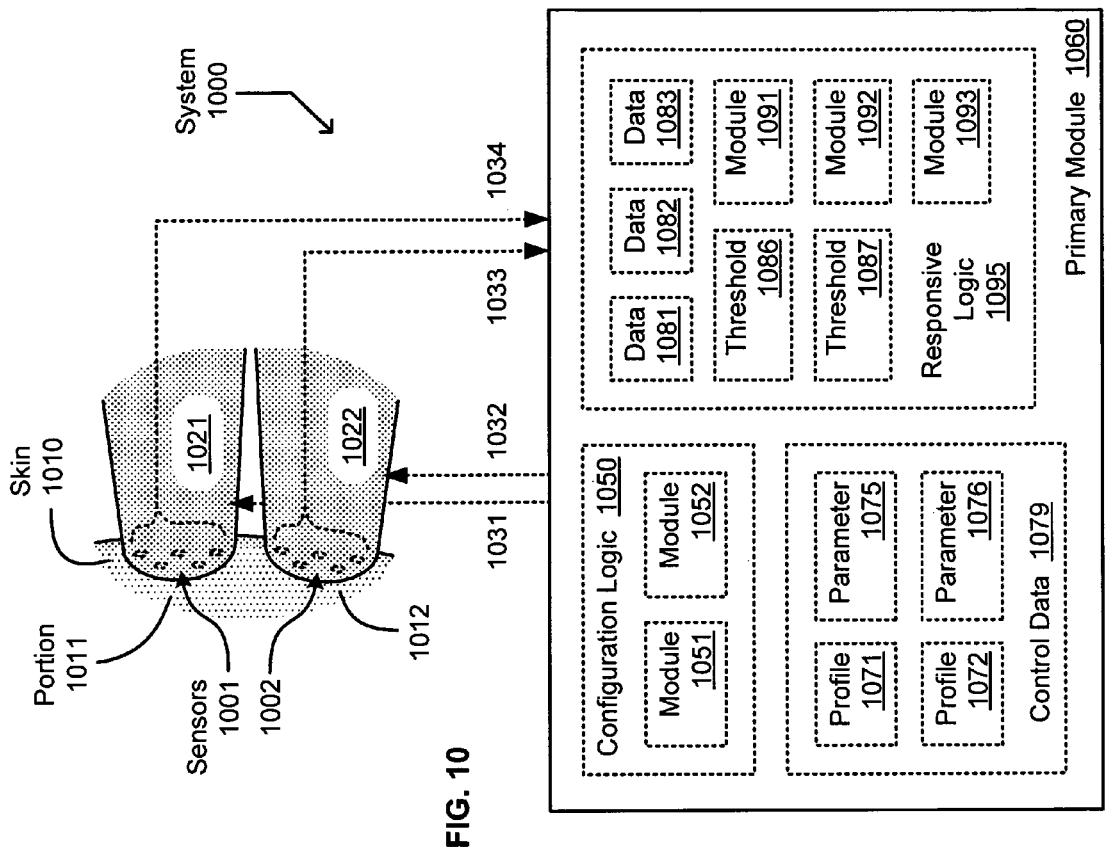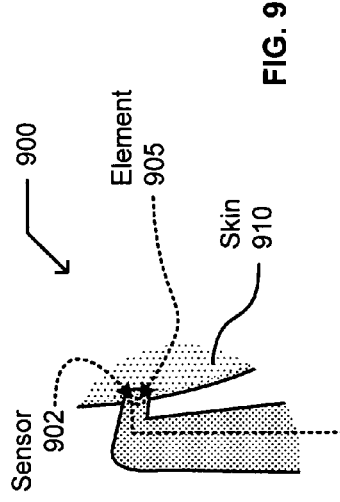

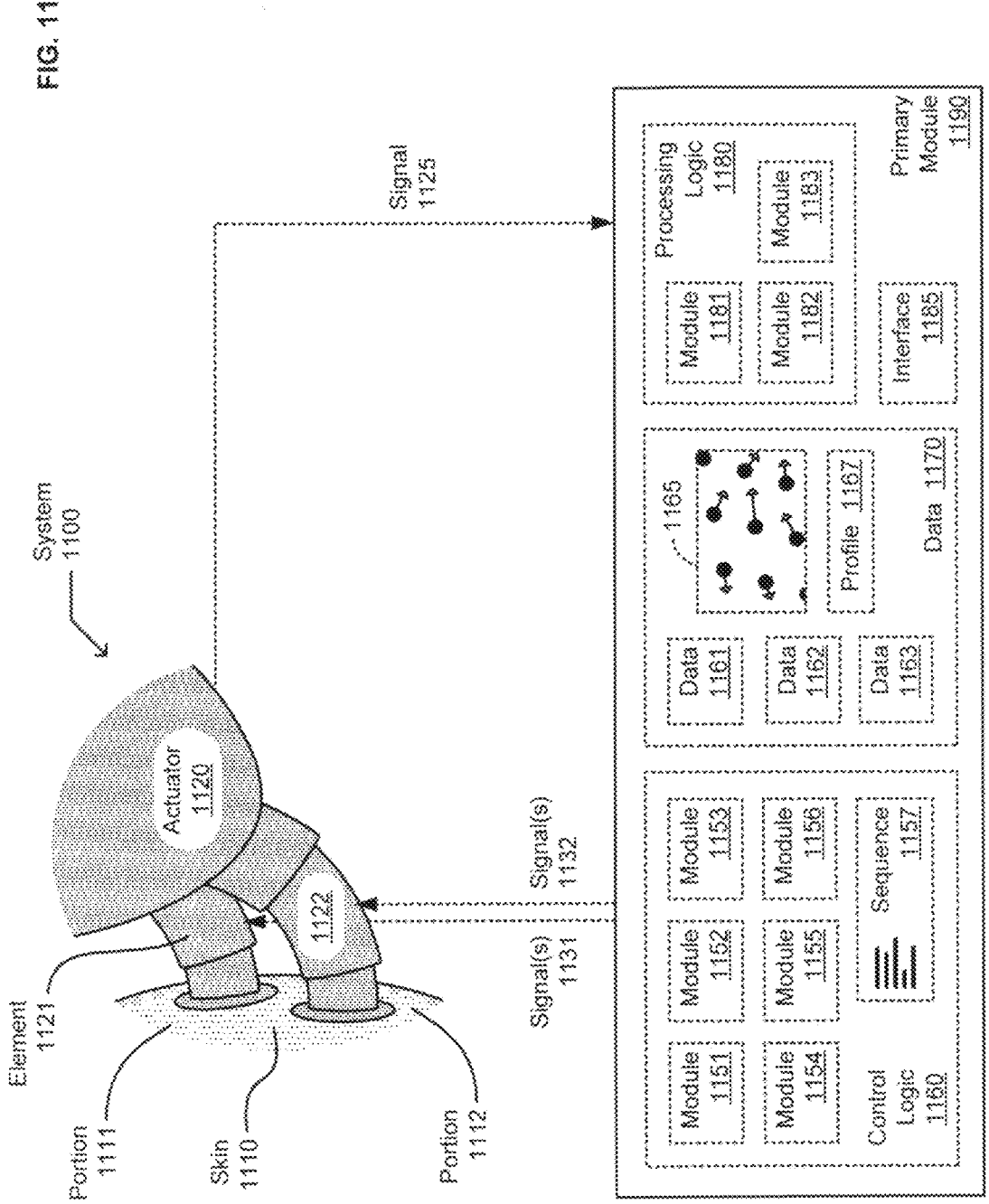

FIG. 22
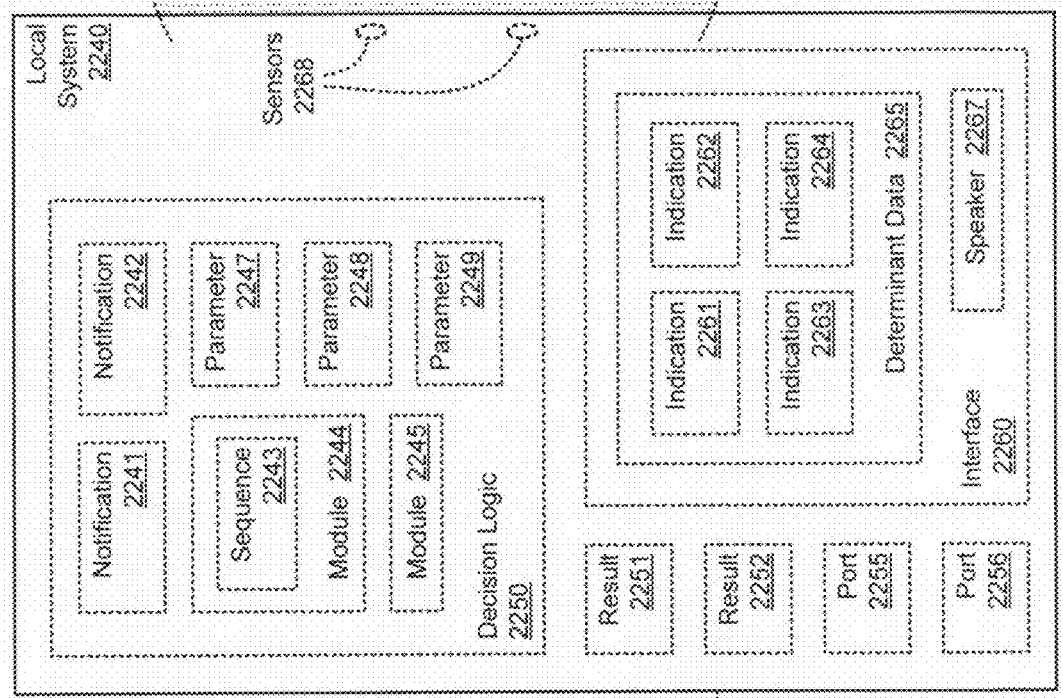
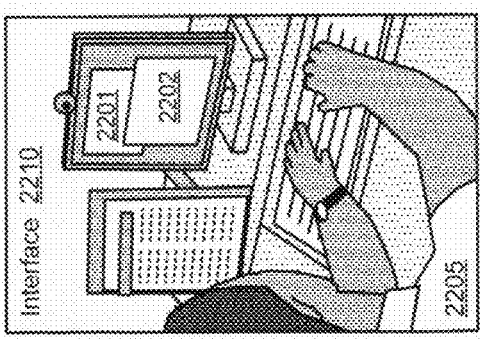

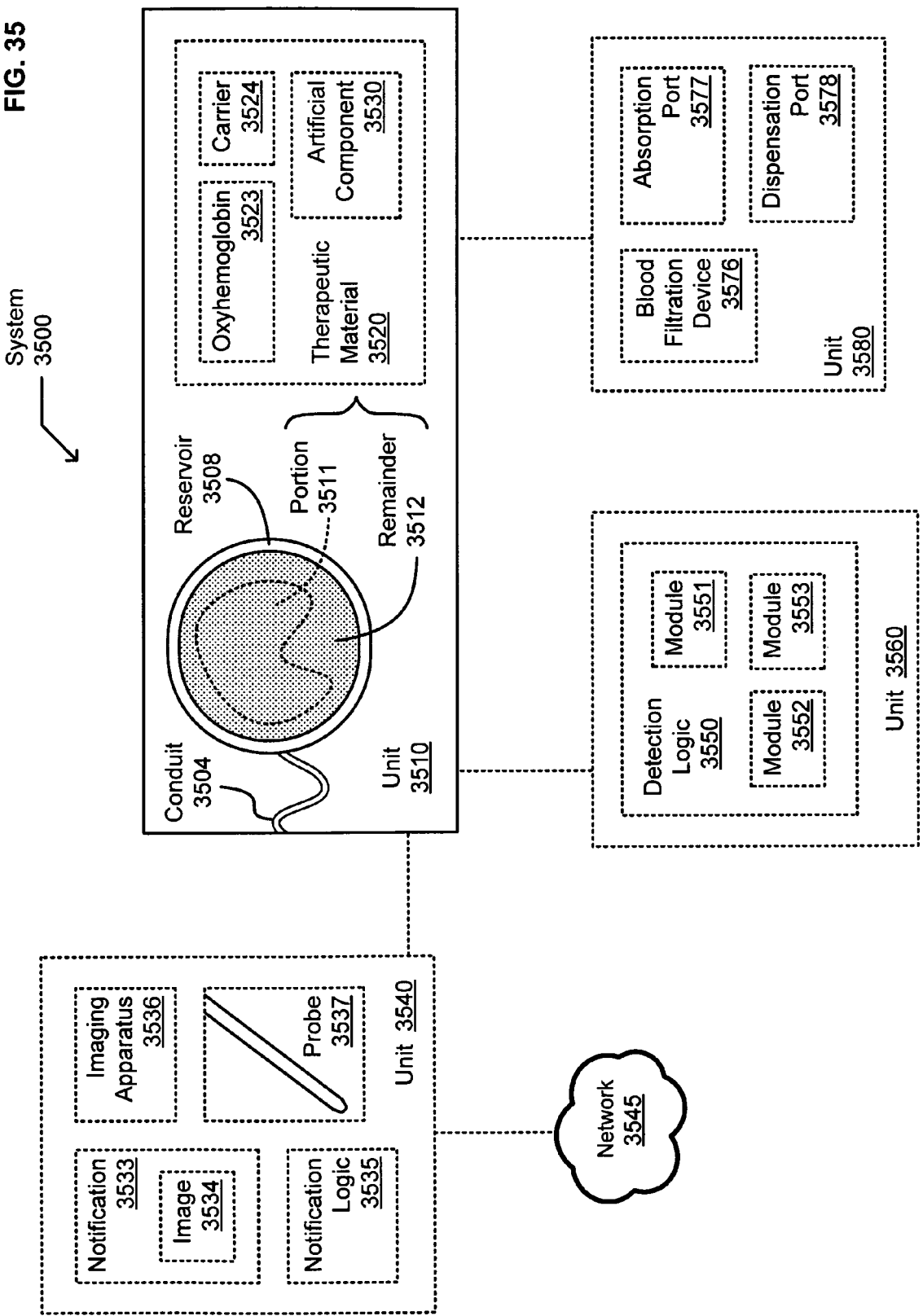

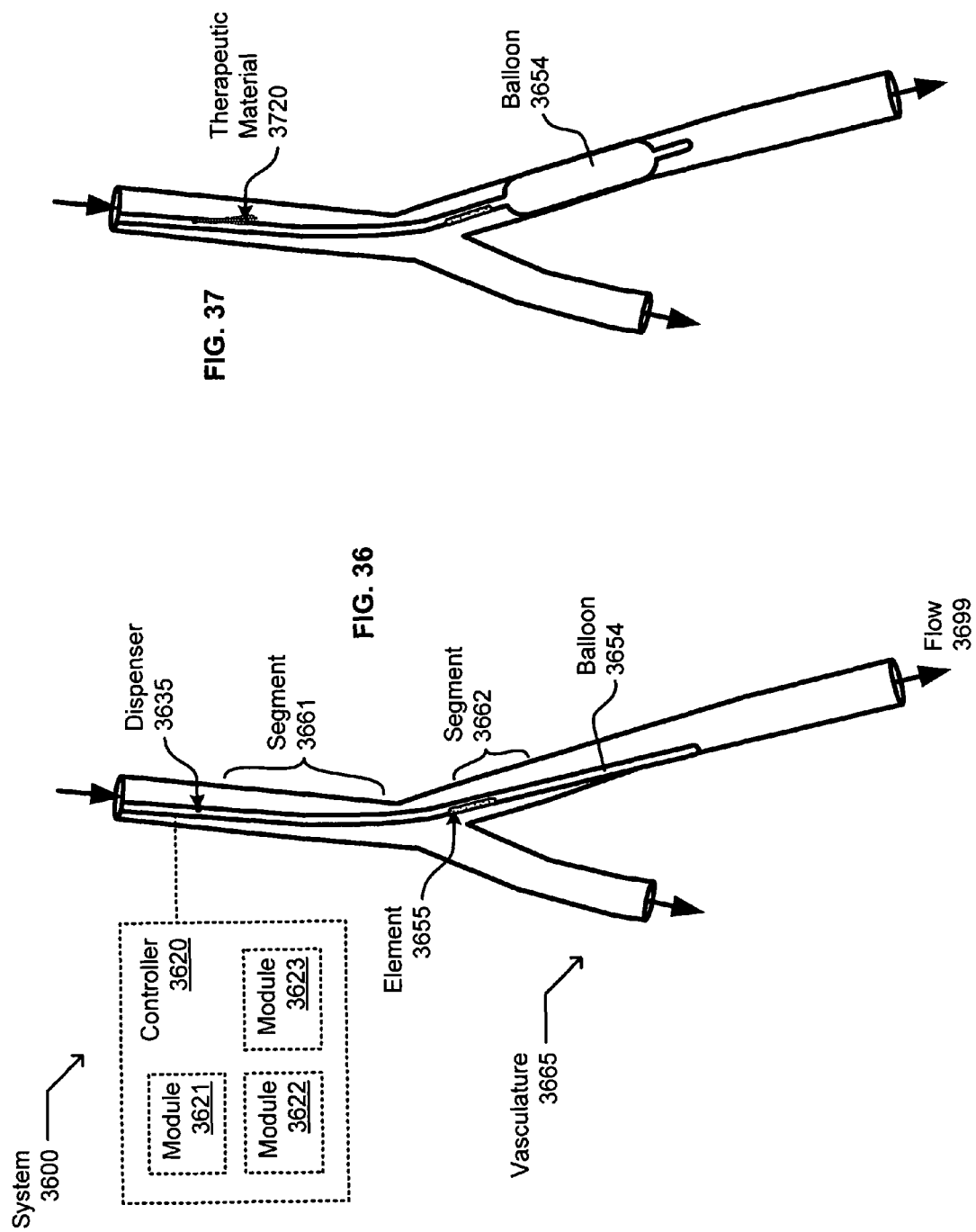

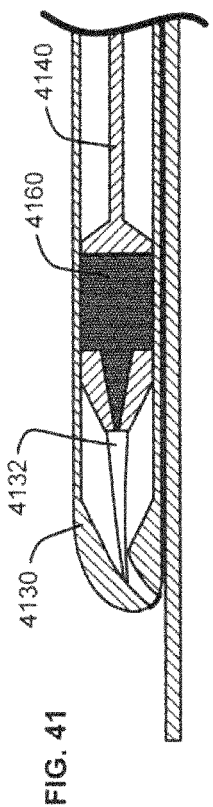
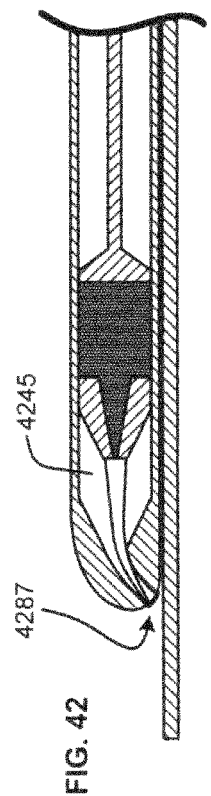
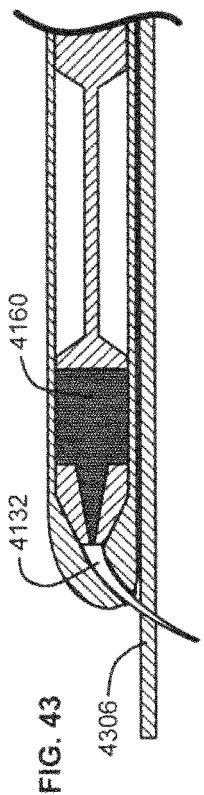
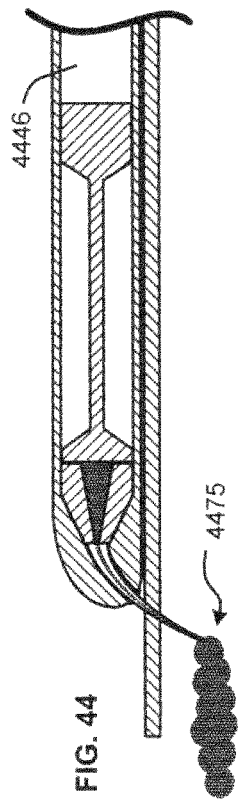
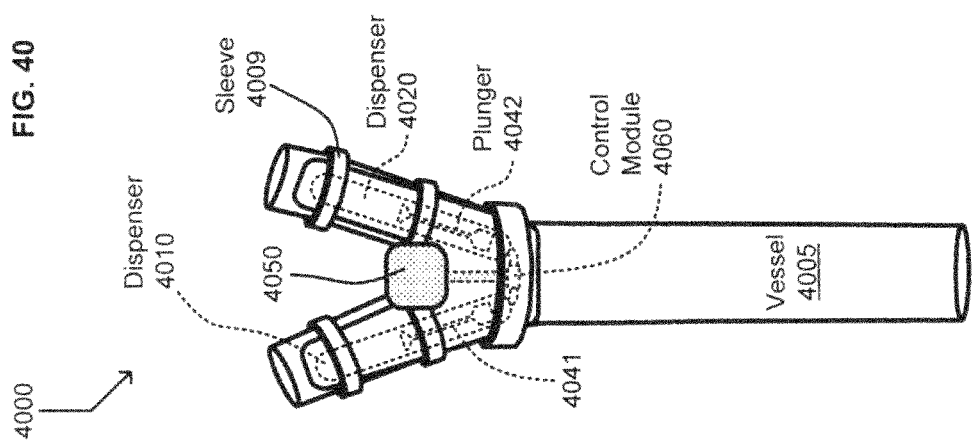

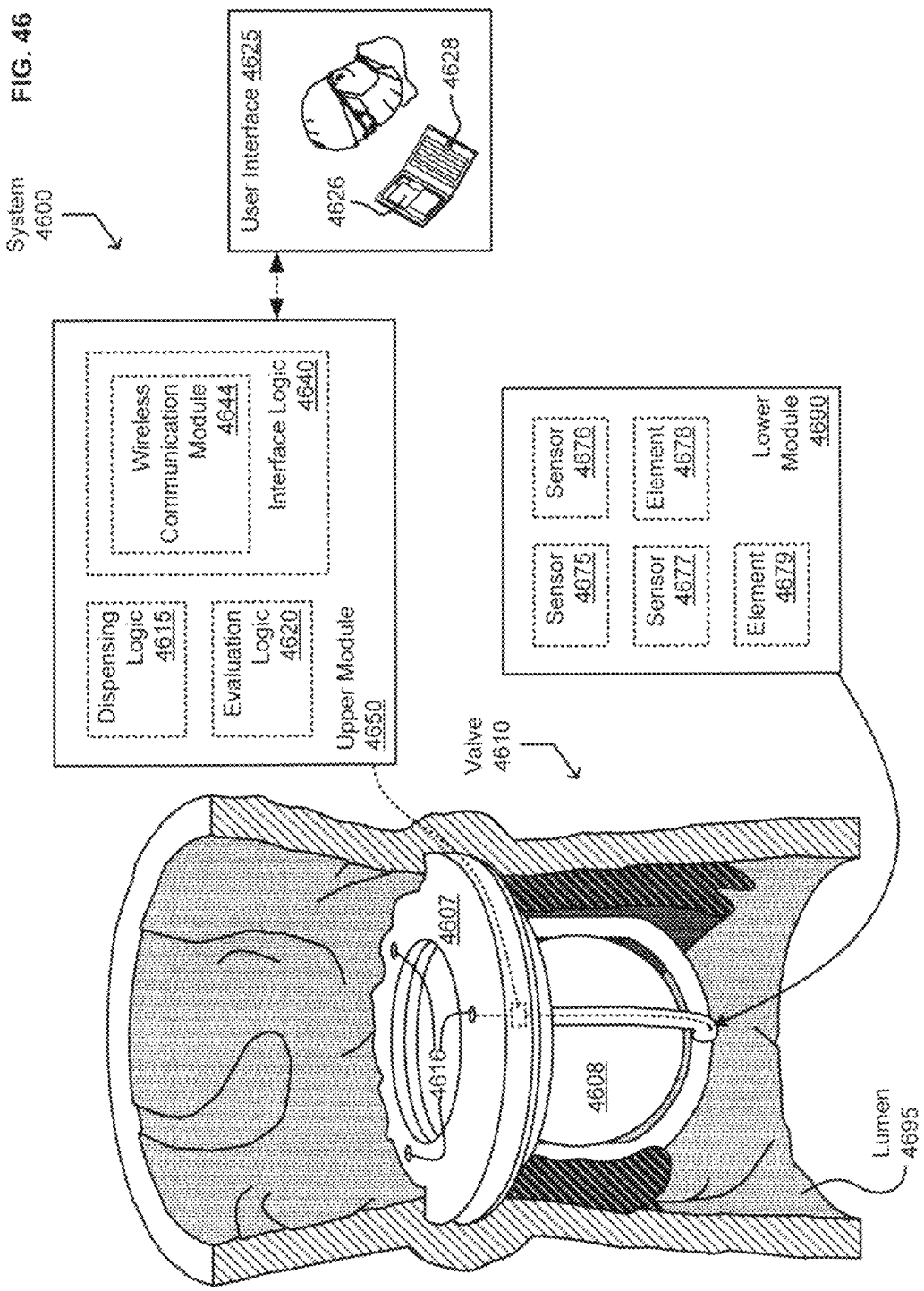

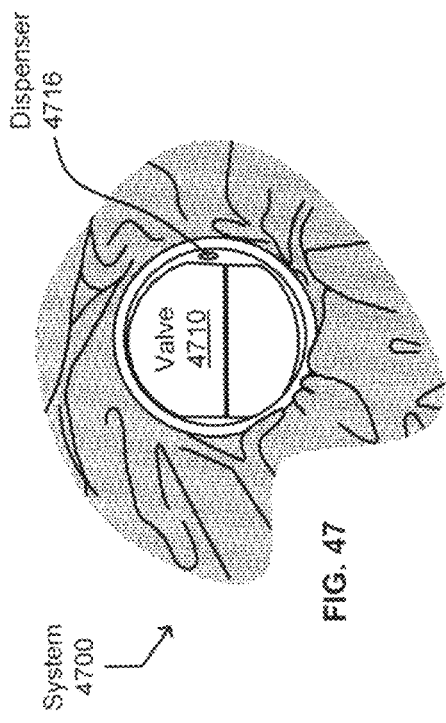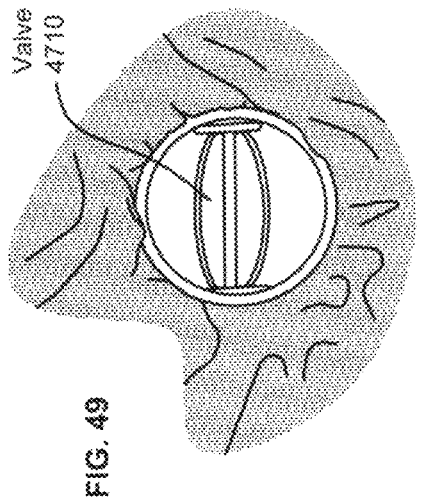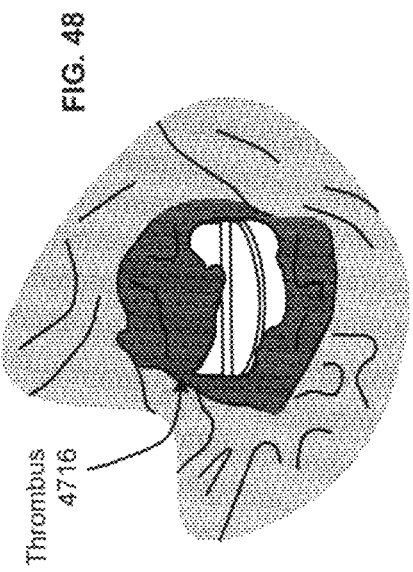

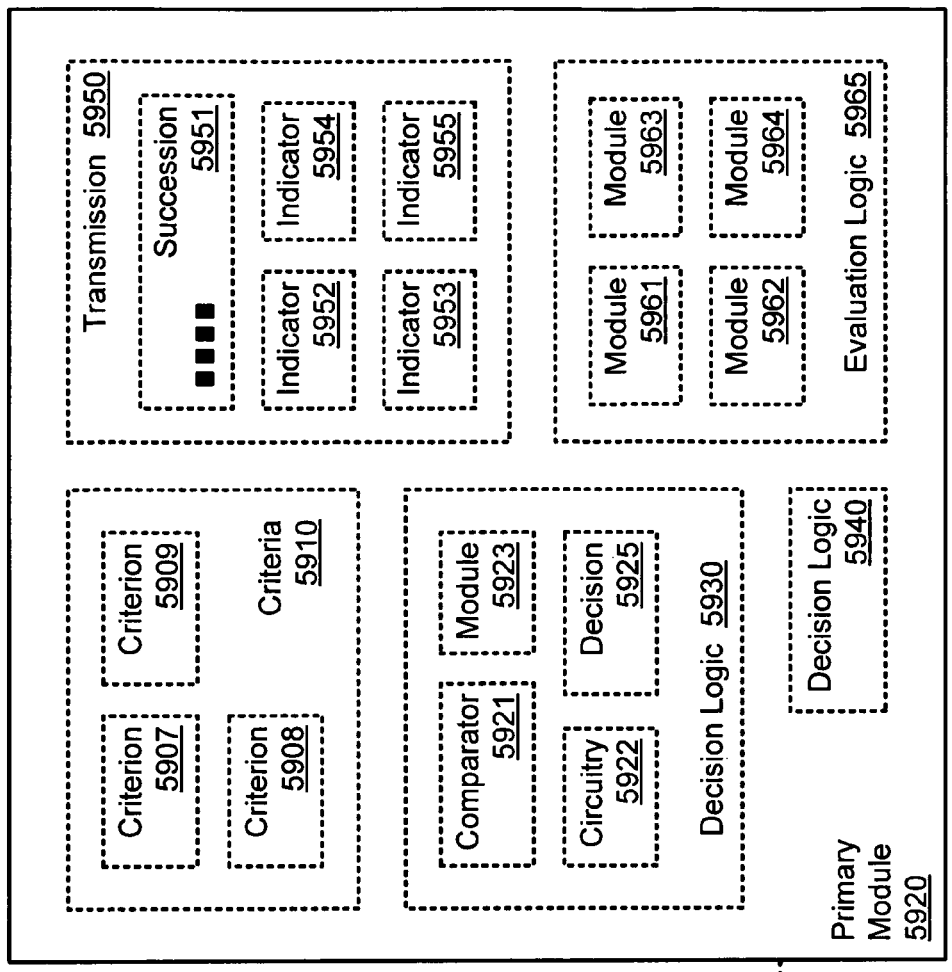
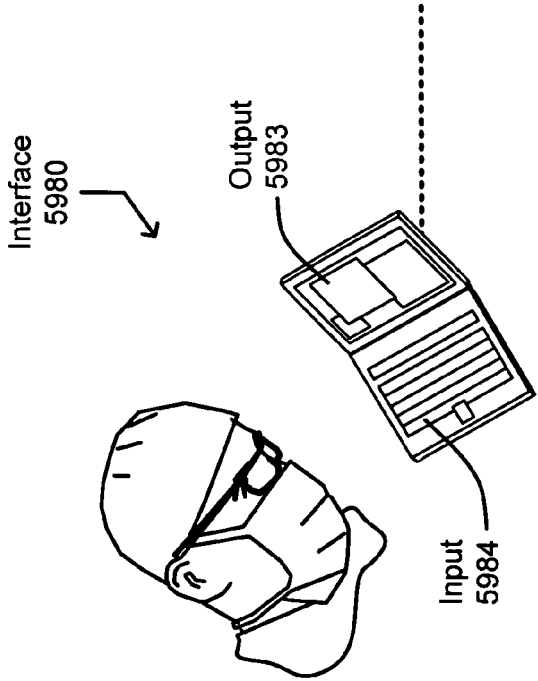
FIG. 59

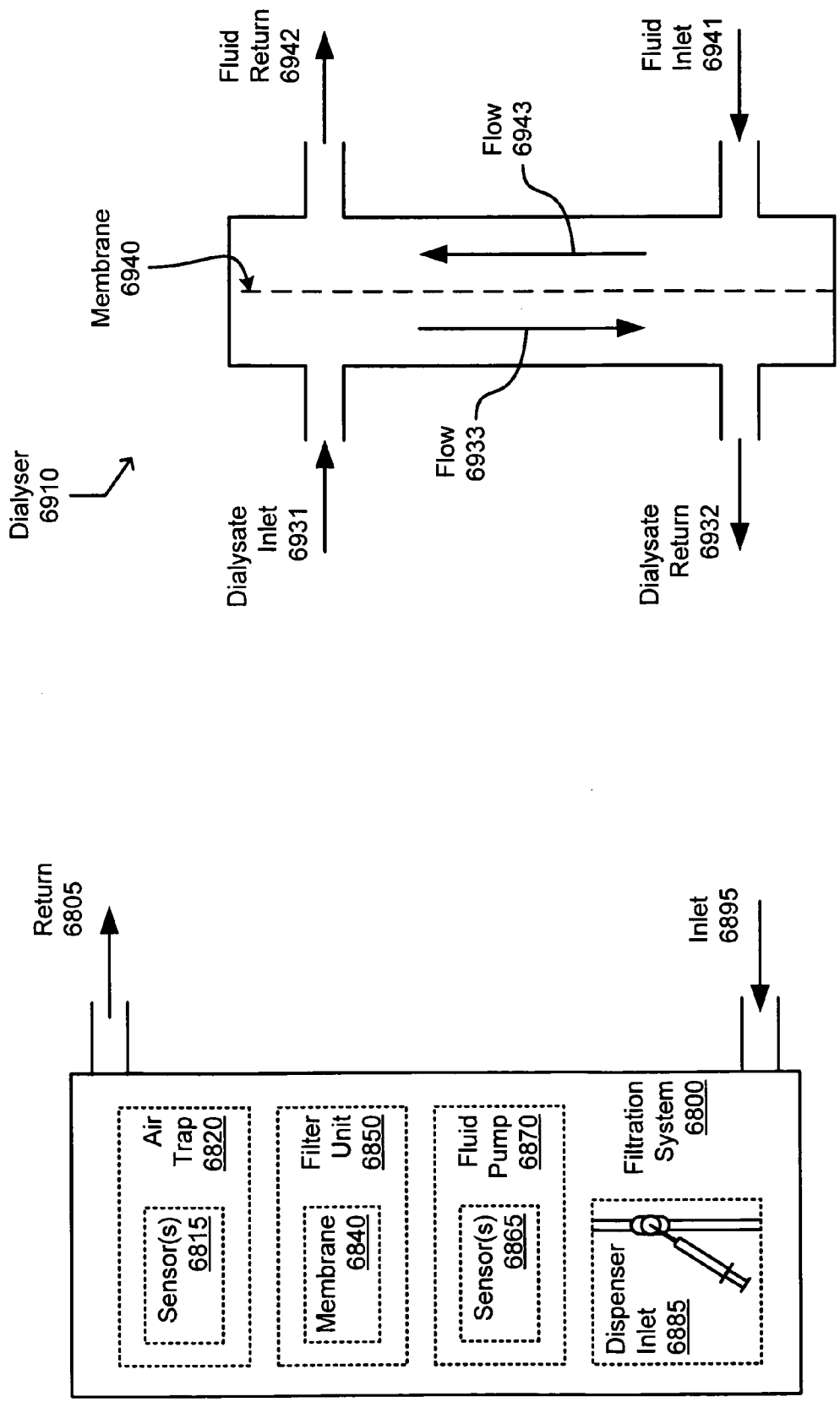

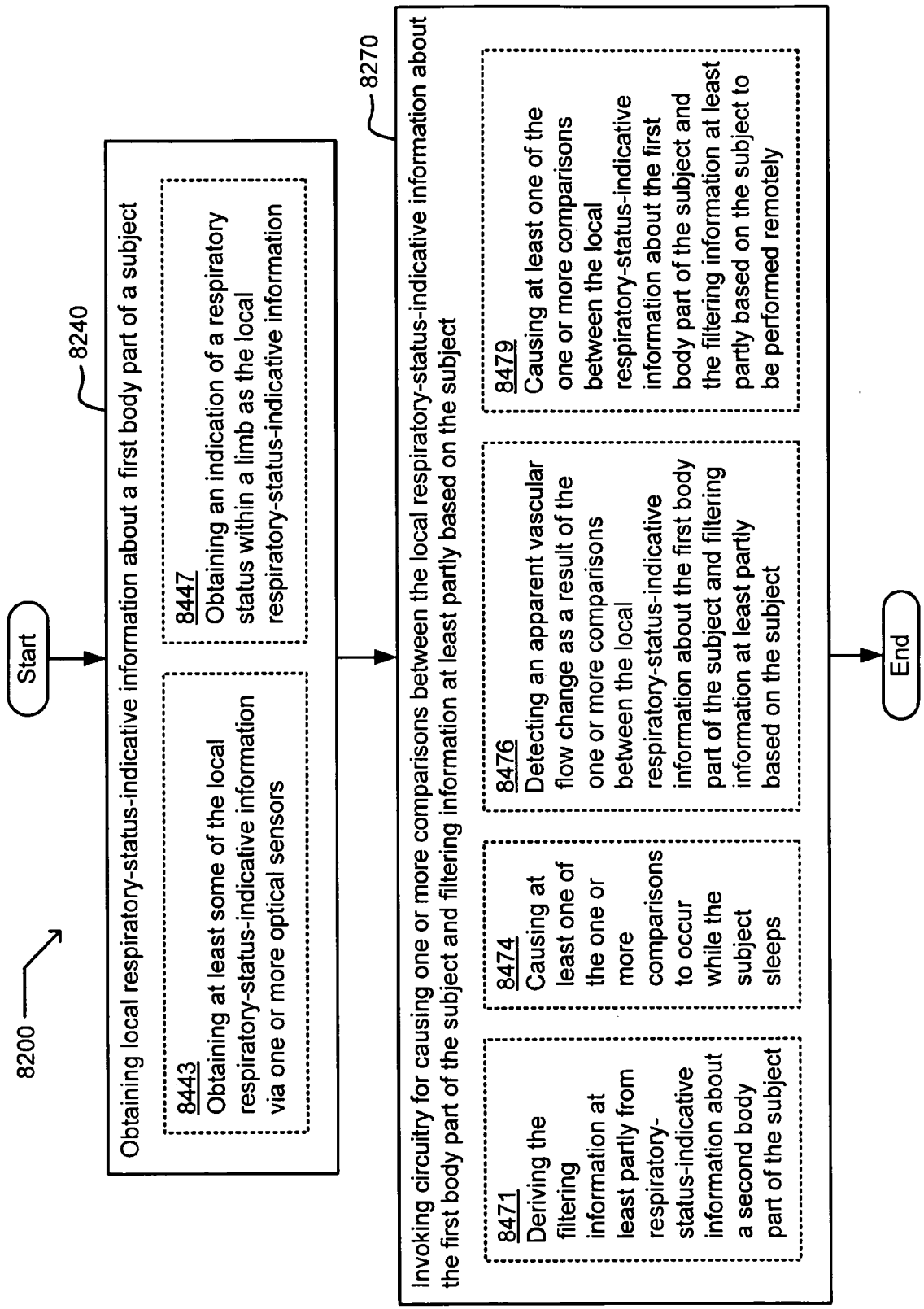

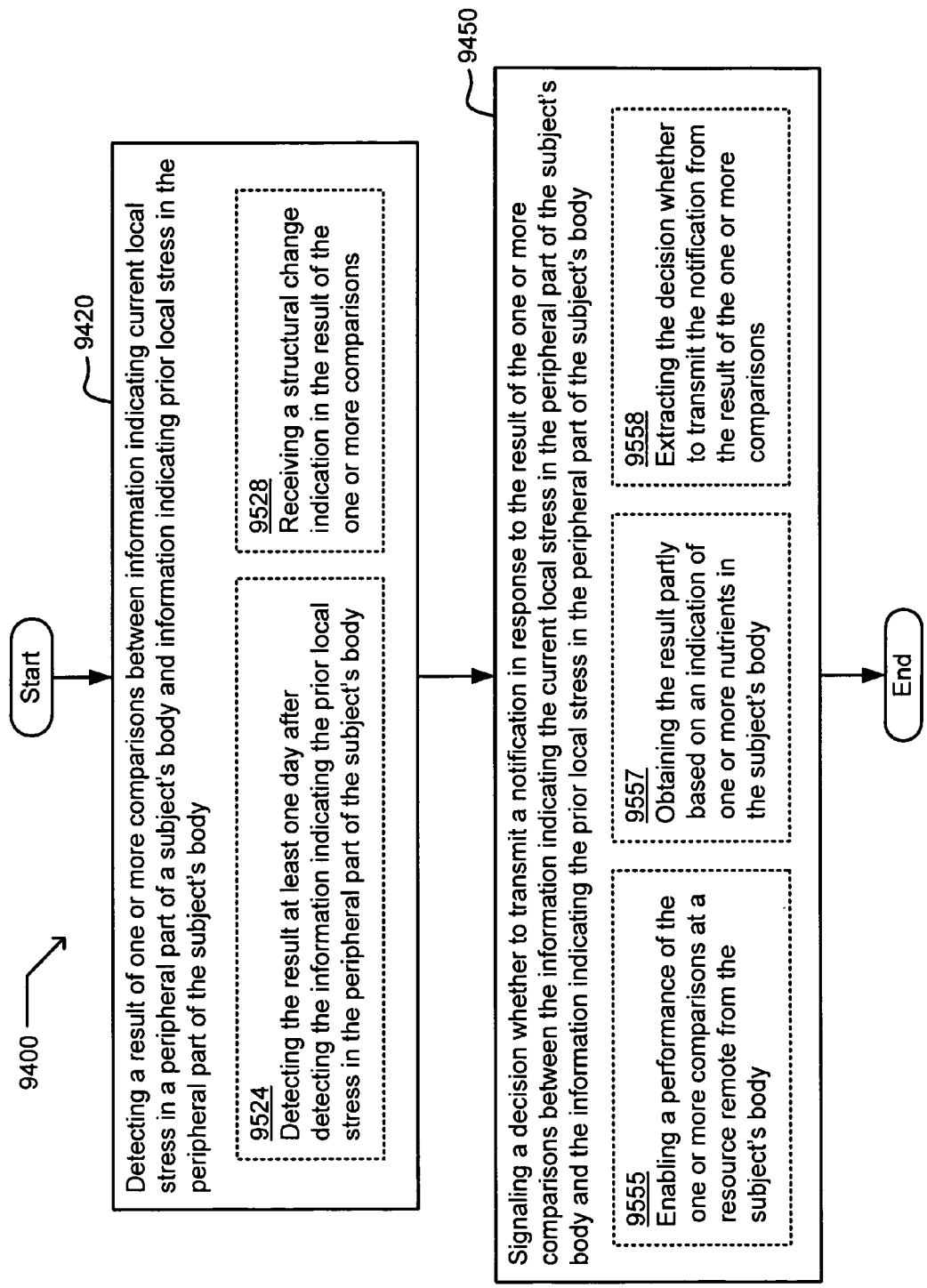

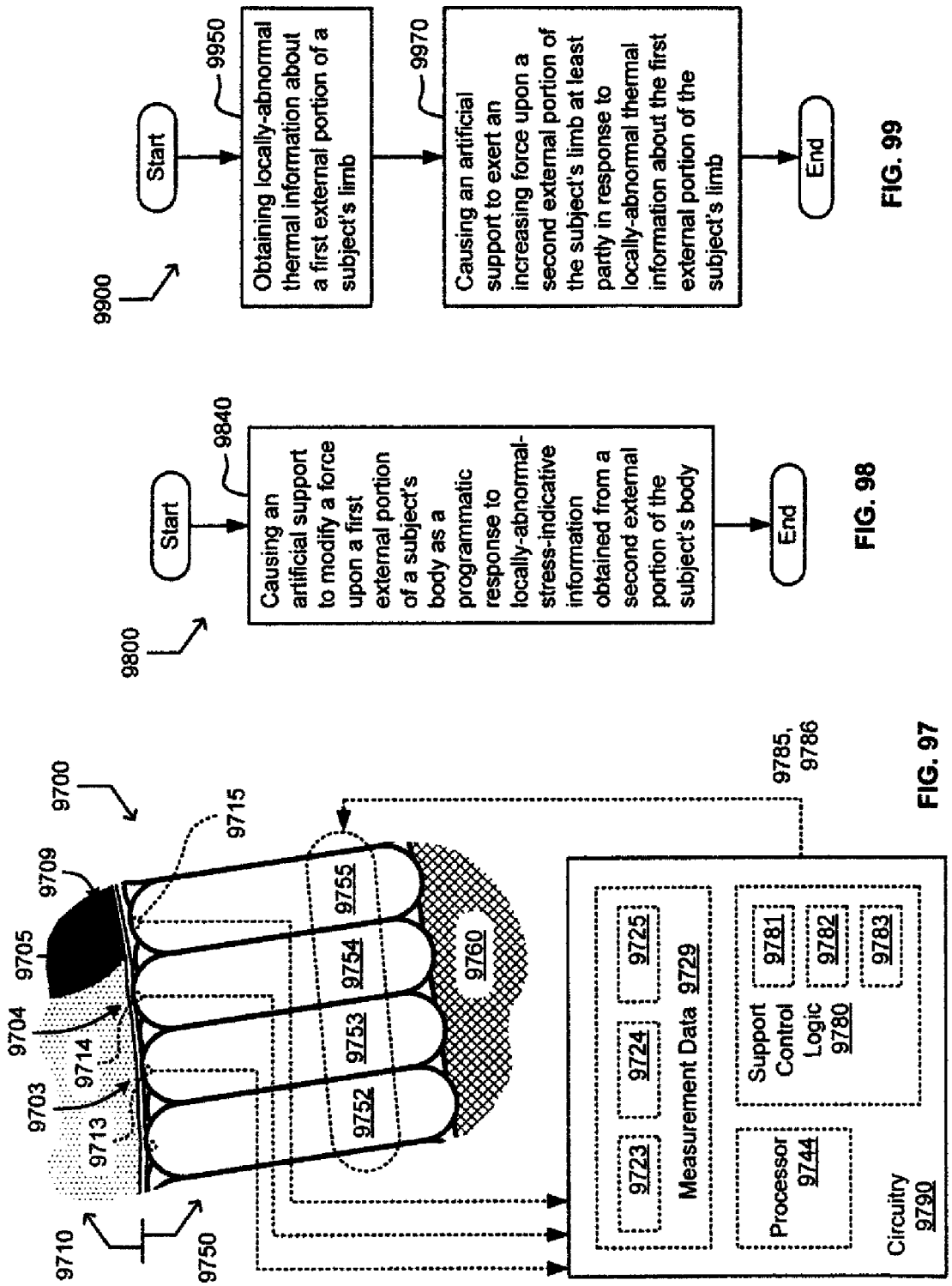

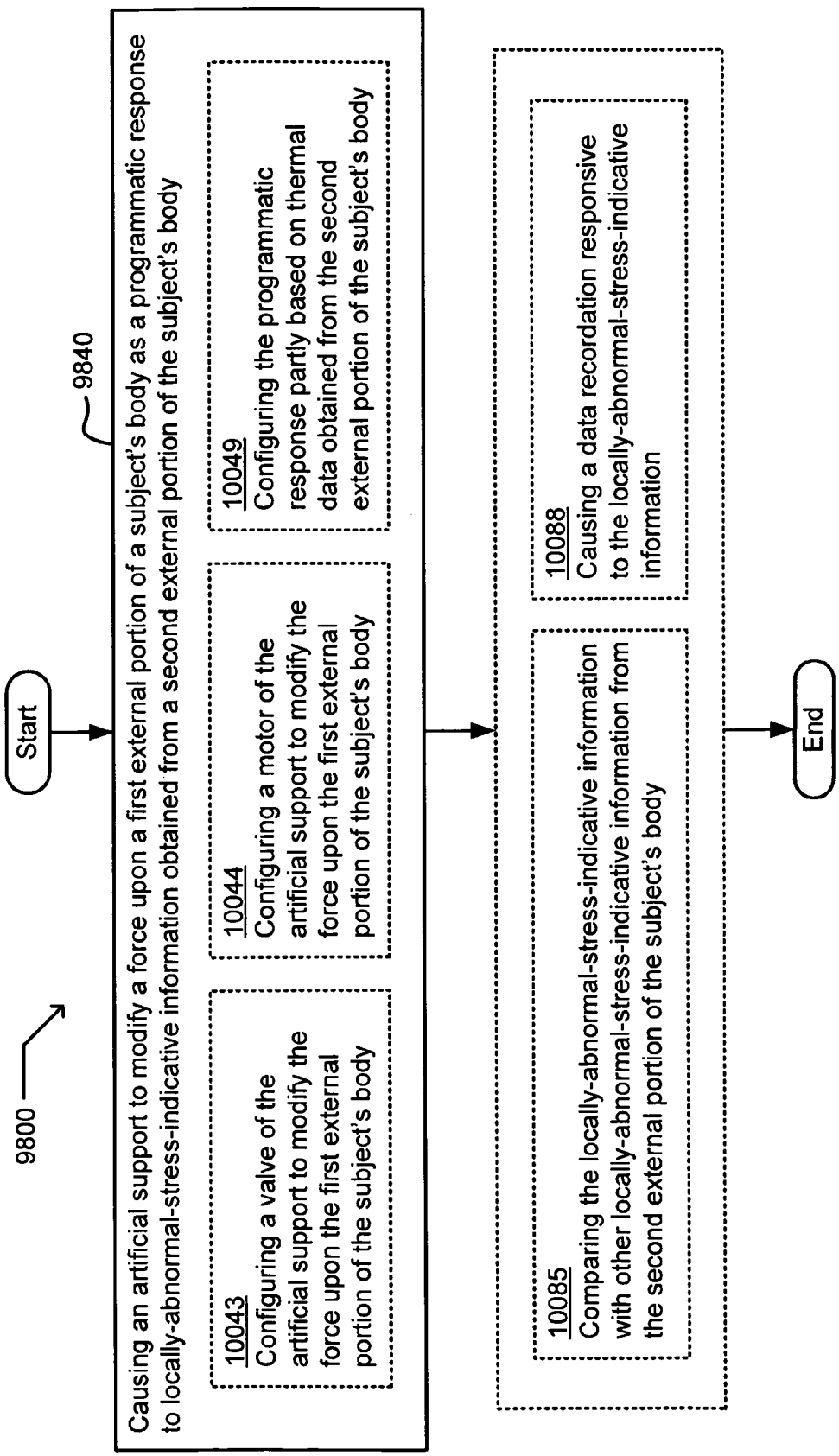

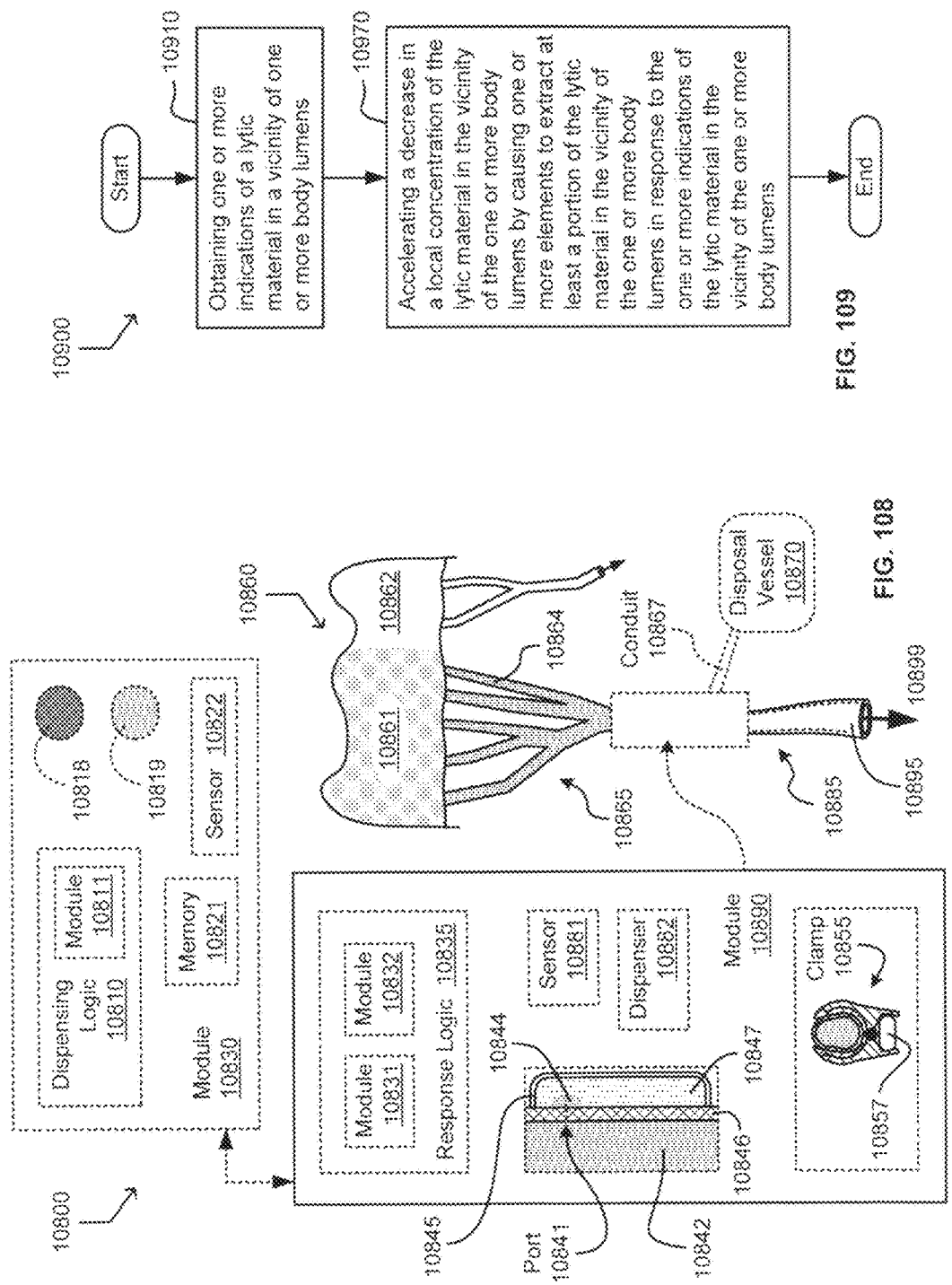

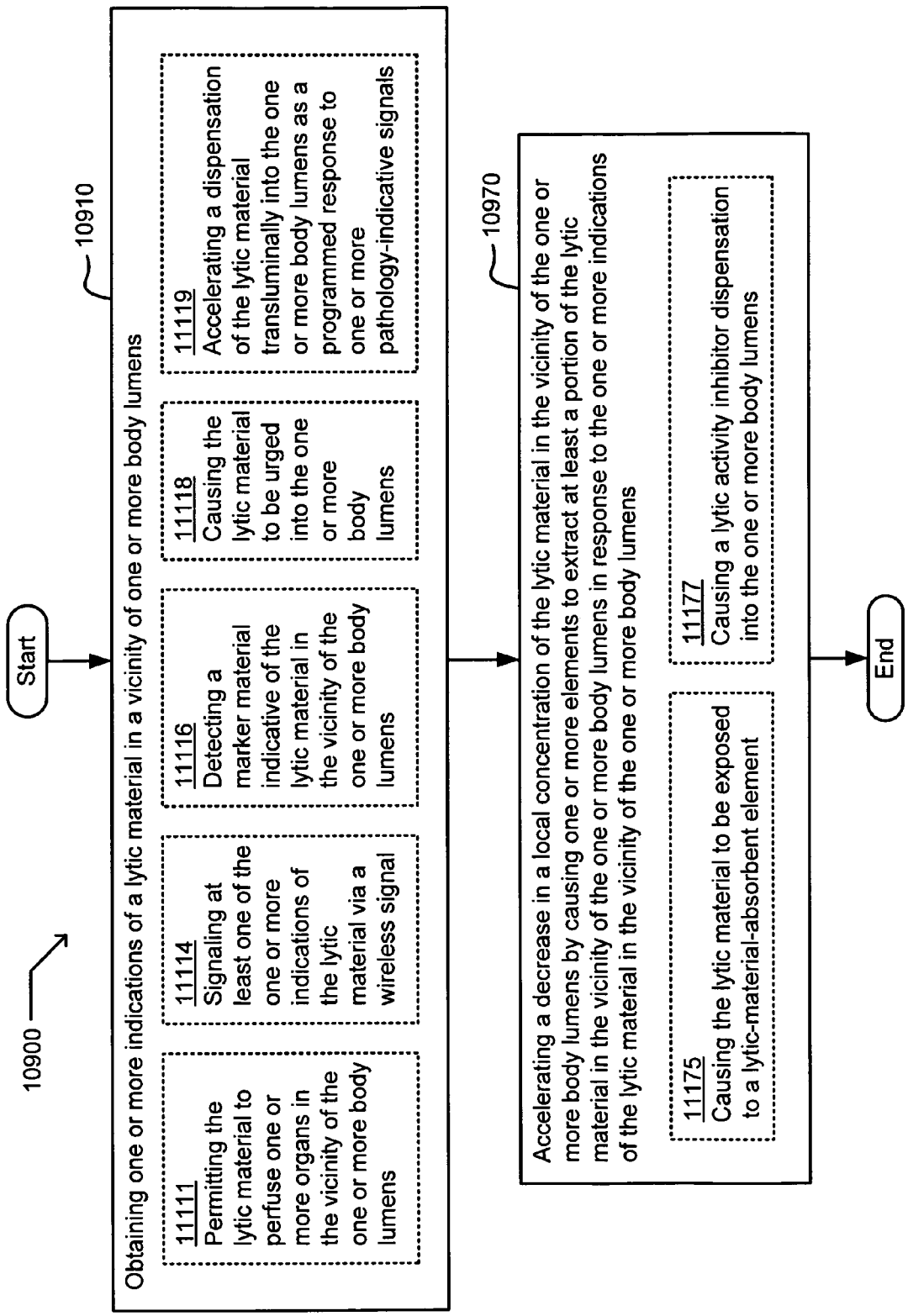

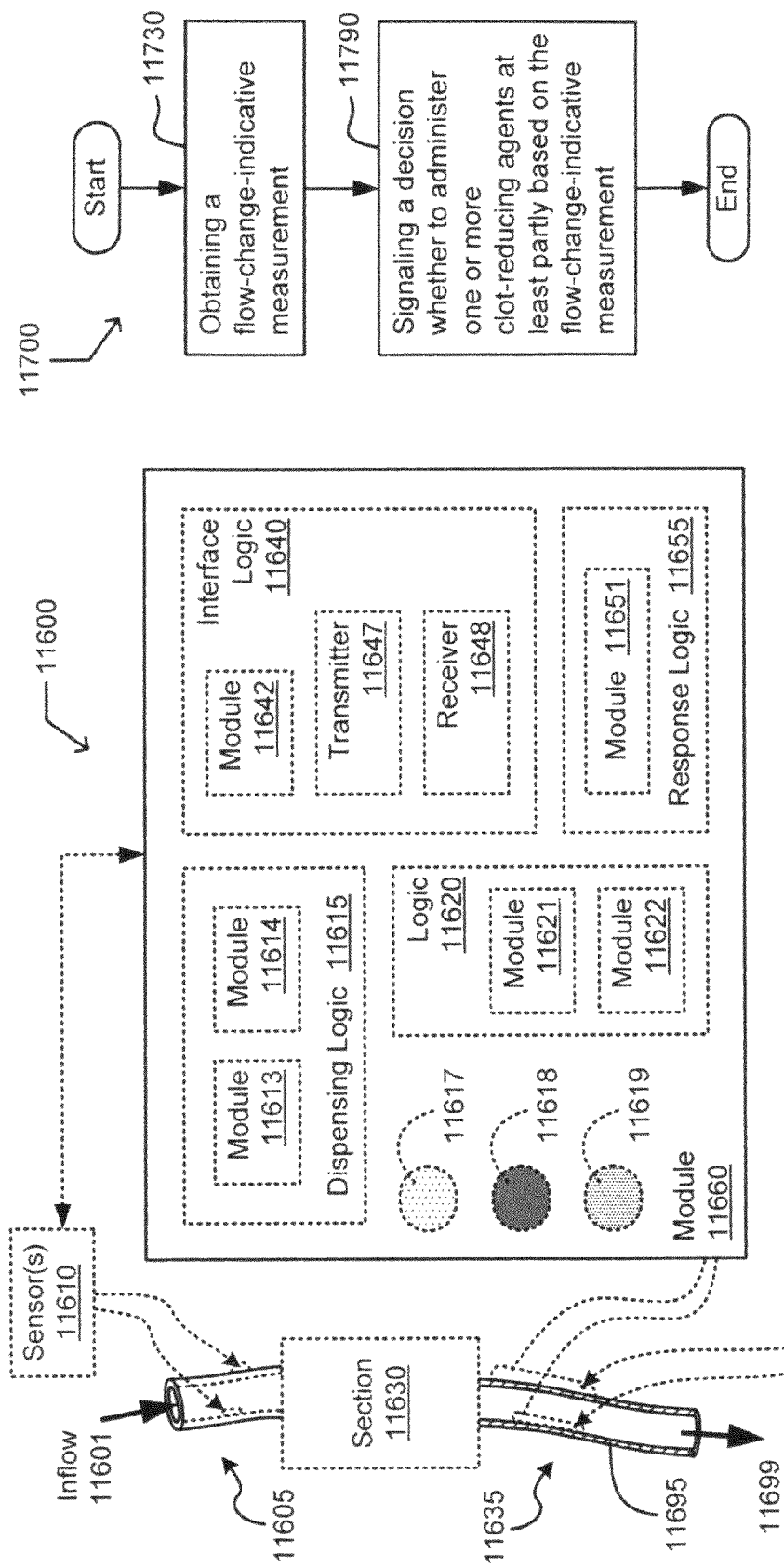

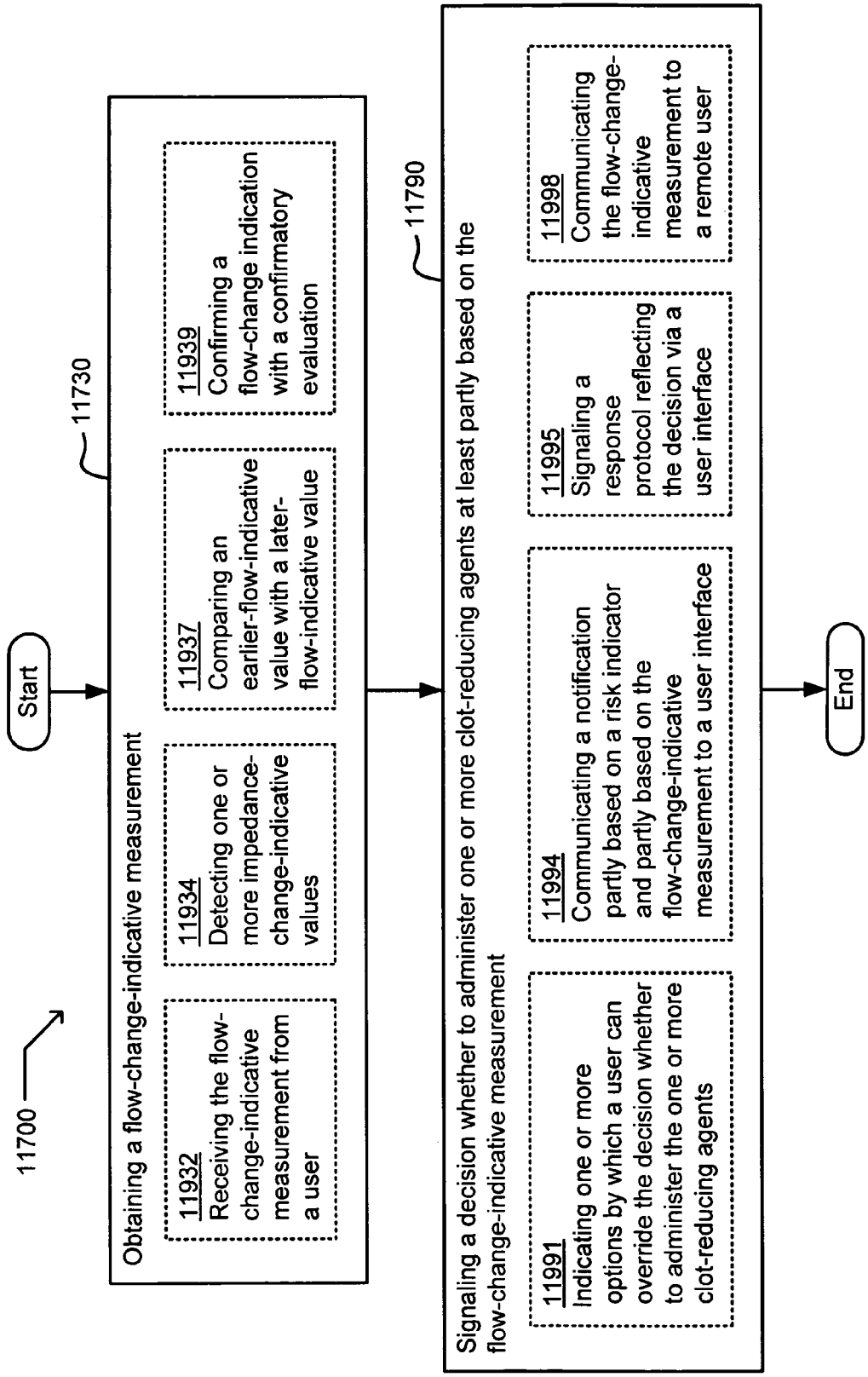

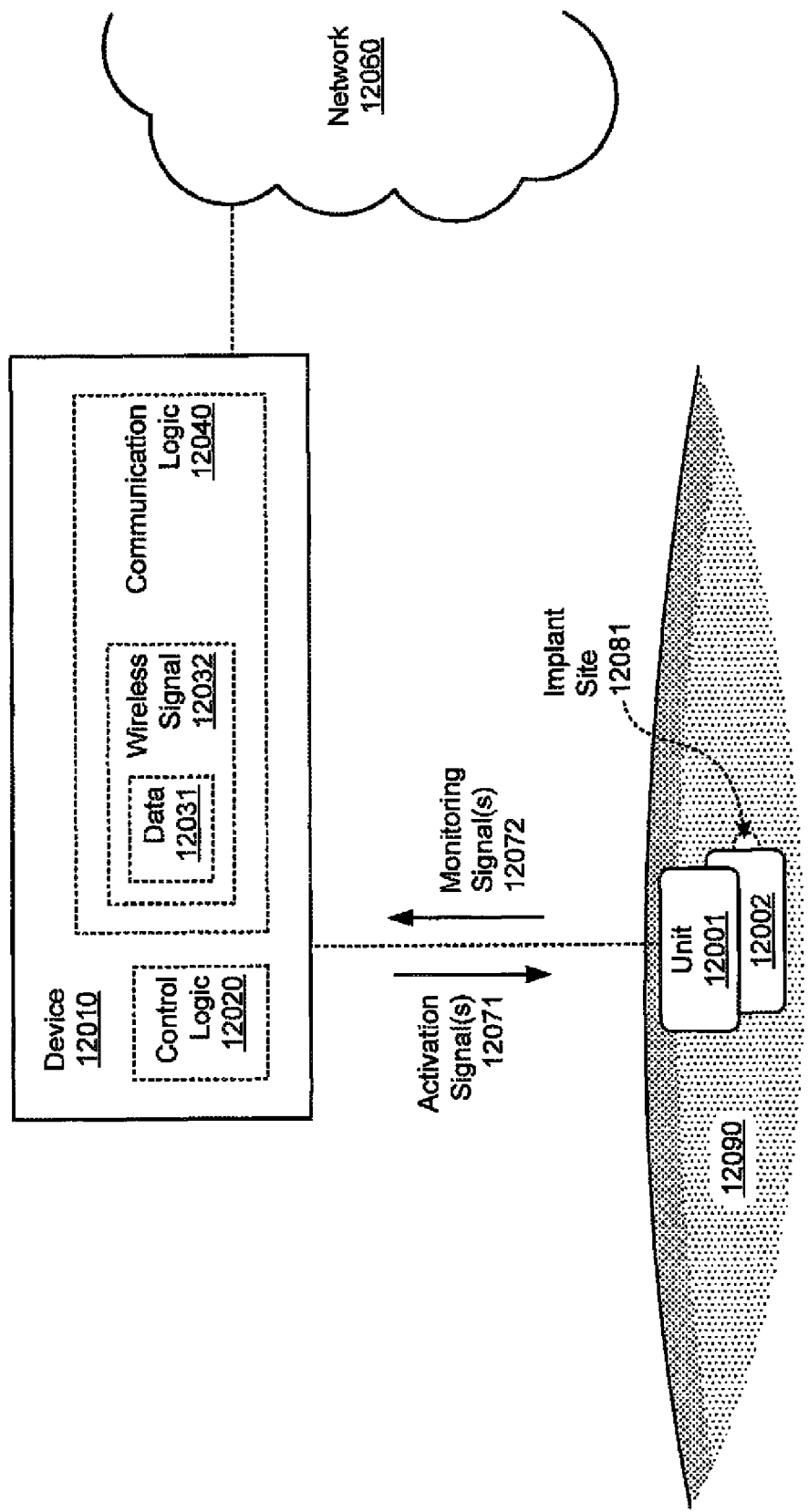

CIRCULATORY MONITORING SYSTEMS AND METHODS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications:

For purposes of the USPTO extra-statutory requirements, the present application constitutes a continuation-in-part of U.S. patent application Ser. No. 12/004,107, entitled TREATMENT INDICATIONS INFORMED BY A PRIORI IMPLANT INFORMATION, naming Bran Ferren, Roderick A. Hyde, Muriel Y. Ishikawa, Eric C. Leuthardt, Dennis J. Rivet, Lowell L. Wood, Jr. and Victoria Y. H. Wood as inventors, filed Dec. 18, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a method includes but is not limited to obtaining local circulatory information relating to a leg of a subject and signaling a decision whether to transmit a notification in response to one or more comparisons between filtering information specific to the subject and the local circulatory information relating to the leg of the subject. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining local circulatory information relating to a leg of a subject and circuitry for signaling a decision whether to transmit a notification in response to one or more comparisons between filtering information specific to the subject and the local circulatory information relating to the leg of the subject. In addition to the foregoing, other system aspects are described in the claims, drawings, and text forming a part of the present disclosure.

In one aspect, a method includes but is not limited to obtaining local respiratory-status-indicative information about a first body part of a subject and causing one or more comparisons between the local respiratory-status-indicative information about the first body part of the subject and filtering information at least partly based on the subject. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining local respiratory-status-indicative information about a first body part of a subject and circuitry for causing one or more comparisons between the local respiratory-status-indicative information about the first body part of the subject and filtering information at least partly based on the subject. In addition to the foregoing, other system aspects are described in the claims, drawings, and text forming a part of the present disclosure.

In one aspect, a method includes but is not limited to obtaining local thermal information about a peripheral part of a body of a subject and signaling a decision whether to transmit a notification in response to one or more comparisons between filtering information specific to an attribute of the subject and the local thermal information about the peripheral part of the body of the subject. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining local thermal information about a peripheral part of a body of a subject and circuitry for signaling a decision whether to transmit a notification in response to one or more comparisons between filtering information specific to an attribute of the subject and the local thermal information about the peripheral part of the body of the subject. In addition to the foregoing, other system aspects are described in the claims, drawings, and text forming a part of the present disclosure.

In one aspect, a method includes but is not limited to obtaining information indicating a current thermal condition in a peripheral part of a subject's body and signaling a decision whether to transmit a notification at least partly in response to one or more comparisons between the information indicating the current thermal condition in the peripheral part of the subject's body and information indicating a prior thermal condition in the peripheral part of the subject's body. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining information indicating a current thermal condition in a peripheral part of a subject's body and circuitry for signaling a decision whether to transmit a notification at least partly in response to one or more comparisons between the information indicating the current thermal condition in the peripheral part of the subject's body and information indicating a prior thermal condition in the peripheral part of the subject's body. In addition to the foregoing, other system aspects are described in the claims, drawings, and text forming a part of the present disclosure.

In one aspect, a method includes but is not limited to detecting a result of one or more comparisons between information indicating current local stress in a peripheral part of a subject's body and information indicating prior local stress in the peripheral part of the subject's body and signaling a decision whether to transmit a notification in response to the result of the one or more comparisons between the information indicating the current local stress in the peripheral part of the subject's body and the information indicating the prior local stress in the peripheral part of the subject's body. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for detecting a result of one or more comparisons between information indicating current local stress in a peripheral part of a subject's body and information indicating prior local stress in the peripheral part of the subject's body and circuitry for signaling a decision whether to transmit a notification in response to the result of the one or more comparisons between the information indicating the current local stress in the peripheral part of the subject's body and the information indicating the prior local stress in the peripheral part of the subject's body. In addition to the foregoing, other system aspects are described in the claims, drawings, and text forming a part of the present disclosure.

In one aspect, a method includes but is not limited to causing an artificial support to modify a force upon a first external portion of a subject's body as a programmatic response to locally-abnormal-stress-indicative information obtained from a second external portion of the subject's body. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for causing an artificial support to modify a force upon a first external portion of a subject's body as a programmatic response to locally-abnormal-stress-indicative information obtained from a second external portion of the subject's body. In addition to the foregoing, other system aspects are described in the claims, drawings, and text forming a part of the present disclosure.

In one aspect, a method includes but is not limited to obtaining locally-abnormal thermal information about a first external portion of a subject's limb and causing an artificial support to exert an increasing force upon a second external portion of the subject's limb at least partly in response to locally-abnormal thermal information about the first external portion of the subject's limb. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining locally-abnormal thermal information about a first external portion of a subject's limb and circuitry for causing an artificial support to exert an increasing force upon a second external portion of the subject's limb at least partly in response to locally-abnormal thermal information about the first external portion of the subject's limb. In addition to the foregoing, other system aspects are described in the claims, drawings, and text forming a part of the present disclosure.

In one aspect, a method includes but is not limited to obtaining a priori implant information and signaling a decision whether to initiate implant-site-targeting treatment partly based on the a priori implant information and partly based on one or more other clot-indicative determinants. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining a priori implant information and circuitry for signaling a decision whether to initiate implant-site-targeting treatment partly based on the a priori implant information and partly based on one or more other clot-indicative determinants. In addition to the foregoing, other system aspects are described in the claims, drawings, and text forming a part of the present disclosure.

In one aspect, a method includes but is not limited to obtaining a flow-change-indicative measurement and signaling a decision whether to administer one or more clot-reducing agents at least partly based on the flow-change-indicative measurement. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining a flow-change-indicative measurement and circuitry for signaling a decision whether to administer one or more clot-reducing agents at least partly based on the flow-change-indicative measurement. In addition to the foregoing, other system aspects are described in the claims, drawings, and text forming a part of the present disclosure.

In one aspect, a method includes but is not limited to obtaining one or more indications of a lytic material in a vicinity of one or more body lumens and accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a system includes but is not limited to circuitry for obtaining one or more indications of a lytic material in a vicinity of one or more body lumens and circuitry for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens. In addition to the foregoing, other system aspects are described in the claims, drawings, and text forming a part of the present disclosure.

In one aspect, a method includes but is not limited to causing one or more evaluations of local respiratory-status-indicative information about a first body part of an occupant of a vehicle. In addition to the foregoing, other method aspects are described in the claims, drawings, and text forming a part of the present disclosure.

In one or more various aspects, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer.

In one aspect, a vehicle includes but is not limited to circuitry for causing one or more evaluations of local respiratory-status-indicative information about a first body part of an occupant and a seat configured to bear the occupant. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 83-84 depict variants of the flow of FIG. 82.

FIGS. 95-96 depict variants of the flow of FIG. 94.

FIG. 97 depicts an exemplary environment in which one or more technologies may be implemented.

FIGS. 98-99 depict high-level logic flows of operational processes.

FIGS. 100-101 depict variants of the flow of FIG. 98.

FIG. 108 depicts an exemplary environment in which one or more technologies may be implemented.

FIG. 109 depicts a high-level logic flow of an operational process.

FIGS. 110-111 depict variants of the flow of FIG. 109.

FIG. 116 depicts an exemplary environment in which one or more technologies may be implemented.

FIG. 117 depicts a high-level logic flow of an operational process.

FIGS. 118-119 depict variants of the flow of FIG. 117.

FIG. 120 depicts another exemplary environment in which one or more technologies may be implemented.

DETAILED DESCRIPTION

Figure 1:
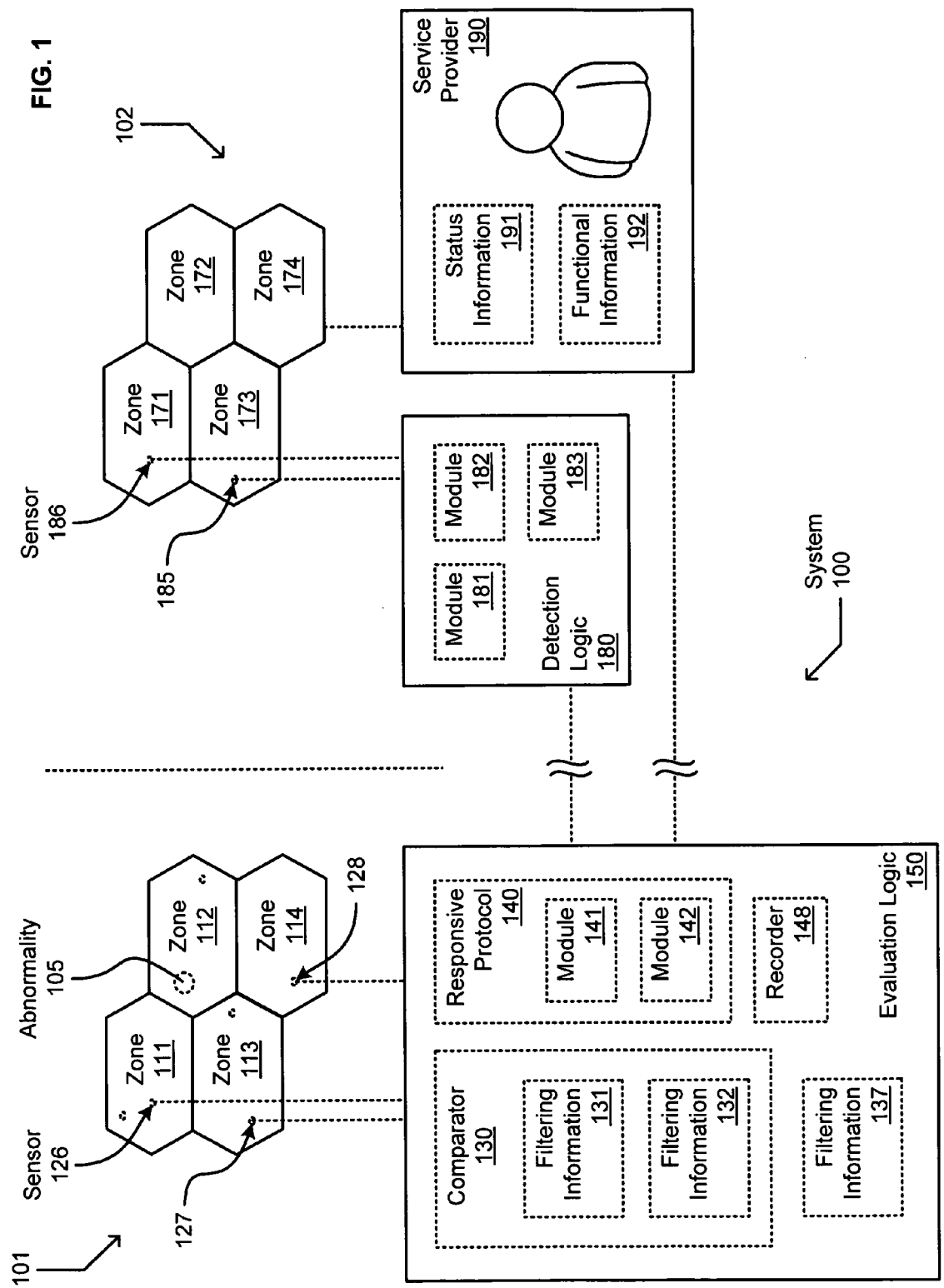
FIGS. 1-81 depict exemplary envirnments in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

With reference now to FIG. 1, shown is a system 100 configured to monitor at least one detection site 101 comprises several zones 111, 112, 113, 114 of a subject's body, any of which may contain an infection or other physiological abnormality 105. Such anomalies may manifest as physical phenomena detectable by a comparator 130 applying various filtering information 131, 132, 137 to output from one or more sensors 126, 127, 128 in a proximity of the detection site(s) 101 as exemplified below. (In some variants, for example, such features of zone 112 may be detected by a ranged sensor 127 in other zones 113 or by a portable sensor 126 that enters zone 112.)

Other such detection sites 102 may likewise include several zones 171, 172, 173, 174 sometimes accessible to system 100, any of which may be detectable at various times by one or more sensors 185, 186. In some variants, also, a clinician or other service provider 190 may be able inspect a patient's leg or other zone 174 of interest, status information 191 which may be acted upon according to a triage protocol or other such functional information 192 from evaluation logic 150. In some contexts, service provider 190 may likewise apply status information 191 at site 102, such as by determining whether a symptom has changed. Functional information 192 may likewise flow to evaluation logic 150, such as by service provider 190 identifying what treatments or other events occurred.

In some variants, module 182 of detection logic 180 may be configured to notify evaluation logic 150 only in the event of input from one or more sensors 185, 186 at site 102. (A "module" may include special-purpose hardware, general-purpose hardware configured with special-purpose software, or other circuitry configured to perform one or more functions recited in this document.) In various embodiments as described below, one or more modules 141, 142 of protocols may likewise be invoked in response to symptoms indicated by such detection logic 180 and/or service providers 190. In some contexts, for example, one or more service providers 190 may orally or otherwise report status information 191 to evaluation logic 150 based upon visual or other preliminary examination of particular zones 173, 174 of a patient's body. Alternatively or additional, the service provider(s) may perform a diagnostic procedure or other evaluation according to programmatic or other functional information 192 specified by evaluation logic 150 (implementing, for example, an expert system).

Module 142 or other such components, for example, may be configured to apply one or more types of filtering information as exemplified below in deciding one or more of (a) whether to warn an individual or otherwise transmit a notification to an interface; (b) whom to notify; (c) when to transmit a notification; (d) what to include with a notification; (e) whether to adapt detection logic to reduce a frequency of detection events or other undesirable notifications, such by configuring inclusion criteria to be more selective; (f) whether to include one or more modules of detection logic in an update operation; (g) whether to retain or otherwise act upon one or more data samples; (h) which actuator drivers, relays, or other hardware control circuitry to activate; (i) whether to trigger one or more emitters or other active elements of sensors; (j) what conditions indicate an actionable health risk; and/or (k) when and which subjects warrant other such responsive actions. One or more instances of responsive protocols 140, recorders 148, or other components of evaluation logic 150 may be provided, in some variants, at a central processing facility that is remote from one or more of site 102, detection logic 180, and/or service provider 190.

In some variants, evaluation logic 150 may be configured to rank conditions or otherwise combine data effectively from two or more subjects, such as by using data from one subject (received via detection logic 180 or service provider 190, e.g.) to generate or update filtering information 132, 137 to be applied to data from another subject (at site 101, e.g.). Other such embodiments are described, for example, with reference to FIGS. 2, 3, 8, 25, and 74 below.

In some variants, two or more sensors 126, 127, 128 may (optionally) implement a sensor array, an assay, or other such combinations of two or more sensor types and/or testing modes configured to detect a potential combination of aspects indicative and confirmatory of a circulatory problem or other pathology of particular concern. Other such embodiments are described, for example, with reference to FIGS. 3, 6, 8, 9, 10, 12, 19, 22-28, 32, 52, 74, and 76 below.

Figure 2:
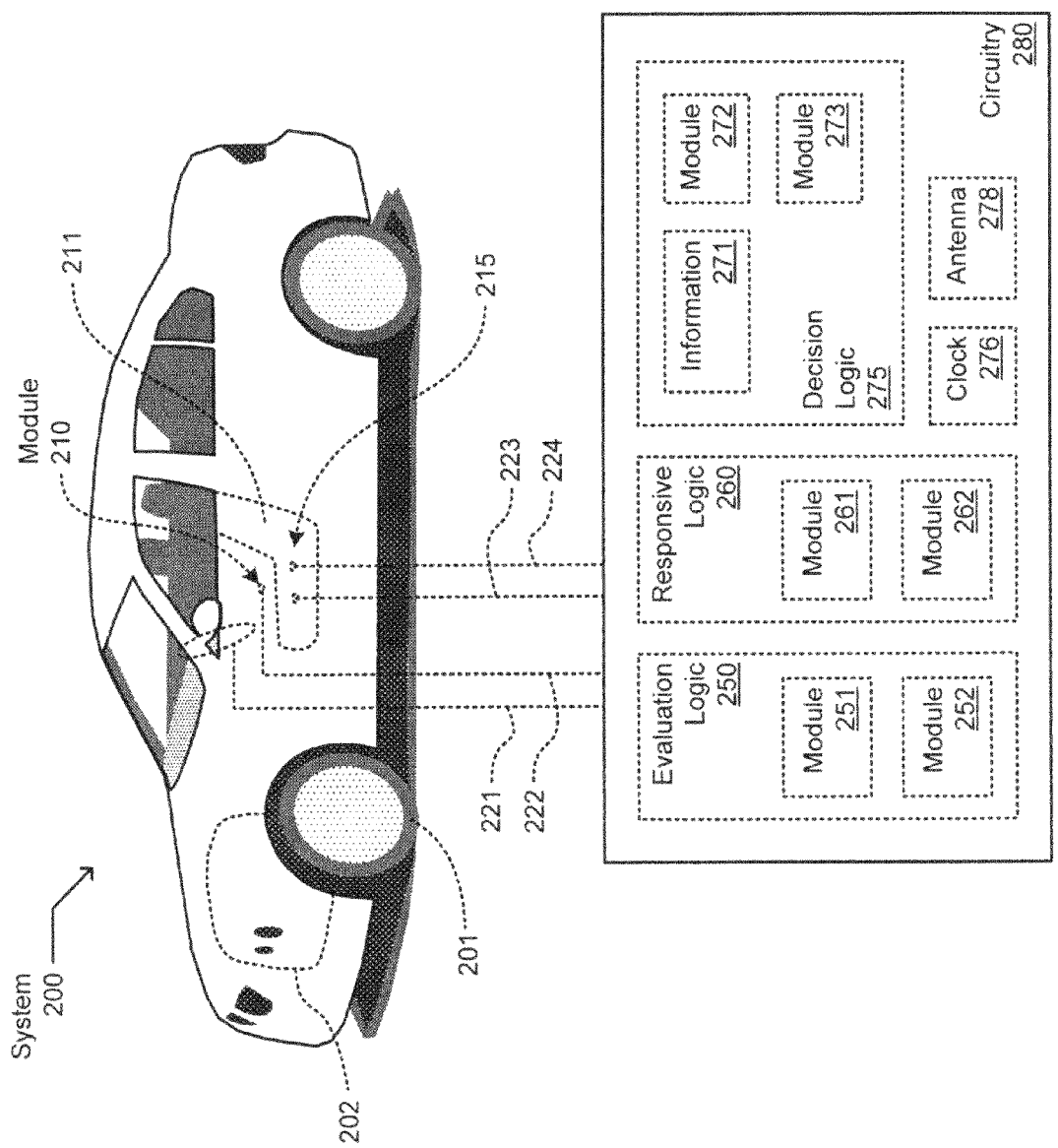

With reference now to FIG. 2, shown is a system 200 in which one or more technologies may be implemented, a sedan comprising wheels 201, an engine 202, and one or more modules 210, 215 configured to provide one or more types of information 221 from controls or information 222, 223, 224 from within or around one or more seats 211 or other locations inside the vehicle. System 200 may further include or otherwise interact with one or more modules 251, 252 of evaluation logic 250, one or more modules 261, 262 of responsive logic 260, and/or one or more modules 272, 273 of decision logic 275 operable for transmitting or otherwise selectively acting upon such information 271 as described below. In some variants, for example, one or more clocks 276 or antennas 278 may facilitate selective notifications, aggregations, evaluations, or other programmatic responses as described herein. Alternatively or additionally, one or more stationary instances of circuitry 280 may communicate with system 200, for example, via antenna 278.

An embodiment provides a vehicle having one or more modules 251, 252 of evaluation logic 250 configured as circuitry for causing one or more evaluations of local respiratory-status-indicative information 222, 223, 224 about a driver's or other occupant's weight-bearing body parts. Other such embodiments may, for example, include features described with reference to each of FIGS. 3-16 and 22-33. Such systems may include or otherwise interact with a steering wheel or other such utility device configured to be handled by an occupant. Alternatively or additionally, such embodiments may include one or more engines 202 operable for conveying one or more seats 211—such as by applying a torque (via one or more axles, e.g.) to wheels 201.

In some embodiments, "respiratory" status may refer generally to oxygen saturation within a blood vessel segment, pH indications indicating a degree of regional exertion or elevation, a presence or absence of hypercapnea, or other such detectable conditions directly or indirectly reflecting discernable cellular respiration. In some embodiments, information "about a body part" may refer to a flow that enters or leaves the body part, a current position or other variable attribute of the body part, eye color or other such body part categories, injuries or other such historical data, tumors or their attributes, or other such information relating to vital organs or other such sub-structures within an individual or demographic grouping. In some embodiments, a conduit or other circuitry may be "invoked" by initiating a reboot or other such hardware function, by calling a procedure or other such identifiable objects, or otherwise by transmitting a pulse or other signal feature configured to trigger an execution of special-purpose functionality.

With reference now to FIG. 3, shown is a system 300 in which one or more technologies may be implemented. System 300 may be positioned centrally or local to subjects 310, 320, for example, and/or configured to invoke one or more interfaces 330 or other response logic 335 in response to one or more indications 311, 312, 313, 314, 321 from sensors 317, 326, 327 in, on, or near extremities 328 or other body parts of interest. This can occur, for example, in a context in which hosiery 318, clothing, or one or more utility devices 325 within a detection range of sensors 317, 326, 327 implements or otherwise interacts with system 300. In some embodiments, such sensors may be implanted in a body tissue of interest or in a structure with which subjects 310, 320 may interact. Alternatively or additionally, some such sensors may be worn as clothing, a support, a patch, a bandage, a watch, or some other article in the subjects' vicinity. Such articles may (optionally) include one or more instances of storage or transmission media 340 configured to bear one or more percentages 343 or other indications 341, 342, 344 such as content 345; information 346; decisions 347; or notifications 348 containing content 349, for example, in any of the flows described below in relation to FIGS. 82-119.

Figure 4:
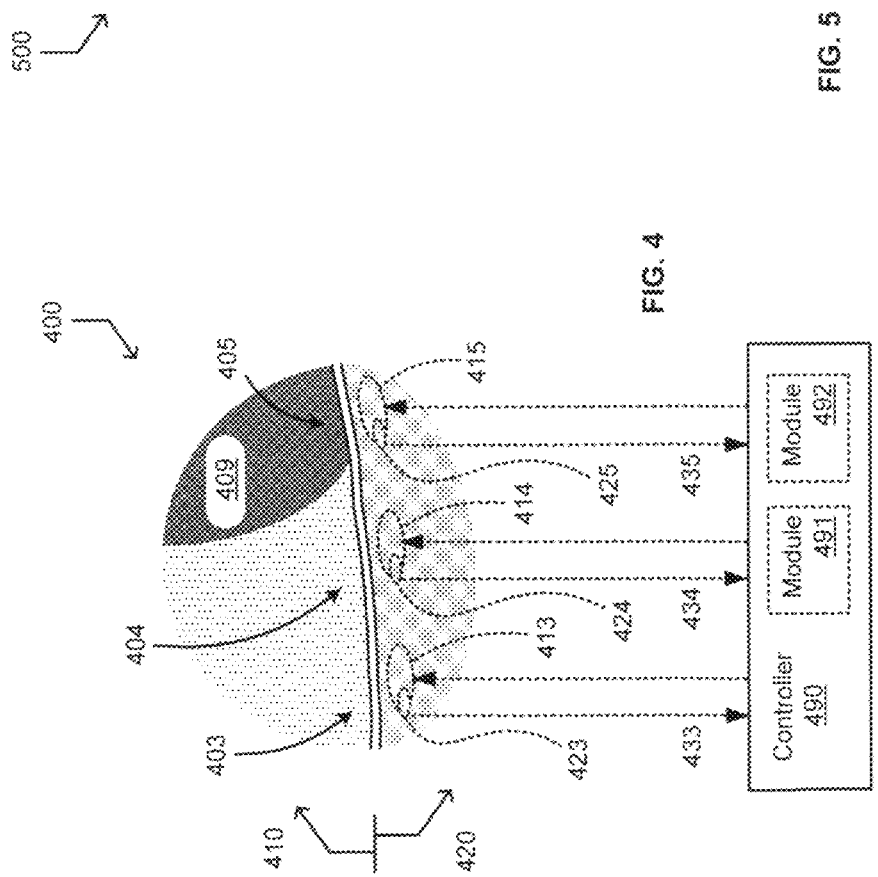

With reference now to FIG. 4, shown is a system 400 in which one or more technologies may be implemented. System 400 comprises a support 420 configured to contact or otherwise remain adjacent one or more external portions 403, 404, 405 of body 410 in such a way as to permit a detection of surface roughness, discoloration, or other detectable anomalies 409. As shown, support 420 includes one or more components 413, 414, 415 that each include one or more sensors 423, 424, 425 respectively adjacent external portions of interest. In some variants, one or more modules 491, 492 of controller 490 are configured to receive one or more sensor inputs 433, 434, 435, for example, and (optionally) to invoke a therapeutic dispensation as an optional feature of any of the flows described below in relation to FIGS. 82-119, such as by a drug dispenser or other suitable component(s) 413, 414, 415.

An embodiment provides a variant of module 491 configured as circuitry for deciding whether to transmit measurement content or other blood clot indications and one or more components 413, 414, 415 each coated with an ultrasound gel or other such medium to facilitate acoustic energy passing from a subject body 410 to respective sensors 423, 424, 425. (Other such embodiments are described, for example, with reference to FIGS. 23-27 below.)

Figure 5:
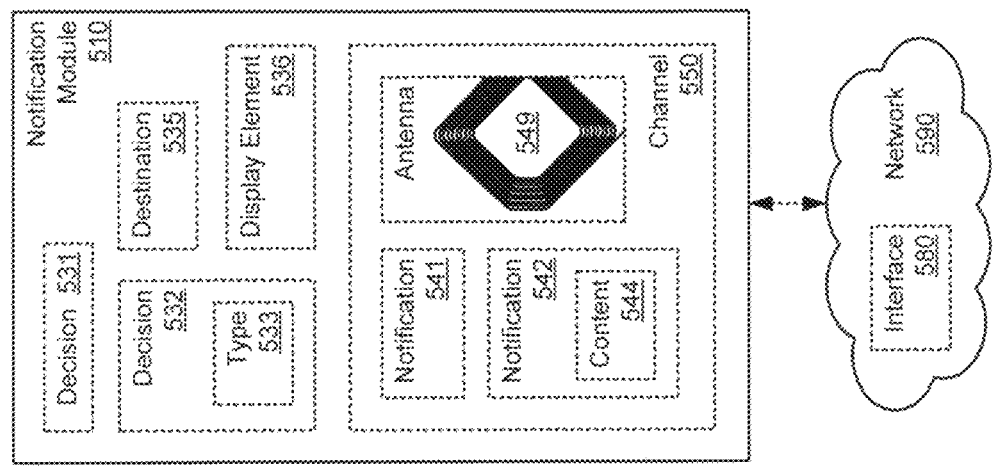

With reference now to FIG. 5, shown is a system 500 in which one or more technologies may be implemented comprising one or more notification modules 510 operably coupled with one or more interfaces 580 in a network 590. Notification module 510 may handle or otherwise include one or more decisions 531, 532 of various types 533, destinations 535, display elements 536, or channels 550 operable for transmitting one or more notifications 541, 542 such as content 544, optionally via one or more radio-frequency or other antennas 549. Such antennas may be used in an implanted or other portable article, for example, as described throughout this document.

In some variants, such notification logic may be configured to provide timely information or advice to one or more individuals in a subject's vicinity. Other such embodiments are described, for example, with reference to FIGS. 2, 3, 6, 8, and 29. Alternatively or additionally, one or more such network components may include media configured for display: flat screen displays, image-projecting devices, touch screens, or other such display media. Other such embodiments are described, for example, with reference to FIGS. 8, 11, 14, 22, 29, and 30.

With reference now to FIG. 6, shown is a wheelchair 600, a system in which one or more technologies may be implemented. Wheelchair 600 includes a seat 610 having one or more signal paths 631, 632, 633, 634 operably coupled with one or more monitoring apparatuses 660, such as for detecting weight or local phenomena. Monitoring apparatus 660 may, for example, comprise one or more modules 641, 642, 643 of detection logic 640, modules 651, 652 of responsive logic 650, antennas 654, or other circuitry for generating or using detection results 655 as described herein.

An embodiment provides a wheelchair or other vehicle comprising one or modules 642 of detection logic 640 configured as circuitry for causing one or more evaluations of incoming signals (arriving along selected paths 631, 632, 633, 634, for example) indicating a status of an occupant's seat, back, feet, or other force-bearing body parts that may suffer local (cellular) respiratory problems for long periods. Such embodiments may be used, for example, in a context in which an occupant is cognitively or otherwise unable to respond to such problems. In some variants, seat 610 may include or otherwise support elastic or other tensile elements configured to urge sensors 617 toward a sitting subject. Other such vehicles configured to monitor a health status of one or more occupants are described, for example, with reference to FIGS. 2 and 8. In some embodiments, "health status" indicative data can reflect a physiological trend or other time-dependent phenomenon indicating some aspect of a subject's condition. Alternatively or additionally, a health status indicative data set can include portions that have no bearing upon a given subject's health. Although some types of distillations can require authority or substantial expertise (e.g. making a final decision upon a risky procedure or other course of treatment), many other types of distillations can readily be implemented without undue experimentation in light of teachings herein.

With reference now to FIG. 7, shown is system 700 in which one or more technologies may be implemented, including one or more actuator arrays 705 operable for responding to controller 775. Array 705 comprises several actuators 701. A first actuator 701 comprises at least two actuator elements 711, 712 each operable to move cell 710 (such as by motor 715) relative to structure 765 selectively in response to controller 775. One or more actuator elements 722 are likewise operable to move cell 720 relative to structure 765 and/or cell 740, also in response to controller 775. One or more actuator elements 741, 742, 743 are likewise operable to move cell 740 relative to structure 765 in response to controller 775. (In some contexts, for example, one or more pumps or valves 746, 747 may be configured to permit a fluid to enter and/or leave actuator element 743 to control its expansion and contraction, for example.) One or more actuator elements 752, 753 are likewise operable to move cell 750 relative to structure 765 in response to controller 775. Controller 775 may thus effectuate local position and/or tension control a selective invocation of such actuators. Controller 775 may comprise one or more instances of configuration modules 777, support control logic 780, or profile data 790 comprising operating parameters 791, 792, 793, 794, 795 or other aspects of one or more profiles 796. In some variants, implementing or using such control logic may include configuring a seat or other mechanical support. Other such embodiments are described, for example, with reference to FIGS. 2, 3, 6, 12, 89, and 97-99. In some variants, moreover, one or more modules 781, 782, 783, 784 may be configured to control one or more such cells 730 comprising, for example, a selectable heating or liquid dispensation element. Any of the local modules described throughout this document may (optionally) include one or more of such an array 705, structure 765, or controller 775 for tissue manipulation, examples of which are described below in relation to the flows of FIGS. 82-119.

Figure 8:
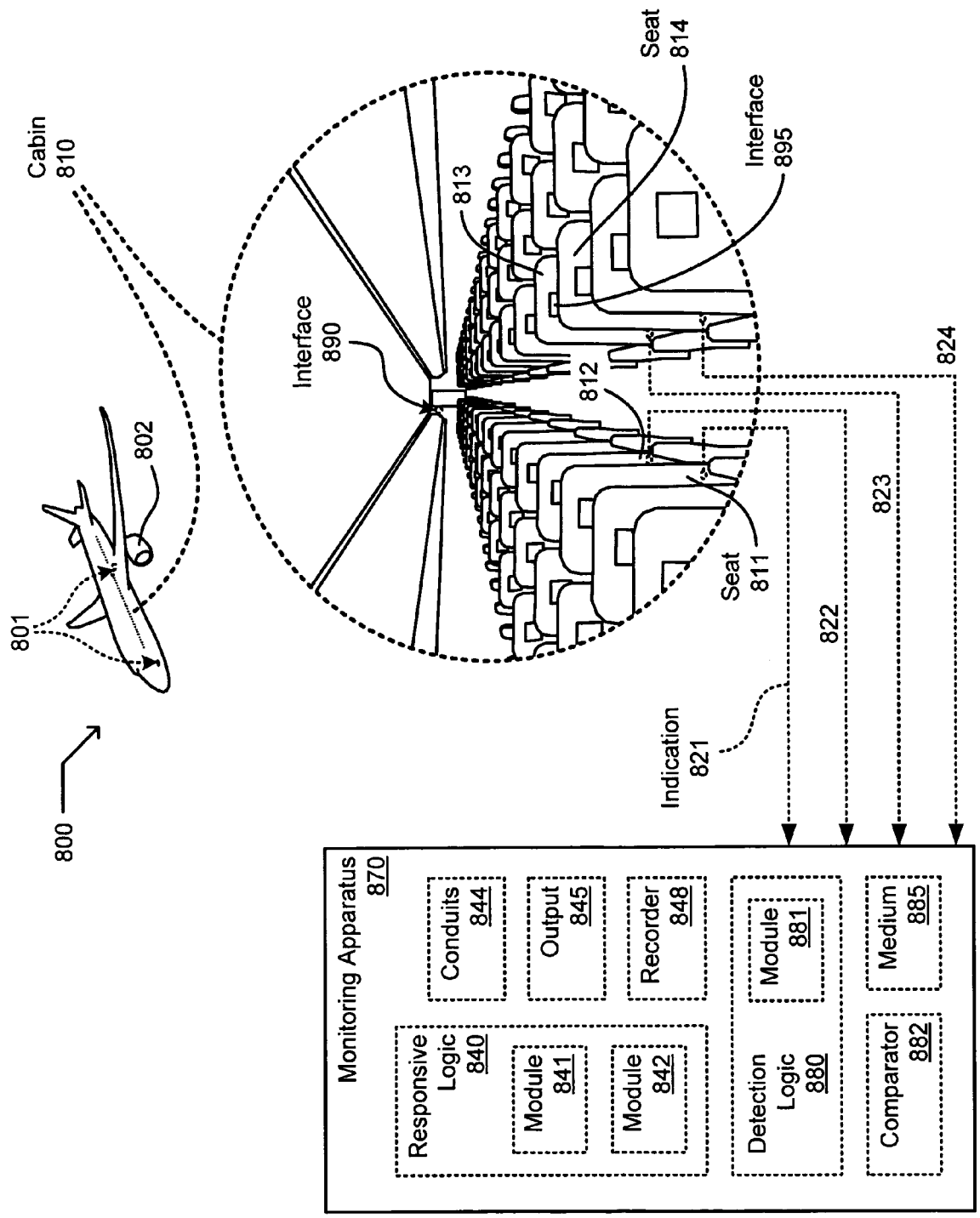

With reference now to FIG. 8, shown is a system 800 in which one or more technologies may be implemented, an airplane comprising wheels 801, engines 802, and a cabin 810 configured to include one or more interfaces 890 configured to receive output 845 from an instance of monitoring apparatus 870. Each monitoring apparatus 870 may be configured to receive one or more sensed indications 821, 822, 823, 824 from respective seats 811, 812, 813, 814 in which passengers may suffer circulatory or other actionable health risks. Each monitoring apparatus 870 may likewise include one or more instances of conduits 844, recorders 848, modules 881 of detection logic 880, or modules 841, 842 of other responsive logic 840 as described below. In some variants, for example, an interface 895 may be configured to display an output 845 selectively in a vicinity of a seat 814 that has generated one or more indications 824 of a circulatory obstruction or other such actionable health risk. Alternatively or additionally, prolonged or other more serious indications 824 (an apparent stroke, for example, or a sleeping passenger with a large clot forming) may be configured to activate a beacon, alarm, or other interface 890 more readily visible and/or audible from a front portion of cabin 810 or from other passengers' seats 812, 813 nearby. A variety of local sensors described in this document are suitable for use in a context like that of system 800, especially those described with reference to FIGS. 23-26.

An embodiment provides an airplane or other vehicle comprising one or comparators 882 or other modules 881 of detection logic 880 configured as circuitry for causing one or more evaluations of incoming indications 821, 822, 823, 824 from seats occupied by respective occupants. Such embodiments may likewise include a cabin 810 or other such enclosure configured to shelter the occupant(s). Alternatively or additionally, such embodiments may include one or more engines 802 operable for conveying one or more seats 811, 812, 813, 814—such as by causing a force to be applied at least to a fuselage or other structure supporting the seat(s). In some variants, an embodiment may further include an auditory or other interface configured to handle user information; software or other modules configured as circuitry for comparing local respiratory-status-indicative information with filtering information selected in response to one or more attributes of occupant(s).

In some variants, such one or more modules 841 of responsive logic 840 may be configured to provide timely information or advice to others who may be near an at-risk vehicle occupant. Other such embodiments are described above, for example, with reference to FIGS. 3, 5, and 6.

With reference now to FIG. 9, shown is a tonometer 925 or other instrument 900 configured to facilitate one or more sensors 902 being positioned adjacent a subject's skin 910. One or more sensor elements 905 may relay or otherwise facilitate a transmission of images 931, signals 932, 933, or other data 935 to a primary module 920. Then or later, one or more modules 943 of evaluation logic 950 may apply one or more thresholds 941 or other criteria 942 to such data as described below.

With reference now to FIG. 10, shown is a system 1000 in which one or more technologies may be implemented comprising two or more actuators 1021, 1022 each configured to support corresponding sensors 1001, 1002 on or near respective portions 1011, 1012 of a subject's skin 1010. In various configurations, primary module 1060 may include one or more modules 1051, 1052 of configuration logic 1050; one or more profiles 1071, 1072 or other parameters 1075, 1076 of control data 1079; and/or responsive logic 1095. As exemplified below, one or more modules 1091, 1092, 1093 of responsive logic 1095 may trigger configuration logic 1050 to update one or more signals 1031, 1032 configured to control respective actuator sets in response to one or more thresholds 1086, 1087 or other criteria being applied to data 1081, 1082, 1083 and/or signals 1033, 1034 received from sensors 1001, 1002. In a variant in which such signals 1033, 1034 signify a local force minimum in portion 1012, configuration logic 1032 may (optionally) be configured to energize actuator 1022, for example, to maintain a nominal contact force with skin 1010.

In some variants, one or more actuators or other circuitry may be configured to include or receive data indirectly from one or more sensor arrays and other combinations of sensor elements. Other such embodiments are described, for example, with reference to FIGS. 1-9, 12, 22-28, 52, 74, and 76.

With reference now to FIG. 11, shown is a system 1100 in which one or more technologies may be implemented. One or more actuators 1120 each comprise a plurality of elements 1121, 1122 configured to respond to one or more signals 1131, 1132 by exerting a controlled force upon respective portions 1111, 1112 of skin 1110. An assembly of one or more actuators 1120 may likewise provide one or more signals 1125 to primary module 1190. Primary module 1190 may include one or more instances of device-executable command sequences 1157 or other modules 1151, 1152, 1153, 1154, 1155, 1156; sensor-derived data 1161, 1162, 1163 and/or vector grids 1165 or other profiles 1167 of data 1170 suitable for use by control logic 1160; one or more modules 1181, 1182, 1183 of processing logic 1180 configured to handle the data 1170 and other aspects of incoming signals 1125; and/or one or more interfaces 1185 configured to facilitate downloads, operational updates, or other such external interactions as described herein. In some variants, implementing or using such control logic may include configuring a seat or other mechanical support. Other such embodiments are described, for example, with reference to FIGS. 6, 7, 12, or 89.

Figure 12:
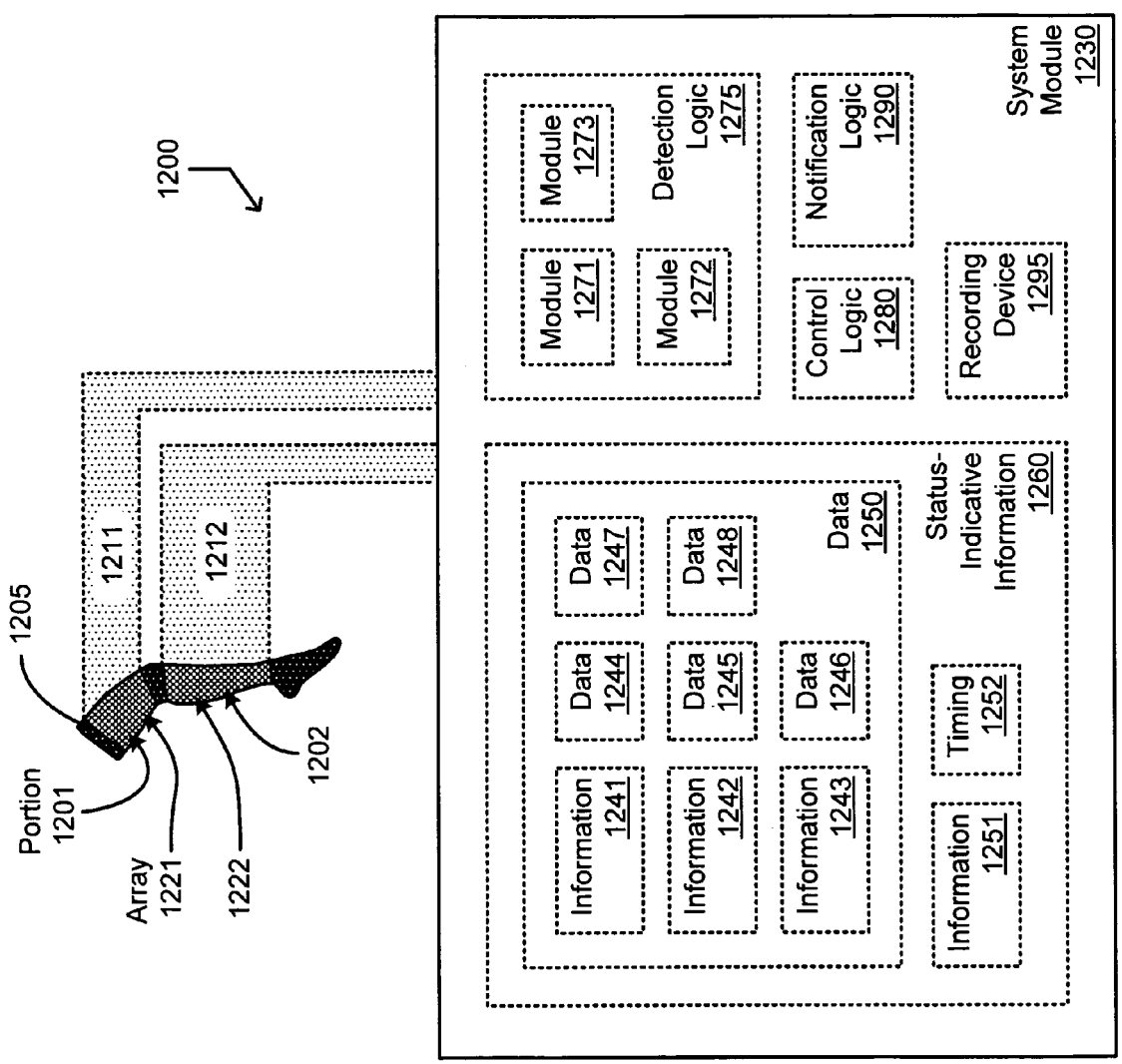

With reference now to FIG. 12, shown is a system 1200 in which one or more technologies may be implemented for use with a custom cast, a fitted stocking, or other such special-purpose apparatus 1205 configured to support a subject's limb as described herein. An array 1221 of sensors, actuators, and/or other such devices may be configured to interact with a portion 1201 of the subject's limb and/or to handle control and/or sensed information 1211. At least one other array 1222 of devices may likewise be configured to interact with one or more respective portions 1202 of the subject's limb and/or to handle respective information 1212 passing to and/or from system module 1230. System module 1230 may include one or more components supported by apparatus 1205, on a nearby utility device, in other (optionally centralized) facilities, or distributed across a plurality of such locations. System module 1230 may include one or more media bearing various types of sensed information 1241, 1242, 1243 or other data 1244, 1245, 1246, 1247, 1248, 1250 as described herein. Other such data and/or thermal information 1251 may be provided roughly contemporaneously as (current) status-indicative information 1260, in some variants, or may indicate timing 1252 associated therewith, such as in a series of periodic measurements reflecting a health status trend in the status-indicative information 1260. System module 1230 may likewise include one or more instances of modules 1271, 1272, 1273 of detection logic 1275, control logic 1280, notification logic 1290, recording devices 1295, or other such components as described herein.

In some variants, such detection logic may be implemented in hosiery, wristbands, bandages, or other such worn articles. Other such embodiments are described, for example, with reference to FIGS. 2, 3, 17, 20, 25, and 29. In some variants, such embodiments may incorporate one or more existing technologies like those of the "BT2" wristwatch design, described at www.exmocare.com and in the Information Disclosure Statement filed herewith.

Figure 13:
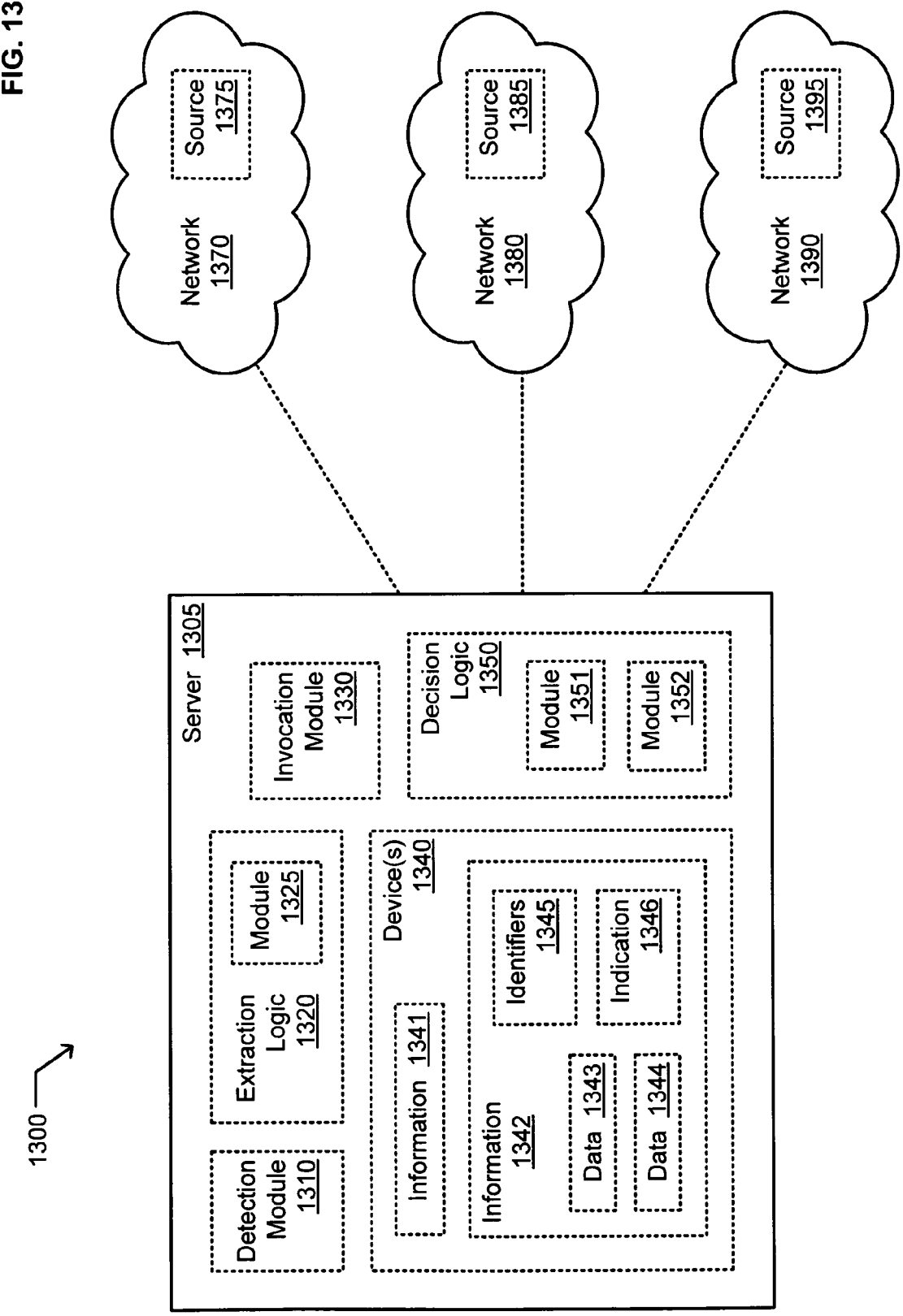

With reference now to FIG. 13, shown is a system 1300 in which one or more technologies may be implemented, a server 1305 configured to communicate with one or more sources 1375, 1385, 1395 in a each of plurality of networks 1370, 1380, 1390. One or more such servers 1305 may include instances of detection modules 1310; modules 1325 of (data) extraction logic 1320; remote-resource invocation modules 1330; devices 1340; or modules 1351, 1352 of decision logic 1350. In some variants, an instrument or other device 1340 as described herein may handle various data 1343, 1344; identifiers 1345; indications 1346; or other information 1341, 1342 as described herein for generating and/or responding to evaluation requests or other such remote invocations.

Figure 14:
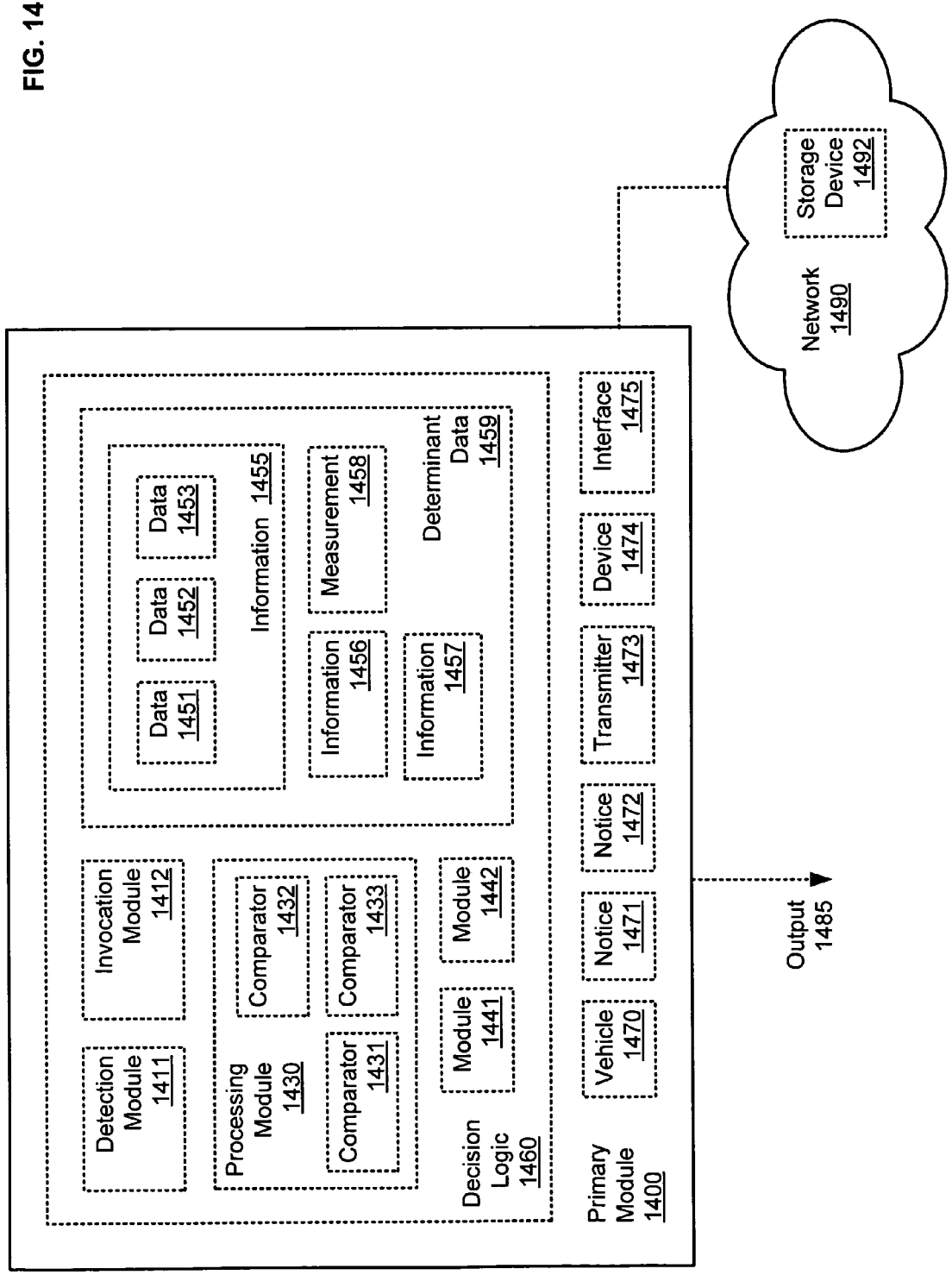

With reference now to FIG. 14, shown is a system in which one or more technologies may be implemented, a vehicle 1470 or other primary module 1400 configured to display or otherwise transmit output 1485 and/or to interact with one or more storage devices 1492 in network 1490. Primary module 1400 may include or otherwise handle one or more instances of decision logic 1460; notices 1471, 1472; transmitters 1473; local devices 1474; or interfaces 1475 as described herein. Decision logic 1460 may include one or more instances of detection modules 1411; invocation modules 1412; comparators 1431, 1432, 1433 or other processing modules 1430; or other modules 1441, 1442 configured to perform or otherwise generate decisions upon images or other data 1451, 1452, 1453 or other such information 1455, 1456, 1457; measurements 1458; or other such determinant data 1459. Primary module 1400 may archive such decisions or other data remotely upon one or more such storage devices 1492, in some implementations as described herein, and/or may retrieve pathological models, thresholds, or other such programmatic information remotely from one or more such storage devices 1492.

Figure 15:
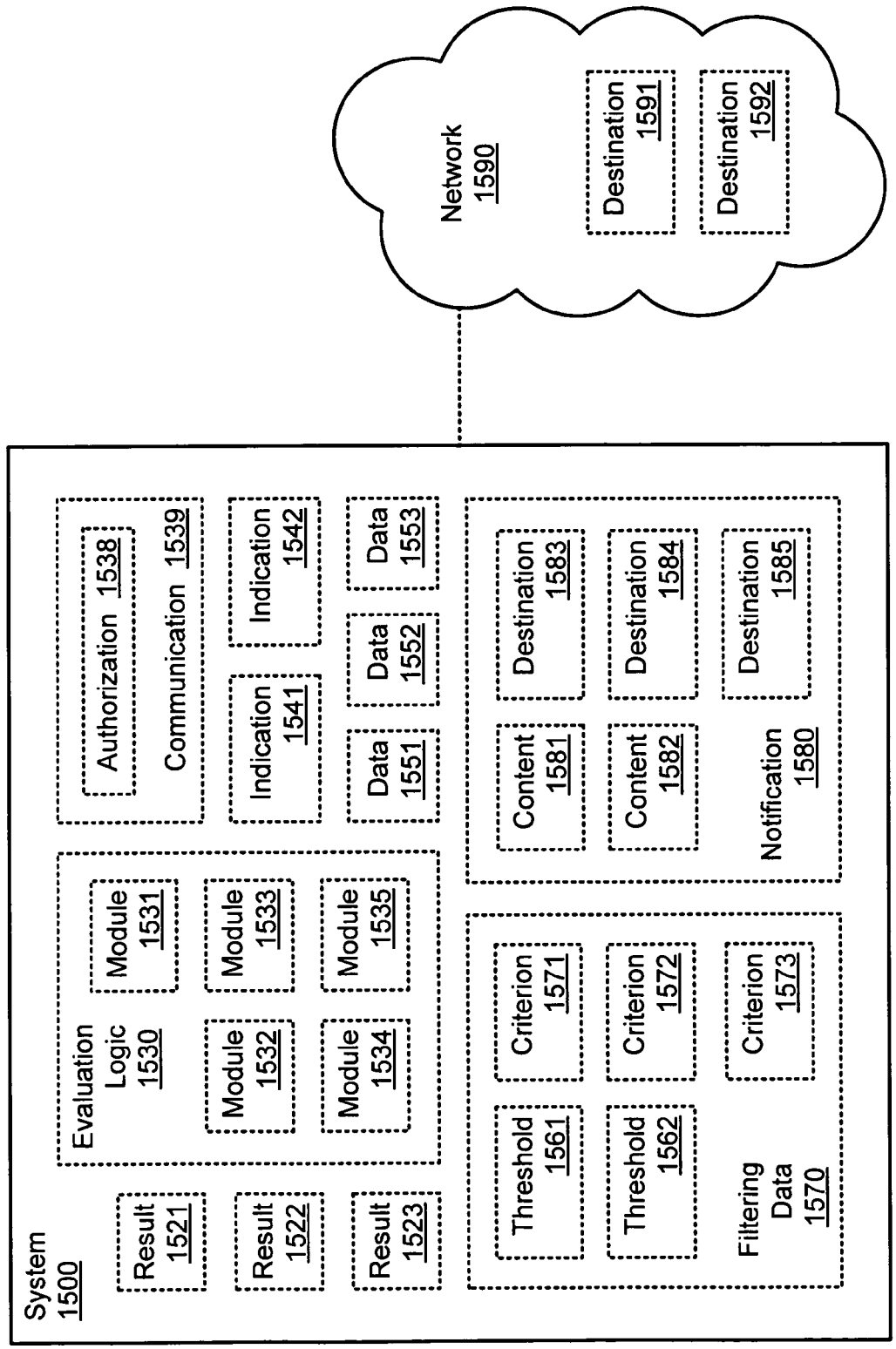

With reference now to FIG. 15, shown is a system 1500 in which one or more technologies may be implemented for relaying or otherwise notifying one or more destinations 1591, 1592 (in a network 1590 of care providers, e.g.) of one or more results 1521, 1522, 1523, authorizations 1538, or other substantive communications 1539. In some variants, for example, one or more modules 1531, 1532, 1533, 1534, 1535 of evaluation logic 1530 may generate or select content 1581, 1582 and/or destinations 1583, 1584, 1585 of such communications 1539 or other notifications 1580 in response to temporal indications 1541, 1542 or other such data 1551, 1552, 1553. In some variants, for example, such evaluation logic may generate or otherwise facilitate such communications or other notifications 1580 by applying one or more thresholds 1561, 1562; criteria 1571, 1572, 1573; or other filtering data 1570 as described herein to symptom-indicative or other subject status data as described herein.

Figure 16:
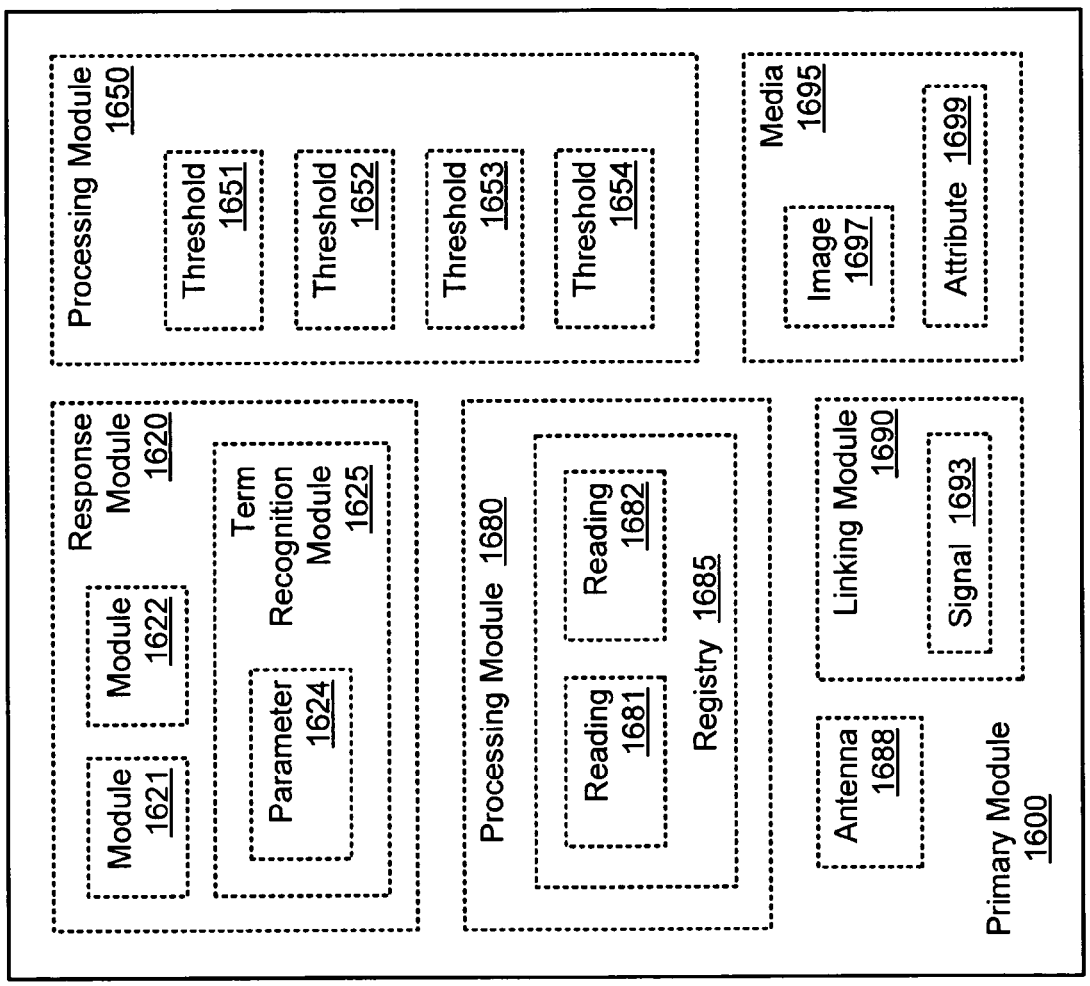

With reference now to FIG. 16, shown is a system in which one or more technologies may be implemented, for example, on an implantable chip or other apparatus suitable for long-term operation in a close vicinity of a subject. A primary module 1600 may comprise one or more instances of response modules 1620; processing modules 1650, 1680; antennas 1688, linking modules 1690, or other components suitable for bearing signals 1693; or other media 1695 configured to hold or otherwise bear images 1697 or other attributes 1699 of potential relevance to a subject's status. Response module 1620 may include one or more instances of term recognition modules 1625 or other modules 1621, 1622 operable for handling one or more parameters 1624. Processing modules 1650, 1680 may be configured to apply one or more thresholds 1651, 1652, 1653, 1654, for example, and/or to hold one or more readings 1681, 1682 in a registry 1685.

In some variants, one or more such media may be configured to contain images or otherwise handle shape-indicative data. Other such embodiments are described, for example, with reference to FIGS. 9, 35, 52, 74, 75, 77, and 79.

Figure 17:
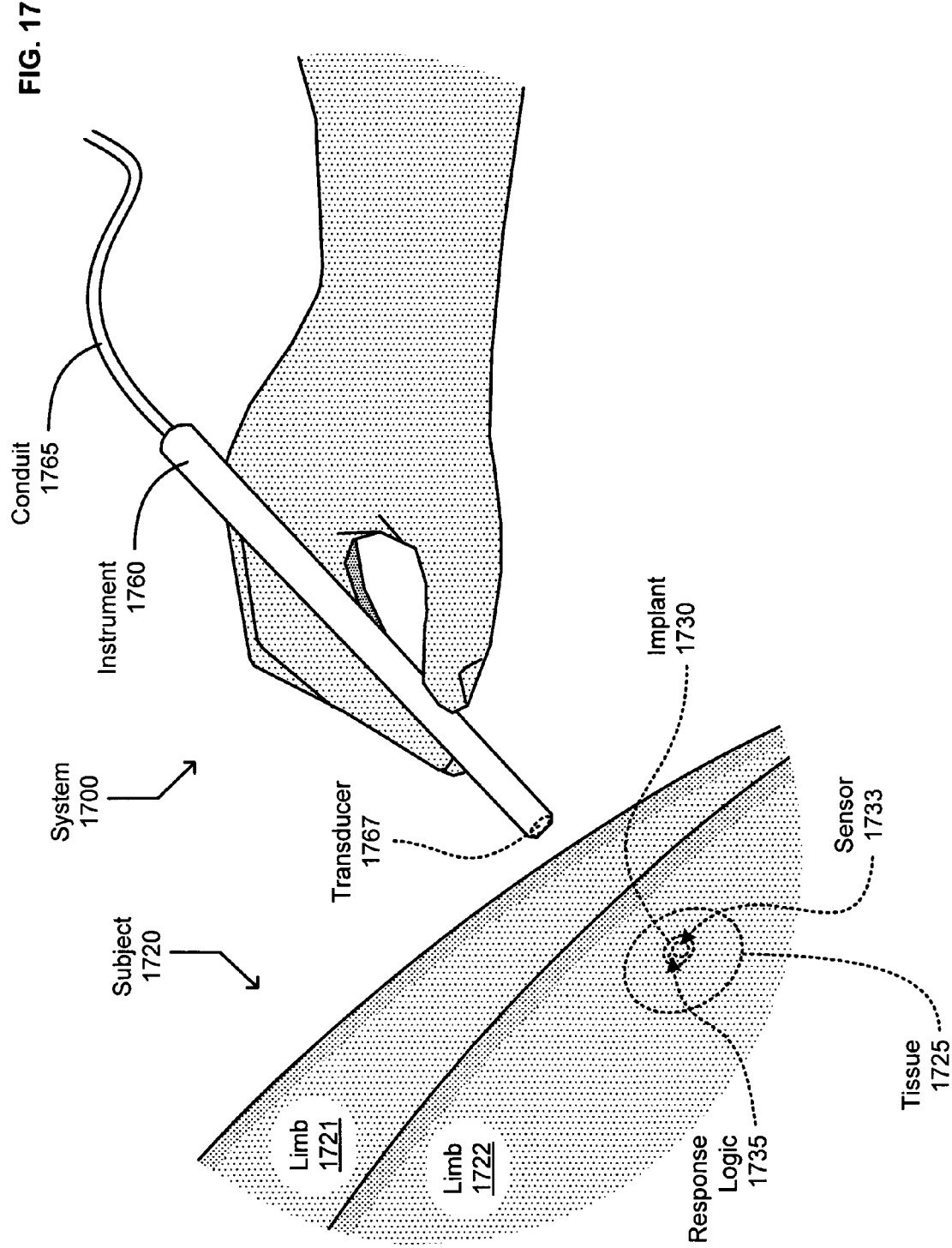

With reference now to FIG. 17, shown is a context in which one or more technologies may be implemented, for example, for using a system 1700 to examine tissue 1725 in one or more limbs 1721, 1722 of a subject 1720. System 1700 comprises one or more transducers 1767 supported on a hand-held instrument 1760 operably coupled to an external module as shown herein via a continuous signal-bearing conduit 1765. In some variants, such examination may be facilitated by one or more sensors 1733 in or on such tissue, optionally comprising an implant 1730 and/or response logic 1735 configured to process or otherwise respond to sensed data therefrom even before becoming operable to forward any indication of the data to transducer 1767.

Figure 18:
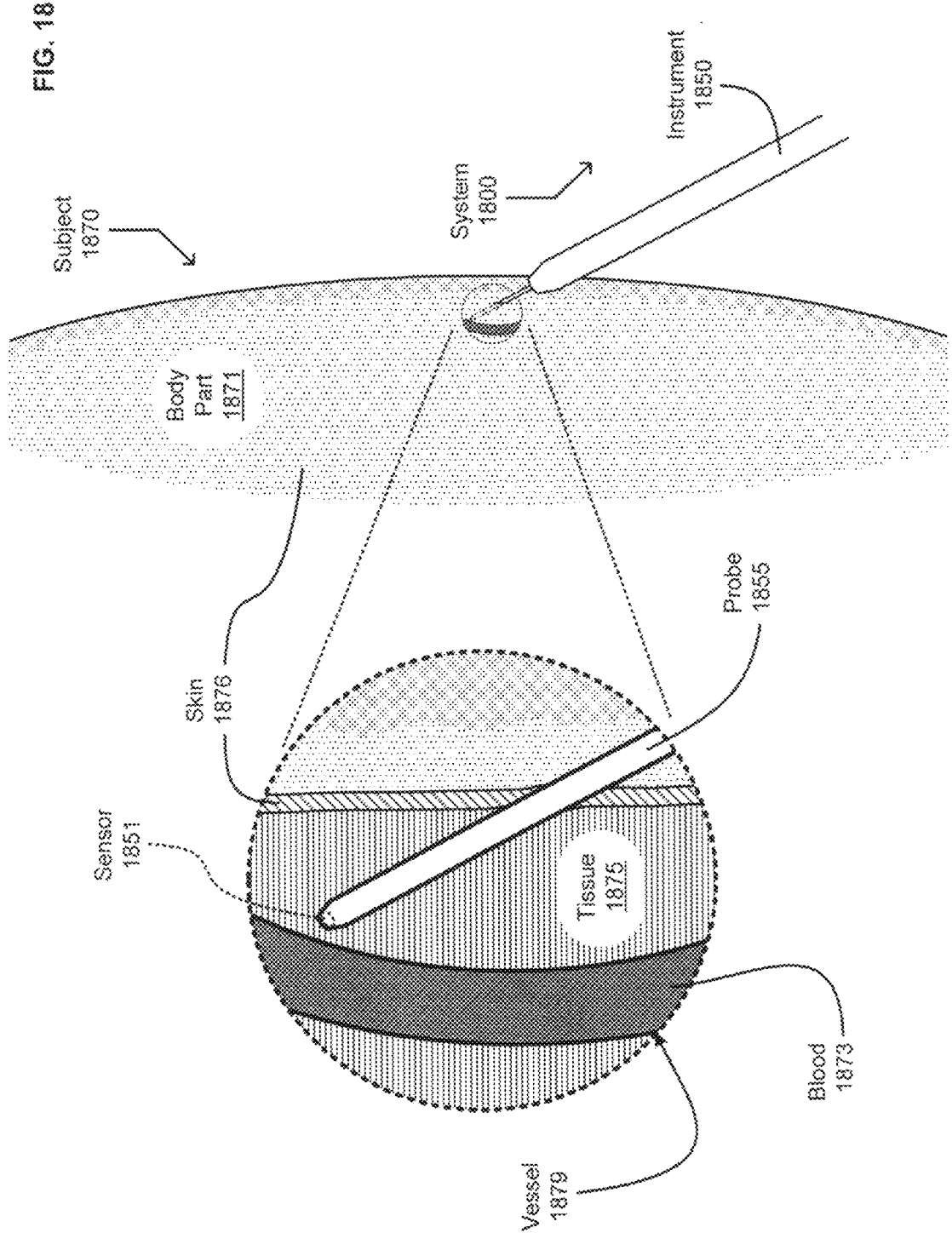

With reference now to FIG. 18, shown is a system 1800 in which one or more technologies may be implemented that include one or more instruments 1850 configured to position one or more sensors 1851 subcutaneously within tissue 1875 of body part 1871, for example. Variant configurations of commercially-available probes or other such instruments may be used to implant one or more sensors 1851, dispensers, or other such modules through skin 1876 of subject 1870 via one or more probes 1855, for example, adjacent or extending into vessel 1879. Such configurations may (optionally) be configured, for example, to detect one or more attributes of and/or administer one or more treatments via blood 1873. Laparoscopic and thoracoscopic systems suitable for accessing a vasculature are in common use, for example, and readily adapted to implement various configurations described herein without undue experimentation.

Figure 19:
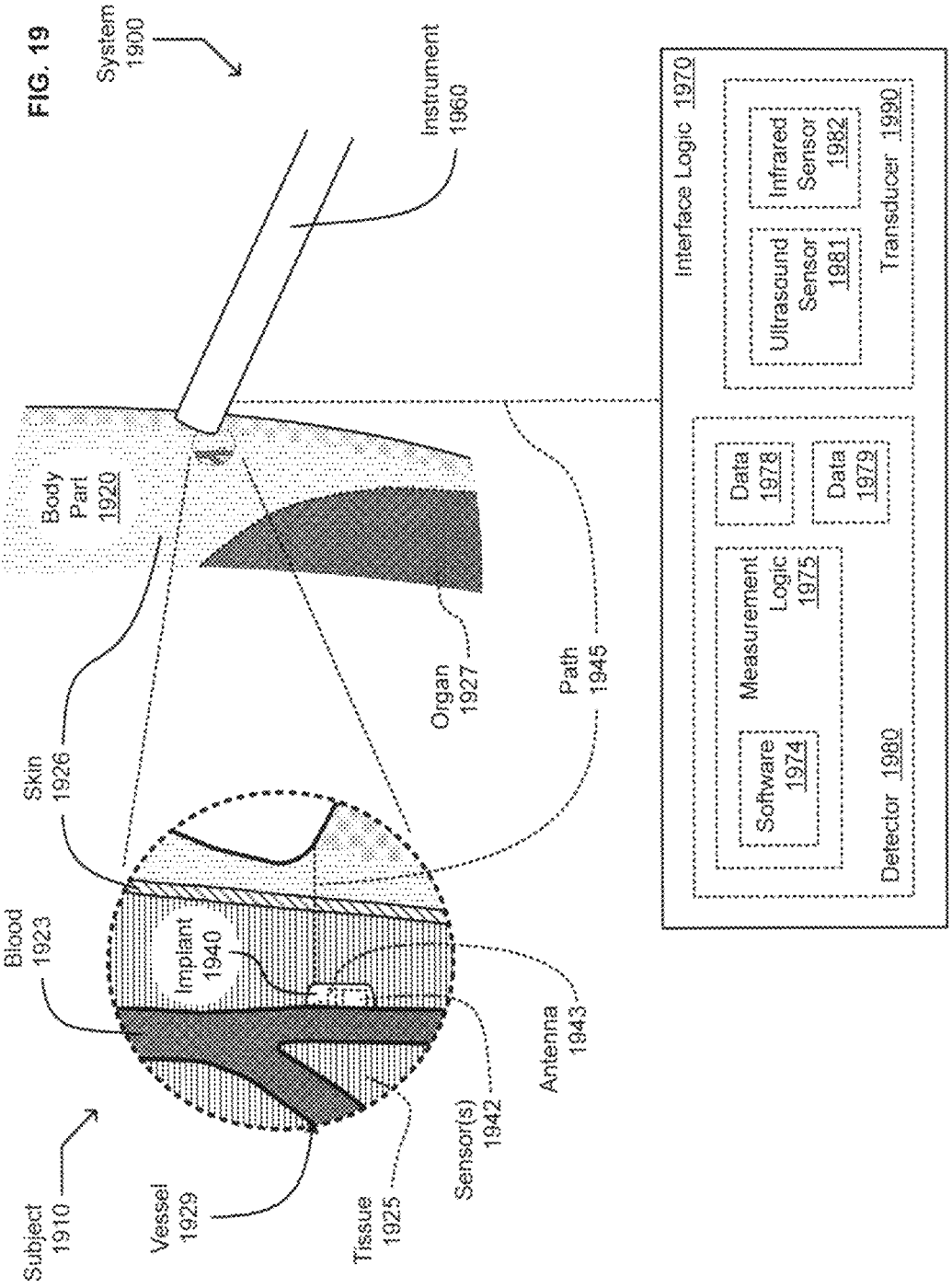

With reference now to FIG. 19, shown is a system 1900 in which one or more technologies may be implemented, such as for one or more body parts 1920 of subject 1910 to interact with interface logic 1970 via one or more hand-held instruments 1960. As shown, body part 1920 contains one or more vessels 1929 bearing blood 1923 into or out of organ 1927. One or more chips or other implants 1940 may be positioned under the subject's skin 1926 in tissue 1925 adjacent vessel 1929, and optionally extending into the vessel(s). Implant 1940 may (optionally) include one or more sensors 1942 as described below and/or one or more antennas 1943 operable for receiving and/or transmitting data along wireless data path 1945 as shown. Interface logic 1970 may include one or more instances of detectors 1980 and/or transducers 1990 such as ultrasound sensors 1981 or infrared sensors 1982. Alternatively or additionally, detector 1980 may include special-purpose software 1974 or other such measurement logic 1975 configured to handle configuration, control, measurement, or other data 1978, 1979 as described below.

Figure 20:
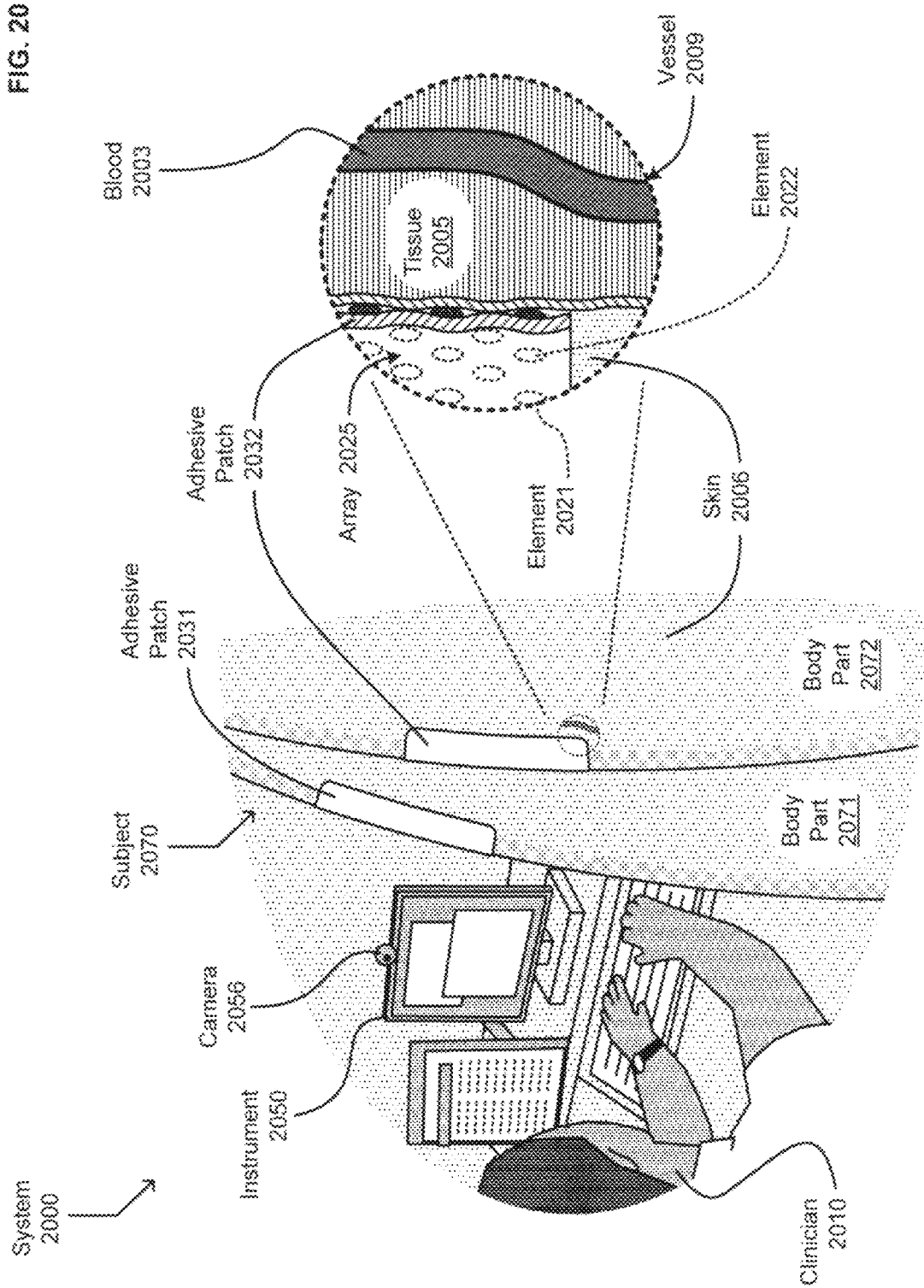

With reference now to FIG. 20, shown is a system 2000 in which one or more technologies may be implemented, such as for observing one or more attributes of body parts 2071, 2072 of subject 2070 via one or more respective adhesive patches 2031, 2032 on the subject's skin 2006. Adhesive patch 2032, for example, holds an array 2025 of sensor elements 2021, 2022 in close contact with skin 2006 so that attributes of subcutaneous tissues 2005, vessels 2009, or blood 2003 or other such materials may be observed. In some contexts, for example, such an array 2025 may implement combinations of two or more types of sensors and/or related logic as exemplified in relation to FIGS. 23-26 below. In some variants, for example, one or more such elements 2021, 2022 may also include a configurable colorant, a light-emitting diode, or other such external feature detectable by a clinician 2010 and/or by an instrument 2050 that contains a camera 2056 or other optical sensor.

An embodiment provides one or more elements 2022 configured as circuitry for deciding whether to transmit one or more blood clot indications (detected with reference, for example, to one or more components sensed within blood 2003 by element 2021) and an adhesive patch 2032 comprising one or more tensile elements configured to hold such elements 2021, 2022 of array 2025 in tight contact with skin 2006. (Other such embodiments are described, for example, with reference to FIG. 3 or 27.) Such embodiments may be used, for example, in a context in which each contact element 2021, 2022 comprises a gel-filled capsule or otherwise includes a liquid-containing medium configured to facilitate acoustic energy passing to or from subject 2070.

In some variants, system components described herein may be configured to include adhesive, fluid, electrically conductive, and/or other special-purpose substances facilitating effective skin contact. Other such embodiments are described, for example, with reference to FIGS. 21 and 32. Alternatively or additionally, system components described herein may be configured to facilitate positioning one or more sensors in contact with or in close proximity to a subject's skin. Other such embodiments are described, for example, with reference to FIGS. 9-11.

Figure 21:
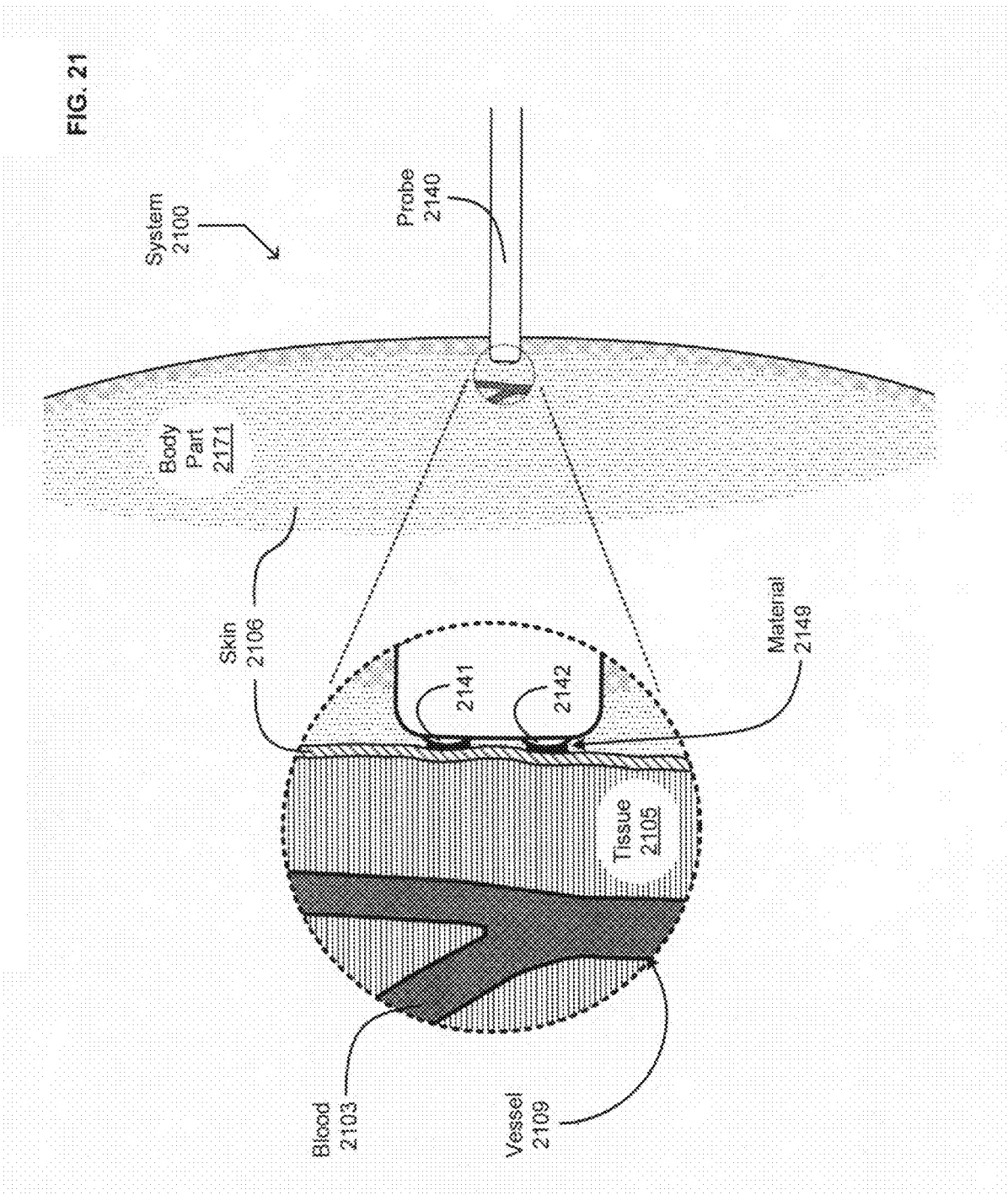

With reference now to FIG. 21, shown is a system 2100 in which one or more technologies may be implemented, such as for detecting one or more attributes of blood 2103 in vessels 2109, for example, or skin 2106 or other tissues 2105 in body part 2171. A hand-held or other probe 2140 may include one or more sensors 2141 or other such elements 2142 operable for detecting such attributes through one or more liquid-containing contact enhancement materials 2149. Such materials may facilitate energy transfer through skin 2106, in some variants, or various modes of chemical detection as described herein.

With reference now to FIG. 22, shown is a network 2215 operable for facilitating communications among one or more interfaces 2210 (of a clinician 2205, e.g.), one or more servers 2220, or one or more local systems 2240 (via one or more media 2225, e.g.). (In some embodiments described herein, sensors 2268 or other such artificial structures are "local" if they are configured to extend into a detection proximity 2277 of one or more parts 2271, 2272 of a subject 2270 of interest.) As shown, local system 2240 may likewise include one or more instances of decision logic 2250; results 2251, 2252; communication ports 2255, 2256; or interfaces 2260. Decision logic 2250 may include one or more instances of notifications 2241, 2242, instruction sequences 2243 or other modules 2244, 2245, or other parameters 2247, 2248, 2249 as described below. Interface 2260 may relay auditory instructions or other such data for use by subject 2270 via one or more speakers 2267 or other output devices. Alternatively or additionally, interface 2260 may receive measurements or other indications 2261, 2262, 2263, 2264 as well as other determinant data 2265 from and/or relating to subject 2270. In some variants, local system 2240 may be configured to facilitate such interchanges with subject 2270 even when only a remote clinician 2205 is available and/or without any contemporaneous involvement with such remote expertise. In some variants described herein, for example, another local system or other intermediary system within network 2215 may decide which notifications 2201, 2202 are suitable in response to a programmatic interaction protocol (with a subject 2270 and/or other individuals, for example, undergoing a triage or other intake) or other such determinant data 2265.

In some embodiments, instructions or other software "relating to" data can include executable code that belongs to a class relating to a class of the data (e.g. "video processing" code relating to "video" data, or "text" data relating to code in a messaging device or other text handling module). The code, data, or class can have a type with a common aspect (e.g. "video" in the type name) or can be related by a table entry (e.g. indicating the code or code type to be used for the data or data type). Code can also relate to data by virtue of a code module call or other invocation containing at least an indication of the data.

In some variants, such local systems may be configured to notify or otherwise interact with care providers or other resources across a foreign or other communication network. Other such embodiments are described, for example, with reference to FIGS. 5, 13, 14, 15, 29, 35, 52, 74, 75, and 78.

Figure 23:
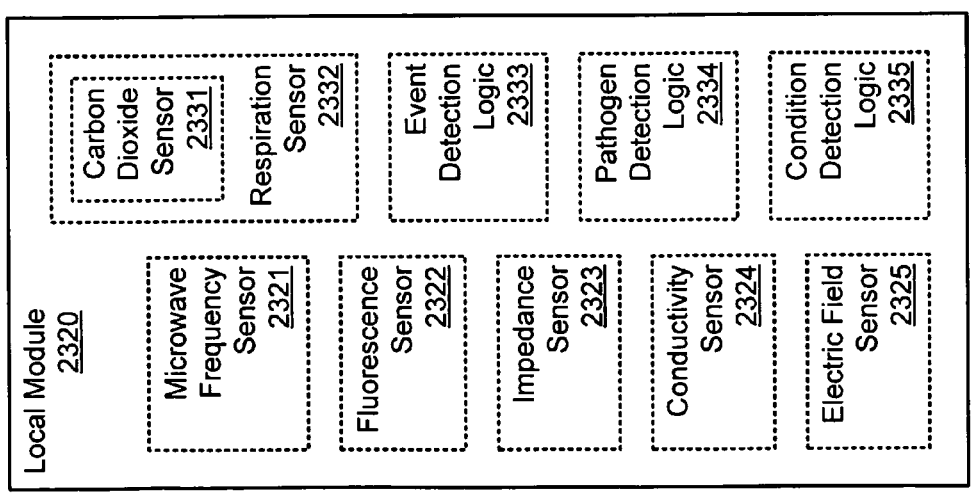

With reference now to FIG. 23, shown is a local module 2320 in which one or more sensor technologies may be implemented, such as for monitoring a device or region, or other such tasks as described herein. In some embodiments as described herein, such modules may include one or more microwave frequency sensors 2321, optionally configured to generate an indication of moisture or related symptoms in or on a subject's body. Alternatively or additionally, local module 2320 may include one or more fluorescence sensors 2322, optionally configured to generate an indication of one or more artificial markers in or on specific tissue. (In many contexts, for example, such markers may be used for monitoring targeted physiological constituents and/or pathogens.) Such modules may likewise include one or more impedance sensors 2323, optionally configured to generate subject respiration rate indications, to detect fractures or other changes in electrode contact surfaces or other such artificial structures, or to detect other such circumstances relating to a subject of interest. Alternatively or additionally, local module 2320 may include one or more conductivity sensors 2324, optionally configured to monitor sweat, apparent urinary incontinence, or other such external circumstances and/or (internally) to monitor blood flow, electrolyte levels, or other such internal conditions. Such modules may likewise include one or more electric field sensors 2325 in some variants as described herein, optionally comprising (a) an implanted sensor configured to monitor nerve traffic, (b) an implanted or contact sensor configured to transmit electrocardiogram signals, brain activity indications, or other such status information about a subject. Alternatively or additionally, local module 2320 may include one or more carbon dioxide sensors 2331 or other respiration sensors 2332, optionally comprising a sensor implanted adjacent a target site and configured to monitor one or more indications of concentration, for example, to detect apparent occlusions of a blood vessel near the site. Such modules may likewise include one or more instances of event detection logic 2333, pathogen detection logic 2334, or other condition detection logic 2335 such as for comparing raw output from sensors as described herein with prior or other sensor output, with threshold values to determine an apparent occurrence of an event, or with other condition attributes as described herein for triggering notification or therapy. In some embodiments, several or all of such items may be included in a single instance of local module 2320.

In some variants, such local modules may be configured to illuminate, exert force upon, or otherwise pass energy into a subject' skin. Other such embodiments are described, for example, with reference to FIGS. 11 & 24.

Figure 24:
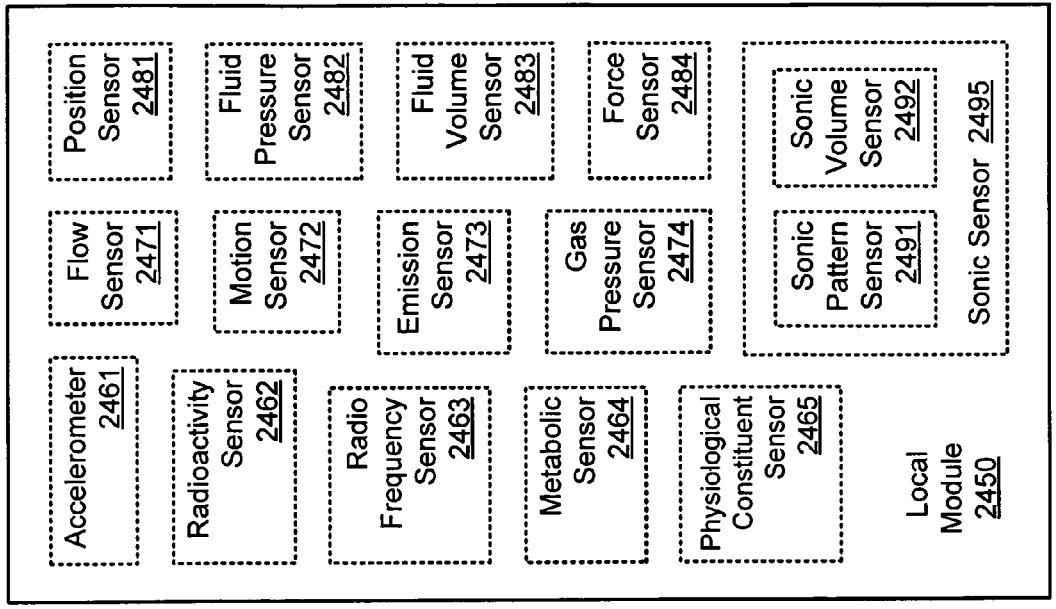

With reference now to FIG. 24, shown is a local module 2450 in which one or more sensor technologies may be implemented, such as for monitoring a device or region, or other such tasks as described herein. In some embodiments as described herein, such modules may include one or more accelerometers 2461, supported in a fixed relation to a target area, optionally configured to generate an indication of the activity, motion, and/or orientation of the subject and/or region. Alternatively or additionally, local module 2450 may include one or more radioactivity sensors 2462, optionally configured internally or externally to generate an indication of one or more artificial markers in or on specific tissue. (In many contexts, for example, such markers may be indicative of levels of administered therapeutic components, rates of adsorption or elimination of components, exposure levels to external radioactive materials, or other pathological or other biological processes.) Such modules may likewise include one or more radio frequency sensors 2463, optionally configured to facilitate communication to, from, or between implanted or external devices, and/or to detect lung- or other such organ-status-indicative information in circumstances in which coupling via a continuous conduit may be undesirable. In some variants, local module 2450 may contain one or more metabolic sensors 2464, optionally configured as an implanted device or an external component configured to monitor the subject or region (ex situ or otherwise) and to generate an indication of uptake, breakdown, elimination, and/or other such metabolic processes relating, for example, to therapeutic materials as described herein. In some contexts, for example, such a metabolic sensor may be configured to indicate a generation and/or elimination of other components resulting from the breakdown of therapeutic components, the use or generation of physiological constituents resulting from glucose transforming into carbon dioxide or other such metabolic processes. Such modules may likewise contain one or more physiological constituent sensors 2465, optionally comprising an implanted or other sensor configured to generate an indication of physiological constituent levels observed in a subject or subject region. This may include items such as chemical components (e.g. calcium, sodium, cholesterol, pH), proteins and protein complexes (e.g. hemoglobin, insulin, binding proteins, antibodies) and/or structures (e.g. red and/or white blood cells, bacteria, viruses, platelets).

Alternatively or additionally, local module 2450 may likewise (optionall) include one or more flow sensors 2471, which may be configured to generate an indication of fluid flow in or across a region of interest. (In many contexts, for example, such phenomena as blood flow through a vein or artery, urine flow through a urethra, bile flow through a bile duct, or other fluid flow from one region to another may be monitored.) Alternatively or additionally, local module 2450 may include one or more motion sensors 2472, optionally configured internally, externally, and/or remotely to give an indication of the motion and/or activity of a device or a portion of a subject. Such modules may likewise include one or more emission sensors 2473, optionally configured to internally or externally give an indication of subject or region status such as using emitted infrared wavelength and intensity levels as an indication of subject or region temperature. Other emission processes may be used to monitor artificial markers in or on tissue, for example, for monitoring specific tissue features, processes, constituents, and/or pathogens. Alternatively or additionally, local module 2450 may include one or more gas pressure sensors 2474 configured to monitor ambient pressure levels, applied pressure levels (in hyperbaric chambers, continuous positive airway pressure machines, respirators, or other such artificial devices) and/or pressure levels observed in a gas-filled support structure. (In some variants, pressure may likewise be indicated by a variety of indirect measures such as blood vessel thickness, pulse energy, position, noise, or other physical phenomena correlated therewith.) Local module 2450 may likewise include one or more position sensors 2481 configured to monitor subject and/or region orientation. Alternatively or additionally, local module 2450 may include one or more fluid pressure sensors 2482, optionally configured to transmit or otherwise respond to physiological fluid pressure (aneurysm sac pressure or cranial pressure, e.g.) or external fluid pressure (as an indication of delivery amount and/or proper function in a therapeutic delivery system, for example, or in a fluid-filled support structure as described herein). Such modules may likewise contain one or more fluid volume sensors 2483, optionally configured to give an indication of fluid volumes within a subject or region such as blood volume in a heart chamber, artery, or lung (as a measure of disease progression or risk, e.g.). Alternatively or additionally, local module 2450 may include one or more force sensors 2484, optionally configured (a) to generate a pressure reading or other indication of force applied to a region (as a measure of tissue rigidity, e.g.) or (b) to indicate glaucoma, compartmental syndromes, abnormal structures, or other such potential pathologies. Such sensors may also be used as an indication of the force applied by a subject and/or region on a support structure to monitor subject activity levels and/or to give an indication of susceptibility to force/pressure related injuries such as pressure ulcers. Such modules may likewise contain one or more sonic sensors 2495, optionally configured to enable communication to, from, and/or between implanted devices, for the recognition of sonic patterns such as heart rate, respiration rates, voice commands and other verbal input (via one or more sonic pattern sensors 2491, e.g.) or of a subject's potential exposure to external stimuli (via one or more sonic volume sensors 2492, e.g.). In some embodiments, several or all of such items may be included in a single instance of local module 2450.

Figure 25:
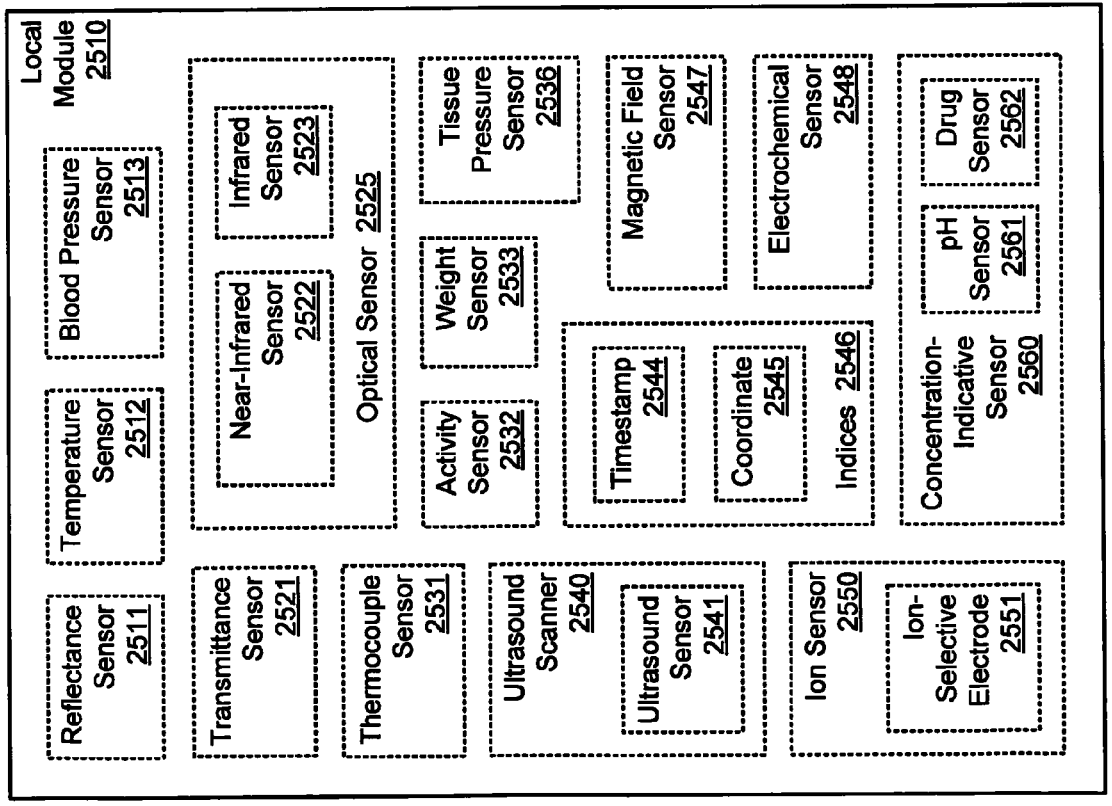

With reference now to FIG. 25, shown is a local module 2510 in which one or more sensor technologies may be implemented, such as for monitoring a device or region. In some embodiments, such modules may (optionally) include one or more temperature sensors 2512, optionally configured to give an indication of ambient thermal conditions around a subject and/or systemic or local thermal conditions of the subject. (In some embodiments, "systemic" information may refer generally to current measurements, body temperature or other such status information, or other data reflecting one or more attributes of a subject as a whole. "Local" information, by contrast, may describe measurements, images, or other such data conventionally pertaining to an identifiable portion of a subject's body.)

Such modules may be implemented using one or more thermocouple sensors 2531, for example, in implanted and/or direct contact devices. Thermal probes may likewise be implemented as optical sensors that are implanted, direct contact, and/or remotely operable. Alternatively or additionally, local module 2510 may include one or more blood pressure sensors 2513, optionally configured to give an indication of peripheral and/or systemic blood pressure of a subject. Such modules may be configured to incorporate one or more fluid pressure sensors 2482 or conductivity sensors 2324 in some implanted contexts. Alternatively or additionally, one or more force sensors 2484 and/or ultrasound sensors 2541 (of ultrasound scanner 2540, e.g.) may be configured in a transdermal mode, for example, to generate information indicative of blood pressure. Local module 2510 may likewise include one or more near infrared sensors 2522 and/or infrared sensors 2523 sensors, optionally configured to determine local oxygenation levels or other such chemical and/or material properties of body tissues or fluids as described herein. Such sensors can likewise be configured as transmittance sensors 2521, for example, receiving radiation that has passed through a subject fingertip or earlobe, or in other such short-path contexts such that the opacity of a tissue region allows for sufficient incident radiation to pass through it to form a usable image. Alternatively or additionally, local module 2510 may comprise one or more reflectance sensors 2511 configured to emit energy into tissue and to capture a portion of the energy reflected.

In some variants, local module 2510 may contain one or more activity sensors 2532, weight sensors 2533 and/or tissue pressure sensors 2536, optionally configured to give an indication of subject activity, motion, or other information indicative of systemic or local physical status. Such modules may likewise include one or more magnetic field sensors 2547, optionally configured to allow for the control and/or inhibition of implanted devices transdermally. Alternatively or additionally, local module 2510 may include mass-indicative or other electrochemical sensors 2548, any of which may (optionally) be configured to give an indication of physiological constituent levels such as by incorporating ion-selective electrodes 2551 (of ion sensor 2550, e.g.) or other concentration-indicative sensors 2560 for the monitoring of potassium, sodium, calcium, and/or other physiologically relevant components (at pH sensor 2561 or other concentration-indicative sensors 2560, e.g.). In some variants, electrochemical sensors 2548 can be used in a faradaic mode to monitor levels of other relevant physiological components such as blood glucose levels, neurotransmitter release, blood oxygen levels, or other useful components either in an implanted setting and/or a contact setting (in which the sensor is inserted through the skin to the detection site, for example, or the target molecules can be isolated from the subject and detected externally. Such modules can also use one or more electrochemical sensors 2548 and/or optical sensors 2525 (including fluorescence sensors 2322, emission sensors 2473, near-infrared sensors 2522, or infrared sensors 2523) individually or in combination to provide information for the monitoring of a drug substance administered to the subject (such as drug sensor 2562, e.g.). Local module 2510 may also implement one or more timestamps 2544, location coordinates 2545, or other such indices 2546 relating to measurements or other aspects of subject status information. In some embodiments, several or all of such items may be included in a single instance of local module 2510.

Figure 26:
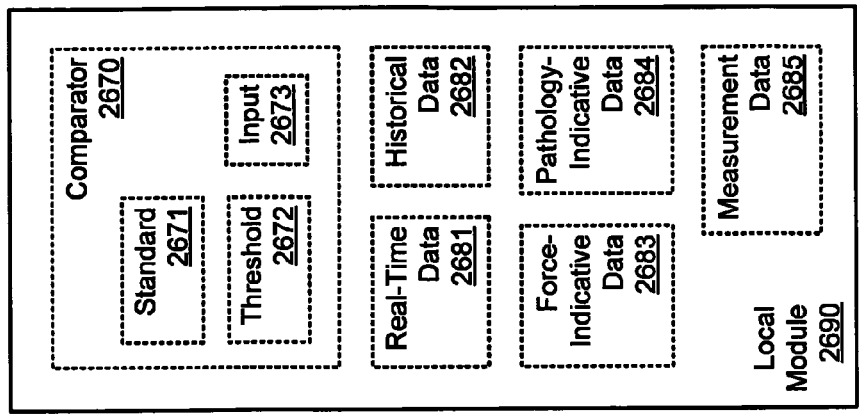

With reference now to FIG. 26, shown is a local module 2690 in which one or more technologies may be implemented, optionally within a sensor, sensor-containing module, or other local instrumentation. Any of local modules 2320, 2450, 2510 may (optionally) include one or more instances of differential or other comparators 2670 configured to process one or more instances of real-time data 2681, historical data 2682, force-indicative data 2683, pathology-indicative data 2684, measurement data 2685 using one or more standards 2671, thresholds 2672, or other input 2673. Those skilled in the art will recognize, for example, how to apply one or more thresholds 2672 configured to implement conditional retention, conditional transmission, or other such selective treatment to pressure-indicative, shear-indicative, strain-indicative, stress-indicative, deformation-indicative, acceleration-indicative, or other such force-indicative data 2683 in light of teachings herein.

Figure 27:
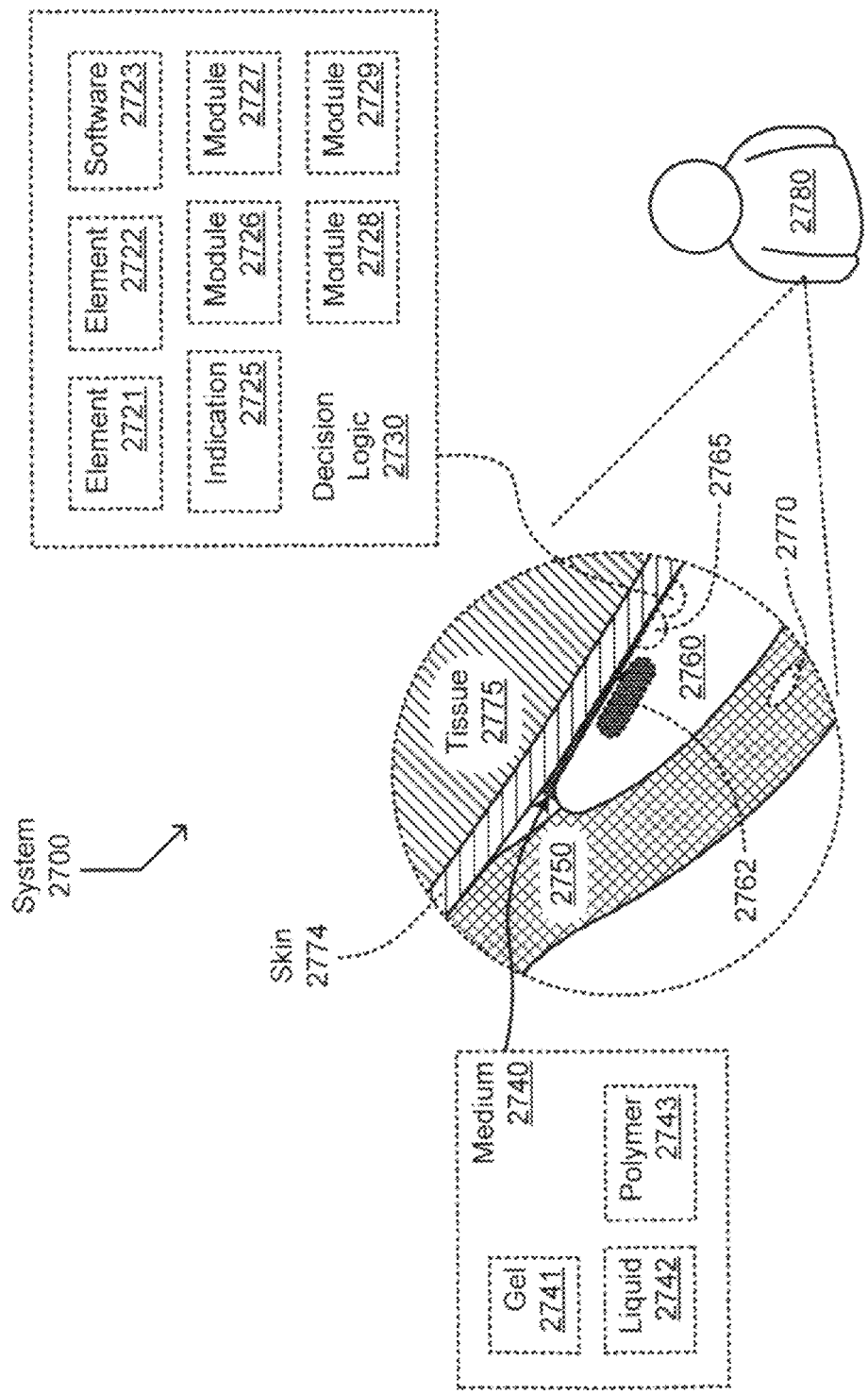

With reference now to FIG. 27, shown is a system 2700 in which one or more technologies may be implemented for periodically or otherwise monitoring skin 2774 or subcutaneous tissue 2775 of a subject 2780 via one or more sensor elements 2760. One or more such modules may be remain adjacent tissue 2775, for example, by hand, by gravity, by one or more media 2740, and/or by one or more straps or other tensile elements 2750 as described herein. In some variants, for example, one or more such media 2740 may contain a gel 2741, a bioadhesive, a liquid 2742, a therapeutic material, a polymer 2743, a carrier, or other such components as described herein. Alternatively or additionally, element 2760 may include one or more instances of dispensers 2762 configured to inject such media so that they spread into direct contact with one or more sensors 2765. Alternatively or additionally, one or more such sensors 2765 may transmit energy indicating one or more physical phenomena in tissue 2775 to one or more elements 2721, 2722, software, indications 2725, or modules 2726, 2727, 2728, 2729 of decision logic 2730 as described below.

An embodiment provides a variant of decision logic 2730 configured as circuitry for deciding whether to transmit one or more blood clot indications 2725, for example, and a liquid-containing medium 2740 configured at least to facilitate acoustic energy passing between subject 2780 and one or more sensors 2765 of the decision logic 2730. In some embodiments, data may be captured from a direct or indirect interaction between a device and a user that also involves other users or devices. Such devices may relay information passively between the user and the device, for example, or may constitute additional embodiments of teachings herein. In some embodiments, an intercommunication "between" a device and a user can include a session at a network terminal, retrieving messages, receiving tactile feedback from actuating an electromechanical device, having a telephone conversation, or other electrical, optical, auditory, or other information flowing from a source to a destination, with some information also flowing to the source. Alternatively or additionally, the intercommunication can include a "forward" and "reverse" flow that include common information, that are causally related, that flow along a common conduit, or that are at least partly simultaneous. In some embodiments, the "device" can include a memory, a display, a transducer, or some other data handling capability. Other such embodiments are described, for example, with reference to FIG. 4 or 23-26 above.

Some implementations include one or more polymers 2743 or other liquids 2742 configured to adhere at least some of the decision logic 2730 in contact with or otherwise within a close proximity to subject 2780. Such sensors may (optionally) include a conductivity sensor and/or other sensors, as well as (a variant of) condition detection logic 2335 configured to infer a presence of the liquid-containing medium in response to a low-enough electrical resistance measurement. In some variants, each instance of element 2760 may implement one or more instances of local modules 2320, 2450, 2510, 2690 as described herein. Such embodiments may further comprise one or more dispensers 2762 configured to dispense a supplemental amount of the liquid containing medium and/or a therapeutic material.

A variant embodiment provides special-purpose software 2723 or other decision logic 2730 implementing circuitry for deciding whether to transmit one or more blood clot indications and one or more elastomeric or other tensile elements configured to exert force upon one or more sensors 2765 of the decision logic 2730 toward subject 2780. (Other such embodiments are described, for example, with reference to FIG. 6 or 20.) Such embodiments may be used, for example, in a vehicle or other context in which one or more lengths of a woven fiber or other seat material are under tension. In some variants, such tension may be measured, for example, by a force sensor of the tensile elements (optionally configured, for example, like sensor 2770). In some variants, decision logic 2730 may include an executable instruction sequence or other modules 2728 configured to capture and/or evaluate one or more ultrasound images indicative of the one or more blood clot indications. Alternatively or additionally, decision logic 2730 may include an implantable antenna 1943, a vehicle antenna 278, or other such wireless communication conduits configured to transmit information from one or more sensors 2765. In some variants, decision logic 2730 may also include or otherwise receive data from one or more flow sensors 2471, one or more respiration sensors 2332 or other concentration-indicative sensors 2560, or other sensors or related logic described above with reference to FIGS. 23-26.

In some variants, such decision logic may be implemented in worn articles. Other such embodiments are described, for example, with reference to FIGS. 12, 17, 25, 29, and 32. In some variants, local modules or other sensor-containing components may (optionally) be configured to include one or media 2740 and/or other special-purpose substances facilitating effective skin contact. Other such embodiments are described above, for example, with reference to FIGS. 21-26.

Figure 28:
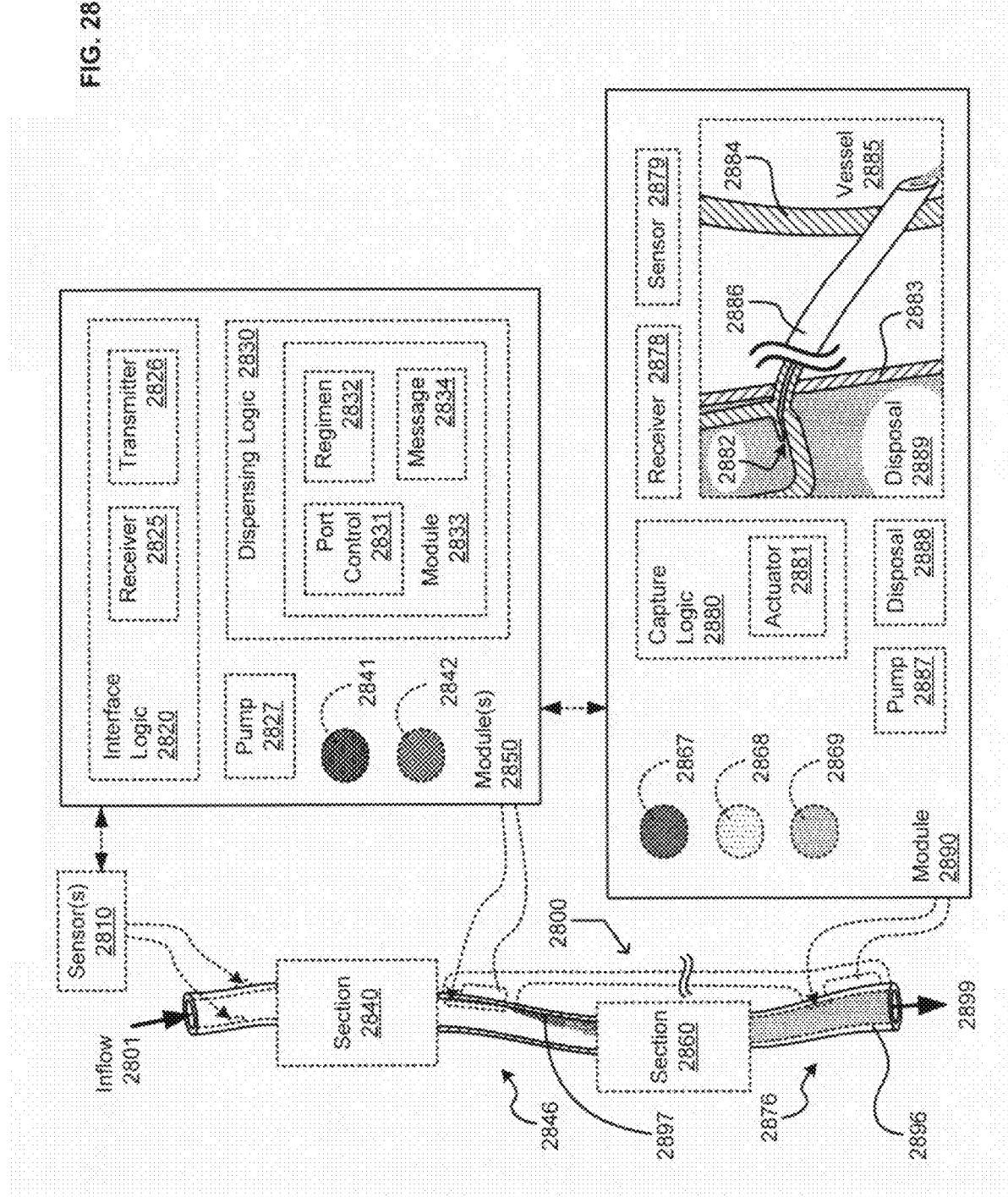

With reference now to FIG. 28, shown is an example of a system that may serve as a context for introducing one or more processes and/or devices described herein. As shown system 2800 may affect or otherwise relate to one or more sections 2840 or other "upstream" portions 2846 of a human or other living subject's vasculature 2896 (receiving inflow 2801) and also to one or more "downstream" portions 2876 of such vasculatures 2896 (bearing outflow 2899). One or more sections 2840, 2860 as shown may comprise one or more of capillary beds, tissues served by vasculature 2896, or other blood vessels.

In some variants, one or more intravascular or other modules 2850 may (optionally) include one or more instances of receivers 2825, transmitters 2826, or other interface logic 2820 such as for communicating (in one or both directions) with one or more sensors 2810 operable for monitoring upstream portion 2846. Module 2850 may likewise include one or more instances pumps 2827 or other hardware controlled by dispensing logic 2830 for selectively releasing one or more (biological, radiotherapy, or other) agents 2841 or other therapeutic structures 2842 into upstream portion 2846. Such module(s) 2850 may also be configured, in some contexts, by including one or more software or other modules 2833 of dispensing logic 2830 comprising one or more instances of port controls 2831, (dispensing or other therapeutic) regimens 2832, or messages 2834 as described below.

As shown, system 2800 may comprise one or more modules 2850 upstream operable for communicating (in one or both directions) with one or more intravascular or other modules 2890 downstream, optionally in an integral and/or implanted structure as shown. Alternatively or additionally, module 2890 may include one or more instances of capture agents 2867, 2868 or other therapeutic agents 2869; receivers 2878; sensors 2879; capture logic 2880 operable for controlling one or more actuators 2881, such as for optically or otherwise controlling the capture agent(s); pumps 2887; or disposals 2888, 2889. As shown, for example, disposal 2889 may include one or more ports 2882 operable for accelerating a decrease in a local concentration of the agent(s) 2841 or other therapeutic structure(s) 2842 along portion 2876 (downstream from dispensation 2897, as shown) by allowing the structure(s) to pass into one or more conduits 2886 traversing one or more vessel walls 2883, 2884. One or more vessels 2885 configured to receive the structure(s) may include, in some embodiments, an esophagus or other natural vessels, implanted artificial vessels, or ex situ vessels.

Figure 29:
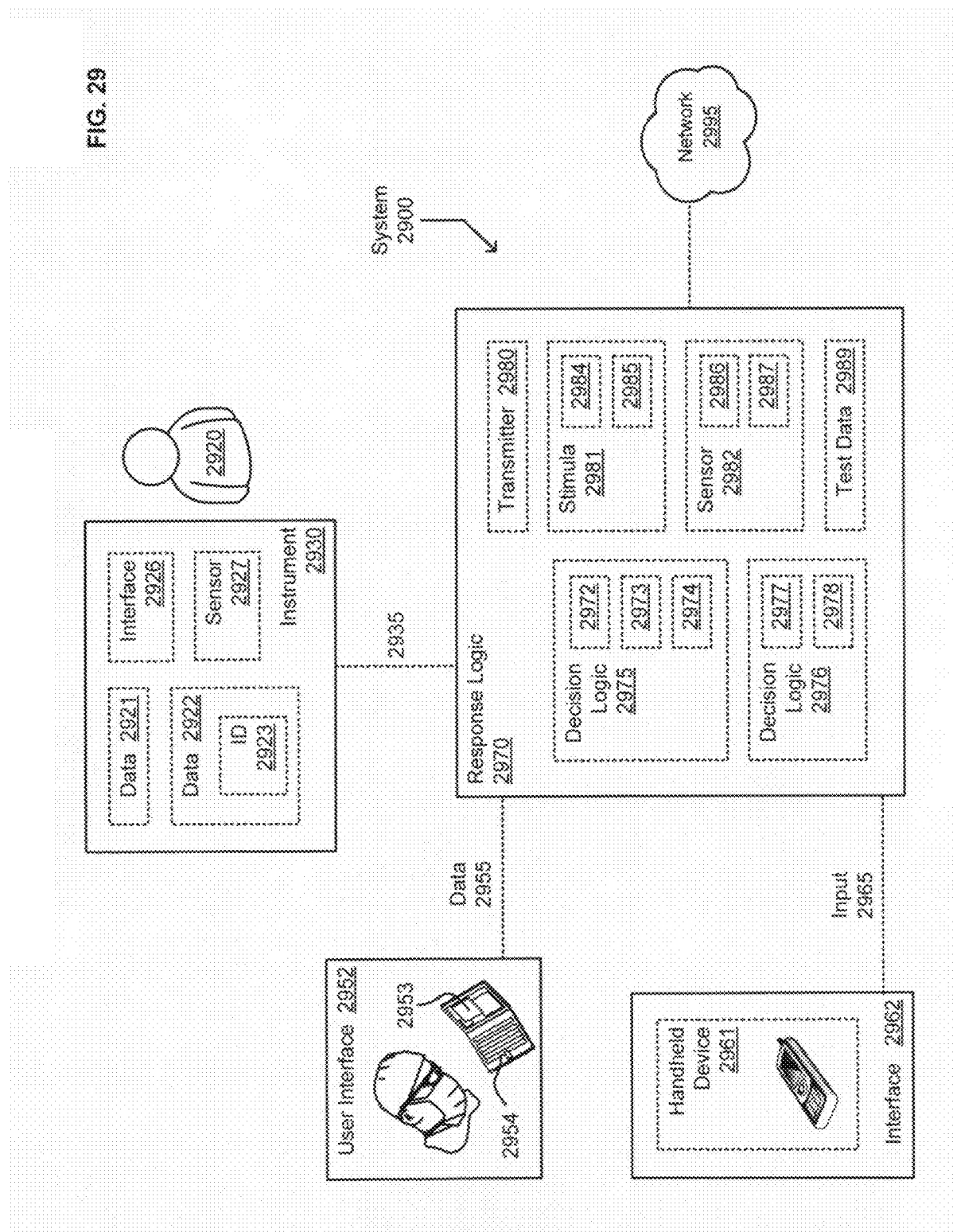

With reference now to FIG. 29, shown is an example of a system 2900 that may serve as a context for introducing one or more processes and/or devices described herein, optionally configured to interact with network 2995. As shown system includes one or more modules 2972, 2973, 2974, 2977, 2978 of decision logic 2975, 2976; one or more transmitters 2980; and/or one or more parameters 2984, 2985 of stimula 2981 selected to facilitate one or more sensors 2982 obtaining sensed values 2986, 2987 or other such test data 2989 about an individual or subpopulation to be monitored. System 2900 may also include or otherwise interact with one or more instances of instruments 2930 configured to obtain data from subject(s) 2920, user interfaces 2952 configured to interact with decision makers or expert resources, or handheld devices 2961 or other such interfaces 2962 for relaying input 2965 to or from other such parties.

One or more instruments 2930 in a vicinity of subject 2920 may include, for example, one or more instances of identifiers 2923 or other data 2921, 2922 about subject 2920 obtained via one or more interfaces 2926 and/or sensors 2927. User interface 2952 may likewise present visual or other output 2953 and/or receive keyed or other input 2954. Response logic 2970 as an entity may receive and/or transmit a variety of communication 2935 or other data 2955 for or from network 2995, in some contexts, as exemplified below. In various examples below, for example, one or more such subjects, caregivers, or others are potential message or other notification recipients. Some such entities have a priori information associating a subject identifier or other indicator with current communications 2935 or other data as described below.

Some variants of decision logic 2975, 2976 may be configured to combine data effectively from two or more subjects, for example, to facilitate comparison at one or more user interfaces or servers. Other such embodiments are described, for example, with reference to FIGS. 2, 3, 13, 22, 25, 26, and 74.

Figure 30:
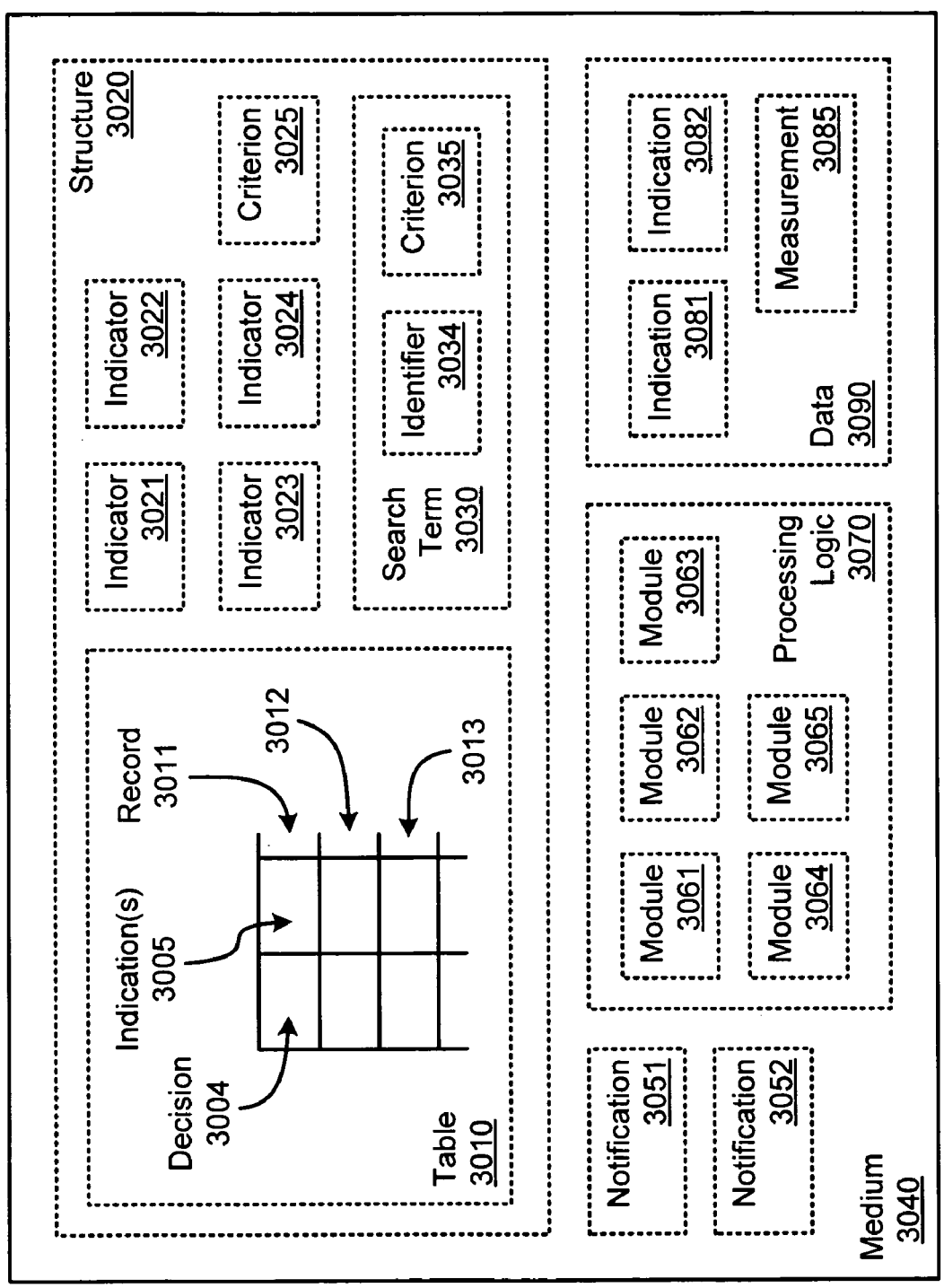

With reference now to FIG. 30, shown is an example of an interface 3000 that may serve as a context for introducing one or more processes and/or devices described herein. Interface 3000 comprises one or more media 3040 configured to contain or otherwise handle one or more tables 3010 or other such informational structures 3020; notifications 3051, 3052; modules 3061, 3062, 3063, 3064, 3065 or other processing logic 3070; indications 3081, 3082 or measurements 3085; and/or other such data 3090. Table 3010 may include one or more instances of decisions 3004, indications 3005, or other such information in each of one or more common records 3011, 3012, 3013. In a context in which structure 3020 includes one or more subjects' medical histories, study data, or other such content, a search agent or other such entity may use one or more indicators 3021, 3022, 3023, 3024 or other criteria 3025 to retrieve suitable information. One or more identifiers 3034 and/or other such criteria 3035 may be used in a search term 3030, for example, in a variety of bots, web crawlers, search engines, or other such implementations.

Figure 31:
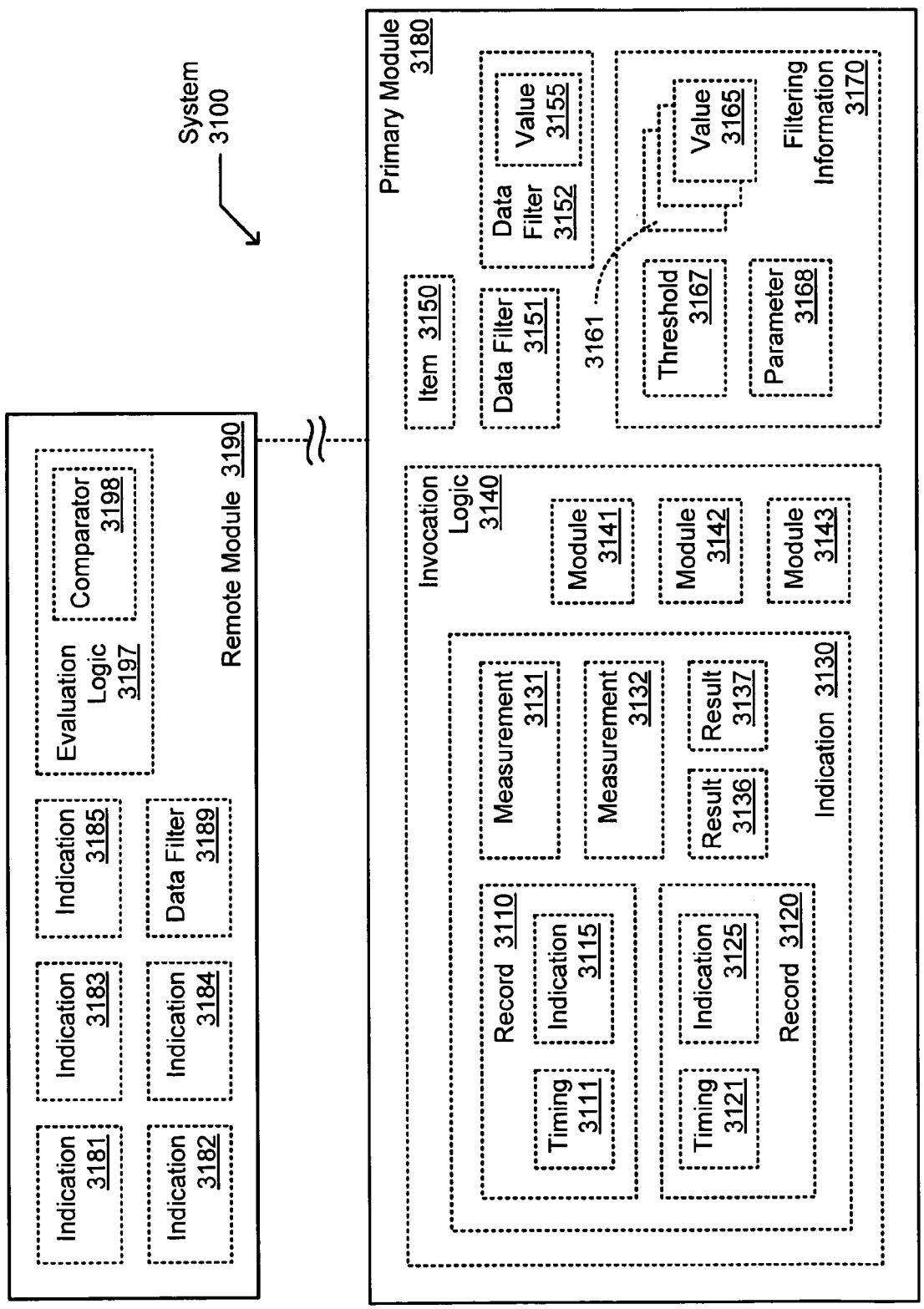

With reference now to FIG. 31, shown is an example of a network or other system 3100 comprising one or more primary modules 3180 operatively linked to one or more remote modules 3190. Remote module 3190 may include or otherwise handle one or more indications 3181, 3182, 3183, 3184, 3185, data filters 3189, or comparators 3198 of evaluation logic 3197. Primary module 3180 may comprise a vehicle or other such item 3150 configured to include or otherwise handle invocation logic 3140 comprising one or more modules 3141, 3142, 3143 responsive to timing 3111, 3121 or other indications 3115, 3125 of records 3110, 3120; measurements 3131, 3132; results 3136, 3137; and/or hybrid or other indications 3130. Primary module 3180 may likewise apply one or more values 3155 as data filters 3151, 3152, or may apply one or more other values 3161, 3165; thresholds 3167; or other such filtering information 3170 for determining whether one or more parameters 3168 warrant a response as described herein.

Figure 32:
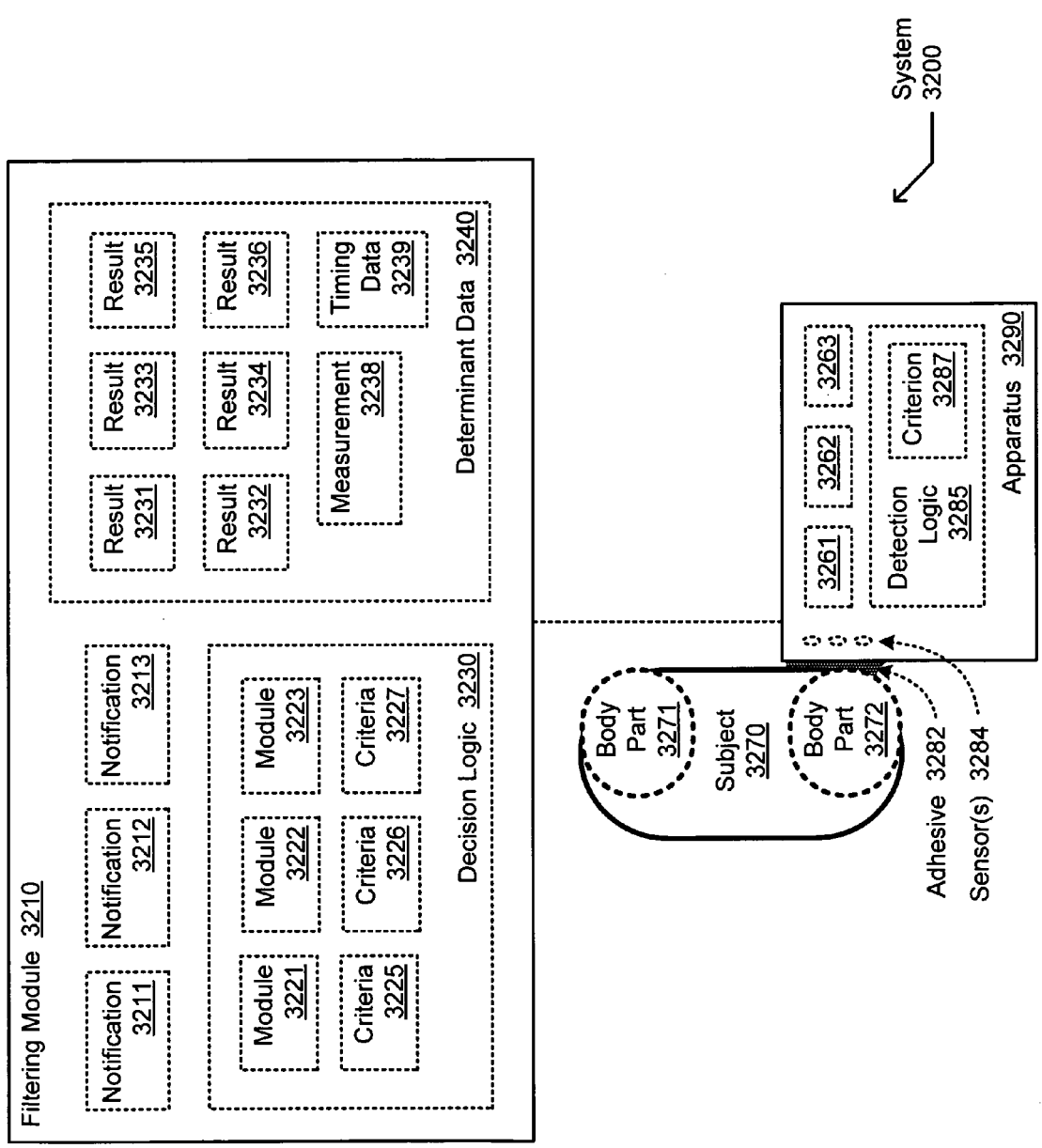

With reference now to FIG. 32, shown is an example of a system 3200 including a filtering modules 3210 configured to process determinant data 3240 about one or more body parts 3271, 3272 of subject 3270. Such data may be received, for example, via one or more sensors 3284 of one or more apparatuses 3290 affixed, such as by one or more adhesives 3282, to body parts 3272 of interest. In some variants, for example, detection logic 3285 produces one or more results 3231, 3232, 3233, 3234, 3235, measurements 3238, and/or timing data 3239 by generating an extraction of data 3261, 3262, 3263 that complies with one or more retention and/or transmission criteria 3287. Alternatively or additionally, one or more modules 3221, 3222, 3223 or other decision logic 3230 may be configured to apply criteria 3225, 3226, 3227 for selectively generating one or more aspects of notifications 3211, 3212, 3213 or other results 3236.

Figure 33:
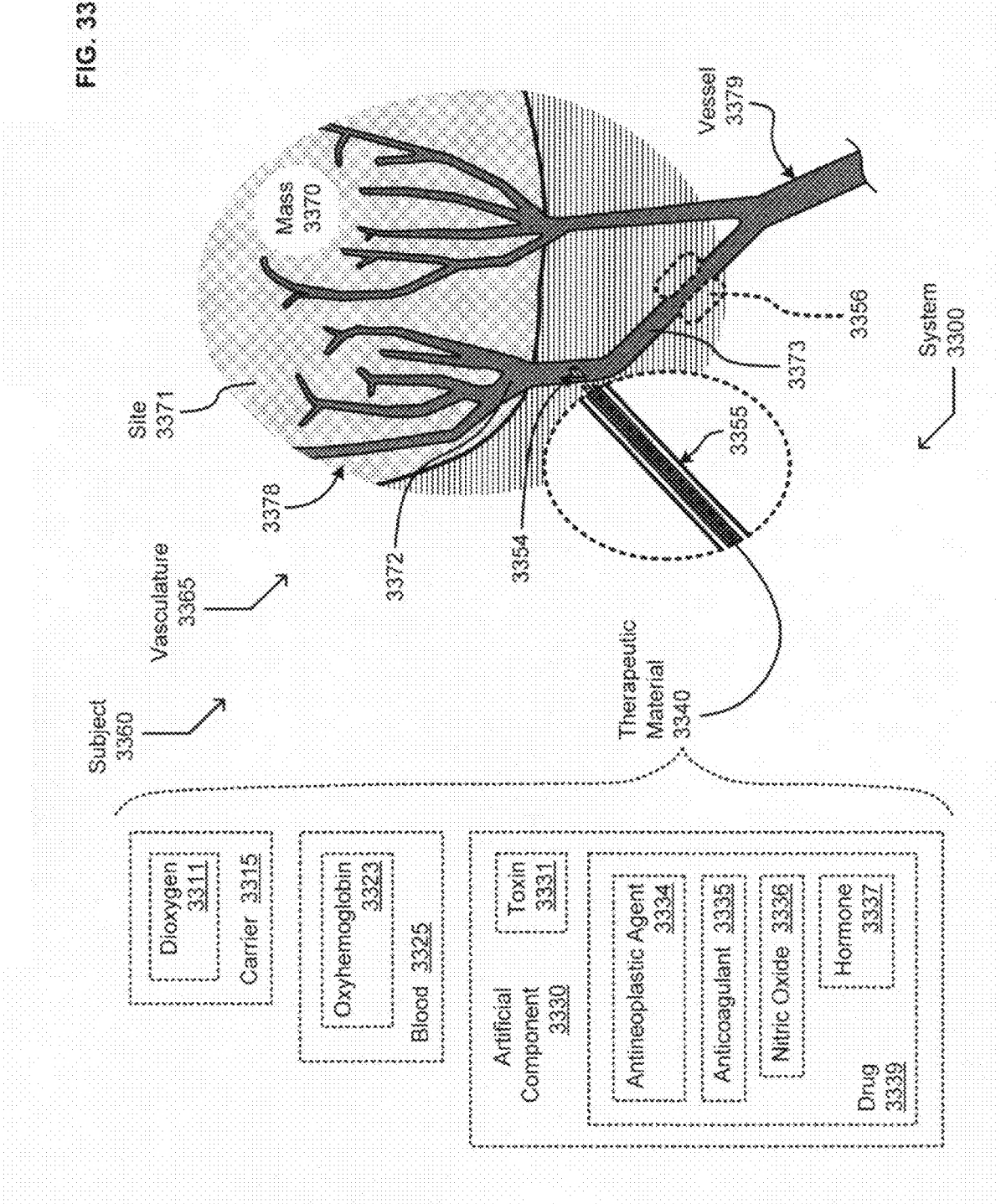

With reference now to FIG. 33, shown is an example of a system 3300 including an in-dwelling catheter or other instrument 3355 suitable for transvascular placement. In some variants, for example, instrument 3355 may couple with a bifurcated catheter or other conduit 3354 suitable to administer one or more therapeutic materials 3340 locally to a treatment site 3371 via one or more capillaries and/or other small vessels 3378. As shown, site 3371 may include some or all of an afflicted organ or other target mass 3370 served by a vasculature 3365 of subject 3360. In some variants, for example, intermediate-size vessels 3372 may include arterioles through which material passes. Alternatively or additionally, a clamp or other such controllable occlusion structure 3356 occludes at least some flow between a vein or other large vessel 3379 and an injection site (segment 3373, e.g.).

An embodiment provides such a transvascular dispenser configured to administer a therapeutic material 3340 containing an artificial component 3330 locally, and in which the therapeutic material(s) 3340 contain dioxygen 3311 in oxyhemoglobin 3323 of blood 3325, for example, or in a carrier 3315. In some variants, oxygen-charged perfluoroheptane may be used, for example, in a context in which a majority of such material may be kept out of general circulation (supplying oxygen by injection and withdrawal of therapeutic material 3340, e.g.). Such therapeutic materials may, for example, include one or more toxins 3331, antineoplastic agents 3334, heparin or other anticoagulants 3335, nitric oxide sources 3336, hormones 3337, or other drugs 3339 or therapeutic materials that may be delivered via a vasculature.

Another embodiment provides an extravascular or other artificial occlusion structure 3356 operable to impede a flow exiting a segment 3373 of a vasculature (into vessel 3379, e.g.) and an instrument 3355 or other artificial structure operable to administer a therapeutic material 3340 locally to the segment 3373. In some embodiments, such a structure may be used for limiting damage to kidneys or other systemic filtration organs.

Another embodiment provides a bifurcated needle or other suitable dispensation conduit 3354 adapted to administer a therapeutic material 3340 locally via (venules or other) intermediate-size vessels 3372 to (capillaries or other small) vessels 3378 and to site 3371. Such conduits may, in some contexts, comprise or otherwise access a reservoir operable for dispensing toxins 3331 or other dangerous dosages locally, some of which may then be absorbed into site 3371 and/or recaptured, for example, back into conduit 3354. In some variants, for example, therapeutic material 3340 may include one or more of dioxygen 3311 in one or more artificial carriers 3315 and/or oxyhemoglobin 3323 borne in blood 3325. Therapeutic material 3340 may likewise include one or more toxins 3331 and/or sources of antineoplastic agents 3334 or anticoagulants 3335 or (supplemental quantities of) nitric oxide 3336, hormones 3337, or other drugs 3339. Such embodiments may also include imaging or other sensing components and/or control or communication components as described herein. Other such embodiments are described, for example, with reference to FIG. 17-32 or 34-43.

Figure 34:
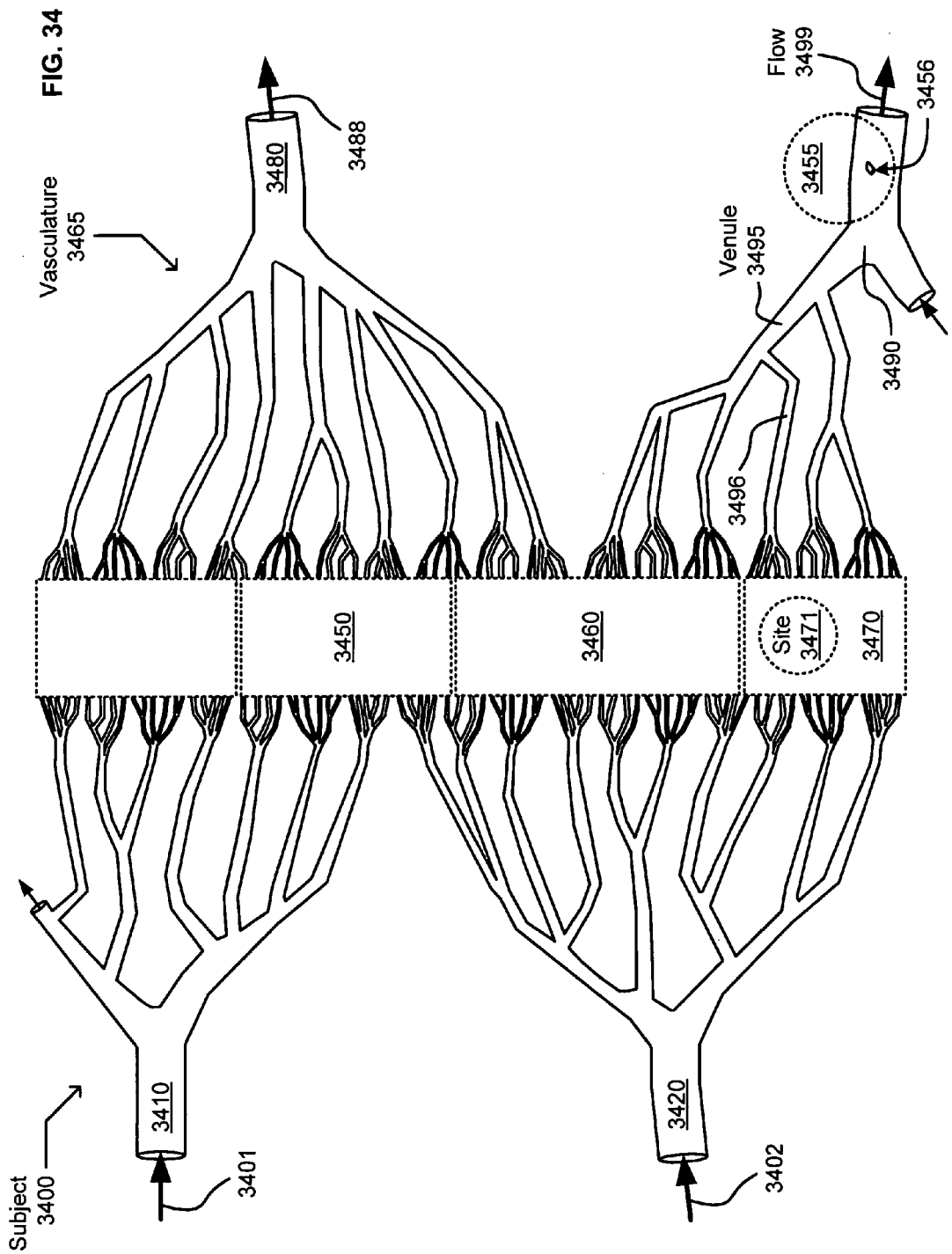

With reference now to FIG. 34, shown is an example of a context in which one or more technologies may be implemented, a quasi-schematic representation of a vasculature 3465 of a mammal or other subject 3400. Two or more systemic or other arterial segments 3410, 3420 receive respective blood flows 3401, 3402, which then diverge into smaller vessels and then to respective capillary beds 3450, 3460, 3470, one or more of which may include a site 3471 of interest for a local treatment. After a nutrient/waste product exchange, blood may exit one or more such beds 3470 via one or more venules 3495, 3496 typically converging into larger flows 3488, 3499 exiting respective venous segments 3480, 3490. In some variants, for example, one or more sites 3471 may receive a local treatment via backflow from one or more artificial structures 3455 that include one or more transvascular or intravascular distal portions 3456 extending within a venule and/or venous segment 3490 as shown. In some variants, injectors or other such structures may be configured to administer a therapeutic material into a vessel within a proximity of one or more occlusion structures operable for blocking most or all of such a flow.

With reference now to FIG. 35, shown is an example of a system 3500 that may serve as a context for introducing one or more processes and/or devices described herein. Unit 3510 of system 3500 may include one or more conduits 3504 configured to dispense therapeutic material 3520 from one or more reservoirs 3508. Such therapeutic material 3520 may include oxyhemoglobin 3523 or other such sources of dioxygen in a pharmaceutically acceptable carrier 3524, for example, that may also include one or more supplemental or other artificial components 3525 susceptible to injection or other vascular administration.

In some variants, unit 3510 may be configured to include or otherwise interact with one or more units 3540 comprising one or more instances of notification logic 3535, imaging apparatuses 3536, and/or sensor-containing probes 3537 configured to detect physical phenomena on or in a subject's body. In a variant containing each, for example, imaging apparatus 3536 may be configured capture one or more images 3534 via probe 3537. Alternatively or additionally, for example, notification logic 3535 may include one or more such images with one or more notifications 3533 to be transmitted to network 3545 as shown.

Alternatively or additionally, unit 3510 may likewise be configured to include or otherwise interact with one or more other modules 3551, 3552, 3553 of detection logic 3550 configured to invoke one or more modules of responsive logic as exemplified herein. In some variants, for example, unit 3560 may include such modules as described herein with reference to FIG. 2, 6, 8, 15, or 83-119.

Alternatively or additionally, unit 3510 may (optionally) be configured to interact with one or more blood filtration devices 3576, absorption ports 3577, dispensation ports 3578 configured to dispense active agent inhibitors, or other such artificial units 3580 effectively configured to extract some portion 3511 of therapeutic material 3520 out of a vasculature. (Apart from such portions, for example, a remainder 3512 of such material may be metabolized, captured locally in tissues, and/or otherwise handled by natural processes.)

An embodiment provides one or more units 3510 as artificial structures configured to administer a therapeutic material 3520 containing at least an artificial component 3530 via one or more capillaries of a vasculature locally and one or more units 3580 as artificial structures configured to extract a portion of the therapeutic material out of the vasculature. One or more such units 3510 may (optionally) include one or more conduits 3504 configured to administer the therapeutic material 3520 via one or more venules of the vasculature locally to one or more capillaries of the vasculature. See, e.g., FIG. 34. In some variants, such a unit 3510 may include one or more reservoirs 3508 containing at least a (systemically) lethal amount of artificial component 3530, which amount which may be dispensed locally and then extracted in portion 3511. Alternatively or additionally, such a unit may comprise an antineoplastic agent dispenser. Alternatively or additionally, such an artificial component 3530 may include a supplemental or other quantity of a hormone effective for a therapy upon site 3471, for example. In some variants, the embodiment may further include a probe 3537 or other structure configured to facilitate positioning at least a distal portion of conduit 3504 through an arterial segment of the vasculature. Alternatively or additionally, such an embodiment may include one or more units 3580 configured to extract some portion 3511 of therapeutic material 3520 physically out of a vasculature or otherwise to filter a blood flow. Alternatively or additionally, the embodiment may include module 3551 configured as circuitry for detecting a release of therapeutic material 3520 and/or module 3552 configured as circuitry for detecting a presence of therapeutic material 3520. Other such embodiments are described, for example, with reference to FIGS. 10, 11, 19, and 20.

An embodiment provides an in-dwelling catheter or other artificial structure 3455 comprising at least unit 3510 configured to administer a therapeutic material 3520 containing oxyhemoglobin 3523 (or some other form of dioxygen acceptable for administration to a living subject 3400 via a vasculature) and an artificial component 3530 locally to a treatment site 3471 via one or more capillary beds 3470. (Other such embodiments are described, for example, with reference to FIGS. 24 and/or 33.) In some contexts, unit 3510 may further include one or more of a flow sensor 2471, a force sensor 2484, a sonic sensor 2495, an in-dwelling catheter comprising distal portion 3456, a pressure sensor, or other implantable components as described herein. Some variants may further include or otherwise interact with unit 3540, which may comprise one or more instances of notification logic 3535 configured to transmit a notification 3533 relating to the first unit 3510 (via a network as described herein, e.g.), imaging apparatuses 3536 configured to facilitate positioning some or all of unit 3510 (locally to and) upstream or downstream from a target treatment site 3471, or a probe 3537 for moving one or more units 3510, 3540, 3560, 3580 into selected positions in or near vasculature 3465.

A variant embodiment provides an artificial structure comprising one or more instances of unit 3510 configured to administer (an anticoagulant or other artificial components 3530 of) therapeutic materials 3520 locally via capillaries. Another artificial structure comprising unit 3580 may include one or more dispensation ports 3578 configured to extract a portion 3511 of the therapeutic material(s) 3520 out of a vasculature, such as by "getter-"-type removal. Alternatively or additionally, such units 3580 may comprise absorption ports 3577 or other blood filtration devices 3576 configured to extract portion 3511 of the therapeutic material(s) 3520 physically out of the vasculature 3465. Such configurations may permit such high dosages that a reservoir 3508 may contain a (systemically) lethal amount of the artificial component 3530, in a context in which a remainder 3512 will constitute a non-lethal dose. In contexts like that of FIG. 34, unit 3510 may further include one or more transvascular conduits 3504 configured to administer therapeutic material 3520 via one or more venules 3495 of the vasculature 3465 locally to the one or more capillaries.

With reference now to FIGS. 36 & 37, shown is an example of an endoscopic system that may serve as a context for introducing one or more processes and/or devices described herein. System 3600 may include one or more elongate structures comprising one or more instances of dispensers 3635, thermal or other treatment elements 3655, and/or balloons 3654 guided at least partly along a blood flow 3699 of vasculature 3665. Subsequently, at FIG. 37, therapeutic material 3720 may be administered locally and/or one or more balloons 3654 or other occlusion structures may occlude flow 3699 temporarily.

An embodiment provides an occlusive structure operable to impede a flow 3699 exiting one or more segments 3661, 3662 of a vasculature 3665 and a dispenser 3635 and/or other treatment elements 3655 operable to administer chilling or other therapies locally at segment 3662. (Other such embodiments are described, for example, with reference to FIG. 116.) The system may likewise include a controller 3620, optionally operable selectively to invoke one or more instances of modules 3621 configured to trigger the balloon 3654 or other occlusive structure to impede flow 3699; modules 3622 configured to trigger the dispenser 3635 or other therapeutic structure(s); and/or modules 3623 configured to trigger other such local intravascular therapies.

Figure 38:
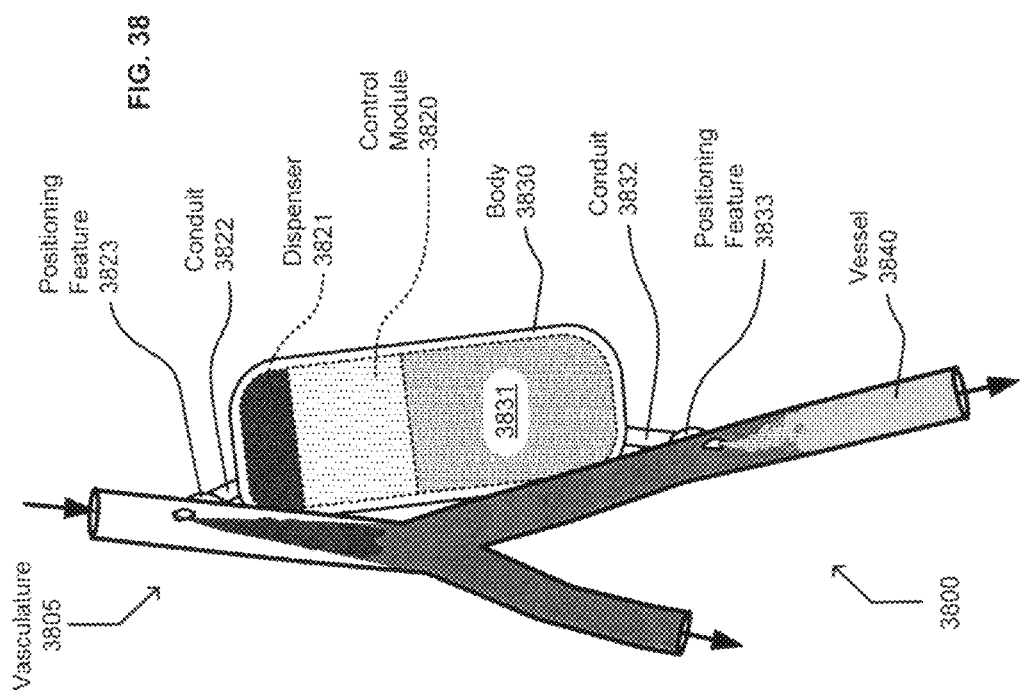

With reference now to FIG. 38, shown is an example of a system that may serve as a context for introducing one or more processes and/or devices described herein. As shown, system 3800 comprises a plurality of dispensers 3821, 3831 operatively coupled with a control module 3820 within body 3830, positioned adjacent a forked vessel 3840 of vasculature 3805. As shown, a dispenser 3821 is configured to dispense a lytic agent through one or more conduits 3822 extending into an upstream portion of vessel 3840, the conduit(s) secured in place by a bioadhesive or other positioning feature 3823. Dispenser 3831 is likewise configured to dispense (at least) a lytic agent inhibitor through one or more conduits 3832 extending into a downstream portion of vessel 3840, the conduit(s) secured in place by a similar positioning feature 3833.

Figure 39:
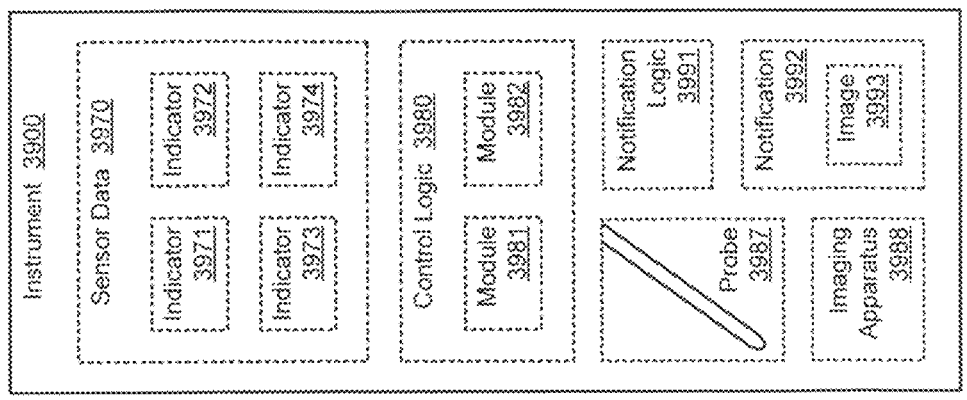

With reference now to FIG. 39, shown is an example of a monitoring and/or control instrument 3900 configured to handle one or more instances of (one or more) indicators 3971, 3972, 3973, 3974 or other sensor data 3970. Instrument 3900 may, for example, comprise one or more instances of control logic 3980 (such as modules 3981, 3982), probes 3987, imaging apparatuses 3988, or notification logic 3991 operable for handling one or more notifications 3992 as described herein, optionally including one or more images 3993.

In some variants, systems described herein may be configured to include transvascular or other implantable articles. Other such embodiments are described, for example, with reference to FIGS. 33 and 40-50.

With reference now to FIG. 40, shown is an example of a system 4000 comprising one or more dispensers 4010, 4020 configured to dispense materials (transvascularly) into respective branches of an artery or other large blood vessel 4005. Such dispensers may, in some variants, be secured in a vicinity of a vessel by one or more sleeves 4009 or other such positioning features. In response to one or more dispensation criteria as described below, control module 4060 is configured to permit a fluid communication between a pressurized reservoir 4050 and one or more plungers 4041, 4042 configured to actuate the respective dispensers.

With reference now to FIGS. 41-44, shown is an operative example of an injector configuration suitable for use, for example, in dispensers like those of FIG. 40. As shown in FIG. 41, a plunger 4140 exerts force (leftward as shown) upon injectable fluid 4160 so that needle 4132 slides along tapered body 4130 (downward as shown). In response to pressure from needle 4132 and/or fluid 4245 (saline, e.g.), as shown in FIG. 42, a containment film 4287 breaks. As shown in FIG. 43, needle 4132 pierces blood vessel wall 4306. As shown in FIG. 44, a portion of injectable fluid 4160 becomes dispensation 4475 at a somewhat lower pressure than that initially present in pressure transfer fluid 4446. In some variants, needle 4132 comprises a blood-soluble portion coated with a film configured so that abrasion with tapered body 4130 exposes the blood-soluble portion. In others, a spring or other actuation mechanism may be used, optionally configured to withdraw a needle after the injection. Alternatively or additionally, an adhesive or other sealing mechanism may be applied at the point of injection.

Figure 45:
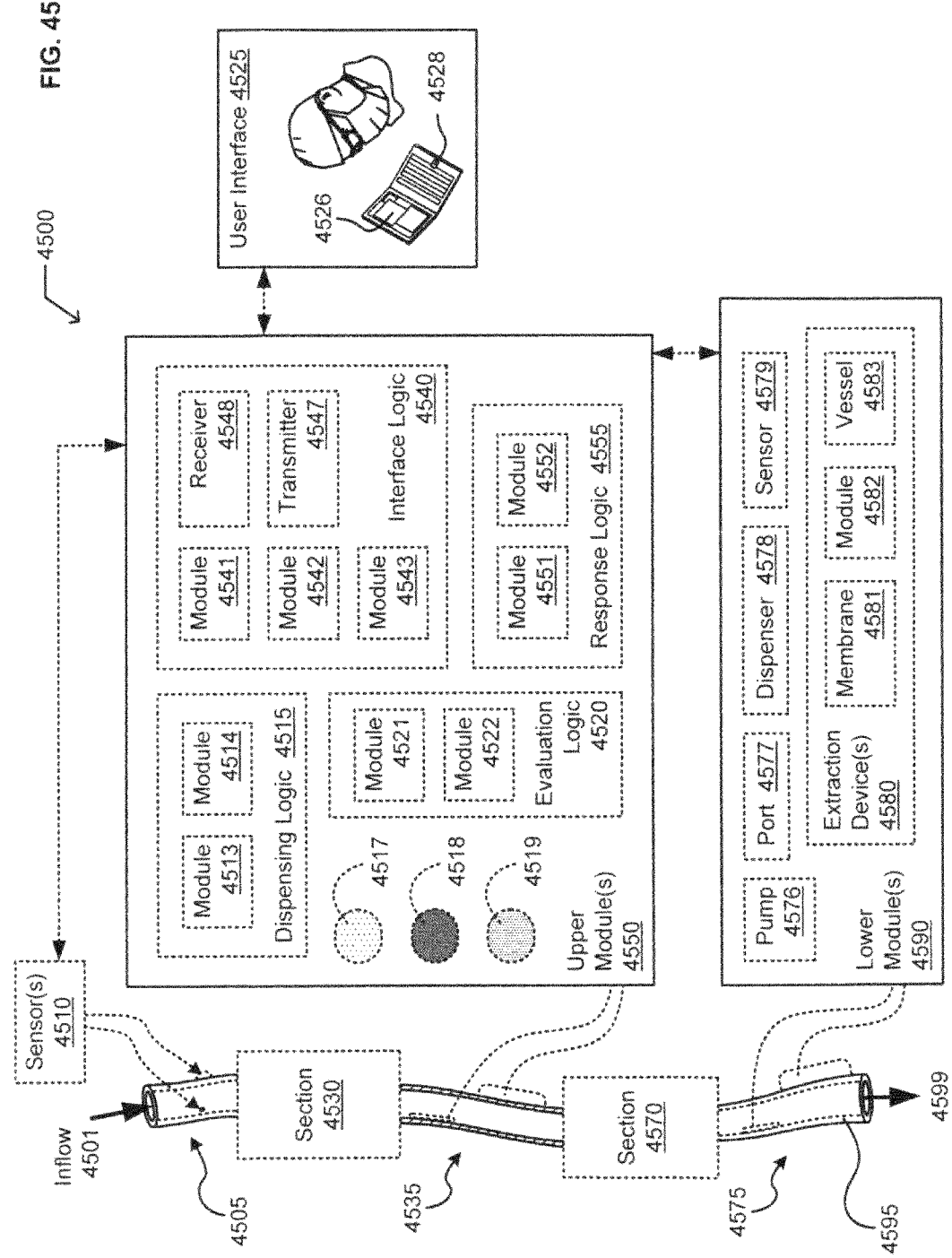

With reference now to FIG. 45, shown is an example of a system that may serve as a context for introducing one or more processes and/or devices described herein. As shown system 4500 may affect or otherwise relate to vicinity 4505, section 4530, vicinity 4535, section 4570, and vicinity 4575 of a vascular lumen 4595 through which one or more blood components may flow. One or more inflows 4501 of blood enter respective portions of lumen 4595 as shown, pass through sections 4530, 4570 and exit as one or more outflows 4599. In respective variants, arteries, veins, or smaller vessels of lumen 4595 may traverse respective vicinities 4505, 4535, 4575 as shown. Sections 4530, 4570 may likewise comprise one or more capillary beds as well as implants or other entities with which lumen 4595 interacts.

In some variants, one or more upper modules 4550 in vicinity 4535 may (optionally) send data to and/or receive data from one or more instances of intravascular or other sensors 4510 in vicinity 4505. Upper module 4550 may likewise comprise one or more instances of modules 4513, 4514 of dispensing logic 4515; dispensers 4517, 4518, 4519; modules 4521, 4522 of evaluation logic 4520; transmitters 4547, receivers 4548, or other modules 4541, 4542, 4543 of interface logic 4540; or modules 4551, 4552 of response logic 4555. Interface logic may handle data to output device 4526 and/or from input device 4528 as well interacting with one or more lower modules 4590. Lower module 4590 may include one or more instances of microfluidic or other pumps 4576, ports 4577, dispensers 4578, sensors 4579, or semi-permeable membranes 4581 or other such modules 4582 or vessels 4583 of extraction devices 4580.

With reference now to FIG. 46, shown is an example of a system that may serve as a context for introducing one or more processes and/or devices described herein. As shown system 4600 may comprise a lumen 4695 comprising a heart valve 4610 including an annular base 4607 containing one or more dispensers 4616, a ball 4608, and one or more upper modules 4650 and lower modules 4690 operatively coupled as shown. Upper module 4650 may comprise one or more instances of dispensation logic 4615, evaluation logic 4620, or wireless communication modules 4644 or other interface logic 4640 operable for communication with one or more user interfaces 4625; for transmitting data to one or more output devices 4626 or receiving data from one or more input devices 4628 thereof as shown. Lower module 4690 may comprise an optical sensor 4675, an auditory sensor 4676, or other sensors 4677; or pressure or force sensors or other a flow-force-responsive elements 4678 or other elements 4679 as described herein.

An embodiment provides a system 4600 comprising dispensing logic 4615 or interface logic 4640 operable for signaling a decision whether to initiate implant-site-targeting treatment and one or more dispensers 4616 responsive to the decision. Each dispenser 4616 may (optionally) include a thrombolytic agent and/or other therapeutic materials as described herein, suitable for targeting a vicinity of valve 4610. The above-described "signaling" circuitry may comprise one or more of optical sensors 4675, auditory sensors, flow-force-responsive elements 4678, or other components suitable for providing thrombus-indicative measurements or other data suitable for informing the decision in light of teachings herein.

In some embodiments, "signaling" something can include identifying, contacting, requesting, selecting, or indicating the thing. In some cases a signaled thing is susceptible to fewer than all of these aspects, of course, such as a task definition that cannot be contacted.

In some variants, systems described herein may be configured to include one or more controllable dispensers or other such control features. Other such embodiments are described, for example, with reference to FIGS. 4, 10, 50, 68, and 71.

An embodiment provides a system 4600 comprising interface logic 4640 operable for signaling a decision (a) whether to initiate implant-site-targeting treatment or (b) whether to administer one or more clot-reducing agents. Alternatively or additionally, system 4600 comprising may similarly provide dispensing logic using such signaling, for example, for guiding one or more dispensers 4616 accordingly. Each dispenser 4616 may (optionally) contain a thrombolytic agent and/or other therapeutic materials as described herein, suitable for targeting a vicinity of valve 4610. The above-described "signaling" circuitry may comprise one or more of optical sensors 4675, auditory sensors 4676, flow-force-responsive elements 4678, or other components suitable for providing thrombus-indicative measurements or other data suitable for informing the decision in light of teachings herein.

With reference now to FIG. 47, shown is an example of a system that may serve as a context for introducing one or more processes and/or devices described herein. As shown system 4700 comprises (a top view of) a valve 4710 having a dispenser 4716 in an upper portion thereof. Any of the embodiments described herein with reference to FIG. 45 may effectively implement valve 4710 as a combination of upper module 4550 and lower module 4590 within lumen 4595. Any of the embodiments described herein with reference to FIG. 112 may effectively implement valve 4710 as module 11250 within lumen 11295. Any of the embodiments described herein with reference to FIG. 116 may effectively implement valve 4710 as module 11660 within lumen 11695. Any of the embodiments described herein with reference to FIG. 108 may effectively implement valve 4710 as module 10890 within lumen 10895. Any of the embodiments described herein with reference to FIG. 28 or 108 may likewise implement valve 4710 as module 10890 or system 2800 within lumen 10895 or vasculature 2896.

With reference now to FIG. 48, shown is (a bottom view of) a variant of valve 4710 in which a dangerous, partially occlusive thrombus 4716 has formed. An embodiment provides one or more sensors 4579 in a lower module 4590 suitable for detecting thrombus 4716 and able to respond programmatically as described herein.

With reference now to FIG. 49, shown is (a bottom view of) a variant of valve 4710 in which thrombus 4716 has been prevented or removed as described herein. Valve 4710 is accordingly operable for opening and closing effectively in this configuration, unlike that of FIG. 48.

Figure 50:
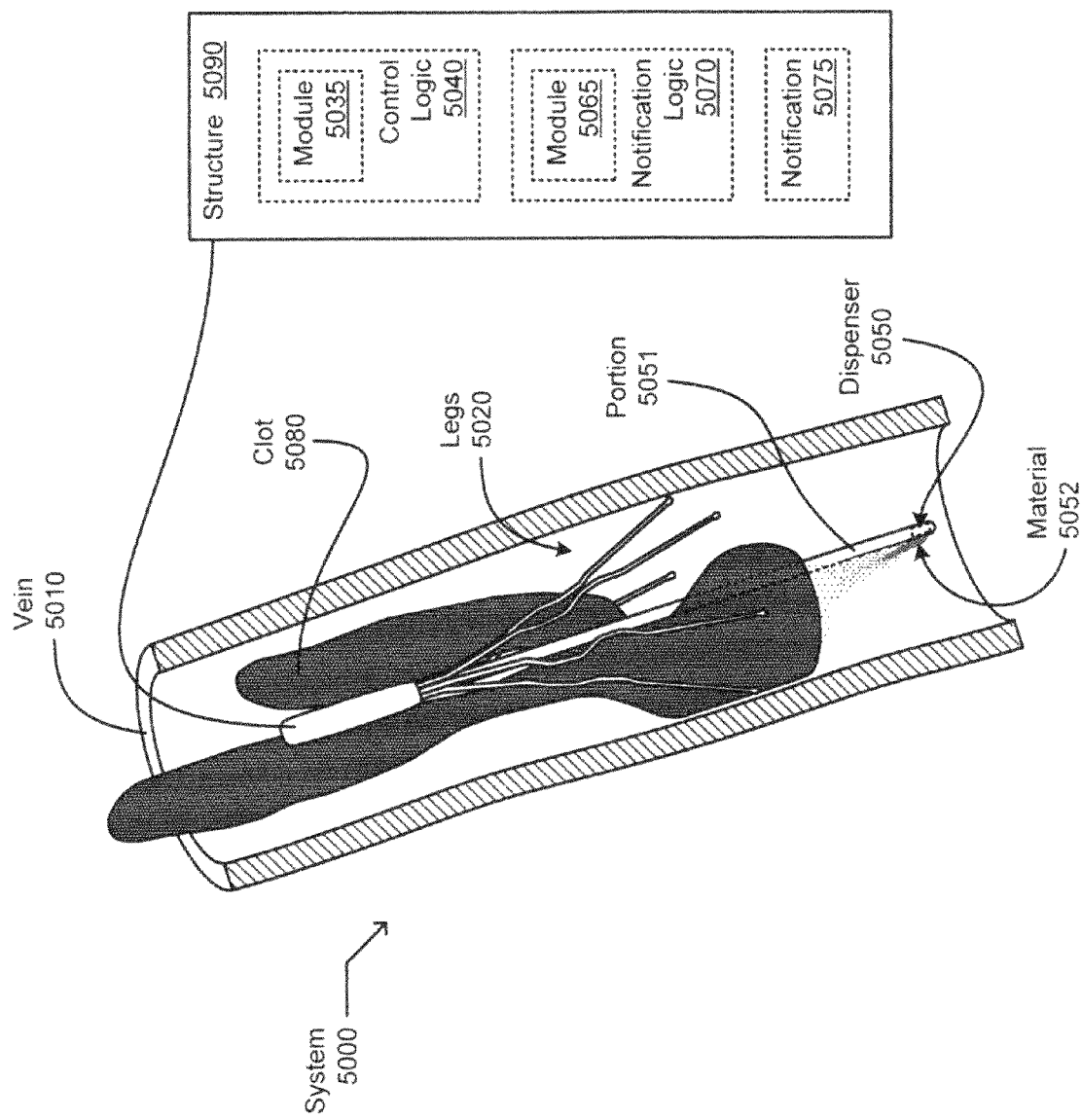

With reference now to FIG. 50, shown is an implanted system 5000 in which one or more technologies may be implemented, a structure 5090 having a plurality of legs 5020 (optionally a variant of a "Gunther Tulip" inferior vena cava filter, for example) engaging a wall of a lerge vein 5010. In response to detecting a large-enough clot 5080 (as a force increase, deformation, or other manifestation described herein, e.g.), one or more modules 5035 of control logic 5040 may cause a dispenser 5050 to inject a concentrated dose of lytic material 5052 locally from an upstream portion 5051 of system 5000. Alternatively or additionally, one or more modules 5065 of notification logic 5070 may cause or enable a notification 5075 to be transmitted, for example, wirelessly to an external device as described herein signaling one or more such events.

In some variants, systems described herein may be configured to include or interact with a pacemaker or other such implantable articles. Other such embodiments are described, for example, with reference to FIGS. 33 and 34.

Figure 51:
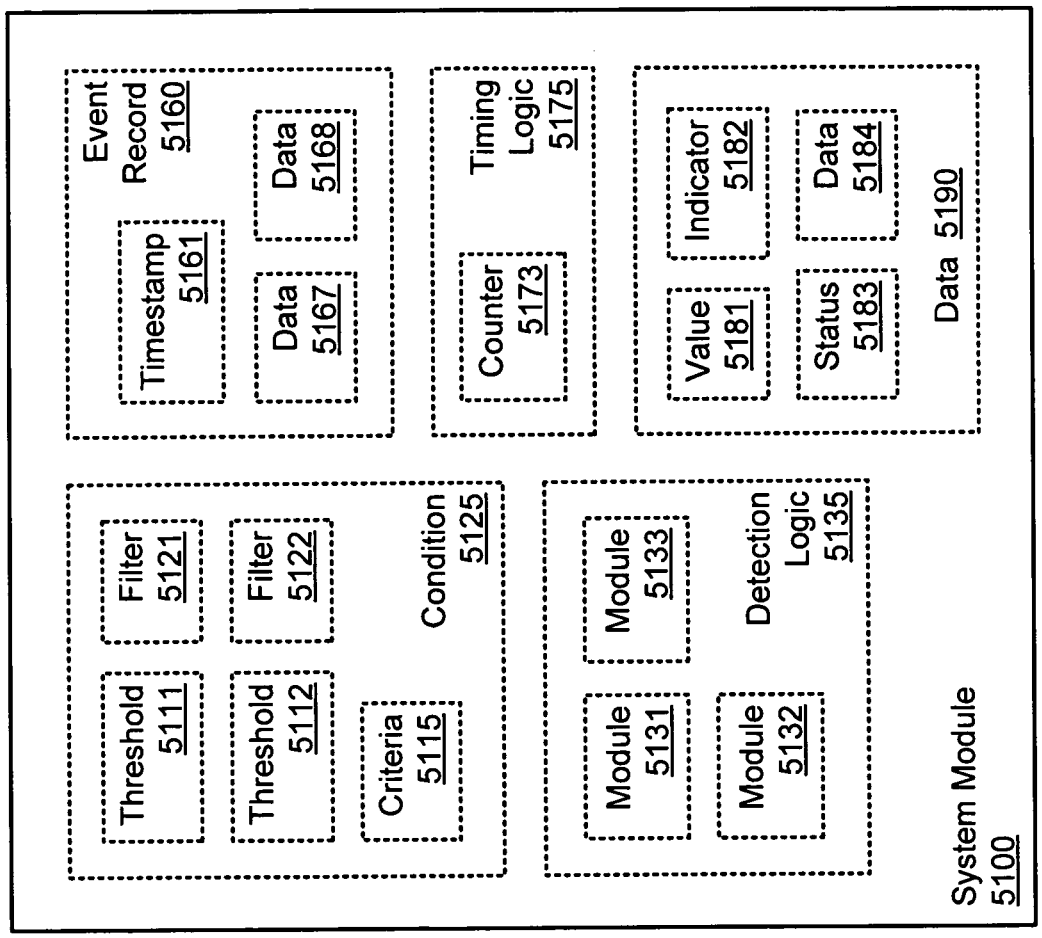

With reference now to FIG. 51, shown is an example of a system that may serve as a context for introducing one or more processes and/or devices described herein. As shown system module 5100 may comprise one or more thresholds 5111, 5112, criteria 5115, filters 5121, 5122, or other conditions 5125 detectable by one or more modules 5131, 5132, 5133 of detection logic 5135. Such logic may be implemented in hardware or software, for example, optionally configured for analyzing values from one or more event records 5160, counters 5173 or other timing logic 5175, or other such data. In some variants, for example, event record 5160 may associate one or more timestamps 5161 with measurements or other data 5167, 5168. Alternatively or additionally, such logic may analyze one or more other values 5181, indicators 5182, statuses 5183, or other such data 5184, 5190 of potential diagnostic utility.

Figure 52:
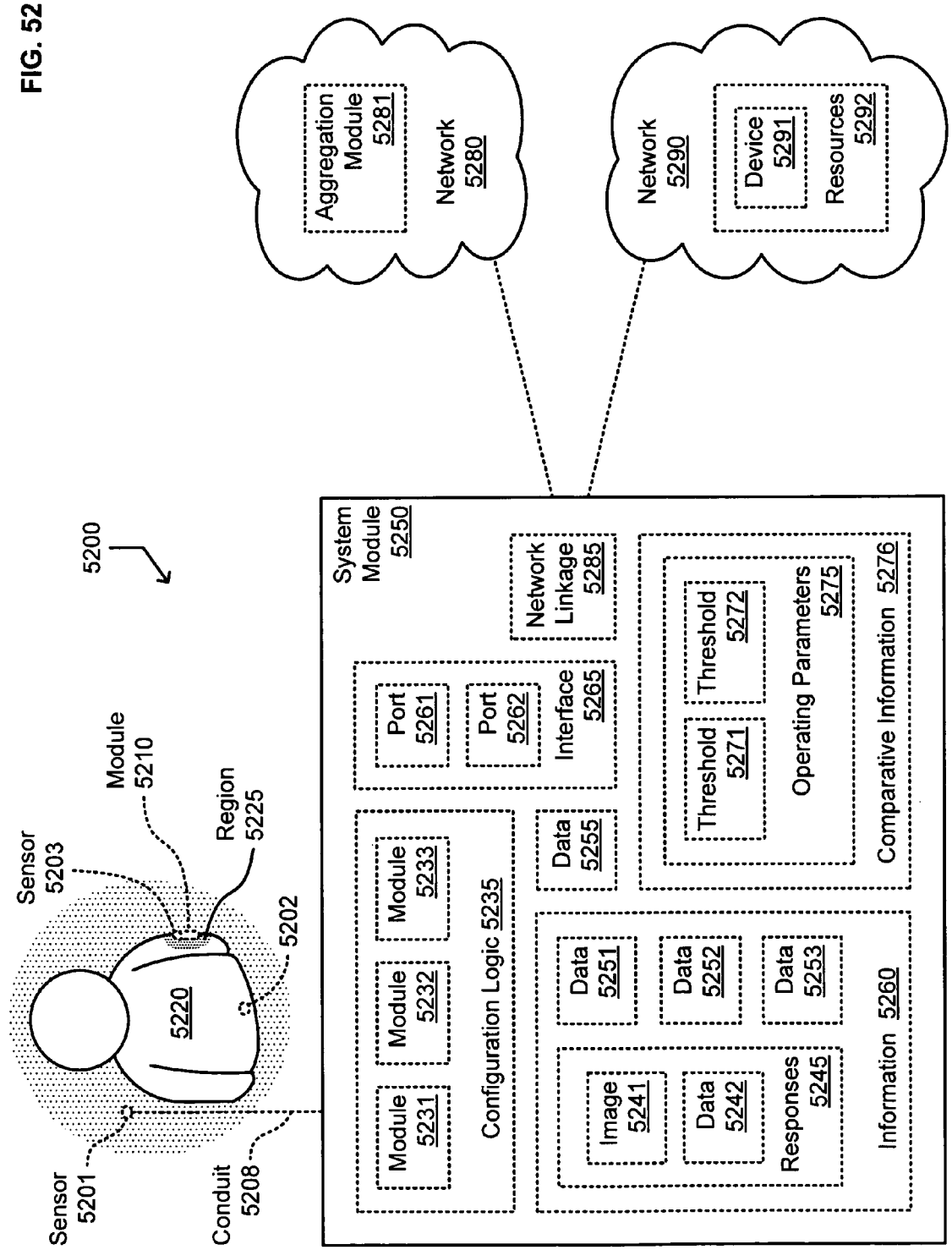

With reference now to FIG. 52, shown is an example of a system 5200 comprising a system module 5250 operable for communicating to and/or from one or more sensors 5201, 5202, 5203; other modules 5210; aggregation modules 5281; devices 5291 or other resources 5292; or other portions of networks 5280, 5290. In some contexts, for example, such sensors may be (a) operatively coupled with system module 5250 via a conduit 5208 and/or (b) near a peripheral region 5225 or core of subject 5220 as shown. In some variants, system module 5250 may include one or more modules 5231, 5232, 5233 of configuration logic 5235 configured to handle one or more images 5241, data 5242, other responses 5245, other data 5251, 5252, 5253, 5255 as described herein, or other information 5260 of potential utility in diagnosing a living subject. Alternatively or additionally, system module 5250 may include one or more ports 5261, 5262 or other features of interface 5265; network linkages 5285 for interacting to and/or from networks; or thresholds 5271, 5272, operating parameters 5275, or other comparative information 5276 potentially useful for diagnostic and/or monitoring purposes.

Figure 53:
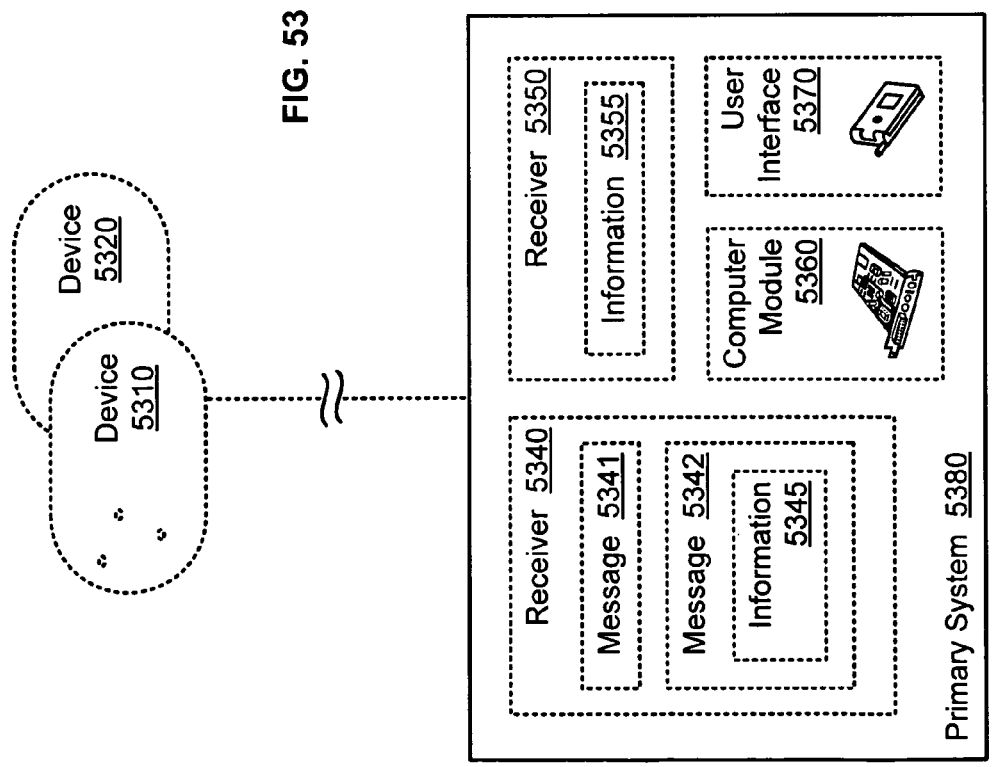

With reference now to FIG. 53, shown is an example of a sensor-containing device 5310 or other device 5320 at least sometimes in communication with one or more primary systems 5380. In some variants, for example, one or more receivers 5340, 5350 may be configured to receive one or more messages 5341, 5342 or other information 5345 from such devices. Alternatively or additionally, primary system 5380 may include one or more controller cards or other computer modules 5360 implementing decision logic 275, 1350, 1460, 2250, 2730, 3230 or other logic as described herein, for example, in hardware or software form. Primary system 5380 may likewise include one or more hand-held or other user interfaces 5370 for relaying notifications or other information to or from care providers or other users 5390.

Figure 54:
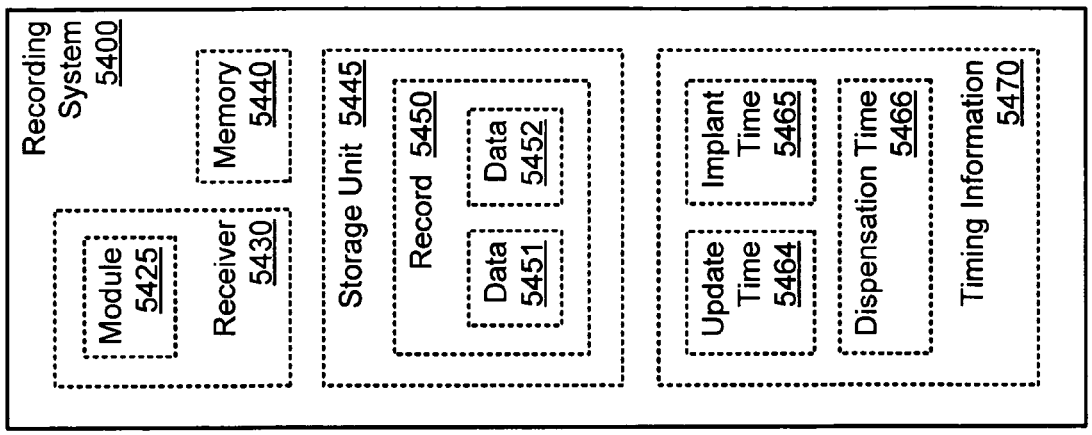

With reference now to FIG. 54, shown is an example of a recording system 5400 comprising one or more receivers 5430 for handling software or other modules 5425, one or more records 5450 associating data 5451, 5452 in a memory 5440 or storage unit 5445, or timing information 5470 as described herein. In some contexts, for example, recording system 5400 may record or otherwise handle one or more update times 5464, implant times 5465, dispensation times 5466, or other such data in association with an event type, a quantity, or other such parameters of potential analytical utility.

In some variants, other system components described herein may be configured to generate or act upon such timing information. Such embodiments are described, for example, with reference to FIGS. 11, 55, 56, and 62-64.

Figure 55:
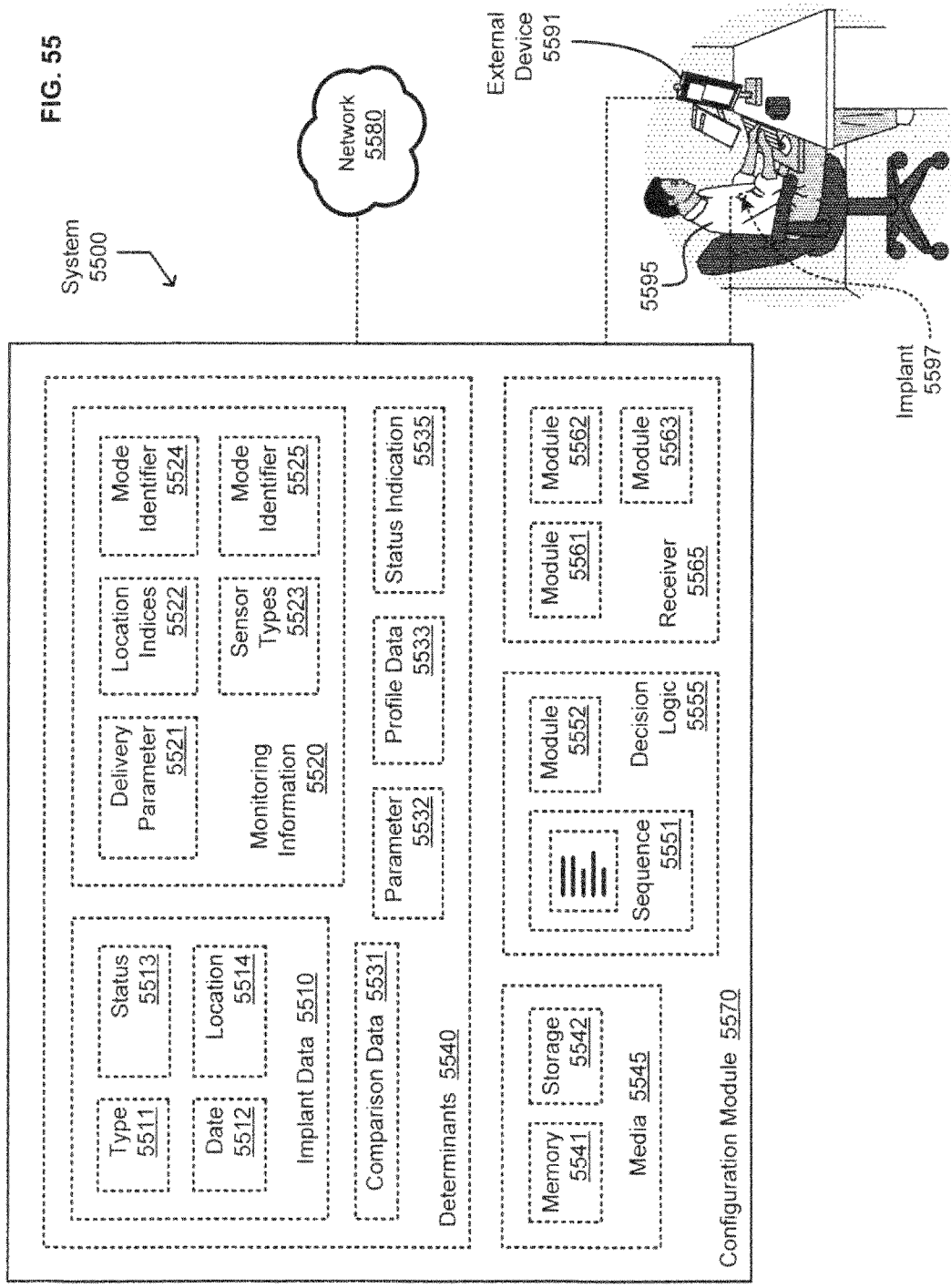

With reference now to FIG. 55, shown is a system 5500 in which one or more technologies may be implemented, a configuration module 5570 wirelessly or otherwise operably coupled to one or more networks 5580, external devices 5591, or implants 5597 in subject 5595. In some variants, configuration module may include one or more determinants 5540 in memory 5541, storage 5542, or other media 5545. In various contexts as described below, for example, one or more instruction sequences 5551 or other modules 5552 of decision logic 5555 may behave in a manner that depends upon one or more of a type 5511, date 5512, status 5513, or location 5514 of implant 5597, or other such implant data 5510, comparison data 5531, parameters 5532, or profile data 5533 as described herein. Alternatively or additionally, one or more 5521, location indices 5522, sensor types 5523, mode identifiers 5524, 5525 or other such monitoring information 5520 and/or status information 5535 may be received by one or more modules 5561, 5562, 5563 of receiver 5565 for potential use by diagnosticians and/or decision logic as described herein.

Figure 56:
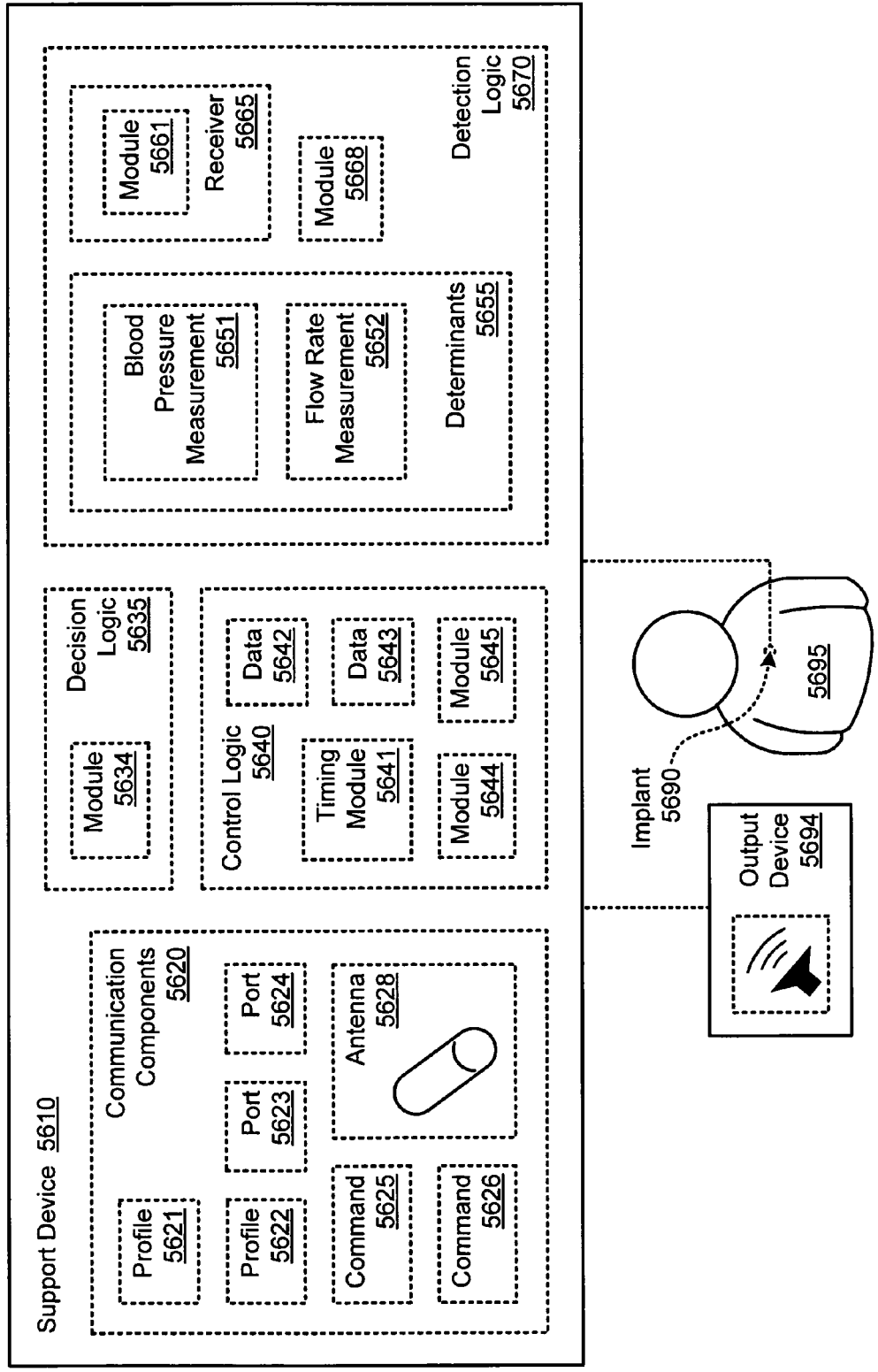

With reference now to FIG. 56, shown is a system 5600 in which one or more technologies may be implemented, configured to receive information from implant 5690 and/or to convey information to a subject or other user 5695 via one or more output devices 5694 (a speaker, e.g.). Support device 5610 may include one or more ports 5623, 5624, antennae 5628, or other such communication components 5620 operable for handling one or more profiles 5621, 5622, commands 5625, 5626 or other such information. Alternatively or additionally, support device 5610 may include one or more modules 5634 of decision logic 5635 or timing modules 5641 or other modules 5644, 5645 of control logic 5640 suitable for handling data 5642, 5643 as described herein. In some variants, detection logic 5670 of support device 5610 may likewise include one or more receivers 5665 or other modules 5661, 5668 configured to handle one or more blood pressure measurements 5651, flow rate measurements 5652, or other such determinants 5655 that depend upon the implant(s) 5690 or other characteristics of subject 5695.

Figure 57:
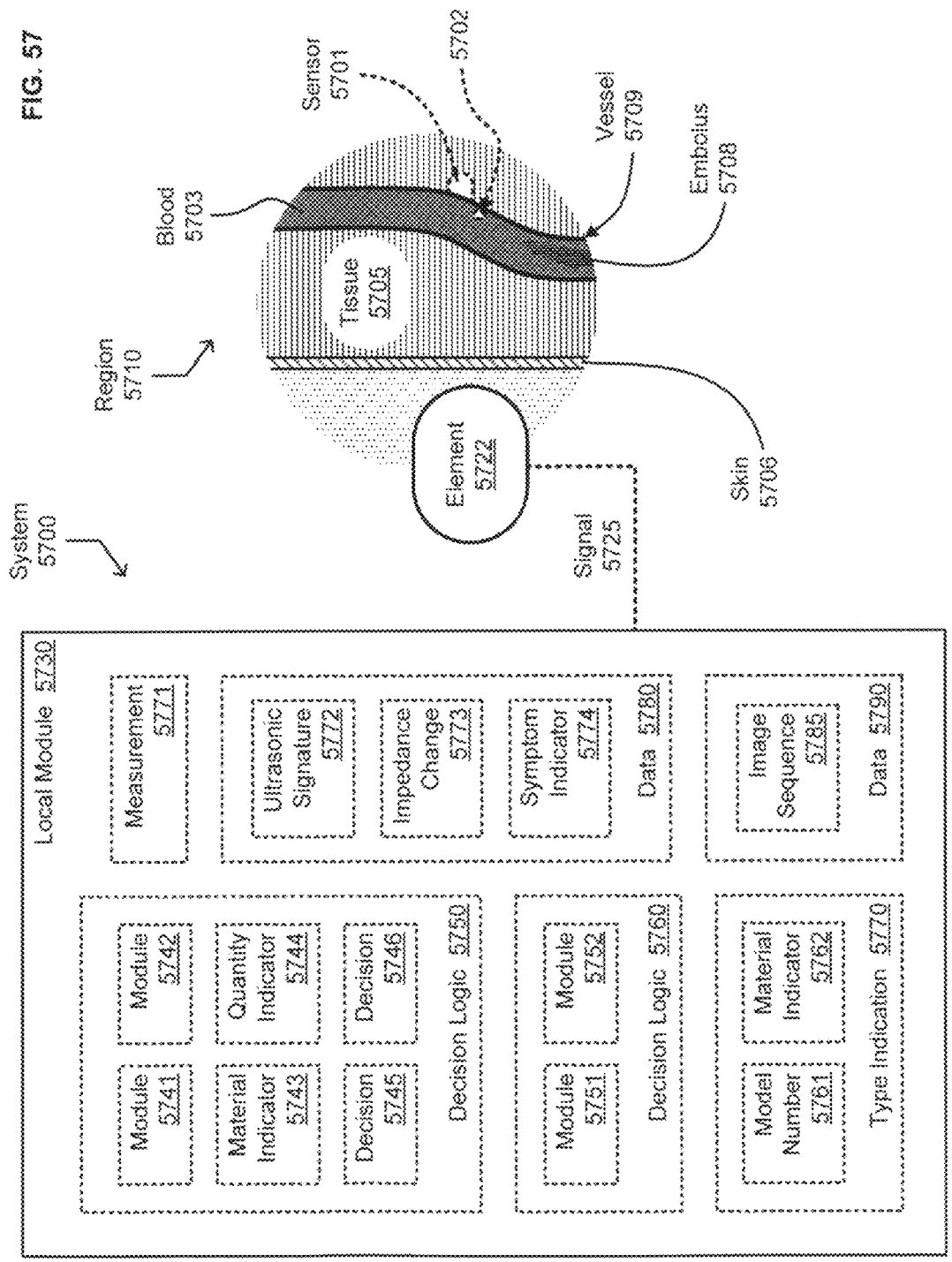

With reference now to FIG. 57, shown is a system 5700 in which one or more technologies may be implemented, a local module 5730 configured to communicate signals 5725 to and/or from one or more sensors 5701 or other such elements 5722 in a region 5710 adjacent a blood vessel 5709. This can facilitate detection of an embolus 5708 or other circulation-related features in blood 5703, skin 5706, or tissue 5705. Such a local module 5730 may include one or more modules 5741, 5742, 5751, 5752 of decision logic 5750, 5760 operable for generating one or more decisions 5745, 5746. Such decisions may depend upon one or more material indicators 5743, 5762, quantity indicators 5744, model numbers 5761, or other type indications 5770. Alternatively or additionally, such decisions may depend upon one or more measurements 5771, ultrasonic signatures 5772, impedance changes 5773, symptom indicators 5774, image sequences 5785, or other such data 5780, 5790.

Figure 58:
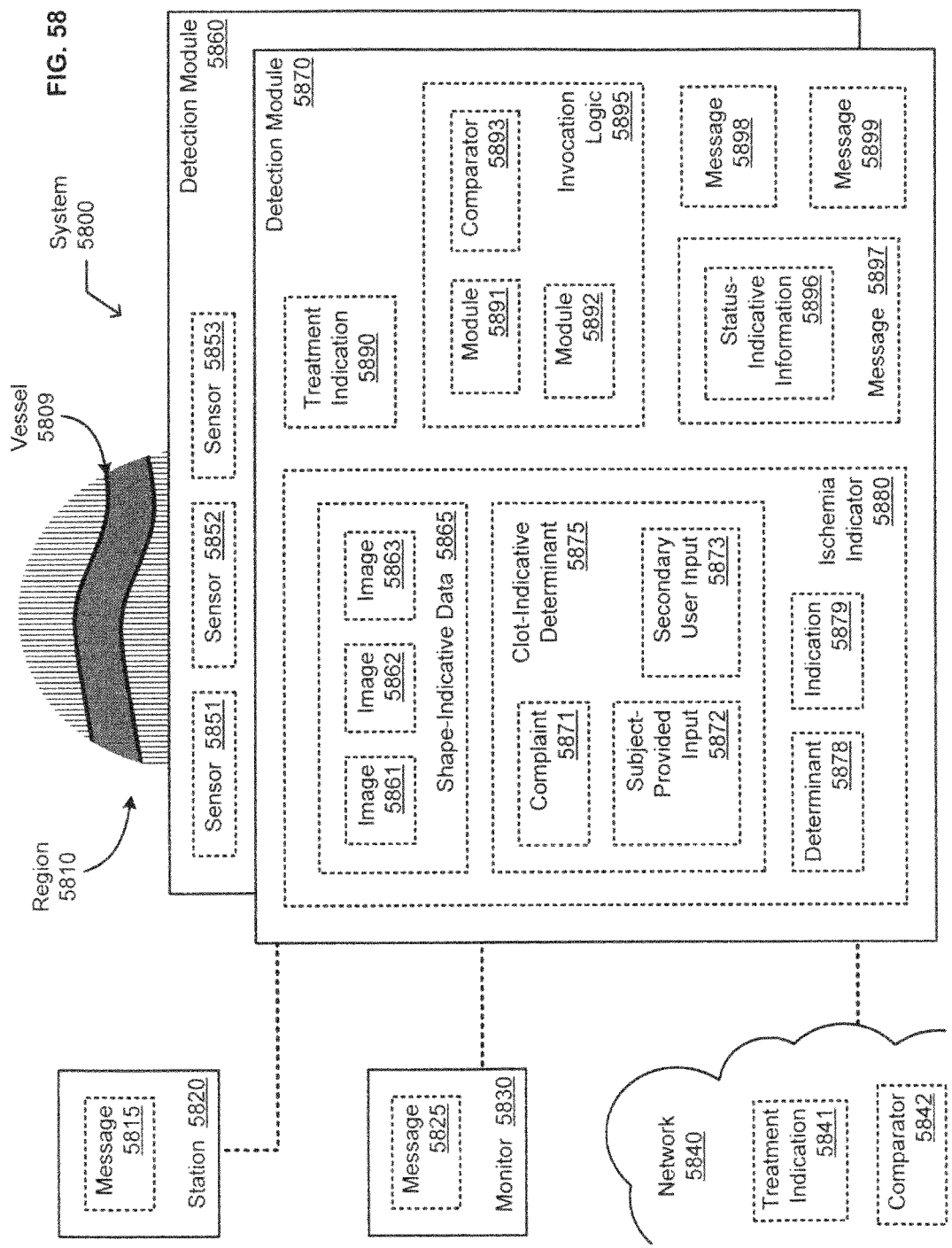

With reference now to FIG. 58, shown is a system 5800 comprising two or more coupled detection modules 5860, 5870 configured to handle sensor data manifesting measurements or other attributes of a region 5810 adjacent blood vessel 5809. In some variants, for example, detection module 5860 includes sensors 5851, 5852, 5853 as described herein operable to transmit the sensor data. Accordingly, detection module 5870 may be configured to handle one or more images 5861, 5862, 5863 or other shape-indicative data 5865; one or more complaints 5871, subject-provided input 5872, secondary user input 5873, or other such clot-indicative determinants; or other determinants 5878 or other indications 5879 comprising ischemia indicators 5880. Detection module 5870 may further include one or more comparators 5893 or other modules 5891, 5892 of invocation logic 5895 for sending and/or receiving a treatment indication 5890, status-indicative information 5896, or other components of messages 5897, 5898, 5899. In various contexts as described herein, one or more such treatment indications 5841 or other messages 5815, 5825 may be transmitted to or received from one or more stations 5820, monitors 5830, comparators 5842, or other components of networks 5840 potentially remote from region 5810.

In some variants, such detection modules may be configured to capture and/or transmit images or otherwise handle shape-indicative data. Other such embodiments are described, for example, with reference to FIGS. 9, 16, 35, 52, 75, 77, and 79.

With reference now to FIG. 59, shown is a system 5900 comprising primary module 5920 configured to transmit output 5983 to and/or receive input 5984 from interface 5980. Primary module 5920 may include one or more comparators 5921, circuitry 5922, module 5923, or other decision logic 5930, 5940 configured to generate one or more decisions 5925 or other data responsive to one or more criteria 5907, 5908, 5909, 5910. Alternatively or additionally, primary module 5920 may include one or more modules 5961, 5962, 5963, 5964 of evaluation logic 5965 configured to generate metadata or other such information responsive to one or more such criteria. Such input or output data may, for example, comprise a succession 5951 or other indicatos 5952, 5953, 5954, 5955 transmitted to or from primary module 5920.

Figure 60:
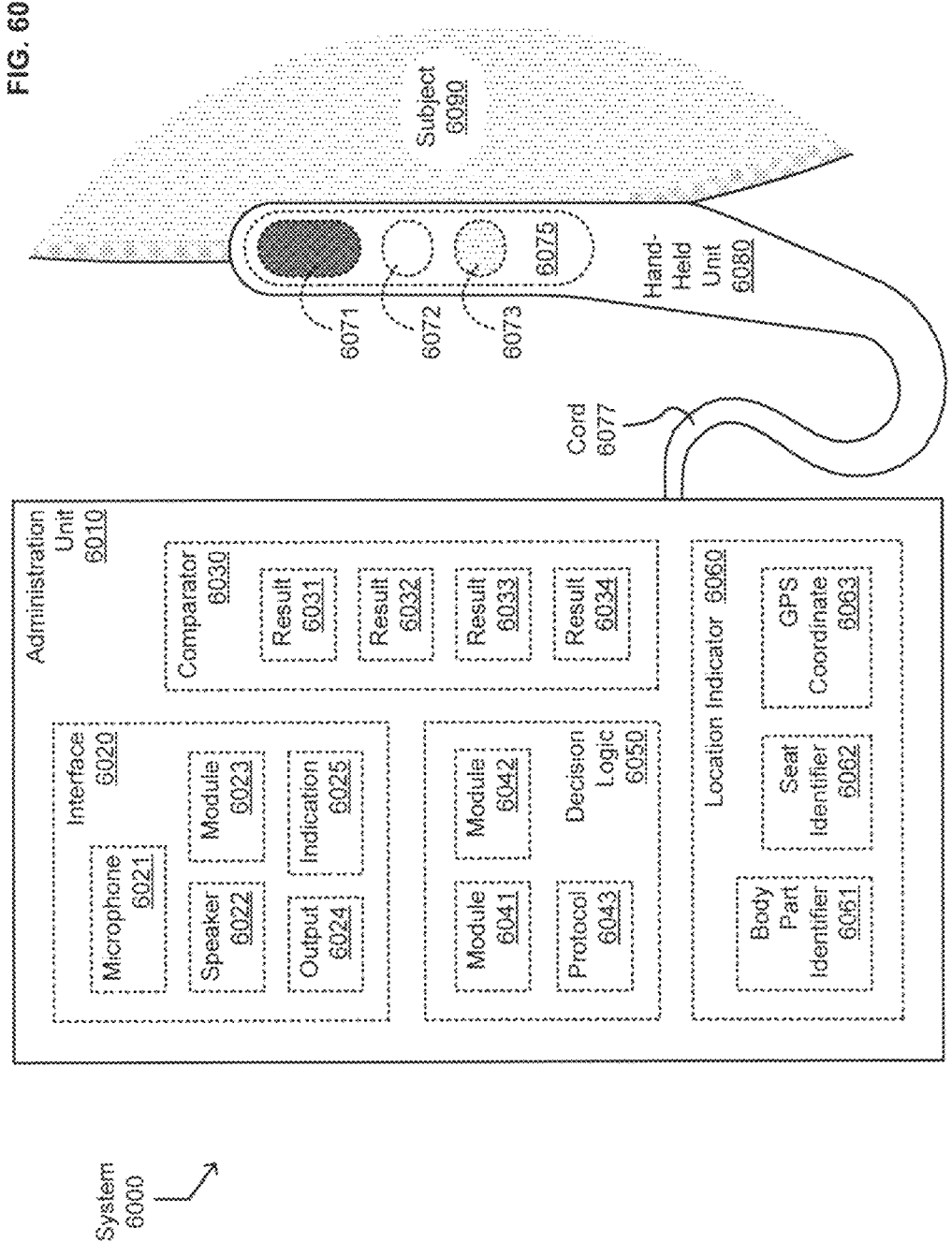

With reference now to FIG. 60, shown is an administration unit 6010 optionally comprising one or more primary modules described herein, and operatively coupled via a cord 6077 with a hand-held unit 6080 positionable adjacent a subject 6090. In some variants, for example, hand-held unit 6080 may include one or more sensors or logic as described herein. Alternatively or additionally, hand-held unit 6080 may include one or more dispensers 6075 of a vasodilator 6071, lytic agent 6072, or other such therapeutic components 6073 (operatively controlled via cord 6077, e.g.). Administration unit 6010 may include one or more microphones 6021, speakers 6022, or other modules 6023 of interface 6020 configured to convey output 6024 or other indications 6025. Such information may be guided by one or more interaction protocols 6043 or other modules 6041, 6042 of decision logic 6050. Alternatively or additionally, such information may be guided by one or more results 6031, 6032, 6033, 6034 from comparator 6030 and/or by one or more body part identifiers 6061, seat identifiers 6062, global positioning system (GPS) coordinates 6063, or other such location indicators 6060.

In some variants, hand-held unit 6080 may be implemented as a handle, a steering wheel, an arm rest, or other feature of a vehicle configured to monitor a health status of one or more occupants. Other such embodiments are described, for example, with reference to FIGS. 2, 6, and 8.

Figure 61:
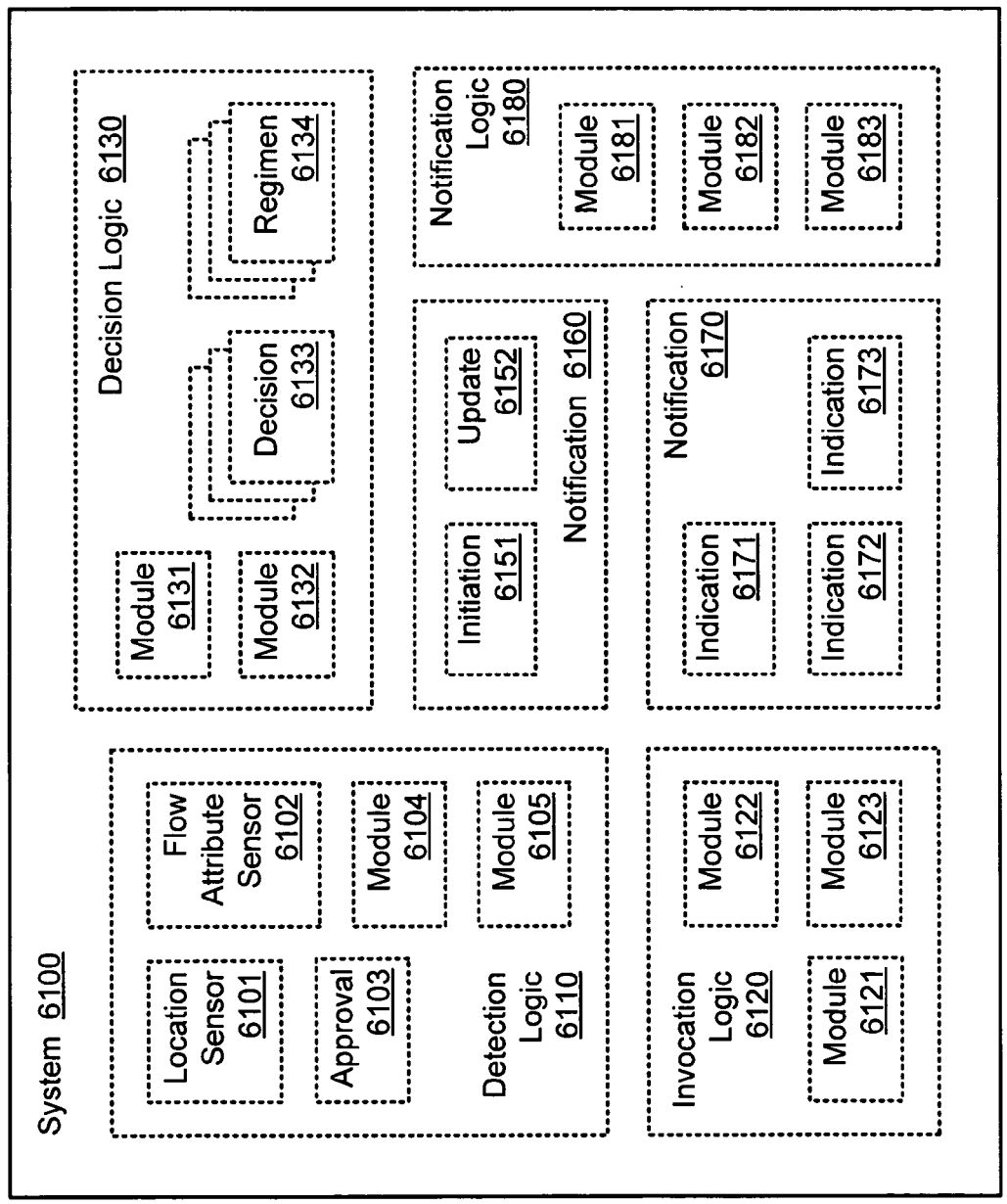

With reference now to FIG. 61, shown is a system 6100 in which one or more technologies may be implemented comprising one or more location sensors 6101, flow attribute sensors 6102, approvals 6103, or other such input components to one or more modules 6104, 6105, 6121, 6122, 6123 of detection logic 6110 or invocation logic 6120. System 6100 may further include one or more instances of decisions 6133 generated by one or more modules 6131, 6132 responsive to a fulfillment of one or more regimens 6134. Alternatively or additionally, system 6100 may further include one or more instances of initiations 6151, updates 6152, indications 6171, 6172, 6173, or other notifications 6160, 6170 configured and/or triggerred by one or more modules 6181, 6182, 6183 of notification logic 6180.

In some variants, such notification logic may be configured to facilitate selective notifications according to one or more controllable parameters. Other such embodiments are described, for example, with reference to FIGS. 3, 5, 12, 15, 22, 29, 30, 32, 35, and 77.

Figure 62:
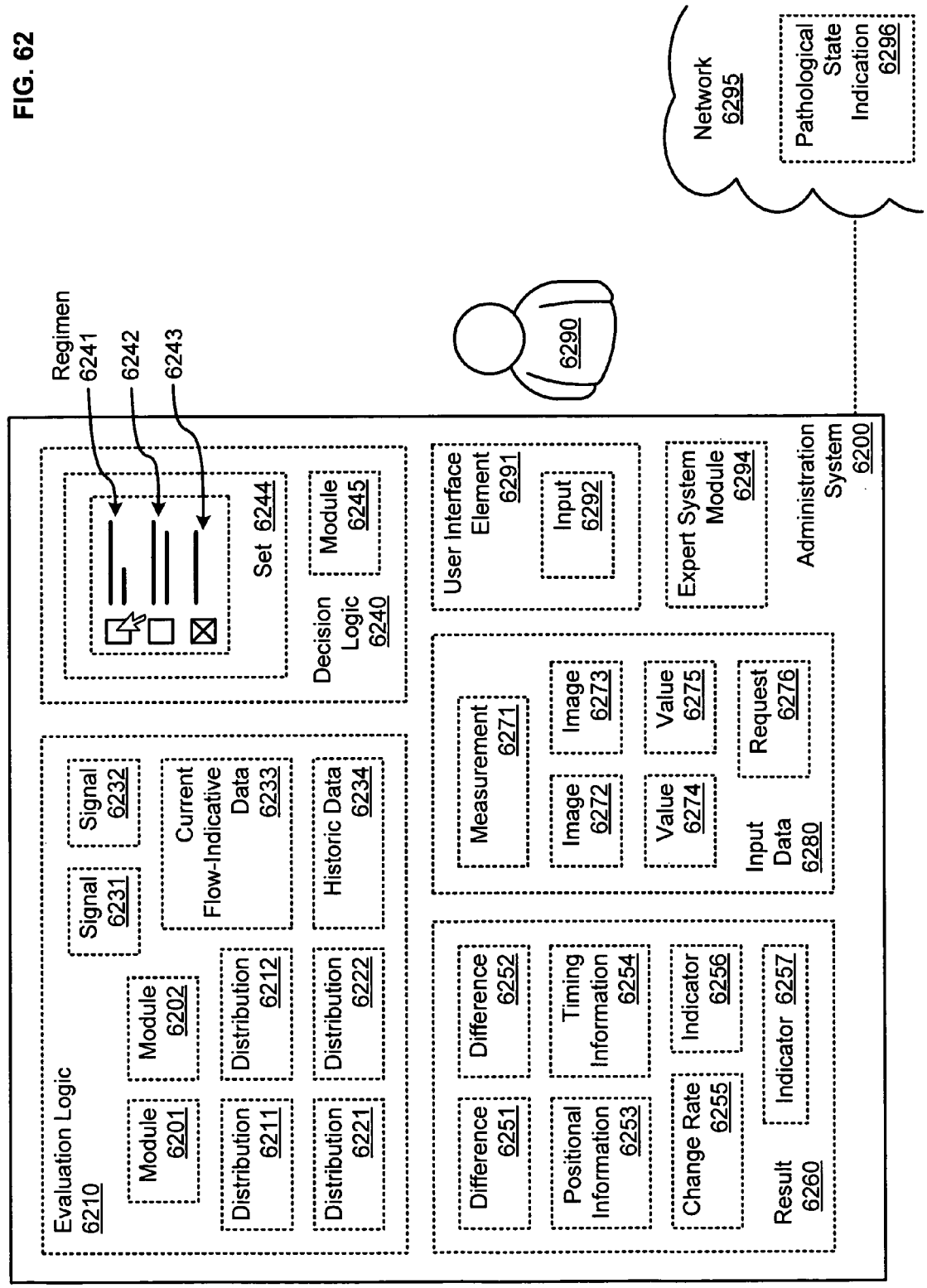

With reference now to FIG. 62, shown is an administration system 6200 comprising one or more modules 6201, 6202 of evaluation logic 6210 configured to generate one or more results 6260 in response to an evaluation of one or more distributions 6211, 6212, 6221, 6222 with one or more signals 6231, 6232, current flow-indicative data 6233, historical data 6234, or other such diagnostically relevant parameters as described herein. Alternatively or additionally, one or more differences 6251, 6252, positional information 6253, timing information 6254, change rates 6255, indicators 6256, 6257 or other results 6260 may manifest or otherwise stem from a set 6244 of one or more regimens 6241, 6242, 6243 (selected as input 6292 from user 6290 at a user interface element 6291, e.g.). Such results 6260 can likewise manifest or otherwise stem from one or more measurements 6271, images 6272, 6273, values 6274, 6275, requests 6276, or other such input data 6280 (from one or more users 6290 and/or expert system modules 6294, e.g.). In some variants, for example, one or more modules 6245 of decision logic 6240 may (a) define a default set of regimens in response to a pathological state indication 6296 or other such data from network 6295 and/or (b) permit the user(s) to configure the set 6244 selectively as a mode of dispensation control.

Figure 63:
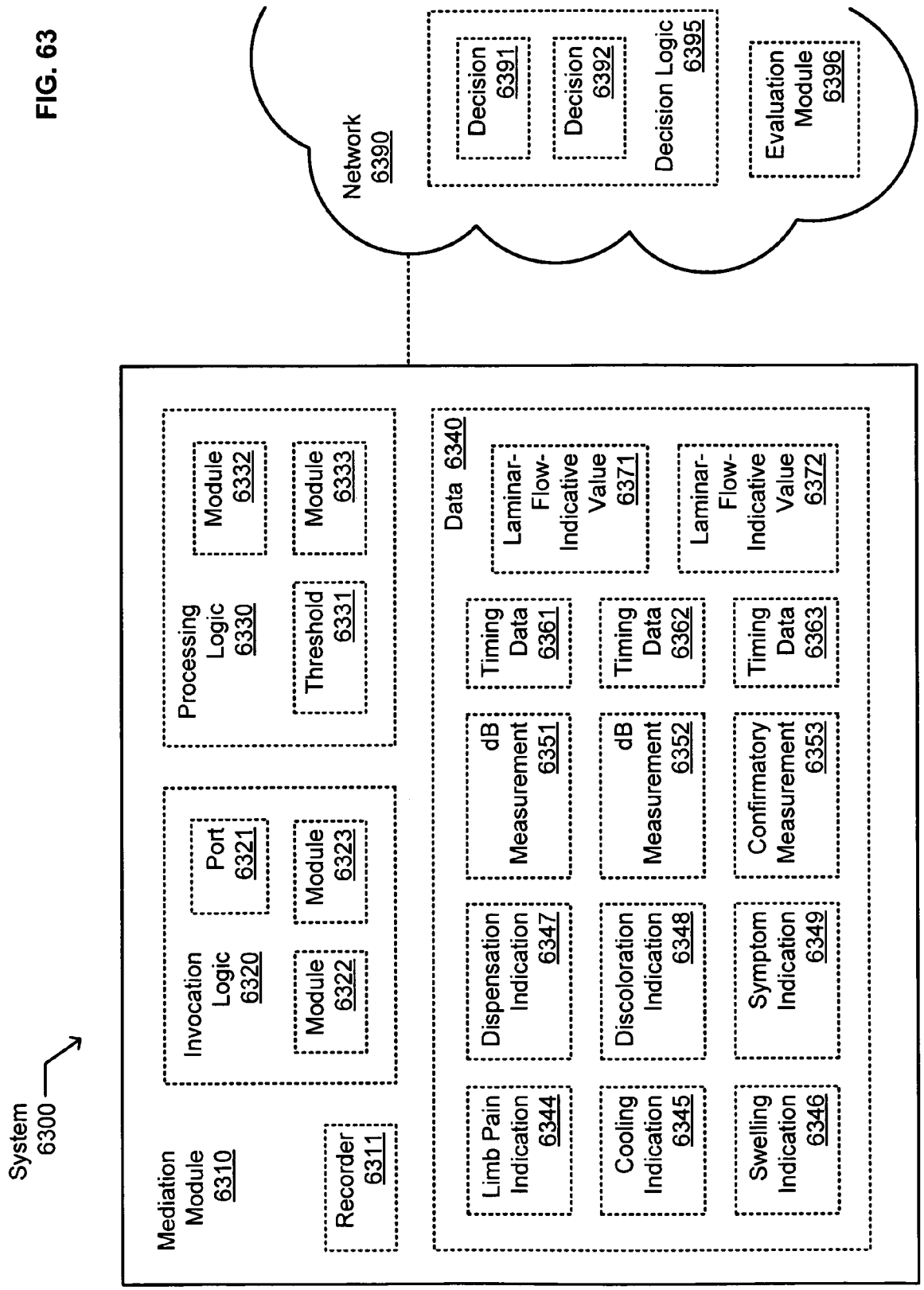

With reference now to FIG. 63, shown is a system 6300 comprising a mediation module 6310, such as may be configured to facilitate data aggregation or other such data-transformative interaction between one or more networks 6390 and a primary or other local system as described herein. Mediation module 6310 may include one or more recorders 6311; ports 6321, modules 6322, 6323 or other invocation logic 6320; or modules 6332, 6333 or other processing logic 6330, such as for applying a threshold 6331. Such components may, for example, trigger a recording or analysis in response to one or more instances of limb pain indications 6344, cooling indication 6345, swelling indications 6346, dispensation indications 6347, discoloration indications 6348, symptom indcations 6349, decibel measurements 6351, 6352, timing data 6361, 6362, 6363, or a low-enough Reynolds number computation or other laminar-flow-indicative value 6371, 6372. In some variants, moreover, these or other data types may be used as confirmatory measurements 6353 or other data configured for a contingent confirmation of a follow-up evaluation, a diagnosis, a referral, a prognosis, or some other hypothesis of potential therapeutic relevance. In some variants, for example, invocation logic 6320 may trigger one or more decisions 6391, 6392 or other responses from decision logic 6395, a remote evaluation module 6396, or other such entities. Alternatively or additionally, some or all such data 6340 may be transmitted to network 6390, for example, to permit such recording or other functions to be performed remotely.

Figure 64:
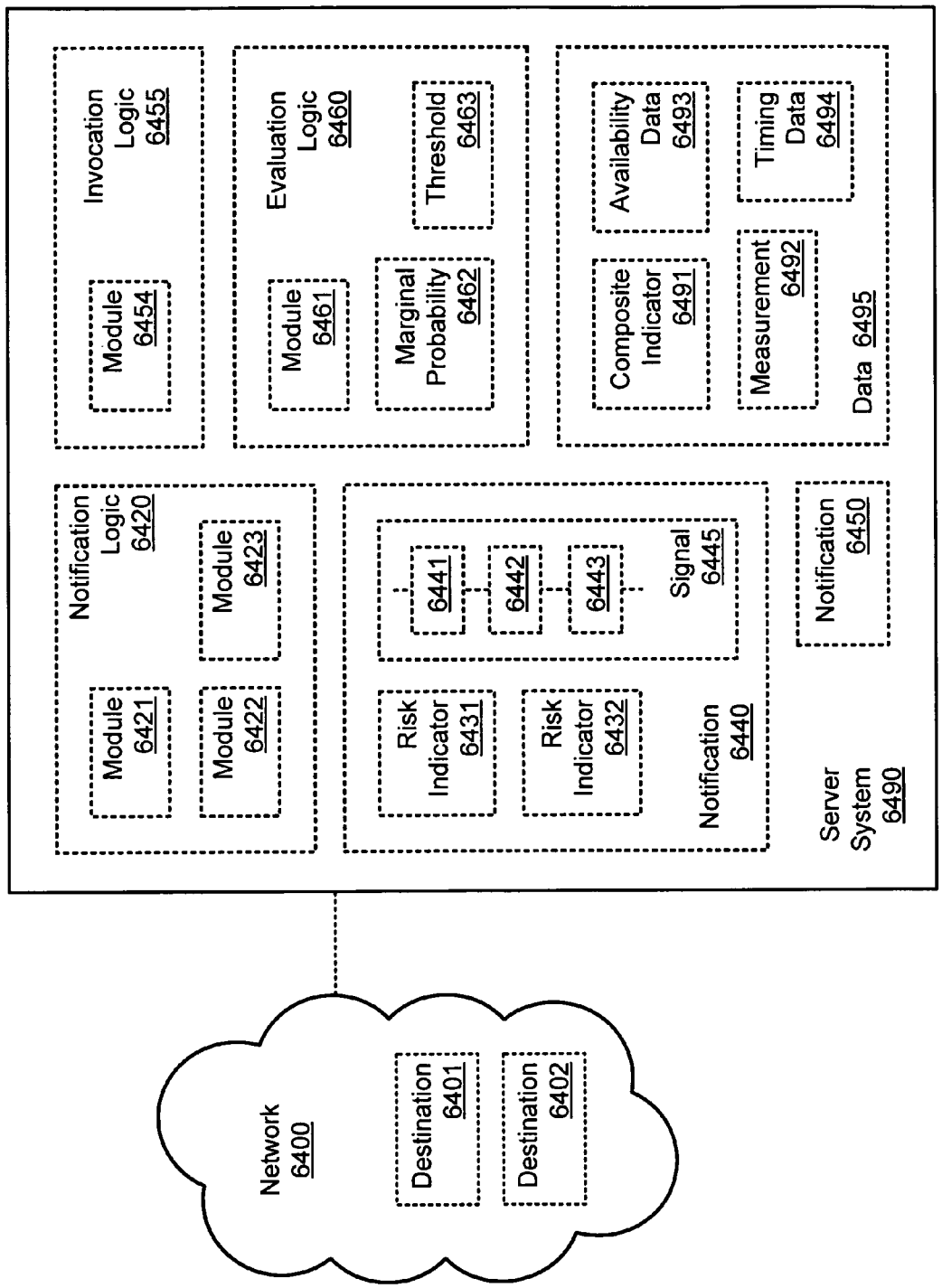

With reference now to FIG. 64, shown is a network 6400 comprising a plurality of addressable destinations 6401, 6402 supported by one or more server systems 6490. In some variants, server system 6490 may include one or more modules 6421, 6422, 6423, 6454, 6461 of notification logic 6420, invocation logic 6455, or evaluation logic 6460. Such logic may generate one or more risk indicators 6431, 6432 and/or data samples 6441, 6442, 6443 comprising signals 6445, or other such components of notifications 6440, 6450 including or otherwise manifesting one or more marginal probabilities 6462, thresholds 6463, composite indicators 6491, measurements 6492, availability data 6493, timing data 6494, or other such data 6495 useful for facilitating a diagnosis of a subject's medical or veterinary problem.

In some variants, such notification logic may be configured to facilitate selective notifications according to one or more controllable parameters. Other such embodiments are described, for example, with reference to FIGS. 12, 15, 22, 29, 30, 32, 35, and 74.

Figure 65:
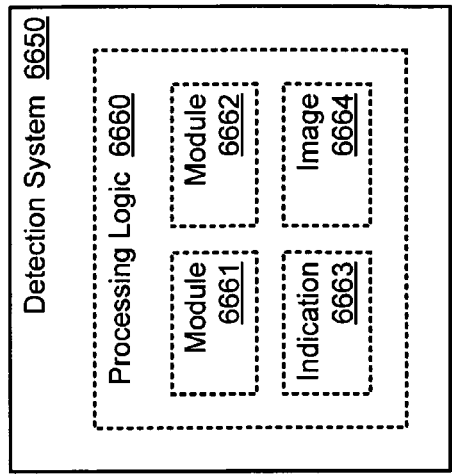

With reference now to FIG. 65, shown is an interface 6500 in which one or more technologies may be implemented. To facilitate providing information to and/or from a user as described herein, such an interface may include one or more comparators 6521, 6522 or other evaluation logic 6520 configured to facilitate an application of one or more criteria 6523 for decisions or other evaluations as described below. Alternatively or additionally, such an interface may include one or more modules 6538 or other notification logic 6540 configured to enable, trigger, configure, or otherwise facilitate one or more notifications 6544 as described herein.

Figure 66:
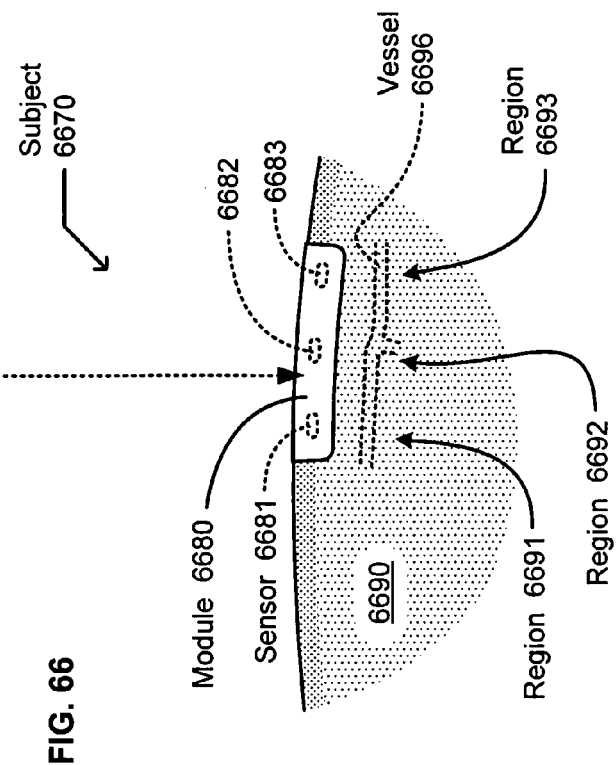

With reference now to FIG. 66, shown is a detection system 6650 comprising one or more modules 6661, 6662 of processing logic 6660 configured to interact with a module 6680 positioned on skin 6690 of subject 6670. Such modules may include one or more sensors 6681 configured to derive shape or other detectable attributes of a region 6691 at a first end of a segment of a vessel 6696 as shown, one or more sensors 6683 configured to derive shape or other detectable attributes of a region 6693 at a second end of the segment as shown, and/or one or more sensors 6682 configured to derive shape or other detectable attributes of a region 6692 at a middle portion of the segment of as shown. One or more such sensors 6681, 6682, 6683 may provide signals from which such logic may derive one or more flow-indicative or other images 6664 or other such circulatory indications 6663, for example, via any of several existing technologies.

Figure 67:
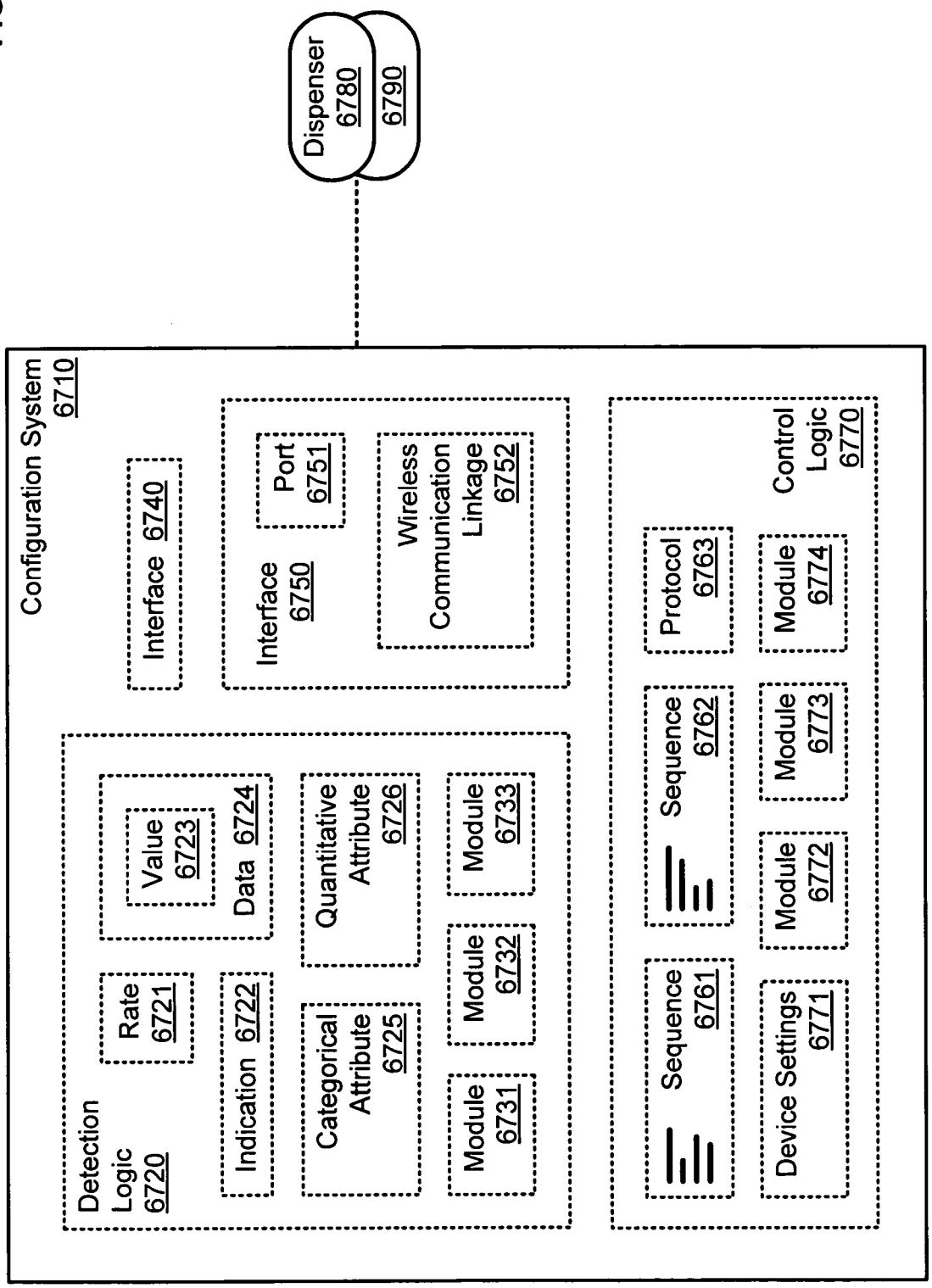

With reference now to FIG. 67, shown is a configuration system 6710 comprising one or more modules 6731, 6732, 6733 or other detection logic 6720 configured to detect one or more rates 6721, indications 6722, categorical attributes 6725, quantitative attributes 6726, or other such values 6723 or other data 6724 indicative of pathologies, therapies, or other such manifestations of conditions described herein. Alternatively or additionally, configuration system 6710 may include one or more interfaces 6740, 6750 configured to transmit data to and/or from a user, a dispenser 6780 or other device 6790 for use in proximity to a subject, or other such resources. In some variants, configuration system 6710 may likewise include one or more sequences 6761, 6762, protocols 6763, device settings 6771, or other such parametric forms configured to guide one or more modules 6772, 6773, 6774 of control logic 6770 as described herein.

With reference now to FIG. 68, shown is a filtration system 6800 configured to provide via one or more returns 6805 at least a portion of a bodily fluid received via one or more inlets 6895. In some variants, filtration system 6800 may include one or more instances of sensors 6815, 6865 in a vicinity of an air trap 6820 and/or fluid pump 6870. Alternatively or additionally, filtration system 6800 may likewise include one or more dispenser inlets 6885, membranes 6840 for use in or more filter units 6850, or other such mechanisms for adding or removing solid or other components of the fluid.

With reference now to FIG. 69, shown is a dialyser 6910 in which one or more technologies may be implemented. Dialyser 6910 may be configured to provide via one or more fluid returns 6942 a portion of a flow 6943 received via one or more fluid inlets 6941. Another portion of flow 6943 merges into a flow 6933 between the dialysate inlet(s) 6931 and dialysate return(s) 6932 through one or more membranes 6940.

Figure 70:
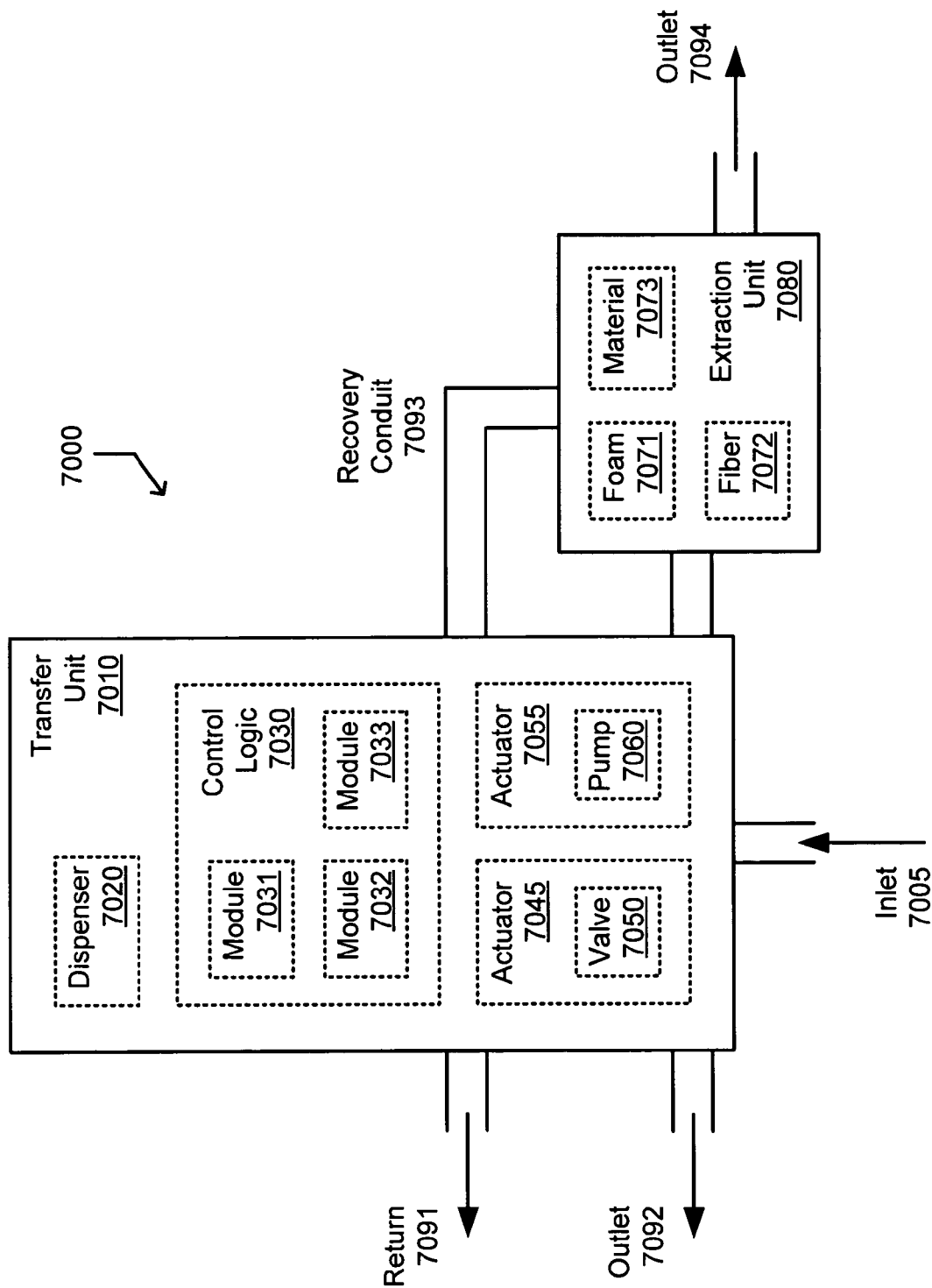

With reference now to FIG. 70, shown is another type of transfer system 7000 in which one or more technologies may be implemented. One or more valves 7050, pumps 7060, or other actuators 7045, 7055 guide blood selectively from inlet 7005 toward return 7091, outlet 7092, or extraction unit 7080. One or more modules 7031, 7032, 7033 of control logic 7030 control such actuation and/or an operation of one or more dispensers 7020 as described herein. Flow into such extraction units 7080 may come into contact with one or more foams 7071, fibers 7072, or other such materials 7073 effective for removing a sample or potentially toxic portion, which can then be removed or guided toward outlet 7094. Alternatively or additionally a remaining portion may be guided back toward transfer unit 7010 (via recovery conduit 7093) as shown. In some variants, transfer unit 7010 may be implanted or otherwise left in place even as cartridges or other such modular extraction units are occasionally replaced.

In some variants, systems described herein may be configured to include one or more mechanical control features. Other such embodiments are described, for example, with reference to FIGS. 4, 7, 10, 28, 45, 68, and 71.

Figure 71:
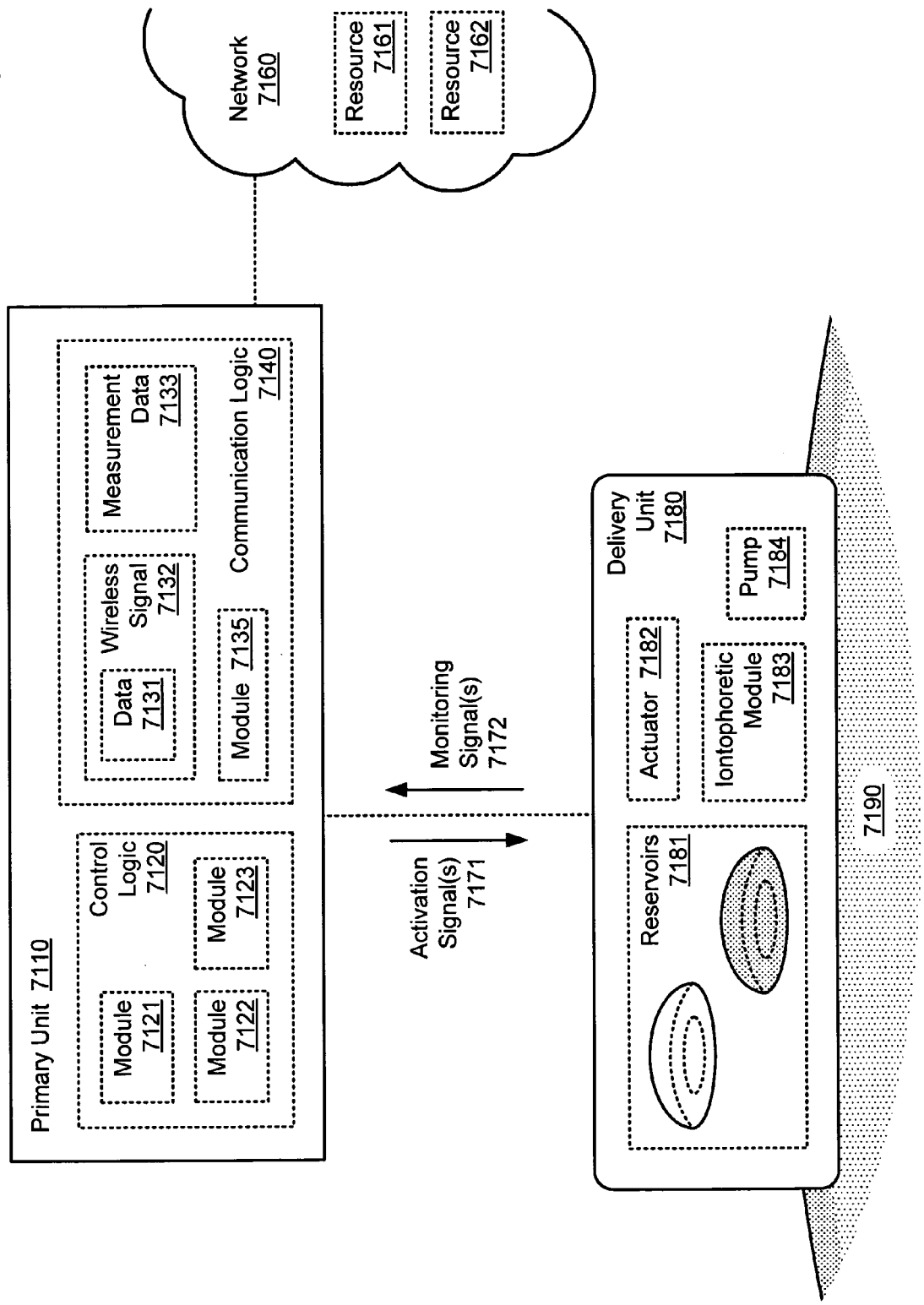

With reference now to FIG. 71, shown is system in which one or more technologies may be implemented comprising at least one primary unit 7110 operable for communication to and/or from one or more delivery units 7180. Delivery unit 7180 may include one or more reservoirs 7181, actuators 7182, iontophoretic modules 7183, or pumps 7184 in a delivery range of subject 7190. In some variants, for example, one or more modules 7121, 7122, 7123 of control logic 7120 may transmit one or more activation signals 7171 to cause a test or other therapeutic regimen relating to subject 7190. Alternatively or additionally, one or more modules 7135 of communication logic 7140 may receive measurement data 7133 or other data 7131, optionally as a component of a wireless signal 7132 or other monitoring signal(s) 7172 received by communication logic 7140 in relation to delivery unit 7180. Alternatively or additionally, such logic may selectively notify or otherwise interact with one or more resources 7161, 7162 in network 7160 as described herein.

With reference now to FIG. 120, shown is system in which one or more technologies may be implemented comprising at least one device 12010 (like primary unit 7110 of FIG. 71, e.g.) operable for communication to and/or from one or more delivery units 12001, 12002 (like delivery unit 7180, e.g.). In some variants, for example, control logic 12020 (like control logic 7120, e.g.) may transmit one or more activation signals 12071 for a therapy relating to subject 12090. Alternatively or additionally, communication logic 12040 (like communication logic 7140, e.g.) may receive data 12031, optionally as a component of a wireless signal 12032 or other monitoring signal(s) 12072 received by communication logic 12040 in relation to delivery units 12001, 12002. Alternatively or additionally, such logic may implement an interface (like user interface 4625, e.g.) or interact with a network 12060 (like network 7160, e.g.). In some variants, such systems may include a first dispenser (comprising unit 12001, e.g.) operable for dispensing lytic material, a second dispenser (comprising unit 12002, e.g.) operable for targeting an implant site 12081 by dispensing at least the lytic material, and a device 12010 operable for communicating a selection (as data 12031, e.g.) of one or more of the first dispenser or the second dispenser. This exemplifies a first dispenser operable for dispensing at least the lytic material, a second dispenser operable for targeting an implant site by dispensing at least the lytic material, and a wireless-communication device operable for communicating a selection of one or more of the first dispenser or the second dispenser.

An embodiment provides one or more instances of control logic 7030, 7270 configured to accelerate a decrease in a local concentration of one or more lytic materials 7284 in a vicinity of a blood vessel by causing one or more elements (pumps or instances of extraction unit 7080, e.g.) to extract at least a portion of such material in response to one or more lytic material indications from one or more sensors or dispensers 7290 in the vicinity. This can occur, for example, when the sensor(s) include one or more reflectance sensors 2511, transmittance sensors 2521, sonic sensors 2495, ion sensors 2550, or other suitable modes of detecting a lytic material. In some variants, such one or more such elements exemplify circuitry or other means for obtaining one or more indications of a lytic material in a vicinity of one or more body lumens comprising one or more of a reflectance sensor or a transmittance sensor. Alternatively or additionally, such software or other logic may be configured to cause a transluminal dispensation into one or more venules or other vessels 3379, 3840, 4005 as a programmed response to one or more pathology-indicative signals.

Figure 73:
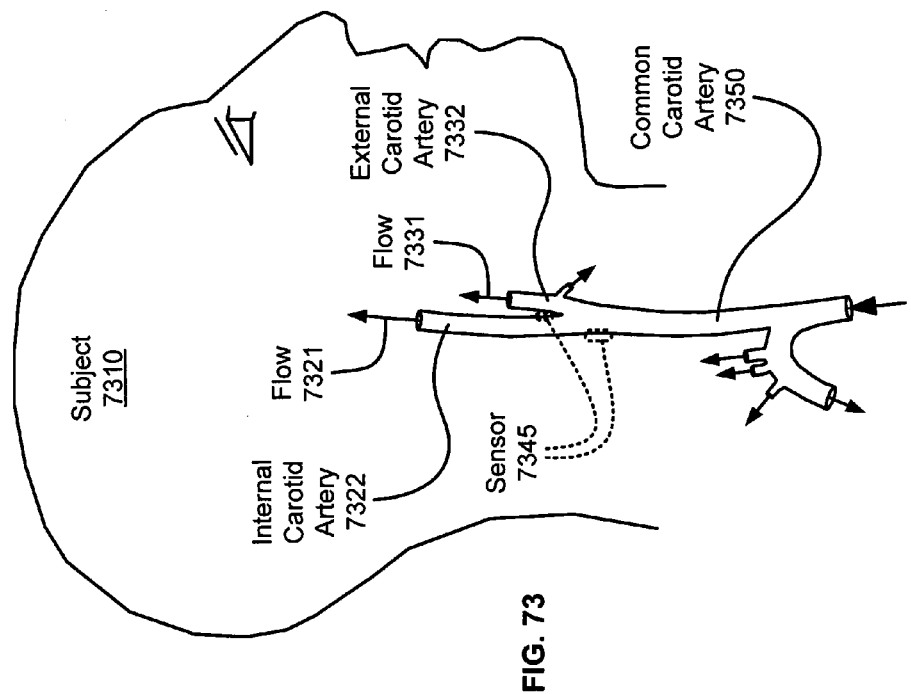
Figure 72:
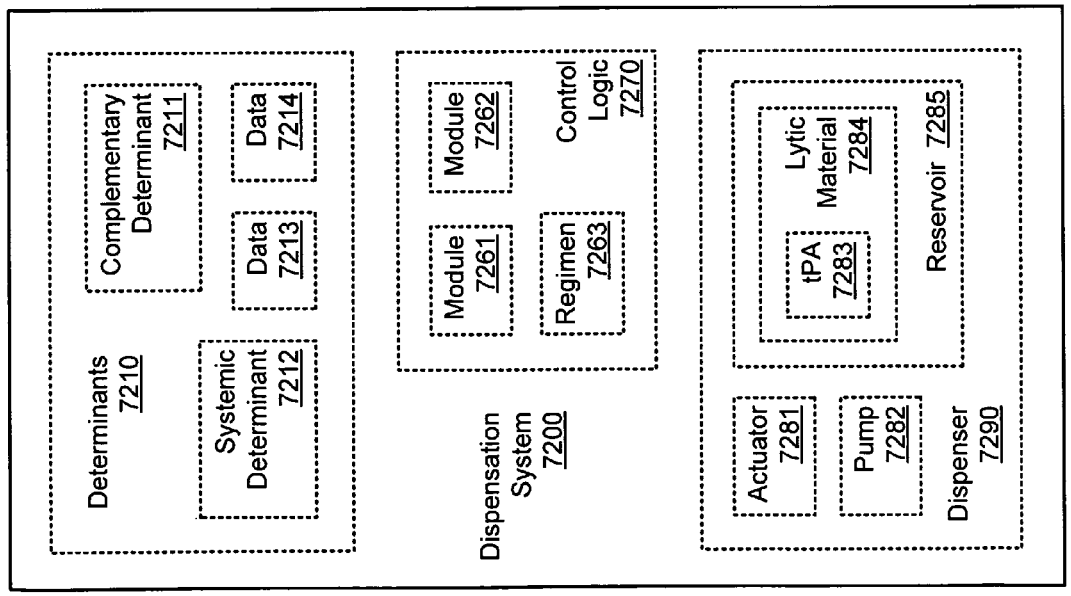

With reference now to FIG. 73, shown is a subject 7310 for whom one or more technologies may be implemented. A (right) common carotid artery 7350 bifurcates into a flow 7321 through internal carotid artery 7322 and a flow 7331 through an external carotid artery 7332. One or more sensors 7345 may be implanted or otherwise configured to detect such flows and/or arteries, optionally triggering one or more programmatic notifications, dispensations, or other such responses as described herein. In some variants, for example, apparent warning signs of a stroke may trigger a (confirmatory) diagnostic interaction with subject 7310 and/or a warning or other advice to a caregiver or others in a vicinity of subject 7310.

Figure 74:
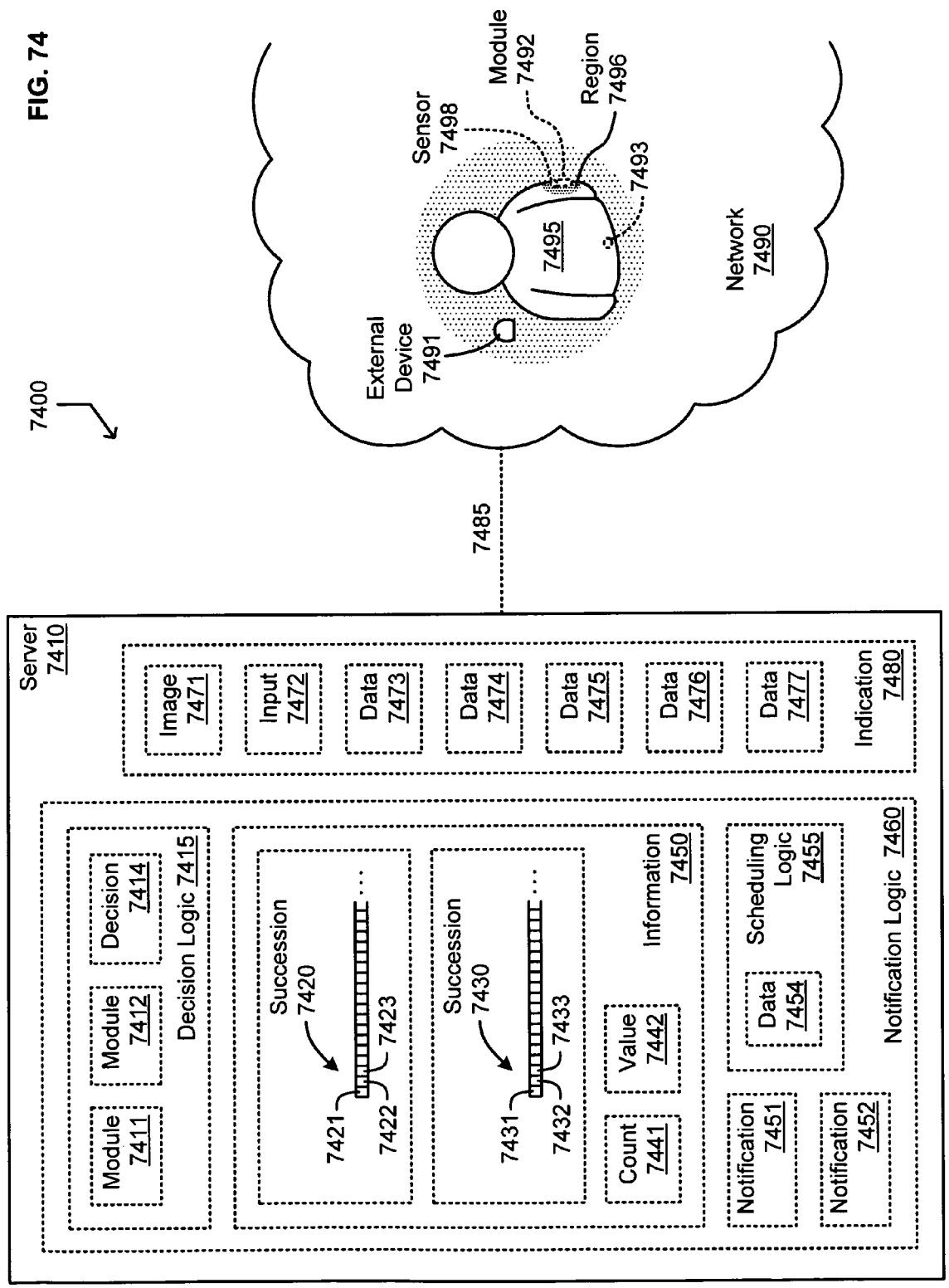

With reference now to FIG. 74, shown is a distributed system 7400 in which one or more technologies may be implemented comprising a server 7410 remote from an at-risk subject 7495 in network 7490. In some variants, for example, one or more sensors 7498 or other modules 7492 may be configured to detect or otherwise interact with an afflicted region 7496 on a limb of a subject 7495. Alternatively or additionally, external device 7491 or other such modules 7493 may be configured to facilitate communications 7485 to and/or from server 7410 and/or to detect systemic or complementary determinant conditions relating to subject 7495.

In some variants, external device 7491 may comprise a vehicle of network 7490 configured to monitor a health status of one or more occupants. Other such embodiments are described, for example, with reference to FIGS. 2, 6, and 8.

In some variants, server 7410 may include one or more special-purpose circuits or other modules 7411, 7412 of decision logic 7415 configured to generate one or more decisions 7414 in response to various indications 7480 as described herein. These may include one or more images 7471, inputs 7472, or other such sensor data or other data 7473, 7474, 7475, 7476, 7477. Alternatively or additionally, scheduling logic 7455 or other notification logic 7460 may generate notifications 7451, 7452 and/or other such consequential data 7454 derived from event counts 7441, variable values 7442 used for computations as described herein, or other such information 7450. In some contexts, such information may (optionally) include at least one succession 7420 of differences or other such indications 7421, 7422, 7423 computed, for example, from one or more successions 7430 of measurements 7431, 7432, 7433 or other values as exemplified below. Such successions 7420, 7430 may signify an amount of moisture on a subject's skin, an indication of how long a body part has been stationary, an indicator of flow, a partial pressure or other manifestation of concentration, or other such information of diagnostic utility.

Figure 75:
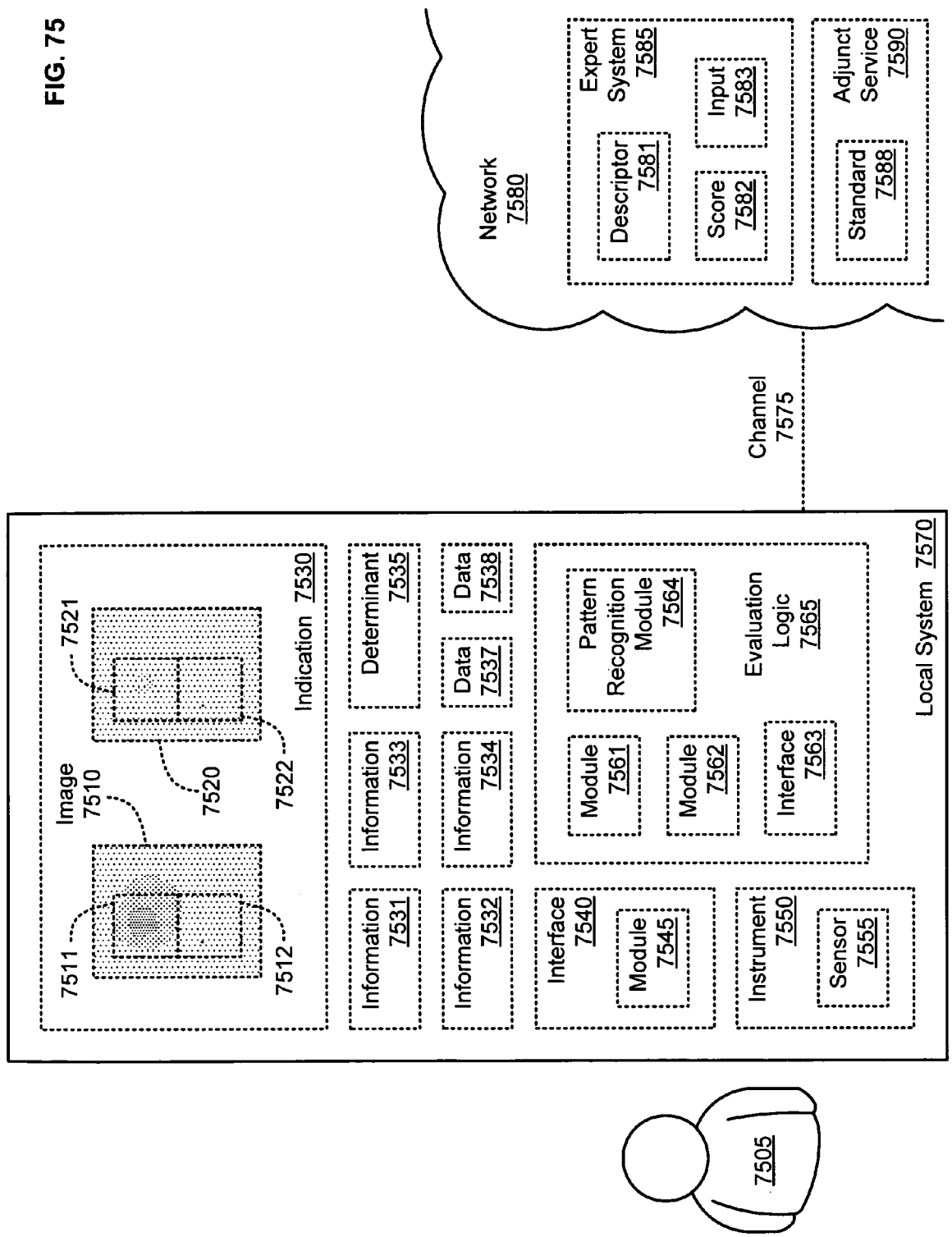

With reference now to FIG. 75, shown is a local system 7570 configured to communicate with expert system 7585 or other parts of network 7580 in relation to one or more descriptors 7581, scores 7582, or inputs 7583 as described herein. Alternatively or additionally, network 7580 may contain one or more adjunct services 7590 configured to apply one or more standards 7588 to various indications 7530 or information 7531, 7532, 7533, 7534; determinants 7535; or other data 7537, 7538 transmitted across channel 7575. In some variants, for example, such indications may include one or more images 7510, 7520 having portions 7511, 7512, 7521, 7522 of potential diagnostic utility recognizable by a remote specialist, a pattern recognition module, or other such entity. In some variants, local system 7570 may further include one or more extraction modules 7545 or other logic in a local interface 7540 configured to present abnormal indications selectively to a clinician, for example, holding an instrument 7550 (supporting one or more sensors 7555 in a vicinity of a subject 7505, e.g.). Alternatively or additionally, local system 7570 may include one or more pattern recognition modules 7564, interfaces 7563, or other modules 7561, 7562 of evaluation logic 7565 as described herein.

Figure 76:
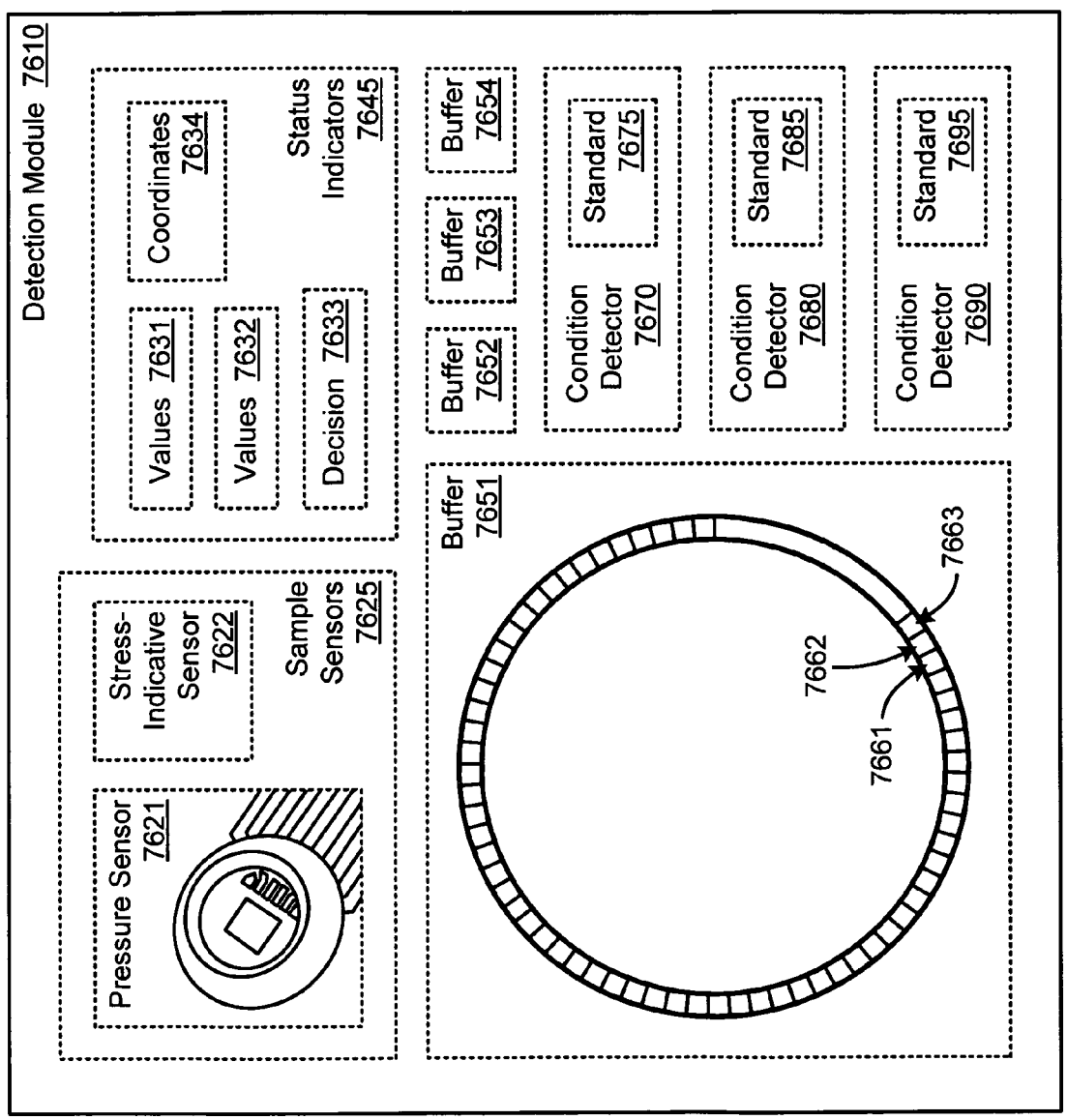

With reference now to FIG. 76, shown is a system 7600 in which one or more technologies may be implemented. A detection module 7610 as described herein may include one or more pressure sensors 7621, stress-indicative sensors 7622, or other sample sensors 7625 configured to generate values 7631, 7632, notification decisions 7633 or other such manifestations of preference, coordinates 7634, or other status indicators 7645 relating to a subject. See FIGS. 23-26. Such information can, for example, be held in a circular buffer 7651 (as successive samples 7661, 7662, 7663, for example) or other buffer 7652, 7653, 7654 configured to permit one or more condition detectors 7670, 7680, 7690 to apply standards 7675, 7685, 7695 as exemplified herein.

Figure 77:
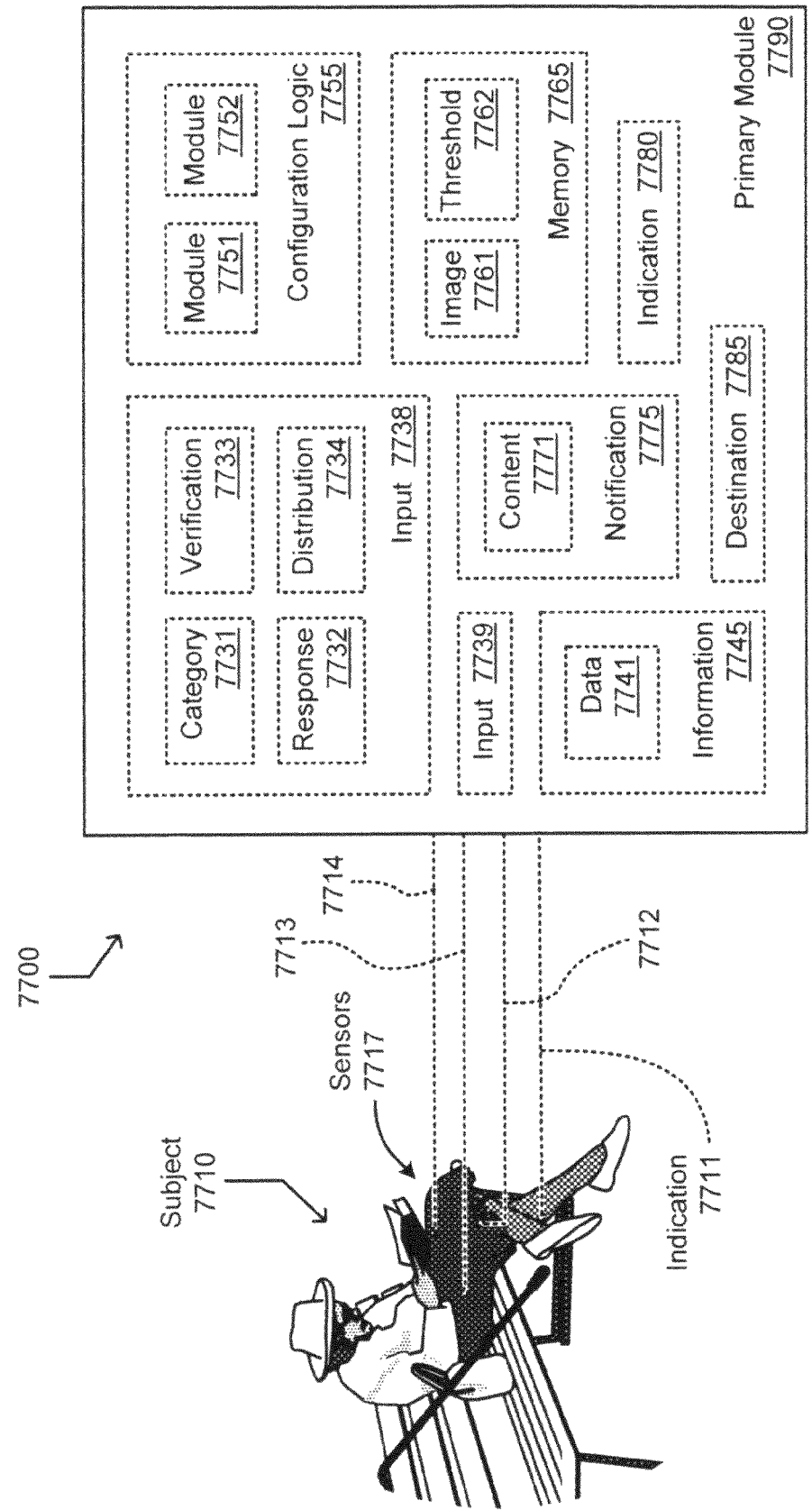

With reference now to FIG. 77, shown is a system 7700 comprising a primary module 7790 configured to accept indications 7711, 7712, 7713, 7714 from one or more auditory or other sensors 7717 in, on or about a subject 7710 of observation. Such modules may be implemented, for example, to include or interact with one or more components or contexts of FIGS. 1-76. In some variants, inputs 7738, 7739 or other information 7745 as described herein may include one or more categories 7731, responses 7732, verifications 7733, distributions 7734, or other such data 7741 suitable for inclusion, for example, as content 7771 of a notification 7775. Alternatively or additionally, one or more modules 7751, 7752 or other configuration logic 7755 may maintain one or more images 7761, apply one or more thresholds 7762, or otherwise provide one or more indications 7780 or notification destinations 7785 in response to then-current contents of memory 7765.

In some variants, system 7700 may be configured to include a vehicle configured to monitor a health status of one or more occupants. Other such embodiments are described, for example, with reference to FIGS. 2, 6, and 8.

In some embodiments, data can be "acceptable" to a data analysis module if some or all of the data can be processed by the module with success. An indication of acceptable data can be appropriate in response to detecting an apparent presence or absence of a pattern in the data, for example, or to determining that the data has a file size or header format that is typical for data processed by the analysis module.

Figure 78:
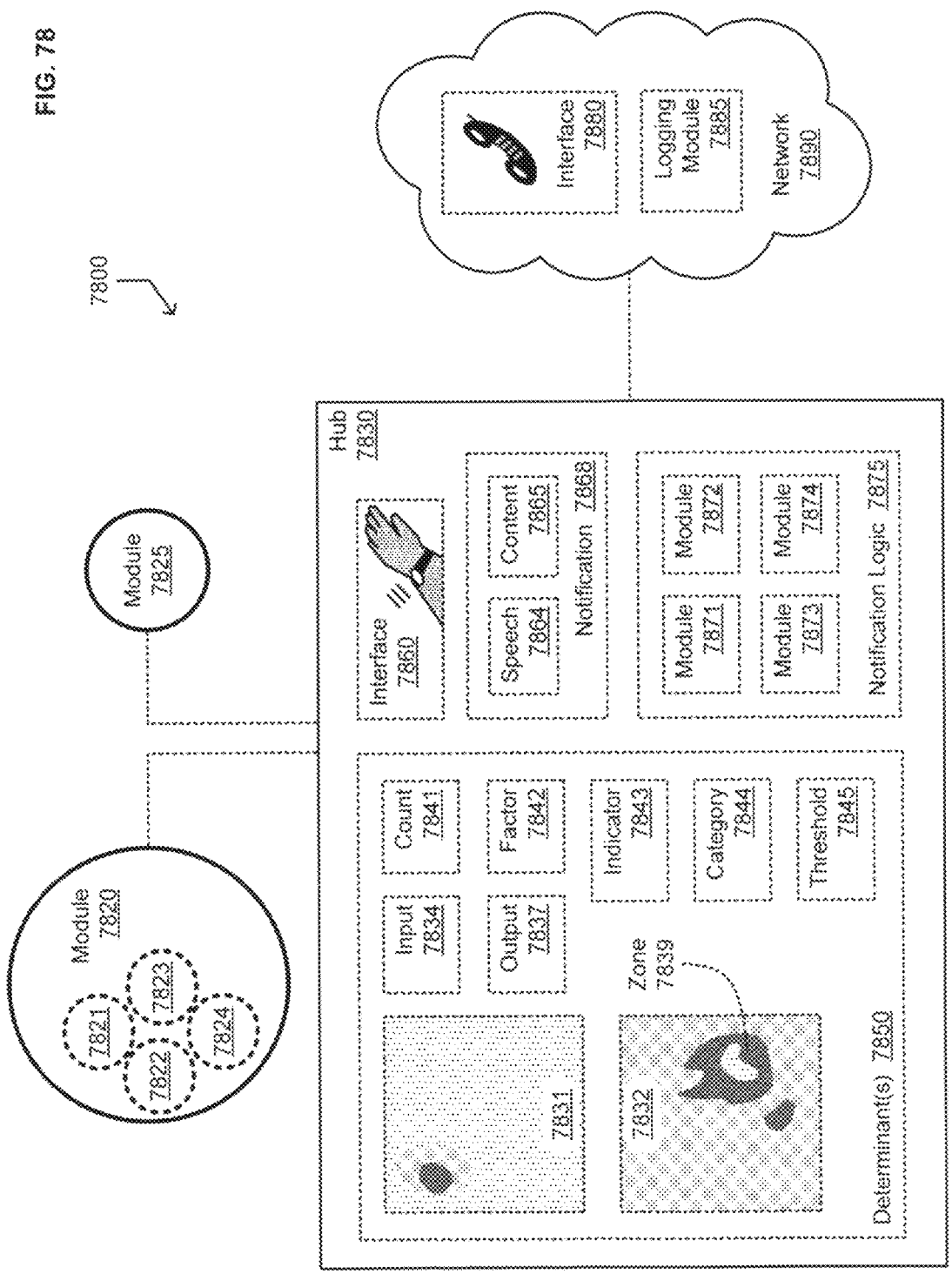

With reference now to FIG. 78, shown is a system 7800 comprising one or more modules 7820, 7825 in communication with a hub 7830 having access to one or more networks 7890. In some variants, for example, a module 7820 positioned on or near a subject may include one or more sensors 7821, 7822, 7823, 7824 operable for transmitting one or more images 7831, 7832 (depicting zone 7839, e.g.), counts 7841, outputs 7837 from sensors, indicators 7843, thresholds 7845 or other factors 7842 to be applied, or other such determinants 7850. Alternatively or additionally, hub 7830 may receive (via one or more interfaces 7860, e.g.) one or more categories 7844 or other such input 7834 from a user or other local entity. In response to such determinants, one or more modules 7871, 7872, 7873, 7874 of notification logic 7875 may configure one or more notifications 7868 for local delivery (via interface 7860, e.g.) and/or delivery to one or more interfaces 7880 or logging modules 7885 of network 7890. In some contexts, module 7872 may configure notification 7864 to include a raw sample of slurred speech 7864 provided by a subject in response to programmatic queries, for example, or other such content 7865 of an established diagnostic regimen. Such content may be omitted, in some contexts, in response to a determination that such content is normal (not slurred, e.g.) as described herein.

Figure 79:
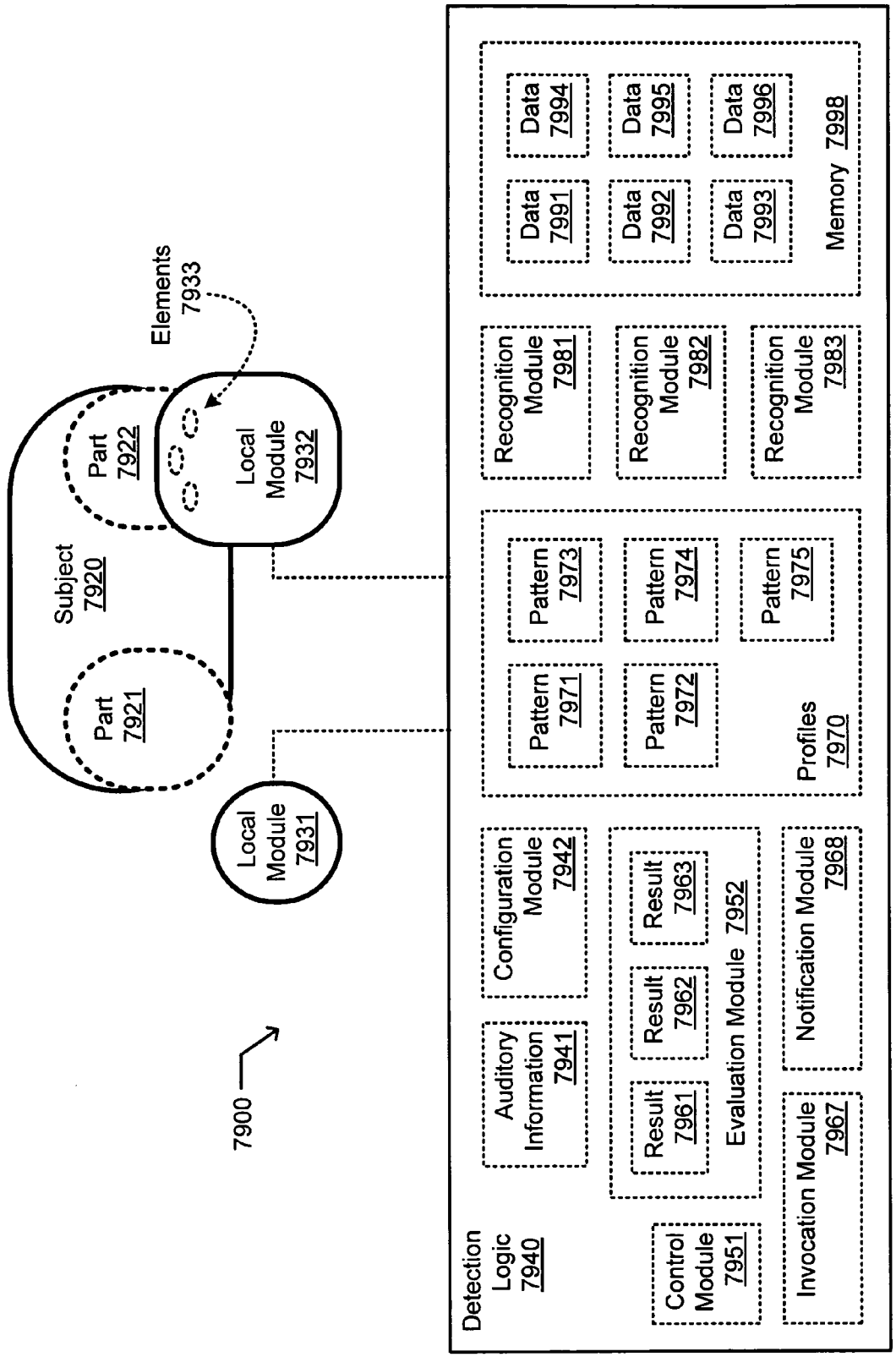

With reference now to FIG. 79, shown is a system 7900 comprising one or more local modules 7931, 7932 each in a vicinity of one or more body parts 7921, 7922 of subject 7920. In some contexts, such local modules 7932 may include one or more sensors, support elements, dispensers, or other such elements 7933 positioned in contact with or otherwise adjacent a body part 7922 of interest. In various applications, detection logic 7940 may include one or more instances of configuration modules 7942, control modules 7951, invocation modules 7967, notification modules 7968, or various recognition modules 7981, 7982, 7983 configured to process auditory information 7941 or other input data as described herein. Detection logic 7940 may (optionally) include one or more evaluation modules 7952 configured to implement one or more computed results 7961, comparison results 7962, user selections, or other such evaluation results 7963. Such results may arise from a recognition of one or more patterns 7971, 7972, 7973, 7974, 7975 or profiles 7970 (combinations of patterns, e.g.) evident in data 7991, 7992, 7993, 7994, 7995, 7996 residing in memory 7998. In some variants, for example, recognition module 7981 may be configured to recognize one or more extended measurement trends or other such pathological patterns 7971 even in data 7993 still in a normal range, in some contexts. Alternatively or additionally, one or more recognition modules 7982 may be configured to detect a shape, color, or other optical pattern 7975 characteristic of a scar, birthmark, or other common and/or unchanging irregularity manifested in data 7996 and not indicative of a circulatory pathology.

In some variants, such notification logic may be configured to facilitate selective notifications according to one or more controllable parameters. Other such embodiments are described, for example, with reference to FIGS. 30, 32, 35, 74, 77, 78, 80, 85-96, and 104-107.

Figure 80:
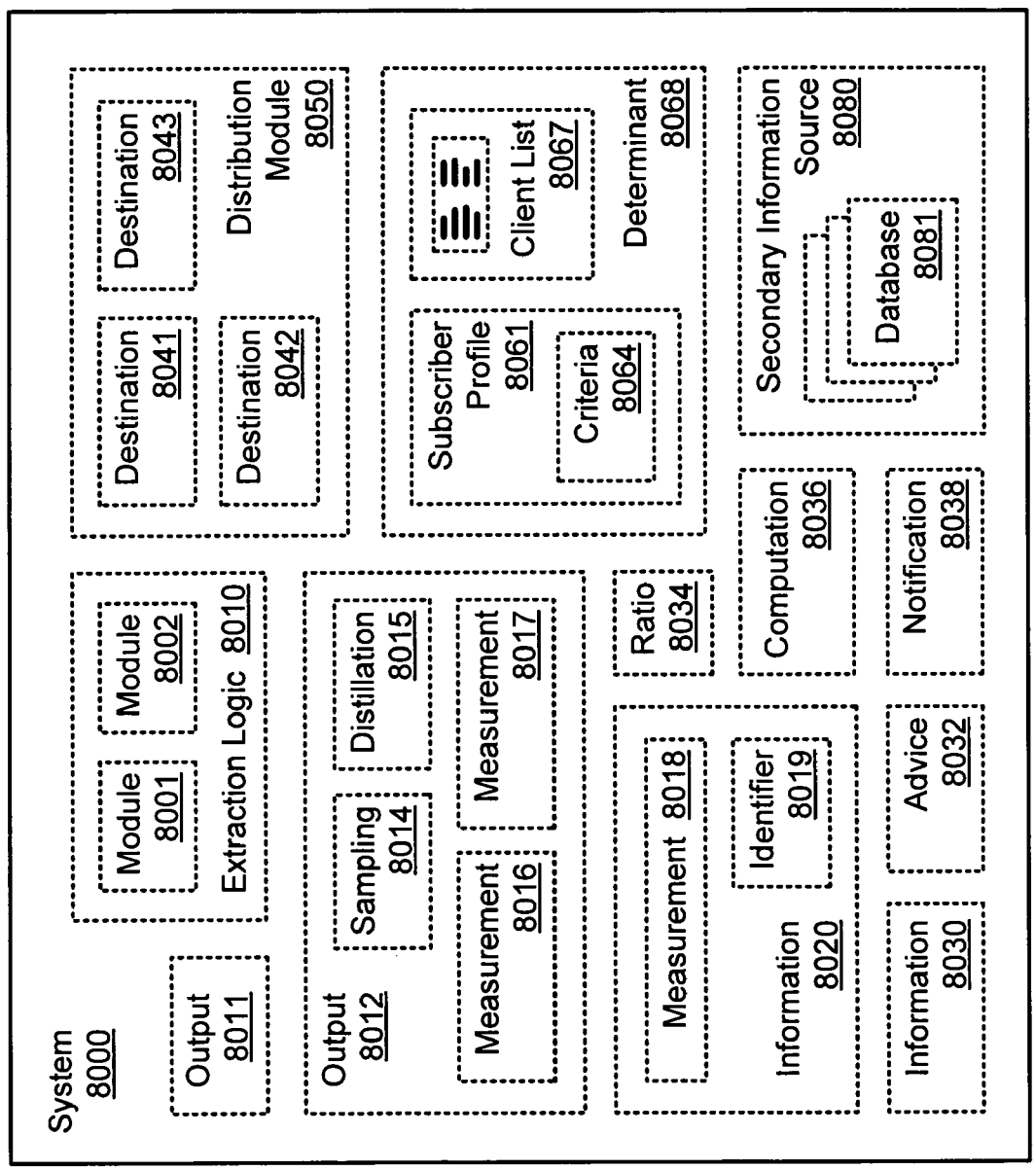

With reference now to FIG. 80, shown is a system 8000 comprising one or more modules 8001, 8002 of extraction logic 8010 configured to process one or more samplings 8014, distillations 8015, measurements 8016, 8017, 8018, identifiers 8019, or other such output 8011, 8012 from sensors or other detection logic described herein. In some embodiments, such a "distillation" can comprise an average, estimate, range, or other computation at least partly distilling a set of data. It can likewise include an indexing, sorting, summarization, distributed sampling, or other process having a purpose or effect of showing some aspect of the data more concisely or effectively than a conventional display of the entire data. Selecting a last portion of a data set can constitute a distillation, for example, in a context in which the data's utility apparently increases. Those skilled in the art will recognize many useful modes of distilling data in light of the state of the art and of teachings herein.

Such information 8020, 8030 may further include one or more instances of programmatic advice 8032, ratios 8034, computations 8036, or other such components of notifications 8038. In some variants, for example, at least one distribution module 8050 may be configured to use such information to select one or more destinations 8041, 8042 among a plurality of destinations 8041, 8042, 8043 in response to these or other criteria 8064 (defined in one or more subscriber profiles 8061, e.g.) or to a client list 8067. Alternatively or additionally, notification logic 1290, 3535, 3991, 6180, 7460, 7875 or other responsive logic described herein may use one or more such determinants 8068 to select among one or more databases 8081 or other secondary information sources 8080 to draw upon for contextual information to be included in such notifications.

In some variants, logic for applying one or more thresholds or other such criteria may be configured to preserve relevant data selectively, to generate a summary or evaluation, or otherwise to perform suitable data extractions. Other such embodiments are described, for example, with reference to FIGS. 1, 8, 12, 31, 32, 59, 65, and 85. In some embodiments, such data extraction criteria can include maxima or other comparison values applied to durations, counts, lengths, widths, frequencies, signal magnitudes or phases, digital values or the like. Such criteria can be applied by determining when or how often a definable pattern can be found: a text string, a quantity, a cough-like sound, an arrhythmia, a visible dilation, a failure to respond, a non-change, an allergic response, a symptom relating to an apparent condition of the user, or the like.

Figure 81:
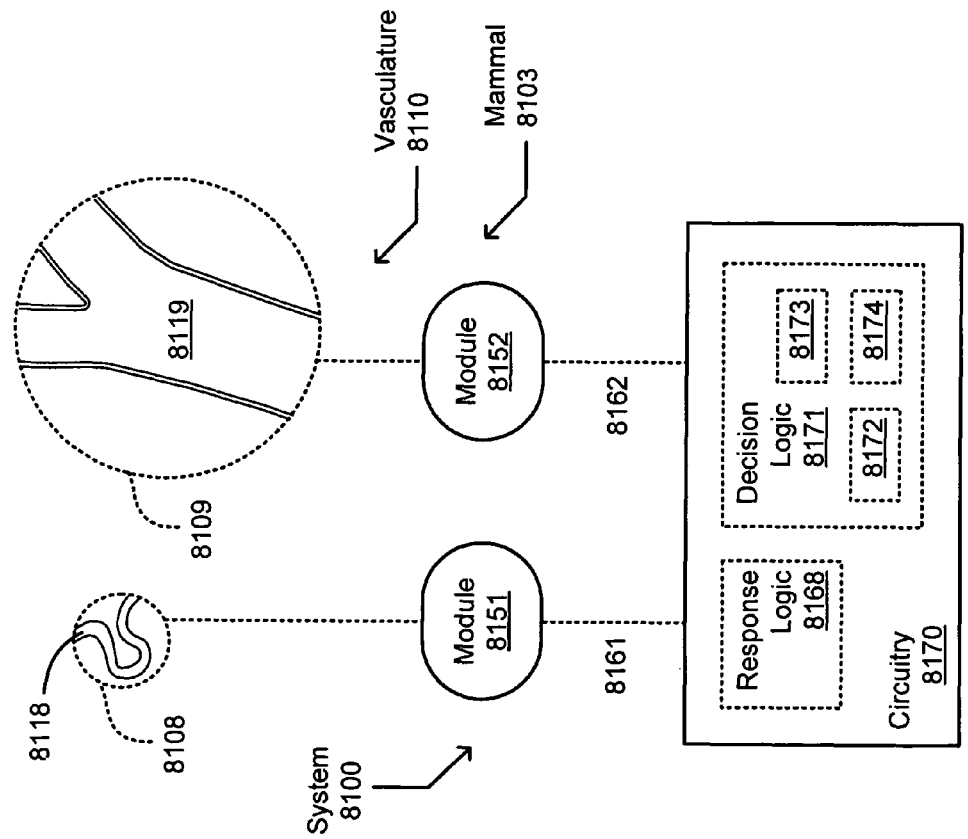

With reference now to FIG. 81, shown is a system 8100 in which one or more technologies may be implemented. Respective information 8161, 8162 may be obtained about two or more body parts 8108, 8109 respectively containing blood vessels 8118, 8119 of a vasculature 8110 of a mammal 8103. Circuitry 8170 configured to receive such information 8161, 8162 may include one or more instances of modules 8151, 8152, response logic 8168, or modules 8172, 8173, 8174 of decision logic 8171.

Figure 82:
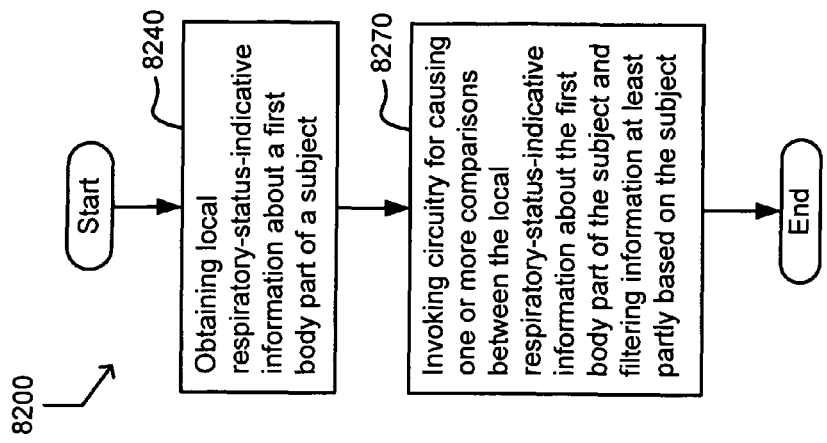
FIG. 82 depicts a high-level logic flow of an operational process.

With reference now to FIG. 82, shown is a flow 8200 comprising operation 8240—obtaining local respiratory-status-indicative information about a first body part of a subject (e.g. response logic 8168 receiving one or more measurements or other information 8161 indicative of a past or present respiratory status of organ tissues or other parts of a patient under observation). This can occur, for example, in a context in which response logic 8168 receives the information 8161 via a sensor-containing module 8151 or other direct mode of observation.

In light of teachings herein, numerous existing techniques may be applied for detecting respiratory transitions or other phenomena from measurements or other raw data as described herein without undue experimentation. See, e.g., U.S. Pat. No. 7,308,292 ("Optical-based sensing devices"); U.S. Pat. No. 7,305,262 ("Apparatus and method for acquiring oximetry and electrocardiogram signals"); U.S. Pat. No. 7,200,431 ("Implantable blood flow monitoring system"); U.S. Pat. No. 7,136,704 ("Blood oxygen monitoring system and a lead therefor"); U.S. Pat. No. 7,025,778 ("Endovascular graft with pressure temperature flow and voltage sensors"); U.S. Pat. No. 7,011,633 ("Blood flow measuring apparatus"); U.S. Pat. No. 7,006,858 ("Implantable retrievable sensors and immunosensors"); U.S. Pat. No. 7,004,907 ("Blood-pressure monitoring device featuring a calibration-based analysis"); U.S. Pat. No. 6,895,265 ("Implantable sensor"); U.S. Pat. No. 6,731,976 ("Device and method to measure and communicate body parameters"); U.S. Pat. No. 6,682,490 ("Apparatus and method for monitoring a condition inside a body cavity"); U.S. Pat. No. 6,475,170 ("Acoustic biosensor for monitoring physiological conditions in a body implantation site"); U.S. Pat. No. 6,268,161 ("Biosensor"); U.S. Pat. No. 6,206,835 ("Remotely interrogated diagnostic implant device with electrically passive sensor"); U.S. Pat. No. 6,047,203 ("Physiologic signs feedback system"); U.S. Pat. No. 6,015,387 ("Implantation devices for monitoring and regulating blood flow"); U.S. Pat. No. 5,967,986 ("Endoluminal implant with fluid flow sensing capability"); U.S. Pat. No. 5,833,603 ("Implantable biosensing transponder"); U.S. Pat. No. 5,601,811 ("Substantive water-soluble cationic UV-absorbing compounds"); U.S. Pat. No. 5,593,431 ("Medical service employing multiple DC accelerometers for patient activity and posture sensing and method"); U.S. Pat. No. 5,188,106 ("Method and apparatus for chronically monitoring the hemodynamic state of a patient using doppler ultrasound"); U.S. Pat. No. 4,536,274 ("pH and CO.sub.2 sensing device and method of making the same").

Operation 8270 describes invoking circuitry for causing one or more comparisons between the local respiratory-status-indicative information about the first body part of the subject and filtering information at least partly based on the subject (e.g. module 8172 of decision logic 8171 triggering one or more other modules 8174 to compare information 8161 with information 8162 received from another module 8152 configured for observing another body part 8109 in a vicinity of blood vessel 8119). This can occur, for example, in a context in which decision logic 8174 receives at least some of the information 8161 about body part 8108 via response logic 8168 and in which one or more modules 8172, 8174 of decision logic 8171 perform such a comparison within a proximity of mammal 8103. In some variants, for example, some or all of the filtering information may be derived from similar measurements of nearby tissue and/or other information about the "first" body part. Alternatively or additionally, one or more of the modules 8174 of decision logic 8171 may retain and/or forward a sample of the information to a central facility for other such comparisons or for further evaluation.

In some embodiments, "causing" events can include triggering, producing or otherwise directly or indirectly affecting the events. This can include causing the events remotely, concurrently, partially, or otherwise as a "cause in fact," whether or not a more immediate cause also exists.

In some embodiments, an action can be taken "at least partly based on" some data or event. This can include a context in which the event directly or indirectly triggers or directs the action, or otherwise in which the outcome of the action can depend upon some aspect of the data. Those skilled in the art will recognize many such relationships that are useful in light of the state of the art and of teachings herein.

In light of teachings herein, numerous existing techniques may be applied for generating and applying quantitative or other comparative criteria as described herein without undue experimentation. See, e.g., U.S. Pat. No. 7,304,580 ("Intelligent medical vigilance system"); U.S. Pat. No. 7,286,872 ("Method and apparatus for managing data from multiple sensing channels"); U.S. Pat. No. 7,218,966 ("Multi-parameter arrhythmia discrimination"); U.S. Pat. No. 7,200,431 ("Implantable blood flow monitoring system"); U.S. Pat. No. 7,113,819 ("Method and apparatus for monitoring the condition of a fetus"); U.S. Pat. No. 7,065,465 ("Method and system for multi-sensor data fusion"); U.S. Pat. No. 6,983,178 ("Probe for use in non-invasive measurements of blood related parameters"); U.S. Pat. No. 6,942,616 ("System and method for collecting and transmitting medical data"); U.S. Pat. No. 6,908,431 ("System and method for providing feedback to an individual patient for automated remote patient care"); U.S. Pat. No. 6,809,653 ("Telemetered characteristic monitor system and method of using the same"); U.S. Pat. No. 6,802,811 ("Sensing, interrogating, storing, telemetering and responding medical implants"); U.S. Pat. No. 6,731,976 ("Device and method to measure and communicate body parameters"); U.S. Pat. No. 6,478,737 ("System and method for analyzing normalized patient voice feedback an automated collection and analysis patient care system"); U.S. Pat. No. 6,416,471 ("Portable remote patient telemonitoring system"); U.S. Pat. No. 6,387,048 ("Implantable sensor and integrity tests therefor"); U.S. Pat. No. 6,336,900 ("Home hub for reporting patient health parameters"); U.S. Pat. No. 6,312,378 ("System and method for automated collection and analysis of patient information retrieved from an implantable medical device for remote patient care"); U.S. Pat. No. 6,149,674 ("Patient thermal regulation system"); U.S. Pat. No. 6,047,203 ("Physiologic signs feedback system"); U.S. Pat. No. 5,833,603 ("Implantable biosensing transponder"); U.S. Pat. No. 5,558,638 ("Patient monitor and support system").

Figure 83:
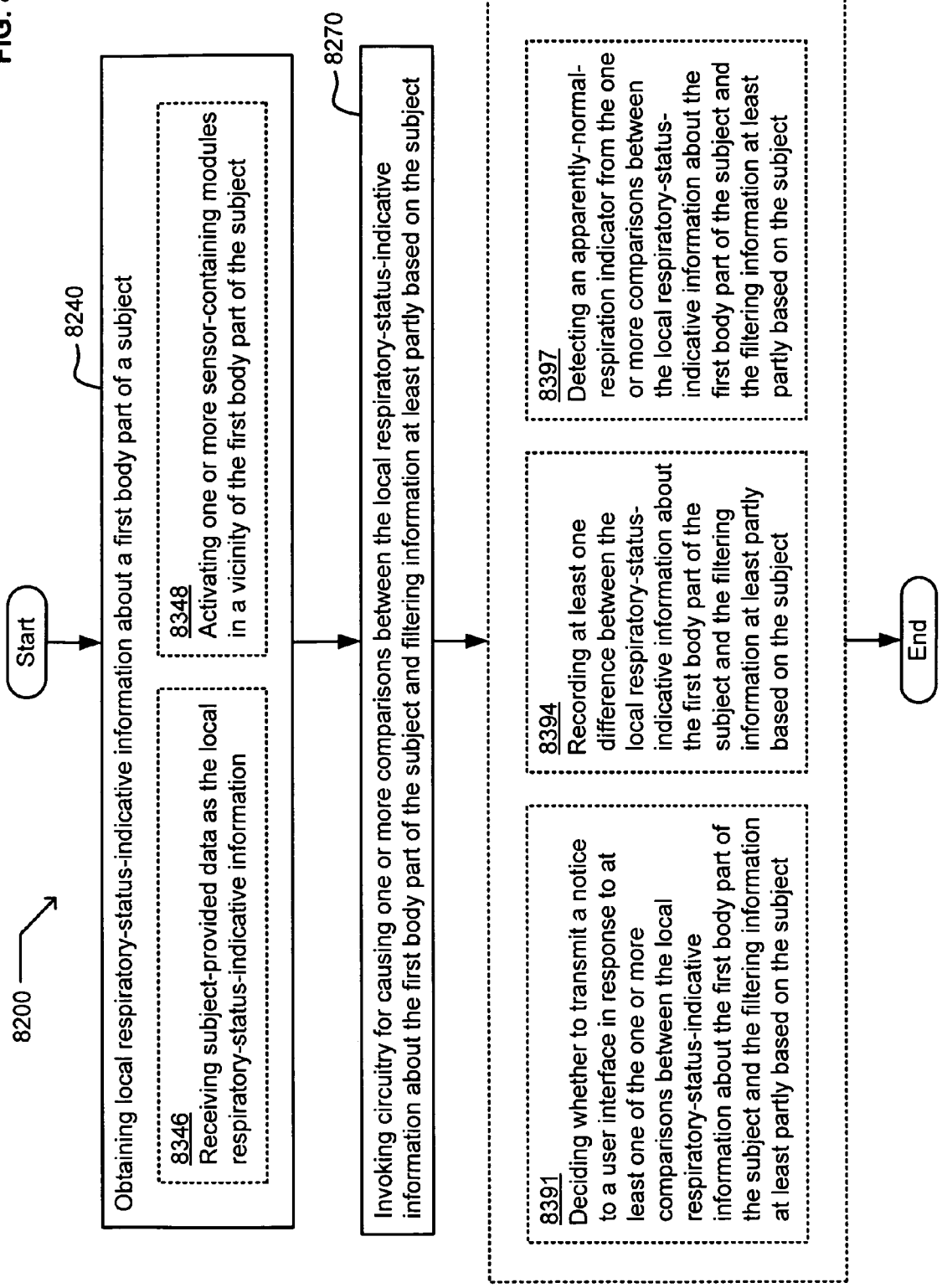

With reference now to FIG. 83, there are shown several variants of the flow 8200 of FIG. 82. Operation 8240—obtaining local respiratory-status-indicative information about a first body part of a subject—may (optionally) include one or more of the following operations: 8346 or 8348. In some embodiments, variants of operation 8240 may be performed by one or more instances of processing modules 1430, 1650, 1680; response modules 1620; or decision logic 275, 1350, 1460, 2250, 2730, 3230, 5750, 5930, 6130, 6395, 7415. Flow 8200 may likewise (optionally) include one or more of the following operations: 8391, 8394 or 8397. Alternatively or additionally, flow 8200 may be performed in a context as described above with reference to any of FIGS. 1-80 and/or in conjunction with other flow variants as described below.

Operation 8346 describes receiving subject-provided data as the local respiratory-status-indicative information (e.g. term recognition module 1625 or other components of response module 1620 receiving subject-provided data 2921, 2922 directly or indirectly from one or more interfaces 2962 or other instruments 2930). This can occur, for example, in a context in which an instance of primary module 1600 of FIG. 16 resides within network 2995 and performs operation 8240 by interacting with one or more instruments 2930 in a proximity of subjects. In some variants, for example, a software or other term recognition module 1625 identifies one or more diagnoses or other symptom-indicative parameters 1624 within a subject's speech or other communication 2935. Alternatively or additionally, one or more other modules 1621 may be configured to record, report, or otherwise respond to such communication 2935 conditionally as described herein, such as by a timely reciprocal communication 2935 with subject 2920. In some variants, moreover, one or more handheld devices 2961 or other interfaces 2962 may perform operation 8346 in relation to a subject within a proximity thereof, such as by receiving keyed or other input 2965.

In light of teachings herein, numerous existing techniques may be applied for requesting or otherwise receiving demographic parameters, event data, or other data via an interface with subjects as described herein without undue experimentation. See, e.g., U.S. Pat. No. 7,258,666 ("System and methods for monitoring a patient's heart condition"); U.S. Pat. No. 6,968,375 ("Networked system for interactive communication and remote monitoring of individuals"); U.S. Pat. No. 6,926,668 ("System and method for analyzing normalized patient voice feedback in an automated collection and analysis patient care system"); U.S. Pat. No. 6,893,396 ("Wireless internet bio-telemetry monitoring system and interface"); U.S. Pat. No. 6,755,783 ("Apparatus and method for two-way communication in a device for monitoring and communicating wellness parameters of ambulatory patients"); U.S. Pat. No. 6,478,737 ("System and method for analyzing normalized patient voice feedback an automated collection and analysis patient care system"); U.S. Pat. No. 6,168,563 ("Remote health monitoring and maintenance system").

Operation 8348 describes activating one or more sensor-containing modules in a vicinity of the first body part of the subject (e.g. linking module 1690 transmitting a sonic, optical, or other activation signal 1693 to an implant 1730 or other suitable device within a proximity of tissue 1725 of subject 1720). This can occur, for example, in embodiments in which such an implant 1730 or hand-held instrument 1760 implements one or more primary modules 1600, in which such signals 1693 trigger or otherwise enable an effective image capture or other detection operation as described herein via one or more transducers 1767 or other sensors 1733, and in which a clot or other circulatory obstruction may otherwise be difficult to locate and treat in time. Alternatively or additionally, such sensors may be configured to include or otherwise provide data to software 1974 or other such measurement logic 1975 operable for performing operation 8348 by detecting a status or other attribute of limb 1722 or other body parts 1920 within an effective detection range of one or more of the sensor(s).

In light of teachings herein, numerous existing techniques may be applied for implementing and interacting with decision logic, data capture or transformation configurations, or other components within or for use with condition or event detection as described herein without undue experimentation. See, e.g., U.S. Pat. No. 7,304,580 ("Intelligent medical vigilance system"); U.S. Pat. No. 7,261,690 ("Apparatus for monitoring health, wellness and fitness"); U.S. Pat. No. 7,155,281 ("Complimentary activity sensor network for disease monitoring and therapy modulation in an implantable device"); U.S. Pat. No. 7,024,234 ("Method and apparatus for monitoring the autonomic nervous system"); U.S. Pat. No. 6,984,207 ("Passive physiological monitoring (P2M) system"); U.S. Pat. No. 6,980,851 ("Method and apparatus for determining changes in heart failure status"); U.S. Pat. No. 6,689,069 ("Apparatus and method for blood pressure pulse waveform contour analysis"); U.S. Pat. No. 6,600,949 ("Method for monitoring heart failure via respiratory patterns"); U.S. Pat. No. 6,358,201 ("Method and apparatus for facilitating physiological coherence and autonomic balance"); U.S. Pat. No. 6,312,378 ("System and method for automated collection and analysis of patient information retrieved from an implantable medical device for remote patient care"); U.S. Pat. No. 6,179,793 ("Cardiac assist method using an inflatable vest"); U.S. Pat. No. 5,978,693 ("Apparatus and method for reduction of motion artifact"); U.S. Pat. No. 4,860,751 ("Activity sensor for pacemaker control").

Operation 8391 describes deciding whether to transmit a notice to a user interface in response to at least one of the one or more comparisons between the local respiratory-status-indicative information about the first body part of the subject and the filtering information at least partly based on the subject (e.g. module 1441 of decision logic 1460 deciding whether to send one or more notices 1472 via transmitter 1473 in response to one or more comparators 1431, 1433). This can occur, for example, in a context in which decision logic 1460 performs operation 8270, in which an interface or other component of remote module 3190 (of FIG. 31) is configured to receive notice 1471, 1472 or other output 1485, and in which the filtering information applied by such comparators 1431, 1433 may each apply an identifier, a type, an evaluation, or some other attribute of a specific subject for which such information is required or forbidden. In some variants, for example, the information transmitted for display may contain all local status indicators derived or otherwise measured for a medical patient. Alternatively or additionally, module 1441 may be configured to cause local interface 1475 to display or otherwise reveal one or more such notice 1471.

In light of teachings herein, numerous existing techniques may be applied for the display of sensor data and/or derived information as described herein without undue experimentation. See, e.g., U.S. Pat. No. 7,321,862 ("System and method for patient-worn monitoring of patients in geographically dispersed health care locations"); U.S. Pat. No. 7,319,386 ("Configurable system for alerting caregivers"); U.S. Pat. No. 7,285,090 ("Apparatus for detecting, receiving, deriving and displaying human physiological and contextual information"); U.S. Pat. No. 6,731,976 ("Device and method to measure and communicate body parameters"); U.S. Pat. No. 6,246,992 ("Multiple patient monitoring system for proactive health management"); U.S. Pat. No. 5,576,952 ("Medical alert distribution system with selective filtering of medical information"); U.S. Publication No. 20040030578 ("Automated clinical system to facilitate secondary review and authentication of clinical laboratory result values"); U.S. Pat. No. 6,332,502 ("Pipe loading device for a directional drilling apparatus"); U.S. Pat. No. 6,893,396 ("Wireless internet biotelemetry monitoring system and interface"); U.S. Pat. No. 7,304,580 ("Intelligent medical vigilance system"); U.S. Pat. No. 6,694,177 ("Control of data transmission between a remote monitoring unit and a central unit"); U.S. Pat. No. 6,035,230 ("Real-time biological signal monitoring system using radio communication network").

Operation 8394 describes recording at least one difference between the local respiratory-status-indicative information about the first body part of the subject and the filtering information at least partly based on the subject (e.g. module 8173 of decision logic 8171 causing a recordation of output 1485 from one or more subtraction modules or other comparators 1433 that receive such inputs). This can occur, for example, in a context in which one or more rotating storage media or other storage devices 1492 are operatively coupled directly or indirectly to primary module 1400, in which primary module 1400 includes or otherwise interacts with circuitry 8170, and in which module 8173 of decision logic 8171 is configured to invoke device 1492 for recording such outputs. Such event information may include an identifier, a type, or some other attribute of a specific subject to which the information pertains. Alternatively or additionally, such recordable output 1485 may likewise contain the respiratory-status-indicative information and the filtering information to which it was compared.

In light of teachings herein, numerous existing techniques may be applied for recording of event information resulting from the comparison of measured and/or derived information to filtering information as described herein without undue experimentation. See, e.g., U.S. Pat. No. 7,226,422 ("Detection of congestion from monitoring patient response to a recumbent position"); U.S. Pat. No. 7,127,370 ("Attitude indicator and activity monitoring device"); U.S. Pat. No. 6,980,851 ("Method and apparatus for determining changes in heart failure status"); U.S. Pat. No. 6,978,182 ("Advanced patient management system including interrogator/transceiver unit"); U.S. Pat. No. 6,881,192 ("Measurement of sleep apnea duration and evaluation of response therapies using duration metrics"); U.S. Pat. No. 6,336,903 ("Automated collection and analysis patient care system and method for diagnosing and monitoring congestive heart failure and outcomes thereof"); U.S. Pat. No. 6,035,230 ("Real-time biological signal monitoring system using radio communication network").

Operation 8397 describes detecting an apparently-normal-respiration indicator from the one or more comparisons between the local respiratory-status-indicative information about the first body part of the subject and the filtering information at least partly based on the subject (e.g. module 3221 of decision logic 3230 determining that no cellular-respiration-abnormality-indicative criteria 3227 are apparently satisfied by recent measurements 3238 of a subject). This can occur, for example, in a context where one or more respiratory-status-indicative information comparisons are used to assess the status of the "first" body part 3272 of subject 3270 and in which such specific detection may help avoid damage to a subject's heart or brain. In one variant, one or more comparison results 3233, 3235 are correlated with one or more prior comparison results 3231, 3232 or other historic filtering information to avoid a (false) positive notification 3212 about a body part in a context in which the body part's respiratory status is apparently normal.

In light of teachings herein, numerous existing techniques may be applied for assessing respiratory-status-indicative information including discrimination against false event recording and notification from the first body part of the subject as described herein without undue experimentation. See, e.g., U.S. Pat. No. 7,277,747 ("Arrhythmia memory for tachyarrhythmia discrimination"); U.S. Pat. No. 7,269,483 ("Multiple algorithm event discrimination method"); U.S. Pat. No. 7,248,921 ("Method and devices for performing cardiac waveform appraisal"); U.S. Pat. No. 7,189,204 ("Sleep detection using an adjustable threshold"); U.S. Pat. No. 6,990,980 ("Carbon dioxide-based Bi-level CPAP control"); U.S. Pat. No. 6,312,378 ("System and method for automated collection and analysis of patient information retrieved from an implantable medical device for remote patient care").

With reference now to FIG. 84, there are shown several variants of the flow 8200 of FIG. 82 or 83. Operation 8240—obtaining local respiratory-status-indicative information about a first body part of a subject—may (optionally) include one or more of the following operations: 8443 or 8447. In some embodiments, variants of operation 8240 may be performed by one or more instances of processing modules 1430, 1650, 1680; transducers 1990; or local modules 2320, 2450, 2510, 2690, 7931, 7932. Operation 8270—invoking circuitry for causing one or more comparisons between the local respiratory-status-indicative information about the first body part of the subject and filtering information at least partly based on the subject—may include one or more of the following operations: 8471, 8474, 8476 or 8479. In some embodiments, variants of operation 8270 may be performed by invocation logic 3140 and/or by one or more instances of decision logic 275, 1350, 1460, 2250, 2730, 3230, 5750, 5930, 6130, 6395, 7415. Alternatively or additionally, flow 8200 may be performed in a context as described above with reference to any of FIGS. 1-80 and/or in conjunction with other flow variants as described below.

Operation 8443 describes obtaining at least some of the local respiratory-status-indicative information via one or more optical sensors (e.g. one or more infrared sensors 1982 or other transducers 1990 detecting calorimetric or other optical data 1978 indicating an oxygenation of blood 1923 in one or more arteries or other vessels 1929 upstream of a subject's brain or other organ 1927). This can occur, for example, in embodiments in which one or more instances of interface logic 1970 perform operation 8240 by sensing or otherwise obtaining indications of blood or other materials from within tissue 1925, such as by implant 1940 and/or an instrument as described herein. Alternatively or additionally, one or more component modules 1621, 1622 of response module 1620 of FIG. 16 may perform operation 8443 by triggering processing module 1680 to derive the local respiratory-status-indicative information from such indications. This can occur, for example, in embodiments in which decision logic 1460 of FIG. 14 performs operation 8270 with other respiratory-status-indicative information 1456 as described herein, such as may be provided by linking module 1690 in a context in which primary module 1600 (of FIG. 16) comprises one or more instances of interface logic 1970 (of FIG. 19) in network 1490. Alternatively or additionally, processing module 1430 may receive fluid movement data 1453, pressure-fluctuation data 1452, or other such information 1455 indicative of an apparently healthy flow of blood 1923 through a vital organ 1927 or other tissue 1925.

In light of teachings herein, numerous existing techniques may be applied for obtaining subject status information through the use of one or more optical measurement systems as described herein without undue experimentation. See, e.g., U.S. Pat. No. 7,308,292 ("Optical-based sensing devices"); U.S. Pat. No. 7,305,262 ("Apparatus and method for acquiring oximetry and electrocardiogram signals"); U.S. Pat. No. 7,280,858 ("Pulse oximetry sensor"); U.S. Pat. No. 7,004,907 ("Blood-pressure monitoring device featuring a calibration-based analysis"); U.S. Pat. No. 5,755,741 ("Body position and activity sensor"); U.S. Pat. No. 5,601,811 ("Substantive water-soluble cationic UV-absorbing compounds"); U.S. Publication No. 20030050542 ("Device for in-vivo measurement of the concentration of a substance contained in a body fluid"); U.S. Publication No. 20020016535 ("Subcutaneous glucose measurement device") or U.S. Pat. No. 7,181,054 ("System for processing image representative data").

Operation 8447 describes obtaining an indication of a respiratory status within a limb as the local respiratory-status-indicative information (e.g. registry 1685 receiving one or more readings 1681, 1682 from a vessel 1929 routing blood 1923 to or from limb tissue). This can occur, for example, in embodiments in which primary system 1600 (of FIG. 16) includes or otherwise interacts with an instrument 1960 configured to monitor a subject's limb, in which one or more such readings are obtained by a transducer 1767 or other sensors 1733 and/or an implant 1730 or other instrument 1760, and in which at least some of primary module 1600 performs operation 8240 using one or more readings 1681, 1682 and/or information derived from such readings by processing module 1680. Alternatively or additionally, subject-provided data 2922 received via a handheld device, microphone, or other component of interface 2926 may include an auditory or other identifier 2923 of a limb experiencing a symptom, for example. Such information may enable or trigger monitoring or other measurements via sensors as described herein, for example, or may enable or trigger a notice to an interface as described below with reference to operation 8471.

In light of teachings herein, numerous existing techniques may be applied for the monitoring of the respiratory-status-information and/or subject evaluation of the respiratory status of a body part or region including remote monitoring and evaluation of this information as described herein without undue experimentation. See, e.g., U.S. Pat. No. 7,077,809 ("System for measuring and analyzing vasodilatation index"); U.S. Pat. No. 6,983,178 ("Probe for use in non-invasive measurements of blood related parameters"); U.S. Pat. No. 6,939,304 ("Method and apparatus for non-invasively evaluating endothelial activity in a patient"); U.S. Pat. No. 6,926,668 ("System and method for analyzing normalized patient voice feedback in an automated collection and analysis patient care system"); U.S. Pat. No. 6,878,111 ("System for measuring subjective well being"); U.S. Pat. No. 6,740,045 ("Central blood pressure waveform estimation device and peripheral blood pressure waveform detection device"); U.S. Pat. No. 6,720,712 ("Piezoelectric identification device and applications thereof"); U.S. Pat. No. 6,540,668 ("Endoscope with a coupling device (video coupler) for connection of a video camera"); U.S. Pat. No. 6,445,945 ("Non-invasive detection of endothelial dysfunction by blood flow measurement in opposed limbs using tracer injection"); U.S. Pat. No. 6,282,441 ("Health monitoring system"); U.S. Pat. No. 6,152,881 ("Calibrated measurement of blood vessels and endothelium after reactive hyperemia and method therefor"); U.S. Pat. No. 5,941,829 ("Concurrent medical patient data and voice communication method and apparatus"); U.S. Pat. No. 5,671,750 ("Peripheral blood-flow condition monitor"); U.S. Pat. No. 5,497,787 ("Limb monitoring method and associated apparatus").

Operation 8471 describes deriving the filtering information at least partly from respiratory-status-indicative information about a second body part of the subject (e.g. module 3142 adjusting one or more thresholds 3167 of filtering information 3170 to a higher value 3165 in response to a higher pressure measurement 3132 or other indication 3130 of a measurable attribute increase in a subject's limb 1722). This can occur, for example, in a context in which invocation logic 3140 performs operation 8270 and in which one or more data filters 3152, 3189 are configured to apply one or more such new values 3165, 3161 to measurements 3131 or other respiratory status indicators 3130 obtained from another limb 1721 of the subject. Alternatively or additionally, some such thresholds 3167 or other values 3155 may be derived by arithmetically combining quantities relating to matched body parts, other subject locations, and/or systemic values. In some variants, moreover, historical data ranges relating to a common sensor, subpopulation, or body part may likewise bear upon such values as described herein.

In light of teachings herein, numerous existing techniques may be applied for the use of historic and/or concurrent status information derived from one or more additional body parts of the subject or from other similar subjects to evaluate status information derived from the first body part as described herein without undue experimentation. See, e.g., U.S. Pat. No. 7,312,619 ("Multiple local probe measuring device and method"); U.S. Pat. No. 7,098,678 ("Multiple local probe measuring device and method"); U.S. Pat. No. 7,098,673 ("Capacitive measuring system"); U.S. Pat. No. 7,052,474 ("Pharyngoesophageal monitoring systems"); U.S. Pat. No. 7,047,149 ("Optical measurement instrument and optical measurement method"); U.S. Pat. No. 6,943,574 ("Multiple local probe measuring device and method"); U.S. Pat. No. 6,822,564 ("Parallel measurement alarm processor"); U.S. Pat. No. 6,798,226 ("Multiple local probe measuring device and method"); U.S. Pat. No. 6,583,411 ("Multiple local probe measuring device and method"); U.S. Pat. No. 6,545,603 ("Measuring device using an indirect measurement of permittivity"); U.S. Pat. No. 6,238,349 ("Method and apparatus for noninvasive determination of cardiac performance parameters").

Operation 8474 describes causing at least one of the one or more comparisons to occur while the subject sleeps (e.g. invocation module 1412 directly or indirectly triggering one or more comparators 1432, 3198 configured to determine whether a sleeping subject's current sense data 1451 apparently indicates an occluded blood vessel or other local respiratory abnormality in a weight-bearing or other peripheral body part). This can occur, for example, in a context in which one or more primary modules 1400, 3180 receives sense data 1451 from sensors 3284 as described herein, such as by implementing system 3200 of FIG. 32, and in which such timely detection may avoid a need for more intrusive measures. In some variants, for example, one or more sensor(s) 3284 and/or detection logic 3285 of apparatus 3290 may make basic or coarse determinations locally and frequently. In various embodiments as described herein, one or more criteria 3226, 3287 may be used in deciding whether to signal a subject, whether to signal a care provider, whether to trigger further measurement and/or analysis, whether to forward data from apparatus 3290 to filtering module 3210, or whether to invoke other modules or protocols as described herein. Invocation module 1412 may (optionally) be configured for triggering one or more comparators remotely if and only if one or more other comparators 1432 signals a positive result, for example. Alternatively or additionally, invocation module 1442 can be implemented in a system comprising one or more of an adhesive 3282, a wearable or other manipulable apparatus 3290, a bed or other item 3150 of furniture, a detection module 1411 operable for determining whether a subject is apparently asleep, a vehicle 1470 as described herein, or otherwise in configurations as described herein.

In light of teachings herein, numerous existing techniques may be applied for obtaining a set of respiratory-status-indicative information based upon and/or independent of the sleep state of the subject as described herein without undue experimentation. See, e.g., U.S. Pat. No. 7,319,899 ("Sensing techniques for implantable medical devices"); U.S. Pat. No. 7,306,565 ("Ear temperature monitor and method of temperature measurement"); U.S. Pat. No. 7,189,204 ("Sleep detection using an adjustable threshold"); U.S. Pat. No. 7,187,960 ("Apparatus and method for measuring biologic parameters"); U.S. Pat. No. 7,164,941 ("Method and system for contactless monitoring and evaluation of sleep states of a user"); U.S. Pat. No. 6,993,380 ("Quantitative sleep analysis method and system"); U.S. Pat. No. 6,835,351 ("Optical-chemical sensor"); U.S. Pat. No. 6,773,404 ("Discriminating between an awake phase and a sleep phase of a patient in an active implantable medical device"); U.S. Pat. No. 6,363,270 ("Monitoring the occurrence of apneic and hypopneic arousals"); U.S. Pat. No. 6,161,041 ("Pacemaker system with diurnal pattern controlled overdrive for prevention of tachycardia"); or U.S. Pat. No. 7,003,340 ("Electrochemical analyte sensor").

Operation 8476 describes detecting an apparent vascular flow change as a result of the one or more comparisons between the local respiratory-status-indicative information about the first body part of the subject and filtering information at least partly based on the subject (e.g. one or more modules 3142, 3143 triggering one or more results 3136, 3137 of one or more comparisons between earlier indications 3115, 3183 and later indications 3125, 3184 of flow in the subject). This can occur, for example, in a context in which one or more such indications 3183-3185 are extracted from measurements or other event-indicative records 3110, 3120, in which invocation logic 3140 performs operation 8270 by invoking evaluation logic 3197 (remotely) or other data filters 3151 that perform such comparisons. Such filtering information 3170 may (optionally) be partly based upon contemporaneous local respiratory-status-indicative information obtained from other body parts of the subject, for example, to ascertain whether a detected change is apparently vascular, as described herein.

In light of teachings herein, numerous existing techniques may be applied for monitoring apparent vascular flow, detecting apparent changes within parts of a subject, or evaluating such phenomena as described herein without undue experimentation. See, e.g., U.S. Pat. No. 7,331,928 ("Ultrasonic doppler bloodstream measurement device"); U.S. Pat. No. 7,297,280 ("Method and apparatus to measure blood flow in hemodialysis shunts"); U.S. Pat. No. 7,289,927 ("Method and apparatus for the monitoring of body temperature and/or blood flow"); U.S. Pat. No. 7,254,432 ("Method and device for non-invasive measurements of blood parameters"); U.S. Pat. No. 7,226,415 ("Microwave hemorrhagic stroke detector"); U.S. Pat. No. 7,200,431 ("Implantable blood flow monitoring system"); U.S. Pat. No. 7,195,598 ("Method for determining the effectiveness of a medical therapy by analysis of collateral vessels"); U.S. Pat. No. 7,171,251 ("Physiological stress detector device and system"); U.S. Pat. No. 7,128,713 ("Doppler ultrasound method and apparatus for monitoring blood flow and hemodynamics"); U.S. Pat. No. 6,740,042 ("Bilateral simultaneous doppler measurement of segmented sphygmomanometry"); U.S. Pat. No. 6,520,919 ("Inferior-and-superior-limb blood-pressure-index measuring apparatus"); U.S. Pat. No. 6,413,223 ("Cuffless continuous blood pressure monitor"); U.S. Pat. No. 6,117,087 ("Method and apparatus for noninvasive assessment of a subject's cardiovascular system"); U.S. Pat. No. 5,724,983 ("Continuous monitoring using a predictive instrument").

Operation 8479 describes causing at least one of the one or more comparisons between the local respiratory-status-indicative information about the first body part of the subject and the filtering information at least partly based on the subject to be performed remotely (e.g. module 3141 transmitting one or more indications 3181, 3182 of an apparent respiratory status of a part of a subject's body to enable remote module 3190 to compare such indications each against one or more comparative determinants as described herein). This can occur, for example, in a context in which invocation logic 3140 performs operation 8270, in which system 300 of FIG. 3 implements primary module 3180, and in which one or more instances of remote modules 3190 receive indications of age, pathology, gender, risk profile, or other such categories or measurements 1458 of determinant data 1459 relating to each of one or more subjects 310, 320 to be used in the comparison(s). In some variants, for example, remote module 3190 may implement a data aggregator, expert system, and/or other system described herein operable for analyzing one or more indications 311-314 of a current status of the legs of subject 310. This may facilitate a health care professional defining, applying, or adjusting the filtering information to update one or more heuristic models, such as by discounting an indication 314 of a respiratory deficiency in a left thigh in response to a corresponding indication 312 of a respiratory deficiency in the corresponding (left) calf. In a context in which one or more such indications suggest a dangerous clot or other urgent situation in a context like that of of FIGS. 3-6, for example, a caregiver station or other entity nearby may receive a timely notification as described herein. In an embodiment in which the context of FIG. 8 or FIG. 2 includes primary module 1400, for example, one or more indications as described herein may include global positioning system (GPS) coordinates, a seat identifier, or other such location-descriptive information 1457 suitable for use by such caregivers.

In light of teachings herein, numerous existing techniques may be applied for the transmission of current information and/or for the programmatic evaluation of subject-health-related information as described herein without undue experimentation. See, e.g., U.S. Pat. No. 7,319,386 ("Configurable system for alerting caregivers"); U.S. Pat. No. 7,311,665 ("Bio-information sensor monitoring system and method"); U.S. Pat. No. 7,304,580 ("Intelligent medical vigilance system"); U.S. Pat. No. 7,258,670 ("System and method for diagnosing and monitoring respiratory insufficiency for automated remote patient care"); U.S. Pat. No. 7,200,431 ("Implantable blood flow monitoring system"); U.S. Pat. No. 6,454,705 ("Medical wellness parameters management system, apparatus and method"); U.S. Pat. No. 6,416,471 ("Portable remote patient telemonitoring system"); U.S. Pat. No. 6,409,662 ("Patient interface system"); U.S. Pat. Pub. No. 2007/0010719 ("Remote access to healthcare device diagnostic information").

Figure 85:
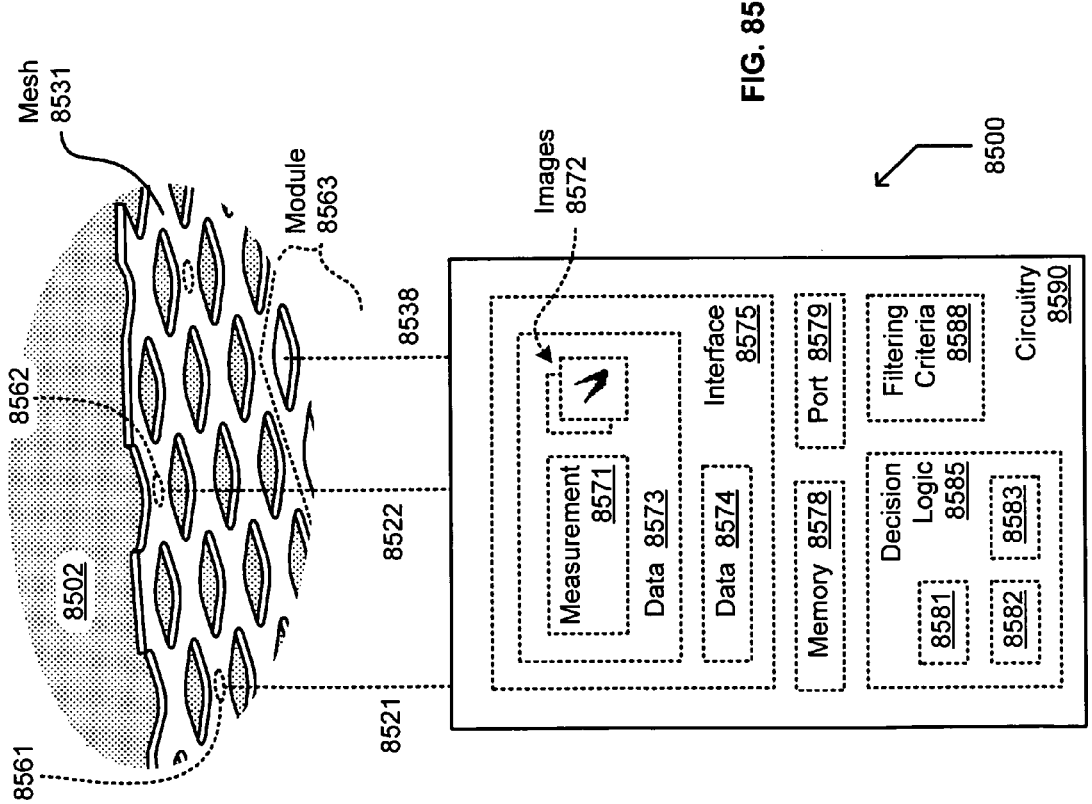
FIG. 85 depicts an exemplary environment in which one or more technologies may be implemented.

With reference now to FIG. 85, shown is a system 8500 in which one or more technologies may be implemented. An adhesive, rigid, or other mesh 8531 is configured to hold one or more sensors 8561, 8562, modules 8563, or other such structures on or near a subject's skin 8502 as described herein. Alternatively or additionally, special-purpose or other circuitry 8590 may include one or more instances of interface 8575, memory 8578, communication ports 8579, decision logic 8585, filtering criteria 8588, or other such structures described herein, for example, configured to receive information 8521, 8522 along respective conduits or other signal paths 8538. Data 8573, 8574 may include one or more instances of measurements 8571 and/or shape-indicative images 8572 in some variants, for example. Decision logic 8585 may likewise handle one or more notifications 8581, modules 8582, or decisions 8583 as described below.

Figure 86:
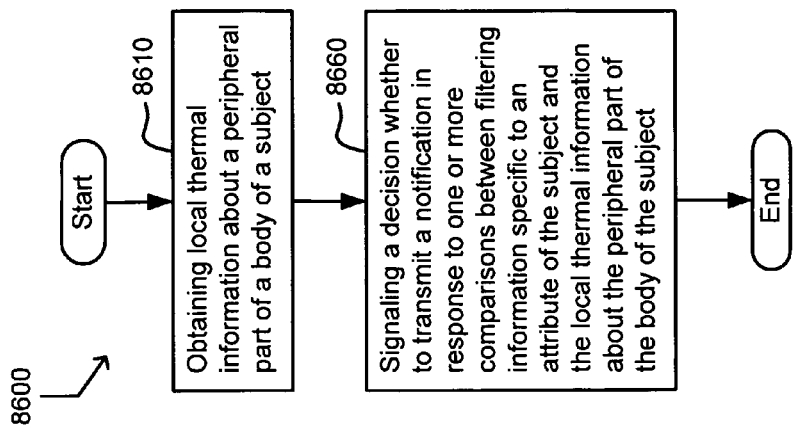
FIG. 86 depicts a high-level logic flow of an operational process.

With reference now to FIG. 86, shown is a flow 8600 comprising operation 8610—obtaining local thermal information about a peripheral part of a body of a subject (e.g. interface 8575 receiving one or more measurements 8571, infrared images 8572, or other information 8521, 8522 indicating local thermal variations in respective portions of the subject's skin 8502). This can occur, for example, in a context in which mesh 8531 is configured to bear the subject's weight and/or hold one or more sensors 8561, 8562 or other modules 8563 adjacent the subject's skin 8502. In some variants, for example, interface 8575 may apply one or more filtering criteria 8588 for extracting a selection or other indication of such data 8573, 8574 for transmission to memory 8578, communication port 8579, and/or decision logic 8585. Alternatively or additionally, such data 8574 may (optionally) contain one or more indications of pressure, pathology, concentration, type, level change, timing, or other such parameters for use by other modules as described herein.

In light of teachings herein, numerous existing techniques may be applied for receiving, extracting, or otherwise obtaining thermal indications via sensors or other structures in, on, or near body parts as described herein without undue experimentation. See, e.g., U.S. Pat. No. 6,983,178 ("Probe for use in non-invasive measurements of blood related parameters"); U.S. Pat. No. 6,975,232 ("Apparatus and method for "seeing" foot inside of shoe to determine the proper fit of the shoe"); U.S. Pat. No. 7,340,293 ("Methods and apparatus for a remote, noninvasive technique to detect core body temperature in a subject via thermal imaging"); U.S. Pat. No. 7,275,867 ("Probe assembly of infrared thermometer"); U.S. Pat. No. 7,087,903 ("Gamma camera and CT system"); U.S. Pat. No. 6,979,293 ("Blood flow reestablishment determination"); U.S. Pat. No. 6,542,767 ("Method and system for controlling heat delivery to a target"); U.S. Pat. No. 6,402,371 ("Axillary infrared thermometer and method of use").

Operation 8660 describes signaling a decision whether to transmit a notification in response to one or more comparisons between filtering information specific to an attribute of the subject and the local thermal information about the peripheral part of the body of the subject (e.g. decision logic 8585 queuing or otherwise causing a transmission of one or more notifications 8581 only if module 8582 generates an affirmative decision 8583). This can occur, for example, in a context in which circuitry 8590 is physically implemented within module 8563 or otherwise near mesh 8531, in which one or more filtering criteria 8588 are suitable for use with at least some thermal component of data 8573, 8574, and in which module 8582 will generate a negative decision if none of the one or more comparisons between the filtering information and the thermal information indicate a roughly simultaneous interpositional temperature difference greater than a given threshold. In some variants, an instance of decision logic 8585 may be configured to detect temperature gradient that exceeds 1° C. for about ten minutes or more, for example, or otherwise to decide whether the subject's skin 8502 apparently indicates a localized area of persistent warmth or coolness. Alternatively or additionally, an instance of decision logic 8585 may be configured to detect a locality of high pressure, discoloration, swelling, or other attributes of an objectively detectable trend that persists for more than a given threshold of time (e.g. on the order of an hour or a day, in some contexts). In some variants in which circuitry 8590 is implemented in a distributed configuration, moreover, one or more modules of decision logic 8585 may be implemented at an aggregation site, optionally remote from one or more subjects, such as to facilitate complex image processing, expert participation, or other such resource-intensive analysis.

In light of teachings herein, numerous existing techniques may be applied for handling destinations, abstentions, conditions, configurations, or other notification decisions as described herein without undue experimentation. See, e.g., U.S. Pat. No. 7,340,687 ("Display control device and method"); U.S. Pat. No. 7,296,042 ("System and method for enabling communication among arbitrary components"); U.S. Pat. No. 7,284,061 ("Obtaining temporary exclusive control of a device"); U.S. Pat. No. 7,263,073 ("Systems and methods for enabling a mobile user to notify an automated monitoring system of an emergency situation"); U.S. Pat. No. 7,216,263 ("Performance monitoring and notification in a threshold sensitive storage management system"); U.S. Pat. No. 7,196,620 ("Sensor monitoring apparatus, monitoring system, sensor monitoring method and program"); U.S. Pat. No. 7,180,983 ("Guidance information notification apparatus in communication network system, communication network system and guidance information notification method"); U.S. Pat. No. 7,174,005 ("School-wide notification and response system"); U.S. Pat. No. 7,155,729 ("Method and system for displaying transient notifications"); U.S. Pat. No. 7,143,222 ("Adaptive message delivery system"); U.S. Pat. No. 7,136,357 ("Transmission path controlling apparatus and transmission path controlling method as well as medium having transmission path controlling program recorded thereon"); U.S. Pat. No. 7,088,993 ("Optimized message notification"); U.S. Pat. No. 7,039,698 ("Notification device interaction"); U.S. Pat. No. 6,886,002 ("Computational architecture for managing the transmittal and rendering of information, alerts, and notifications"); U.S. Pat. No. 6,871,214 ("Generating and providing alert messages in a communications network"); U.S. Pat. No. 6,690,267 ("Remotely controllable bicycle lock and alarm system"); U.S. Pat. No. 6,687,230 ("Routing system and method"); U.S. Pat. No. 6,591,182 ("Decision making process and manual for diagnostic trend analysis"); U.S. Pat. No. 6,513,026 ("Decision theoretic principles and policies for notification"); U.S. Pat. No. 6,438,216 ("Nonintrusive call notification method and system using content-specific information"); U.S. Pat. No. 6,195,571 ("Electronic apparatus capable of automatically switching notification devices"); U.S. Pat. No. 5,740,540 ("Method for telephone number notification and storage in a portable radio").

Figure 87:
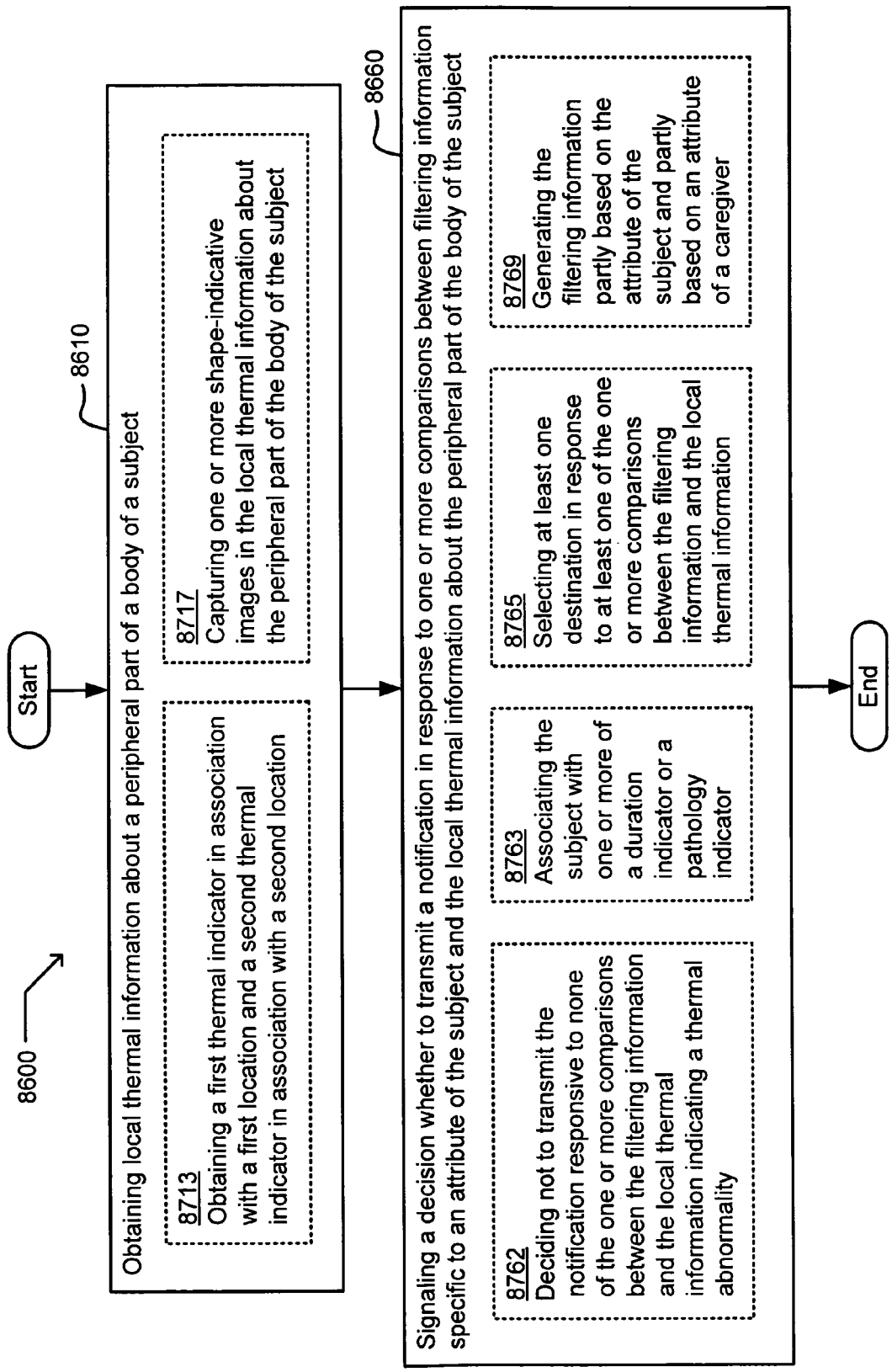
FIGS. 87-88 depict variants of the flow of FIG. 86.

With reference now to FIG. 87, there are shown several variants of the flow 8600 of FIG. 86. Operation 8610—obtaining local thermal information about a peripheral part of a body of a subject—may (optionally) include one or more of the following operations: 8713 or 8717. In some embodiments, variants of operation 8610 may be performed by one or more instances of local modules 2320, 2450, 2510, 2690 configured to handle sensor data; event detection logic 2333 or other detection logic 180, 640, 880, 1275, 3285, 3550, 7940; or other devices configured for thermal imaging, statistical analysis, or other modes of facilitating data evaluations by various users. Operation 8660—signaling a decision whether to transmit a notification in response to one or more comparisons between filtering information specific to an attribute of the subject and the local thermal information about the peripheral part of the body of the subject—may include one or more of the following operations: 8762, 8763, 8765 or 8769. In some embodiments, variants of operation 8660 may be performed by one or more instances of evaluation logic 150, 250, 950, 1530, 7565; decision logic 275, 1350, 1460, 2250, 2730, 3230, 5750, 5930, 6130, 6395, 7415, or other processing or communication devices as described herein. Alternatively or additionally, flow 8600 may be performed in a context as described above with reference to any of FIGS. 1-80 and/or in conjunction with other flow variants as described below.

Operation 8713 describes obtaining a first thermal indicator in association with a first location and a second thermal indicator in association with a second location (e.g. sensors 126, 127, 128 taking temperature-indicative readings at their respective locations in zones 111, 112, 113). This can occur, for example, in embodiments in which module 141 performs operation 8610 and in which comparator 130 performs operation 8660 by applying filtering information 131 to the thermal, temporal, and other data from the sensors. Alternatively or additionally, module 141 may perform operation 8713 by receiving a thermal image of a subject's limb or other such data associated with a range of locations.

In light of teachings herein, numerous existing techniques may be applied for detecting, analyzing, or otherwise handling temperature-indicative data in various contexts as described herein without undue experimentation. See, e.g., U.S. Pat. No. 7,336,202 ("Temperature monitoring device"); U.S. Pat. No. 7,318,004 ("Temperature prediction system and method"); U.S. Pat. No. 7,264,591 ("System and method for monitoring air flow from a person"); U.S. Pat. No. 6,843,774 ("Technique for diagnosing attention deficit hyperactivity disorder"); U.S. Pat. No. 6,445,183 ("Magnetic resonance image diagnosing apparatus"); U.S. Pat. No. 6,299,347 ("Ambient and perfusion normalized temperature detector").

Operation 8717 describes capturing one or more shape-indicative images in the local thermal information about the peripheral part of the body of the subject (e.g. recorder 148 recording one or more images 1697 from a thermal sensor array into a memory or other media 1695). This can occur, for example, in embodiments in which primary module 1600 (of FIG. 16) implements evaluation logic 150 (of FIG. 1) and in which one or more active sets of infrared sensors 1982 or other optical sensors are configured to apply respective-set-specific intensity thresholds 1651, 1653 and/or frequency thresholds 1652, 1654. Such an embodiment may be used, for example, to estimate an areal expansion or other gradient relating to a region of abnormal temperature. Alternatively or additionally, such data may be used to derive an aspect ratio, a shape type, or other such shape-indicative attributes 1699 of developing infections, circulatory problems, or other such thermally detectable local abnormalities 105.

Operation 8762 describes deciding not to transmit the notification responsive to none of the one or more comparisons between the filtering information and the local thermal information indicating a thermal abnormality (e.g. one or more modules 1531 of evaluation logic 1530 deciding whether to transmit notification 1580 in the negative responsive to one or more results 1523 of applying one or more thresholds 1561, 1562 or other criteria 1573). This can occur, for example, in a context in which the result(s) 1523 indicate a normal thermal measurement relative to one or more normality thresholds 1561 such as those described herein and in which one or more users have indicated an availability to receive such notifications. Such decisions may likewise result from one or more auditory or other non-thermal indications of normalcy such as counter-indicia of pathologies identified herein. Alternatively or additionally, one or more such modules 1531, 1532 may be configured to generate such a negative decision in response to a prior notification recipient or other user's response directing or otherwise warranting that notification 1580 not be sent.

In light of teachings herein, numerous existing techniques may be applied for selective communications incorporating triage protocols or other programmatic responses as described herein without undue experimentation. See, e.g., U.S. Pat. No. 7,299,157 ("Event analysis system method and software"); U.S. Pat. No. 7,228,315 ("Computer-automated implementation of user-definable decision rules for medical diagnostic or screening interpretations"); U.S. Pat. No. 7,213,009 ("Systems and methods for manipulating medical data via a decision support system"); U.S. Pat. No. 7,209,671 ("Multiple detector decision receiver"); U.S. Pat. No. 7,116,825 ("Multilevel chain-and-tree model for image-based decisions"); U.S. Pat. No. 6,830,549 ("Method and apparatus for providing patient care"); U.S. Pat. No. 6,751,255 ("Decision feedback analyzer with filter compensation"); U.S. Pat. No. 6,636,621 ("Systems and methods with identity verification by comparison & interpretation of skin patterns such as fingerprints"); U.S. Pat. No. 6,629,937 ("System for processing audio, video and other data for medical diagnosis and other applications").

Operation 8763 describes associating the subject with one or more of a duration indicator or a pathology indicator (e.g. module 3061 providing access to table 3010 or other structures 3020 operable for containing or otherwise facilitating one or more duration or pathology indicators 3023, 3024 or other event or status indicators 3022 responsive to one or more subject identifiers 3034 or other search terms 3030). This can occur, for example, in a context in which at least some such indicators reside in a common record 3013 satisfying one or more search terms 3030. Alternatively or additionally, in some variants, a notification as described herein may refer to a recipient or be sent to a recipient interface or user having a priori knowledge of such an association.

In light of teachings herein, numerous existing techniques may be applied for communicating event or status indications relating to a subject as described herein without undue experimentation. See, e.g., U.S. Pat. No. 7,248,916 ("Automated system and method for establishing a patient status reference baseline"); U.S. Pat. No. 7,232,158 ("Fitting for formation of a fluid-conducting connection"); U.S. Pat. No. 7,177,699 ("Lifestyle management system"); U.S. Pat. No. 7,122,005 ("Remote patient monitoring system with garment and automated medication dispenser"); U.S. Pat. No. 6,840,117 ("Patient monitoring system employing array of force sensors on a bedsheet or similar substrate"); U.S. Pat. No. 6,783,492 ("System and method for monitoring body functions"); U.S. Pat. No. 6,616,606 ("Patient monitoring system"); U.S. Pat. No. 6,584,931 ("System and method for controlling and monitoring the operation of an automatic milking system").

Operation 8765 describes selecting at least one destination in response to at least one of the one or more comparisons between the filtering information and the local thermal information (e.g. one or more modules 1534 selecting one or more first-type destinations 1583, 1591 in response to a comparison result 1522 and otherwise selecting one or more second-type destinations 1584, 1592). This can occur, for example, in a triage protocol in which such results 1522 respectively reflect greater and lesser degrees of urgency or in which the second-type destination 1584 of notification 1580 identifies a notification recipient list and in which a subject is unconscious, unable to communicate, or otherwise vulnerable to such thermally-manifested pathologies. Alternatively or additionally, module 1534 may likewise select among risk-indicative data 1553 or other available content 1581, 1582 for inclusion in each such notification in response to one or more other evaluation results 1521 as described herein.

In light of teachings herein, numerous existing techniques may be applied for notification routing or other modes of destination selection as described herein without undue experimentation. See, e.g., U.S. Pat. No. 7,286,648 ("Emergency locator system"); U.S. Pat. No. 7,260,064 ("Method and apparatus for performing network routing based on queue lengths"); U.S. Pat. No. 7,212,111 ("Method and system for use in emergency notification and determining location"); U.S. Pat. No. 7,203,294 ("System and method for dynamically routing communications"); U.S. Pat. No. 7,116,655 ("Telecommunication system for automatically locating by network connection and selectively delivering calls to mobile client devices"); U.S. Pat. No. 6,970,847 ("Business method for secure document folder distribution"); U.S. Pat. No. 6,638,218 ("System and method for delivering medical examination, diagnosis, and treatment over a network"); U.S. Pat. No. 6,539,302 ("Method, system, and article of manufacture for providing notification of traffic conditions").

Operation 8769 describes generating the filtering information partly based on the attribute of the subject and partly based on an attribute of a caregiver (e.g. module 2244 configuring one or more parameters 2247, 2248 in response to one or more indications 2261, 2263 of the subject's age or apparent pathology and in response to one or more indications 2262, 2264 of a notification recipient's apparent availability). This can occur, for example, in contexts in which decision logic 2250 performs operation 8660 and in which (a) an indication 2261 of an elderly or otherwise at-risk patient and/or (b) an indication 2262 of an "available" caregiver status warrant an incrementally narrower range of "normal" thermal information. Such a narrowing may be accomplished by an increased minimum and/or by a decreased maximum, for example, applied to a measurement or other quantitative determinant as described herein. Alternatively or additionally, one or more other such indications 2263, 2264 may likewise affect one or more parameters used in other filtering as described herein. In some variants, moreover, such filtering information may likewise depend on one or more expert inputs, operational parameters 2248, or other programmatic updates as described herein.

In light of teachings herein, numerous existing techniques may be applied for adaptive or other conditional data evaluation as described herein without undue experimentation. See, e.g., U.S. Pat. No. 7,123,950 ("Nuisance alarm reductions in a physiological monitor"); U.S. Pat. No. 7,079,035 ("Method and apparatus for controlling an alarm while monitoring"); U.S. Pat. No. 6,996,427 ("Pulse oximetry data confidence indicator"); U.S. Pat. No. 6,898,585 ("Fuzzy logic method for adaptively evaluating the validity of sensor data"); U.S. Pat. No. 6,569,095 ("Adaptive selection of a warning limit in patient monitoring"); U.S. Pat. No. 6,473,708 ("Device and method for self-verifying temperature measurement and control"); U.S. Pat. No. 6,241,661 ("Selecting limit values in particular for patient monitoring systems"); U.S. Pat. No. 6,047,201 ("Infant blood oxygen monitor and SIDS warning device").

Figure 88:
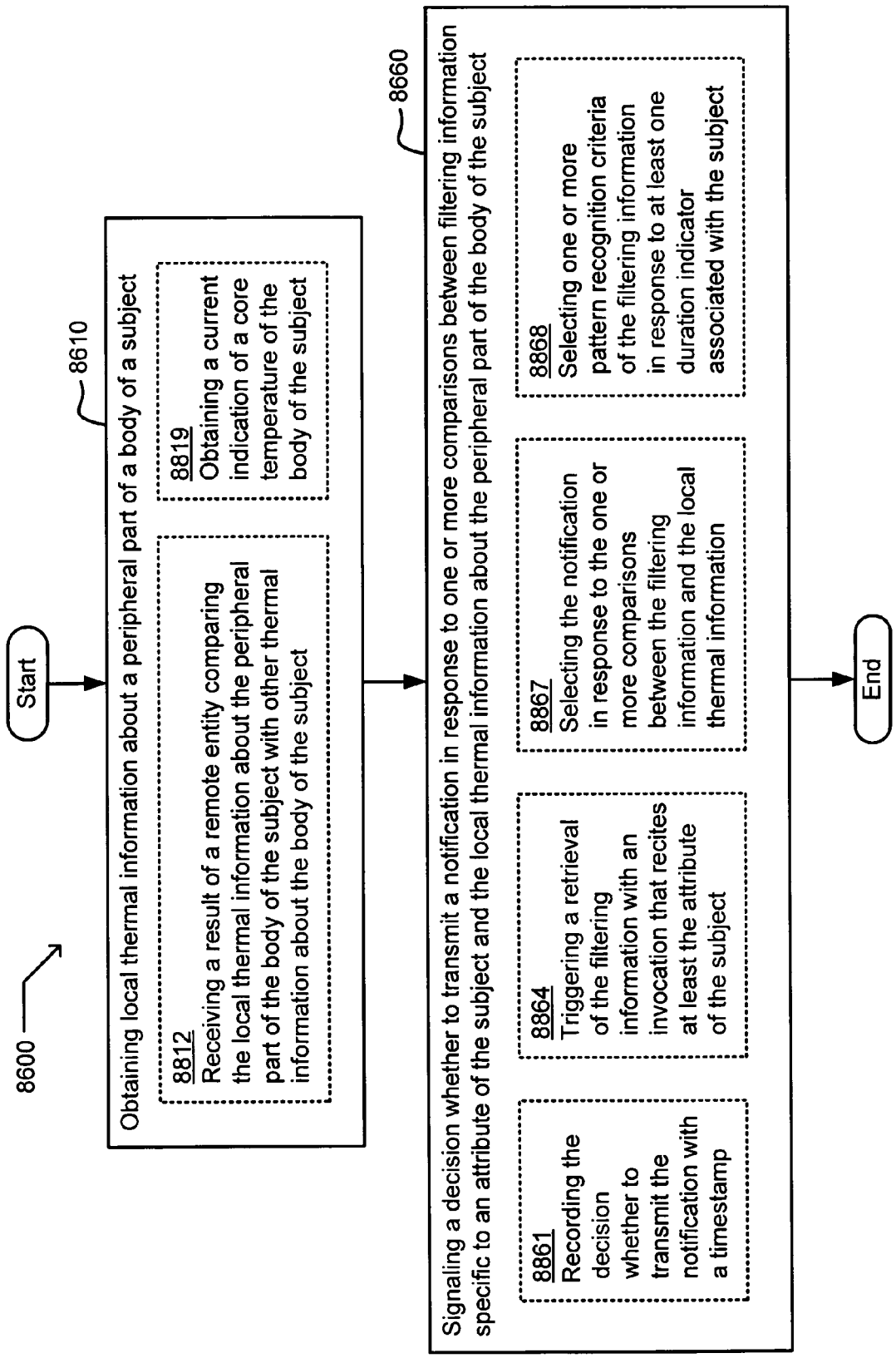

With reference now to FIG. 88, there are shown several variants of the flow 8600 of FIG. 86 or 87. Operation 8610—obtaining local thermal information about a peripheral part of a body of a subject—may (optionally) include one or more of the following operations: 8812 or 8819. In some embodiments, variants of operation 8610 may be performed by one or more instances of interface 2260; apparatus 3290; or other such sensor-containing, communication, or processing devices. Operation 8660—signaling a decision whether to transmit a notification in response to one or more comparisons between filtering information specific to an attribute of the subject and the local thermal information about the peripheral part of the body of the subject—may include one or more of the following operations: 8861, 8864, 8867 or 8868. In some embodiments, variants of operation 8660 may be performed by one or more modules 251 of evaluation logic 150, 250, 950, 1530, 7565; processing logic 1180, 3070; or other circuitry or software as described herein. Alternatively or additionally, flow 8600 may be performed in a context as described above with reference to any of FIGS. 1-80 and/or in conjunction with other flow variants as described below.

Operation 8812 describes receiving a result of a remote entity comparing the local thermal information about the peripheral part of the body of the subject with other thermal information about the body of the subject (e.g. port 2255 receiving one or more results 2251, 2252 from a server 2220, interface 2210, or other resource that is remote from subject 2270). This can occur, for example, in a context in which sensors 2268 and/or interface 2260 facilitates measurements or other indications 2261-2264 being taken from a limb or other peripheral body part 2271 and from another such body part 2272 of subject 2270. In various configurations as described herein, such measurements or other data may be derived from respective sensor-containing modules in, on, or otherwise within a proximity 2277 of such body parts 2271, 2272. Alternatively or additionally, in some variants, a skilled or other user may position one or more sensors successively to take such data at each of such body parts 2271, 2272, optionally in response to audible directions transmitted via an output device such as speaker 2267. See FIGS. 18, 21, & 93.

In light of teachings herein, numerous existing techniques may be applied for transmitting requests, receiving guidance, or otherwise interacting with a remote service as described herein without undue experimentation. See, e.g., U.S. Pat. No. 7,336,166 ("Remote monitoring system and method using the same"); U.S. Pat. No. 7,320,030 ("Remote health monitoring apparatus using scripted communications"); U.S. Pat. No. 7,308,492 ("Method and apparatus for use in remote diagnostics"); U.S. Pat. No. 7,283,153 ("Home-based remote medical assistance"); U.S. Pat. No. 7,202,844 ("Liquid crystal display controller and liquid crystal display"); U.S. Pat. No. 6,984,207 ("Passive physiological monitoring (P2M) system"); U.S. Pat. No. 6,908,431 ("System and method for providing feedback to an individual patient for automated remote patient care"); U.S. Pat. No. 6,847,913 ("Ambulatory surface skin temperature monitor"); U.S. Pat. No. 6,839,455 ("System and method for providing information for detected pathological findings"); U.S. Pat. No. 6,505,196 ("Method and apparatus for improving access to literature").

Operation 8819 describes obtaining a current indication of a core temperature of the body of the subject (e.g. one or more thermometers or other sensors 3284 taking one or measurements 3238 indicative of a core temperature of subject 3270 such as tympanic membrane and/or basal temperature data 3261). This can occur, for example, in a context in which decision logic 3230 and/or apparatus 3290 perform operation 8610 and in which one or more modules 3222 of decision logic 3230 are configured to determine whether a detected temperature change in a peripheral or other body part 3272 apparently reflects a circadian or other systemic phenomenon. Alternatively or additionally, one or more other modules 3223 may apply decision criteria 3226 or other such filtering information derived from other subjects of a common subpopulation (e.g. of the same age as subject 3270), from other data 3262 from one or more comparable body parts 3271 of the same subject 3270, and/or from earlier-acquired data 3263 from the same peripheral part 3272 as described herein.

Operation 8861 describes recording the decision whether to transmit the notification with a timestamp (e.g. module 3063 recording an affirmative or other decision 3004 contemporaneous with a date or other indication 3005 of when such decisions were made or communicated). This can occur, for example, in a context in which system 200 of FIG. 2 or other systems described herein implement module 3063, with or without a common medium holding such modules or other elements. Alternatively or additionally, such records 3011, 3012, 3013 may likewise include one or more supporting items indicative of a destination, a content component, a success, or other such attributes of decision 3004. In some variants, for example, indication 3005 may reflect one or more of (a) when operation 8861 was performed, (b) when decision 3004 was obtained, (c) when such a notification arrived, or (d) when one or more of the comparisons were performed or obtained.

In light of teachings herein, numerous existing techniques may be applied for indicating when a transmission decision was enabled or otherwise acted upon as described herein without undue experimentation. See, e.g., U.S. Pat. No. 7,225,013 ("Adaptive prediction of changes of physiological/pathological states using processing of biomedical signals"); U.S. Pat. No. 7,200,682 ("Time stamp generating system"); U.S. Pat. No. 7,117,037 ("Event marker alignment by inclusion of event marker transmission latency in the real-time data stream"); U.S. Pat. No. 7,062,528 ("Method and system for identifying a time specific event"); U.S. Pat. No. 6,961,327 ("TCP aware local retransmissioner scheme for unreliable transmission network").

Operation 8864 describes triggering a retrieval of the filtering information with an invocation that recites at least the attribute of the subject (e.g. module 3062 requesting or otherwise triggering a search for one or more records 3012 containing suitable quantitative information or other filtering data 3090 by transmitting one or more measurements 3085 as described herein or other indications 3081, 3082 physically obtained from or otherwise specific to the subject). This can occur, for example, in a context in which decision logic 275 of FIG. 2 or response logic 335 of FIG. 3 implements processing logic 3070 configured to interact with any of subjects 310, 1720, 1910, 3270 or others described herein and in which processing logic 3070 performs at least operation 8660 with reference to any of notifications 2241, 2242, 3051, 3052 or others described herein. Alternatively or additionally, in some variants, one or more component indications 3081 of the filtering data 3090 may be derived from current or prior data from a subject as described herein without such retrieval and/or filtering.

In light of teachings herein, numerous existing techniques may be applied for extracting comparative parameters or otherwise configuring suitable data filters as described herein without undue experimentation. See, e.g., U.S. Pat. No. 7,258,670 ("System and method for diagnosing and monitoring respiratory insufficiency for automated remote patient care"); U.S. Pat. No. 7,248,916 ("Automated system and method for establishing a patient status reference baseline"); U.S. Pat. No. 7,225,013 ("Adaptive prediction of changes of physiological/pathological states using processing of biomedical signals"); U.S. Pat. No. 7,147,600 ("System and method for determining a reference baseline of patient information"); U.S. Pat. No. 6,993,167 ("System and method for examining, recording and analyzing dermatological conditions"); U.S. Pat. No. 6,887,201 ("System and method for determining a reference baseline of regularly retrieved patient information for automated remote patient care"); U.S. Pat. No. 6,687,544 ("System and method for determining safety alert conditions for implantable medical devices"); U.S. Pat. No. 6,611,846 ("Method and system for medical patient data analysis").

Operation 8867 describes selecting the notification in response to the one or more comparisons between the filtering information and the local thermal information (e.g. one or more modules 3064 selecting notification 3051 only if the thermal information passes one or more criteria 3035 and notification 3052 otherwise, or only if the thermal information passes one or more other criteria). This can occur in a context in which circuitry 280 includes or otherwise interacts with interface 3000 of FIG. 30, in which information 271 comprises the thermal information and reflects a circulatory obstruction or other pathology local to a limb or other peripheral body part, in which processing logic 3070 performs operation 8660, and in which a circulatory obstruction may be difficult to locate and treat in time. In some variants, for example, one or more modules 272, 273 of decision logic 275 may be configured to sound a local alarm (to notify a passenger, e.g.) for a local thermal deviation of at least X and to sound a remote alarm (to notify a caregiver, e.g.) for a local thermal deviation of at least X+Y. (In such a context, for example, X and Y may each be 0.3° C., 1° C., or 3° C. in respective combinations.) Alternatively or additionally, a subject-independent determinant may affect the filtering information, such as by modulating a systemic temperature estimate according to circadian rhythms based upon a time-of-day indication from clock 276.

In light of teachings herein, numerous existing techniques may be applied for invoking various interfaces or other modes of notifying suitable parties as described herein without undue experimentation. See, e.g., U.S. Pat. No. 7,336,187 ("Patient activity monitor"); U.S. Pat. No. 7,319,386 ("Configurable system for alerting caregivers"); U.S. Pat. No. 7,138,902 ("Personal medical device communication system and method"); U.S. Pat. No. 7,130,396 ("Medical monitoring system having multiple communications channels"); U.S. Pat. No. 7,115,097 ("Positive airway pressure notification system for treatment of breathing disorders during sleep"); U.S. Pat. No. 6,978,169 ("Personal physiograph"); U.S. Pat. No. 6,340,928 ("Emergency assistance system using bluetooth technology").

Operation 8868 describes selecting one or more pattern recognition criteria of the filtering information in response to at least one duration indicator associated with the subject (e.g. module 1535 of evaluation logic 1530 configuring module 1533 to apply one or more lesion monitoring criteria 1571, 1572 in monitoring incoming data 1551 responsive to data 1552 indicating that a subject has been stationary for too many hours). This can occur, for example, in a context in which a user transmits a request, authorization 1538, or other such communication 1539 that one or more such systems locally or remotely monitor a subject as described herein directly at a veterinary clinic, a nursing home, or other such facility. Alternatively or additionally, one or more such determinant indications 1542 may include a counter or other indication of how long a subject remains within a room or other vicinity, how old a subject is, how often a subject is fed or visited, or other such indications 1541 of duration relating to healthcare as described herein.

In light of teachings herein, numerous existing techniques may be applied for organizing, classifying, and recognizing thermal gradients or other patterns indicative of circulatory or other pathologies as described herein without undue experimentation. See, e.g., U.S. Pat. No. 7,276,031 ("System and method for classifying patient's breathing using artificial neural network"); U.S. Pat. No. 7,236,815 ("Method for probabilistically classifying tissue in vitro and in vivo using fluorescence spectroscopy"); U.S. Pat. No. 7,158,692 ("System and method for mining quantitive information from medical images"); U.S. Pat. No. 7,092,970 ("Medical image radiographing system, method for managing medical image and method for displaying medical image"); U.S. Pat. No. 7,058,450 ("Organizing data according to cardiac rhythm type"); U.S. Pat. No. 6,959,211 ("Device for capturing thermal spectra from tissue"); U.S. Pat. No. 6,856,831 ("Method for the early diagnosis of subacute, potentially catastrophic illness"); U.S. Pat. No. 6,611,846 ("Method and system for medical patient data analysis"); U.S. Pat. No. 6,430,430 ("Method and system for knowledge guided hyperintensity detection and volumetric measurement"); U.S. Pat. No. 6,377,834 ("Real time in vivo measurement of temperature changes with contrast enhanced NMR imaging").

Figure 89:
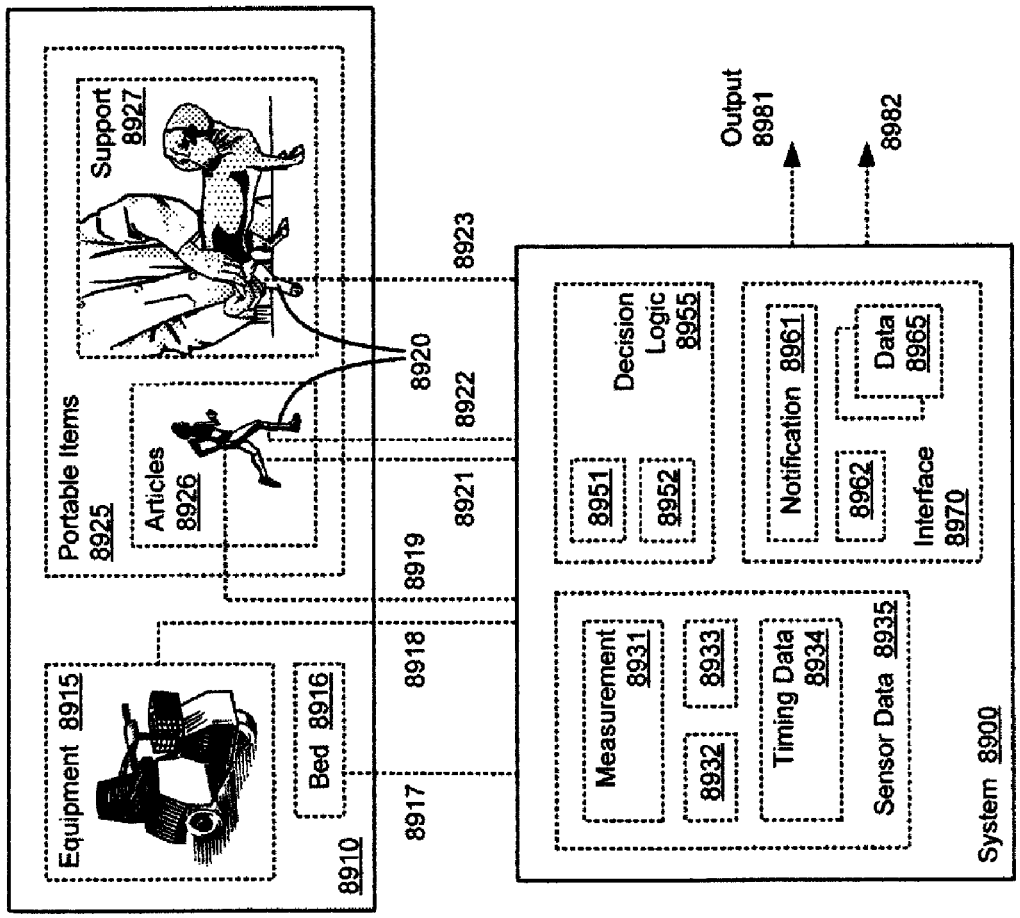
FIG. 89 depicts an exemplary environment in which one or more technologies may be implemented.

With reference now to FIG. 89, shown is a structure 8910 operable in conjunction with system 8900, in which one or more technologies may be implemented. Structure 8910 may include one or more items of transportation or other equipment 8915, beds 8916, and/or handheld or other portable items 8925. Such items may include hosiery, adhesive patches, or other such articles 8926; bandages or other supports 8927; or other such structures as described herein comprising one or more elements 8920 configured to provide information to and/or about such subjects.

In some variants, for example, system 8900 may comprise decision logic 8955 and/or interfaces 8970 operable for receiving or otherwise handling sensor data 8935 such as measurements 8931, timing data 8934, or other data 8932, 8933 as described herein. System 8900 may receive such information 8921, 8922, 8923 or otherwise interact with such structures 8910 via one or more intermittent or other data paths 8917, 8918, 8919. As described herein, decision logic 8955 may use some or all of such temperatures 8951 or other data 8952 as described herein, such as for causing module 8962 or other logic to configure or route notification 8961 or other data 8965 to one or more outputs 8981, 8982.

Figure 90:
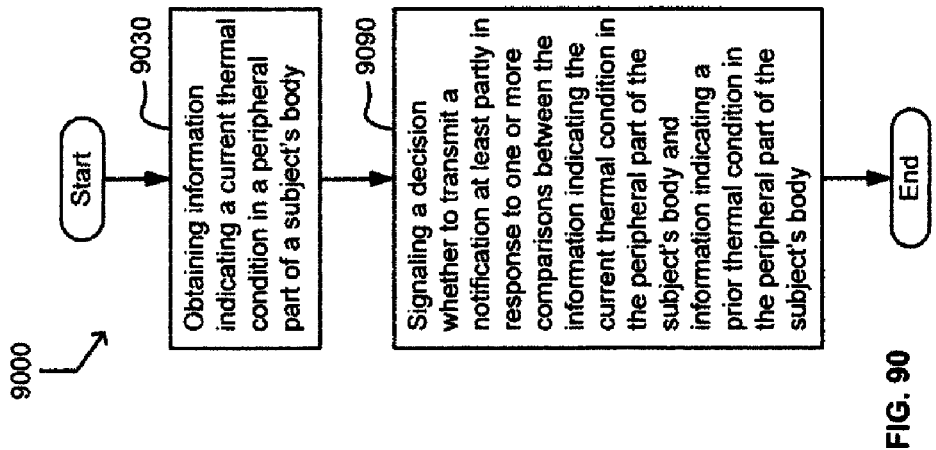
FIG. 90 depicts a high-level logic flow of an operational process.

With reference now to FIG. 90, shown is a flow 9000 comprising operation 9030—obtaining information indicating a current thermal condition in a peripheral part of a subject's body (e.g. decision logic 8955 receiving one or more temperatures 8951 or other such information 8921, 8922, 8923 via one or more portable items 8925 or other equipment 8915 within a proximity of the subject). This can occur, for example, in a context in which system 8900 implements or otherwise interacts with such structures 8910, such as by one or more conduits or other signal paths 8917, 8918, 8919. In some variants, for example, decision logic 8955 may reside within one or more worn articles 8926, a bed 8916, or other equipment 8915 configured to support some or all of a subject. Alternatively or additionally, one or more such structures 8910 may comprise or receive data from one or more implanted or other sensors and/or related circuitry as described above with reference to FIGS. 23-26. Such physical components may likewise incorporate or interact one or more instances of interface 8970 operable for interacting with (some) such subjects or other parties, such as by performing operation 9090.

Operation 9090 describes signaling a decision whether to transmit a notification at least partly in response to one or more comparisons between the information indicating the current thermal condition in the peripheral part of the subject's body and information indicating a prior thermal condition in the peripheral part of the subject's body (e.g. interface 8970 directing one or more notifications 8961 to one or more outputs 8981 corresponding to recipients who have requested or may otherwise benefit from such timely information). This can occur, for example, in a context in which decision logic 8955 has addressed the notifications or otherwise selected the output(s) 8981 according to one or more expert-defined thresholds or other criteria as described herein. In some variants, for example, a recipient or other managing entity associated with output 8982 may choose a more extreme temperature or other threshold as a cutoff in response to receiving an excessive number of notifications that are not actionable. Alternatively or additionally, such an entity may likewise choose a mode of transmission, an inclusion of data 8965, or some other aspect of configuring notification 8961 in response to a recipient's indication of availability as described herein.

Figure 91:
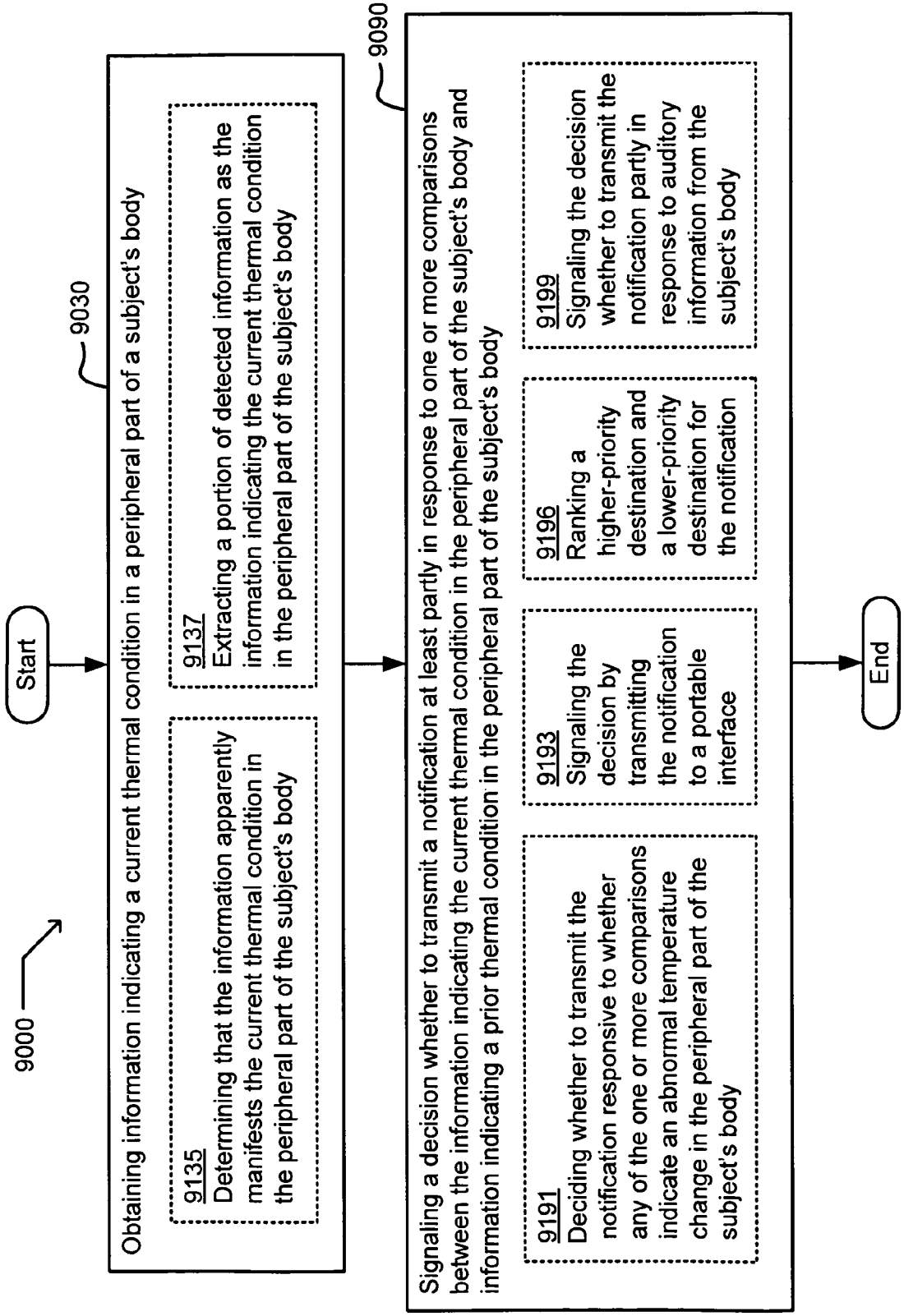
FIGS. 91-92 depict variants of the flow of FIG. 90.

With reference now to FIG. 91, there are shown several variants of the flow 9000 of FIG. 90. Operation 9030—obtaining information indicating a current thermal condition in a peripheral part of a subject's body—may (optionally) include one or more of the following operations: 9135 or 9137. In some embodiments, variants of operation 9030 may be performed by one or more instances of extraction logic, detection logic 640, 7940; or other such data reception or distillation logic as described herein. Operation 9090—signaling a decision whether to transmit a notification at least partly in response to one or more comparisons between the information indicating the current thermal condition in the peripheral part of the subject's body and information indicating a prior thermal condition in the peripheral part of the subject's body—may include one or more of the following operations: 9191, 9193, 9196 or 9199. In some embodiments, variants of operation 9090 may be performed by one or more instances of detection logic 180, 640, 880, 1275, 3285, 3550, 5135, 5670, 6110, 6720, 7940; notification logic 1290, 3535, 3991, 6180, 7460, 7875; or other such processing and/or communication components. Alternatively or additionally, flow 9000 may be performed in a context as described above with reference to any of FIGS. 1-80 and/or in conjunction with other flow variants as described below.

Operation 9135 describes determining that the information apparently manifests the current thermal condition in the peripheral part of the subject's body (e.g. evaluation module 7952 identifying abnormal-temperature-indicative data 7991 received from one or more components of local module 7932 and normal-temperature-indicative data 7992 received from local module 7931). This can occur, for example, in a context in which configuration module 7942 and evaluation module 7952 jointly perform operation 9030; in which other components of detection logic 7940 perform operation 9090; in which evaluation module 7952 implicitly treats such data 7991-7996 as "current" and "spatially separated" for diagnostic purposes; in which at least two such local modules 7931, 7932 each instantiate local module 2510 of FIG. 25 (local to subject 7920, e.g.); and in which local module 7932 detects two or more physical phenomena as described herein from peripheral body part 7922. In some variants, for example, one or more elements 7933 of such local modules 7931, 7932 may comprise respective instances of temperature sensors 2512 or other sensors as shown in FIG. 25. Alternatively or additionally, some or all such data 7991-7996 may (optionally) include (a) color-indicative or other measurement data 7994; (b) timestamps 2544, coordinates 2545, anatomical descriptions, shape data, or other such temporal or spatial indices 2546; and/or (c) pathology profile data 7995; or other such diagnostically useful information.

In light of teachings herein, numerous existing techniques may be applied for determining a data object type, format, or other indication whether data may be evaluated as described herein without undue experimentation. See, e.g., U.S. Pat. No. 7,296,238 ("Method and apparatus for triggering automated processing of data"); U.S. Pat. No. 7,269,718 ("Method and apparatus for verifying data types to be used for instructions and casting data types if needed"); U.S. Pat. No. 7,263,688 ("Method and apparatus for dynamic data-type management"); U.S. Pat. No. 7,020,666 ("System and method for unknown type serialization"); U.S. Pat. No. 7,016,601 ("Method and apparatus for storing different types of data on the same storing medium"); U.S. Pat. No. 6,738,769 ("Sorting multiple-typed data"); U.S. Pat. No. 6,621,506 ("Applying operations to selected data of different types"); U.S. Pat. No. 6,170,997 ("Method for executing instructions that operate on different data types stored in the same single logical register file"); U.S. Pat. No. 5,718,247 ("Apparatus and process for interactive psychotherapy").

Operation 9137 describes extracting a portion of detected information as the information indicating the current thermal condition in the peripheral part of the subject's body (e.g. module 8002 of extraction logic 8010 selectively including one or more measurements 8017 or ratios 8034 or other measurement-based computations 8036 extracted from output 8012 of sensors or other detection circuitry as described herein). This can occur, for example, in a context in which a sampling 8014, a distillation 8015, one or more measurements 8016, 8017 of particular interest, or some other subset of such output 8012 is logged or otherwise retained for comparison and/or included in one or more notifications as described herein. In some variants, for example, such a notification may include a blood pressure measurement 8018, a range or other type identifier 8019, and/or other such extracted information 8020. Alternatively or additionally, such a notification may include advice 8032, a recipient-appropriate translation, or other such categorical information 8030 extracted from a database 8081 or other such secondary information source 8080 using the extracted information 8020, for example, as a search term.

In light of teachings herein, numerous existing techniques may be applied for selectively retaining probative data portions or otherwise sampling or sifting detected information as described herein without undue experimentation. See, e.g., U.S. Pat. No. 7,343,305 ("Method and system for recording carious lesions"); U.S. Pat. No. 7,325,297 ("Automatic assembly machine for mounting bearings onto motors"); U.S. Pat. No. 7,280,992 ("Method for processing medically relevant data"); U.S. Pat. No. 7,254,425 ("Method for detecting artifacts in data"); U.S. Pat. No. 7,076,436 ("Medical records, documentation, tracking and order entry system"); U.S. Pat. No. 6,826,578 ("Method, system, and computer product for collecting and distributing clinical data for data mining"); U.S. Pat. No. 6,611,846 ("Method and system for medical patient data analysis").

Operation 9191 describes deciding whether to transmit the notification responsive to whether any of the one or more comparisons indicate an abnormal temperature change in the peripheral part of the subject's body (e.g. module 643 of detection logic 640 sounding an alarm only if comparison result 655 indicates that any part of a subject's seat 610 is excessively hot or cold). This can occur, for example, in a context in which detection logic 640 is implemented in or otherwise coupled to respective portions of seat 610 via one or more signal paths 631, 632, 633, 634; in which module 641 and/or responsive logic 650 perform operation 9030; in which detection logic 640 performs operation 9090; in which monitoring apparatus 660 resides in or around seat 610, and in which a nearby person may be pre-trained and/or contemporaneously guided to provide adequate and timely aid. Such aid may include talking with or positioning a subject; helping a subject to administer medications; obtaining a defibrillator, ECG monitor, or other such therapeutic or diagnostic instruments; or contacting a physician or ambulance for more extreme situations. In some variants, for example, one or more modules 651 of responsive logic 650 may enable such detection logic only when one or more such signal paths 631-634 indicate an occupant's weight or other indication that wheelchair 600 is occupied. Alternatively or additionally, seat 610 may include one or more instances of local module 2510 of FIG. 25 operable for transmitting comparison results, measurement data, or decisions as described herein along the signal path(s).

Operation 9193 describes signaling the decision by transmitting the notification to a portable interface (e.g. channel 550 transmitting one or more notifications 541, 542 as described herein via one or more antennas 549 to one or more wearable or other portable interfaces 7860, 7880, 580 or other destinations 535). This can occur, for example, in a context in which such a transmission results from one or more hybrid-data decisions 531 or other thermally-dependent decisions 532 and in which one or more controllers as described herein include one or more implementations of notification module 510. In some variants, for example, some or all of the content 544 of such a notification may depend upon a type 533 of one or more such interfaces or other destinations 535. Alternatively or additionally, such a decision may be signaled to a display element 536 or other configurable feature local to notification module 510.

Operation 9196 describes ranking a higher-priority destination and a lower-priority destination for the notification (e.g. module 7871 ranking one or more nearby interfaces 7860 with a higher-priority category 7844 than that of one or more interfaces 7880 of network 7890). This can occur, for example, in a context in which a notification 7868 is first routed to a subject or other higher-priority destination and in which a related notification is routed to another party a few minutes or hours later in the event that module 7872 does not receive input 7834 from the higher-priority destination. In some variants, for example, such input may include an acknowledgment that someone has received the notification. Alternatively or additionally, any such decisions, notifications, or determinants may be logged to other destinations, such as logging module 7885.

Operation 9199 describes signaling the decision whether to transmit the notification partly in response to auditory information from the subject's body (e.g. notification module 510 updating a party partly in response to recognition module 7981 indicating one or more comparison results 7962 and partly in response to recognition module 7983 indicating a recognition of one or more phrases or other patterns 7973, 7974 in speech or other auditory information 7941 from subject 7920). This can occur, for example, in a context in which such auditory information 7941 indicates that subject 7920 may currently be impaired and in which at least one such result 7962 of comparing abnormal-temperature-indicative data 7991 with historical or other filtering data indicates that a hot zone of peripheral body part 7922 has become measurably hotter and that peripheral body part 7921 has apparently remained in a normal condition. In some contexts, for example, such normality may be inferred from abnormal-temperature-indicative data 7991 not referring to part 7921 and/or not coming from one or more local modules 7931 in a vicinity of part 7921. Alternatively or additionally, the decision may depend upon one or more other determinants such as (a) whether a current notification 542 differs from a prior notification 541; (b) whether interface 580 indicates that one or more recipients are apparently online; (c) whether any new comparison result reflects a new, unrecognized, and/or other urgent situation; or other criteria as described herein.

In light of teachings herein, numerous existing techniques may be applied for recognizing words or other auditory patterns as described herein without undue experimentation. See, e.g., U.S. Pat. No. 7,257,531 ("Speech to text system using controlled vocabulary indices"); U.S. Pat. No. 6,990,455 ("Command and control using speech recognition for dental computer connected devices"); U.S. Pat. No. 6,934,579 ("Anaesthesia control system"); U.S. Pat. No. 6,804,654 ("System and method for providing prescription services using voice recognition"); U.S. Pat. No. 6,785,358 ("Voice activated diagnostic imaging control user interface"); U.S. Pat. No. 6,629,937 ("System for processing audio, video and other data for medical diagnosis and other applications"); U.S. Pat. No. 5,335,313 ("Voice-actuated, speaker-dependent control system for hospital bed"); U.S. Pat. No. 5,262,669 ("Semiconductor rectifier having high breakdown voltage and high speed operation").

Figure 92:
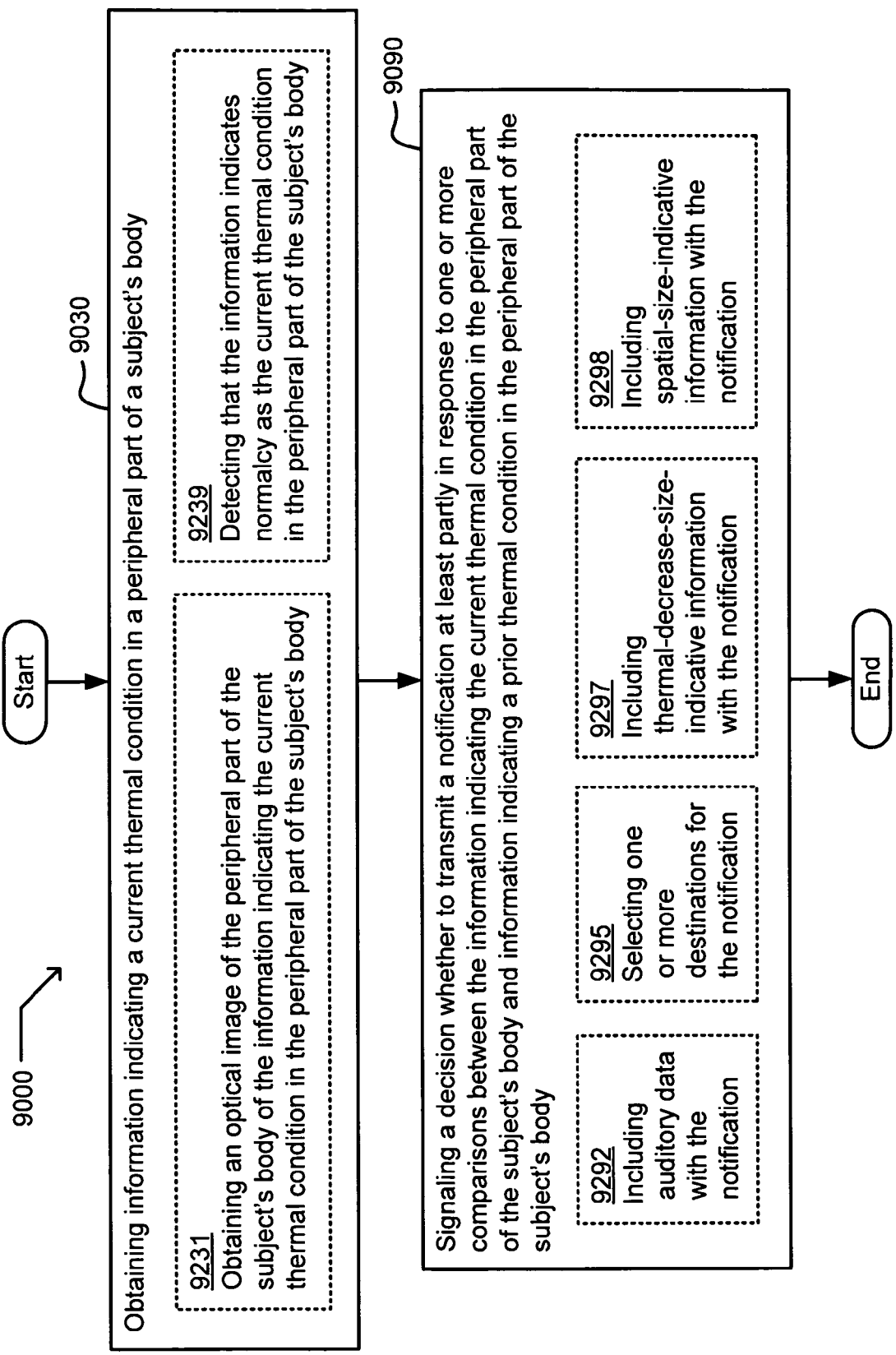

With reference now to FIG. 92, there are shown several variants of the flow 9000 of FIG. 90 or 91. Operation 9030—obtaining information indicating a current thermal condition in a peripheral part of a subject's body—may (optionally) include one or more of the following operations: 9231 or 9239. In some embodiments, variants of operation 9030 may be performed by one or more instances of local modules 2320, 2450, 2510, 2690, 7931, 7932 or other modules 7820 configured to handle sensor data; decision logic 275, 1350, 2730, 2975, 3230, 5750, 5930, 6395, 7415; or other components configured to handle such status information. Operation 9090—signaling a decision whether to transmit a notification at least partly in response to one or more comparisons between the information indicating the current thermal condition in the peripheral part of the subject's body and information indicating a prior thermal condition in the peripheral part of the subject's body—may include one or more of the following operations: 9292, 9295, 9297 or 9298. In some embodiments, variants of operation 9090 may be performed by one or more instances of distribution logic; notification logic 1290, 3991, 6180, 7460, 7875; or other such control or communication components. Alternatively or additionally, flow 9000 may be performed in a context as described above with reference to any of FIGS. 1-80 and/or in conjunction with other flow variants as described below.

Operation 9231 describes obtaining an optical image of the peripheral part of the subject's body of the information indicating the current thermal condition in the peripheral part of the subject's body (e.g. module 7820 receiving image 7831 from infrared sensor 7821 or image 7832 from another optical sensor 7822 from a position adjacent a subject's body part). This can occur, for example, in a context in which a subject or caregiver positions a charge-coupled device or similar image capture mechanism in a vicinity of the body part to monitor a growth or other optically detectable phenomenon, optionally in a manner that captures one or more isotherm-indicative shapes. In some variants, for example, a sensor array comprising infrared-sensitive elements may be used for implementing such data capture. Alternatively or additionally, other radiant-energy-sensitive and/or other elements as described below in FIGS. 23-27 may be used for sensing diagnostically useful information contemporaneously relating to the same part of the subject's body.

Operation 9239 describes detecting that the information indicates normalcy as the current thermal condition in the peripheral part of the subject's body (e.g. one or more modules 2977 of decision logic 2976 indicating normalcy in response to receiving a high-enough and/or low-enough numerical value 2987 directly or indirectly from one or more sensors 2927 operable for detecting a temperature at an extremity of subject 2920). This can occur, for example, in a context in which subject 2920 rests upon or otherwise interacts with instrument 2930, in which decision logic 2976 is capable of detecting and indicating whether value 2987 is too far from a normal temperature, and in which transmitter 2980 is operable for performing operation 9090. In some variants, for example, module 2977 may employ this information as a factor in deciding whether to transmit a notification to user interface 2952 or to other destinations. Alternatively or additionally, in various implementations as described herein, instrument 2930 may include one or more instances of response logic or other circuitry operable for responding conditionally to an identifier 2923 of a subject or other determinants in detected data 2922.

In light of teachings herein, numerous existing techniques may be applied for detecting statistical, anatomical, or other potentially useful thermal aberrations in light of other circumstances as described herein without undue experimentation. See, e.g., U.S. Pat. No. 7,340,293 ("Methods and apparatus for a remote noninvasive technique to detect core body temperature in a subject via thermal imaging"); U.S. Pat. No. 7,226,426 ("Apparatus and method for the detection and quantification of joint and tissue inflammation"); U.S. Pat. No. 6,963,772 ("User-retainable temperature and impedance monitoring methods and devices"); U.S. Pat. No. 6,757,412 ("System and method for helping to determine the condition of tissue"); U.S. Pat. No. 6,126,614 ("Apparatus and method for analysis of ear, pathologies by detecting fluid in the ear measuring body temperature and/or determining a characteristic of a fluid"); U.S. Pat. No. 6,023,637 ("Method and apparatus for thermal radiation imaging"); U.S. Pat. No. 5,999,842 ("Functional thermal imaging apparatus"); U.S. Pat. No. 5,997,472 ("Endodiagnostic method using differential thermal relaxation and IR imaging").

Operation 9292 describes including auditory data with the notification (e.g. one or more modules 7871-7874 of notification logic 7875 configuring notification 7868 to include speech 7864 or other audible data with other content 7865 of notification 7868 delivered to one or more interfaces 7860, 7880). This can occur, for example, in a context in which notification logic 7875 performs at least operation 9090 and in which one or more users or devices have indicated a telephone, computer speaker, or other interface facility for handling such data. In some variants, for example, output 7837 from a microphone or other sensor 7824 may first be detected as speech, a heartbeat or other audible metabolic indicator, or other device-detectable phenomena in a subject's vicinity. Alternatively or additionally, content 7865 provided with a notification 7868 may include one or more instances of translated or other programmatic notifications, for example, suitable for remote delivery at a speaker-containing interface 7880.

In light of teachings herein, numerous existing techniques may be applied for amplifying, recording, translating, selecting, or otherwise facilitating an inclusion of potentially useful auditory data as described herein without undue experimentation. See, e.g., U.S. Pat. No. 7,313,529 ("Portable extender for data transmission within a medical device communication system"); U.S. Pat. No. 7,291,111 ("Apparatus and method for non-invasive diagnosing of coronary artery disease"); U.S. Pat. No. 6,944,497 ("System and method of treating stuttering by neuromodulation"); U.S. Pat. No. 6,878,117 ("Handheld sensor for acoustic data acquisition"); U.S. Pat. No. 6,629,937 ("System for processing audio, video and other data for medical diagnosis and other applications"); U.S. Pat. No. 6,58,2379 ("Apparatus and method of measuring the flow of a liquid, in particular urine, from a patient"); U.S. Pat. No. 6,126,614 ("Apparatus and method for analysis of ear pathologies by detecting fluid in the ear, measuring body temperature and/or determining a characteristic of a fluid"); U.S. Pat. No. 6,014,626 ("Patient monitoring system including speech recognition capability").

Operation 9295 describes selecting one or more destinations for the notification (e.g. distribution module 8050 selecting one or more destinations 8041, 8042 using client list 8067 or other determinants as described herein). This can occur, for example, in a context in which an aircraft or other system 800 implements system 8000 (of FIG. 80) and in which one or more preferences of a client system, member, or other interested party are registered for notification via subscriber profile 8061 or other such indication. In some variants, for example, a passenger in seat 814 of cabin 810 registers for notification of changes in physiological parameters signaled by indication 823 and may receive a notification 8038 via local interface 895, in some variants, in response to a detection of one or more clot-indicative symptoms as described herein. Alternatively or additionally, a flight attendant may receive such a notification 8038, for example via interface 890. In a variety of contexts as described herein, such implementations can facilitate a faster therapeutic response.

In light of teachings herein, numerous existing techniques may be applied for the selection of one or more recipients for medical or other notifications as described herein without undue experimentation. See, e.g., U.S. Pat. No. 7,333,014 ("Notifying users of device events in a networked environment"); U.S. Pat. No. 7,310,615 ("Financial data reporting system with alert notification feature and free-form searching capability"); U.S. Pat. No. 7,308,246 ("Emergency notification system and emergency notification device"); U.S. Pat. No. 7,233,781 ("System and method for emergency notification content delivery"); U.S. Pat. No. 7,180,415 ("Safety/security alert system"); U.S. Pat. No. 7,003,525 ("System and method for defining, refining, and personalizing communications policies in a notification platform"); U.S. Pat. No. 6,834,306 ("Method and apparatus for notifying a user of changes to certain parts of web pages"); U.S. Pat. No. 6,442,241 ("Automated parallel and redundant subscriber contact and event notification system"); U.S. Pat. No. 6,177,873 ("Weather warning apparatus and method"); U.S. Pat. No. 6,014,346 ("Medical timer/monitor and method of monitoring patient status").

Operation 9297 describes including thermal-decrease-size-indicative information with the notification (e.g. module 8962 including a number of degrees or other data 8965 received as information 8922, 8923 from one or more portable items 8925 indicating how much a subject's appendage has apparently cooled). This can occur in a context in which such cooling results from a wound dressing or other article significantly impairing a subject's circulation, for example, or in which such cooling signifies a return to normalcy from an overly-hot condition. In some contexts, for example, a notification recipient may respond with timely advice for treating the subject's leg in response to such quantified notification. Alternatively or additionally, in some contexts, such information may warrant a change in how the subject is monitored, such as by decreasing vigilance and/or by monitoring systemic, environmental, or other information 8921 relating to a subject as described herein.

Operation 9298 describes including spatial-size-indicative information with the notification (e.g. module 7874 of notification logic 7875 including one or more of a scaling factor 7842 or other areal indicator 7843, photographs or other images 7831, 7832, a volumetric or shape-descriptive category 7844, and/or other such information included in or appended to content 7865 of notification 7868). This can occur, for example, in a context in which interface 7860 performs operation 9030, in which module 7873 decides whether to transmit the notification, in which notification logic 7875 performs operation 9090, and in which a subject cannot communicate such information and/or otherwise address a pathology. In some variants, for example, module 7873 signals in the affirmative if a hot zone 7839 of an image 7832 is larger than threshold 7845. Alternatively or additionally, the decision may likewise depend upon one or more of an iteration count 7841 or other indicator of duration, user input 7834, a concentration or other output 7837 from a chemical sensor 7823, and/or other determinants 7850 as described herein.

In light of teachings herein, numerous existing techniques may be applied for shape recognition or other analyses of spatial attributes as described herein without undue experimentation. See, e.g., U.S. Pat. No. 7,346,205 ("System and method for rapidly identifying pathogens, bacteria and abnormal cells"); U.S. Pat. No. 7,340,077 ("Gesture recognition system using depth perceptive sensors"); U.S. Pat. No. 7,331,667 ("Iris pattern recognition and alignment"); U.S. Pat. No. 7,327,861 ("Organism authenticating apparatus"); U.S. Pat. No. 7,317,821 ("Automatic abnormal tissue detection in MRI images"); U.S. Pat. No. 7,242,807 ("Imaging of biometric information based on three-dimensional shapes"); U.S. Pat. No. 7,184,580 ("Fingerprint scar recognition method and apparatus"); U.S. Pat. No. 6,840,117 ("Patient monitoring system employing array of force sensors on a bedsheet or similar substrate"); U.S. Pat. No. 6,675,040 ("Optical object tracking system"); U.S. Pat. No. 6,529,759 ("Method for mapping internal body tissue").

Figure 93:
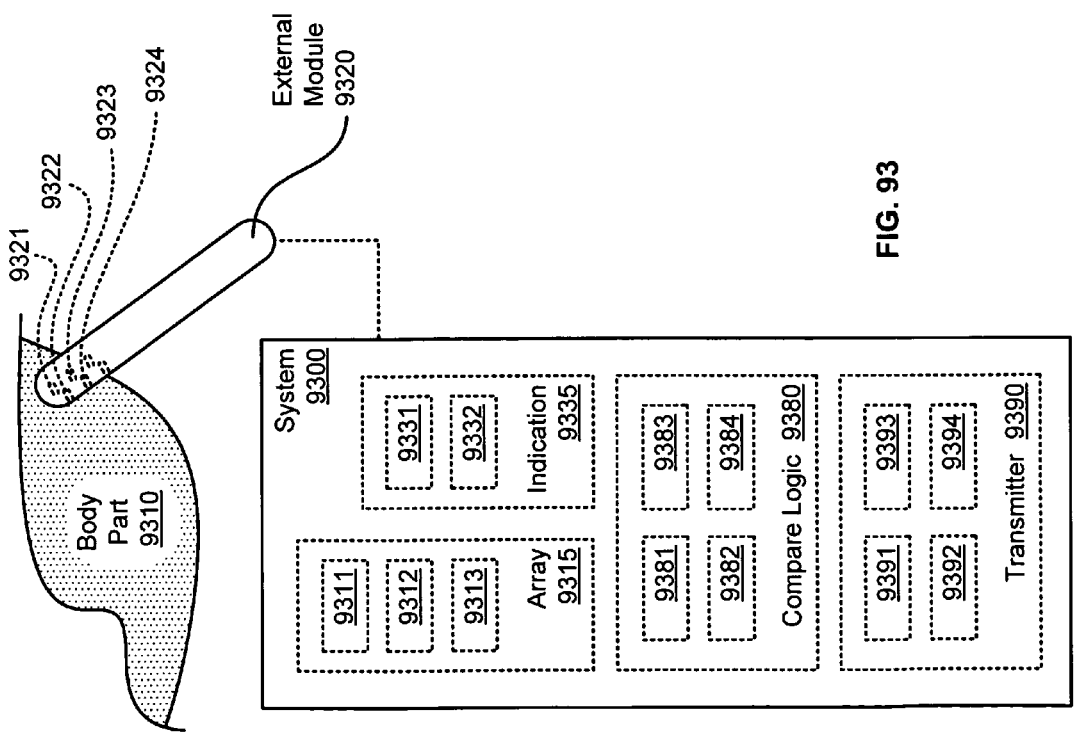
FIG. 93 depicts an exemplary environment in which one or more technologies may be implemented.

With reference now to FIG. 93, shown is a system 9300 in which one or more technologies may be implemented, such as for interacting with external module 9320 to receive information via sensors 9321, 9322, 9323, 9324 about one or more body parts 9310. System 9300 may (optionally) include one or more values 9311, 9312, 9313, 9331, 9332 in an array 9315 or other indication 9335; one or more modules 9381, 9382, 9383, 9384 of compare logic 9380; and/or one or more transmitters 9390 operable to schedule, transmit, identify, or otherwise signal one or more decisions 9391, 9392 or notifications 9393, 9394 as described herein.

Figure 94:
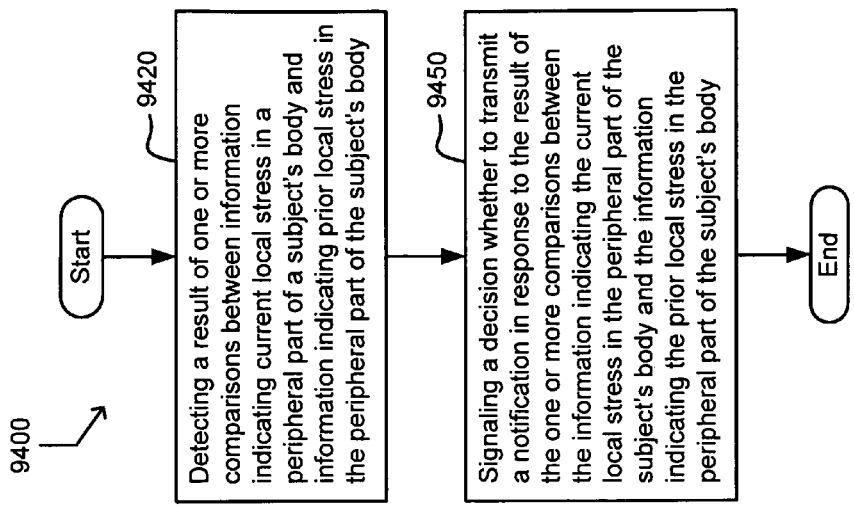
FIG. 94 depicts a high-level logic flow of an operational process.

With reference now to FIG. 94, shown is a flow 9400 comprising operation 9420—detecting a result of one or more comparisons between information indicating current local stress in a peripheral part of a subject's body and information indicating prior local stress in the peripheral part of the subject's body (e.g. external module 9320 transmitting at least one value 9331 manifesting an increasing or decreasing force level in or on body part 9310). This can occur, for example, in a context in which one or more external modules 9320 include one or more microwave frequency sensors 2321, event detection logic 2333, fluid pressure sensors 2482, force sensors 2484, reflectance sensors 2511, weight sensors 2533, comparators 2670, or other components of local modules described herein. In some contexts in which external module 2670 implements local module 2690 of FIG. 26, real-time data 2681 or force-indicative data 2683 may indicate the "current" local stress, for example, and historical data 2682 or other measurement data 2685 may indicate the "prior" local stress. Alternatively or additionally, some such images as described herein (showing swelling, e.g.) or other measurement data 2685 may reside in array 9315 in raw form, optionally to be acted upon by compare logic 9380 or other modes of comparison as described herein.

Operation 9450 describes signaling a decision whether to transmit a notification in response to the result of the one or more comparisons between the information indicating the current local stress in the peripheral part of the subject's body and the information indicating the prior local stress in the peripheral part of the subject's body (e.g. compare logic 9380 activating transmitter 9390 if one or more arrays 9315 or other values 9332 indicate a higher-than-nominal blood pressure or other manifestation of stress increasing repeatedly over a time interval, and otherwise not activating transmitter 9390). This can occur, for example, in a context in which compare logic 9380 includes one or more modules 9381 for comparing pressure levels or other force-level indicators, one or more modules 9382 for comparing event counts, one or more modules 9383 for comparing time intervals, and/or one or more other modules 9384 as described herein. In some variants, a useful time interval (threshold) may be on the order of 2 hours or 2 weeks, for example, or the stress level thresholds may be specified by a notification recipient or other interested party. Alternatively or additionally, in some variants, such a decision may require an intermediary's authorization or may be affected by other determinants as described herein.

With reference now to FIG. 95, there are shown several variants of the flow 9400 of FIG. 94. Operation 9420—detecting a result of one or more comparisons between information indicating current local stress in a peripheral part of a subject's body and information indicating prior local stress in the peripheral part of the subject's body—may include one or more of the following operations: 9524 or 9528. In some embodiments, variants of operation 9420 may (optionally) be performed by one or more modules 261 of evaluation logic 150, 250, 950, 1530, 7565 or other responsive logic as described herein. Operation 9450—signaling a decision whether to transmit a notification in response to the result of the one or more comparisons between the information indicating the current local stress in the peripheral part of the subject's body and the information indicating the prior local stress in the peripheral part of the subject's body—may include one or more of the following operations: 9555, 9557 or 9558. In some embodiments, variants of operation 9450 may be performed by one or more instances of detection modules 5860, 5870; or other such detection and/or evaluation logic as described herein. Alternatively or additionally, flow 9400 may be performed in a context as described above with reference to any of FIGS. 1-80 and/or in conjunction with other flow variants as described below.

Operation 9524 describes detecting the result at least one day after detecting the information indicating the prior local stress in the peripheral part of the subject's body (e.g. module 7561 of evaluation logic 7565 configuring evaluations or other result data 7537 arising from condition detectors, expert systems 7585, or other comparative analysis based upon at least some pressure- or other stress-indicative data 7538 measured one or more days earlier). This can occur, for example, in a context in which evaluation logic 7565 performs operation 9420, in which local system 7570 implements one or more instances of detection modules 7610, in which circular buffer 7651 captures hourly or other successive samples 7661, 7662, 7663 about subject 7505 via one or more sample sensors 7625 over the course of a week or a month and in which one or more condition detectors 7670, 7680 iteratively determine whether such digital or other samples indicate a large-enough and long-enough shift in local tissue stretching or blood pressure measurements, each relative to one or more respective standards 7675, 7685. In some variants, for example, an at-risk patient may use or otherwise interact with one or more wheelchairs, articles of clothing, or other portable systems as described herein repeatedly over a course of weeks or months, so that such an instance of local system 7570 may obtain multiple data points from one or more pressure sensors 7621, stress-indicative sensors 7622, or other sample sensors 7625 thereof. Alternatively or additionally, condition detectors 7680, 7690 may (optionally) access positional coordinates 7634, timing-indicative values 7632, or other such status indicators 7645 as described herein for helping evaluation logic 7565 to identify and avoid transmitting notifications under ordinary circumstances of health indicia.

In light of teachings herein, numerous existing techniques may be applied for recognizing pathologies presenting with a detectable mechanical stress and/or other symptoms as described herein without undue experimentation. See, e.g., U.S. Pat. No. 7,232,415 ("System and method for noninvasively evaluating a limb suspected of compartment syndrome"); U.S. Pat. No. 7,183,057 ("Tape stripping methods for analysis of skin disease and pathological skin state"); U.S. Pat. No. 7,112,318 ("Non-invasive diagnostic imaging technology for mitochondria dysfunction using radiolabeled lipophilic salts"); U.S. Pat. No. 7,110,806 ("Method for imaging an artery using a magnetic resonance contrast agent"); U.S. Pat. No. 7,001,338 ("System and method for diagnosing pathologic heart conditions"); U.S. Pat. No. 6,929,922 ("Methods for the detection of demyelinating diseases"); U.S. Pat. No. 6,847,841 ("Detector of living tissue strength and electrical resistance and activity"); U.S. Pat. No. 6,813,009 ("Detection of metabolic dysfunctions using fluorescence emission from serum"); U.S. Pat. No. 6,735,331 ("Method and apparatus for early detection and classification of retinal pathologies"); U.S. Pat. No. 6,671,540 ("Methods and systems for detecting abnormal tissue using spectroscopic techniques"); U.S. Pat. No. 6,636,755 ("Method and apparatus for obtaining an optical tomographic image of a sentinel lymph node"); U.S. Pat. No. 6,629,937 ("System for processing audio, video and other data for medical diagnosis and other applications"); U.S. Pat. No. 6,620,115 ("Apparatus and method for mechanical imaging of breast"); U.S. Pat. No. 6,507,754 ("Device for the medical monitoring in real time of a patient from the analysis of electroencephalograms").

Operation 9528 describes receiving a structural change indication in the result of the one or more comparisons (e.g. pattern recognition module 7564 of evaluation logic 7565 detecting a swelling, discoloration, or other optically detectable tissue attribute change manifesting as a colorimetric shift between a portion 7511 of a weeks-old image 7510 and a corresponding portion 7521 of a newer image 7520). This can occur, for example, in a context in which evaluation logic 7565 performs operation 9420, in which another portion 7512 of the weeks-old image 7510 resembles a corresponding portion 7522 of the newer image 7520, and in which such resemblance supports a heuristic change model that may likewise be applied to one or more portions 7511, 7521 that have apparently changed. In some variants, for example, such reference portions 7512, 7522 of respective images may be used to establish a position shift or other baseline transfer function for determining whether an area, shape, shade, or other substantial, quantifiable difference between such primary portions 7511, 7521 indicates a structural change. Alternatively or additionally, an expert system 7585 implementing some or all of such evaluation logic 7565 may query a caregiver or other expert for category descriptors 7581 ("site not recognized," "swelling reduced," "emergency," etc.), scores 7582, or other such input 7583 for facilitating subsequent evaluations of such potential structural change indications.

In light of teachings herein, numerous existing techniques may be applied for aggregating symptomatic or other structural data or implementing predictive or other expert systems as described herein without undue experimentation. See, e.g., U.S. Pat. No. 7,315,825 ("Rules-based patient care system for use in healthcare locations"); U.S. Pat. No. 7,272,435 ("System and method for sudden cardiac death prediction"); U.S. Pat. No. 7,225,013 ("Adaptive prediction of changes of physiological/pathological states using processing of biomedical signals"); U.S. Pat. No. 7,027,871 ("Aggregation of data from external data sources within an implantable medical device"); U.S. Pat. No. 6,988,088 ("Systems and methods for adaptive medical decision support"); U.S. Pat. No. 6,643,646 ("Analysis of massive data accumulations using patient rule induction method and on-line analytical processing"); U.S. Pat. No. 6,533,724 ("Decision analysis system and method for evaluating patient candidacy for a therapeutic procedure"); U.S. Pat. No. 6,442,421 ("Method for the medical monitoring in real time of a patient from the analysis of electroencephalograms to characterize and differentiate between physiological or pathological conditions, and a method for anticipating epileptic seizures"); U.S. Pat. No. 6,317,731 ("Method for predicting the therapeutic outcome of a treatment"); U.S. Pat. No. 6,025,128 ("Prediction of prostate cancer progression by analysis of selected predictive parameters").

Operation 9555 describes enabling a performance of the one or more comparisons at a resource remote from the subject's body (e.g. interface 7563 transmitting force estimates or other stress-indicative information 7533 with corresponding locality information 7531, timing information 7532, patient-specific information 7534, or other such comparative parameters). This can occur, for example, in a context in which evaluation logic 7565 performs operation 9450 and in which comparative information and/or other data as described herein is transmitted to or otherwise affects a configuration of one or more standards 7588, logic modules 7562, or other such comparison mode determinants 7535 configured to be applied remotely. In some variants, for example, one or more signal channels 7575 may be implemented in one or more aggregators or other such adjunct services 7590 operable remotely from an external module 9320 or other structures described herein for interacting with subjects. Alternatively or additionally, one or more comparisons or other evaluations as described herein may initially be performed locally to the subject's body.

Operation 9557 describes obtaining the result partly based on an indication of one or more nutrients in the subject's body (e.g. module 181 using one or more sensors 185 to monitor biological-process-indicative changes in zone 171). This can occur, for example, in a context in which detection logic 180 and comparator 130 jointly perform operation 9450 and in which calcium or other nutrients are monitored to give an indication of a deficiency, an excess, or other attributes of subject status. In some variants, for example, sensor 185 may be configured within or adjacent a blood vessel for monitoring and/or controlling blood glucose level. Alternatively or additionally, monitoring of physiological constituents may be used to determine subject compliance with and/or responsiveness to dietary or other therapeutic treatments.

In light of teachings herein, numerous existing techniques may be applied for monitoring nutritional or other physiologically indicative components as an indication of patient status as described herein without undue experimentation. See, e.g., U.S. Pat. No. 7,087,395 ("Vitamin D assay"); U.S. Pat. No. 6,990,365 ("Apparatus for measurement of blood analytes"); U.S. Pat. No. 6,953,666 ("Biomarkers for oxidative stress"); U.S. Pat. No. 6,885,882 ("Method and apparatus for non-invasive glucose sensing through the eye"); U.S. Pat. No. 6,878,518 ("Methods for determining steroid responsiveness"); U.S. Pat. No. 6,671,540 ("Methods and systems for detecting abnormal tissue using spectroscopic techniques"); U.S. Pat. No. 6,573,063 ("Methods and systems for assessing biological materials using optical and spectroscopic detection techniques"); U.S. Pat. No. 6,455,243 ("Nutritional assessment by measuring mitochondrial complex activity"); U.S. Pat. No. 6,300,085 ("Diagnostic method for Alzheimer's disease").

Operation 9558 describes extracting the decision whether to transmit the notification from the result of the one or more comparisons (e.g. condition detector 7690 generating one or more notification decisions 7633 by comparing a sample 7661 against a next sample 7662 or another subsequent sample 7663). This can occur, for example, in a context in which one or more primary and/or local modules include an instance of detection module 7610 configured to perform operation 9450, in which condition detector 7690 generates one or more result values 7631 signifying the necessity of such notifications by applying one or more instances of standard 7695 to successive samples 7661, 7662, 7663 from one or more sample sensors 7625, and in which one or more users or devices might otherwise receive an excessive quantity of such notifications. Alternatively or additionally, such decisions may depend upon each successive ratio or other combination of samples, or upon event counts or other logical combinations of comparison results, or upon other applications of scalar or other standards 7695 as described herein. In some variants, for example, subject measurements exceeding a specified threshold may trigger local and or remote user interface alarms and/or other visual or auditory notifications. Additionally or alternately, notification messages may be sent to a local or remote data processing center for automated analysis and/or recording.

In light of teachings herein, numerous existing techniques may be applied for the transmission of notifications to local and/or remote sites based on one or more evaluation criteria as described herein without undue experimentation. See, e.g., U.S. Pat. No. 7,304,580 ("Intelligent medical vigilance system"); U.S. Pat. No. 7,224,281 ("Patient monitoring and alarm processing system and user interface"); U.S. Pat. No. 7,115,097 ("Positive airway pressure notification system for treatment of breathing disorders during sleep"); U.S. Pat. No. 7,047,083 ("Method and apparatus for identifying lead-related conditions using lead impedance measurements"); U.S. Pat. No. 6,835,553 ("Photometric glucose measurement system using glucose-sensitive hydrogel"); U.S. Pat. No. 6,732,884 ("Bulk medication dispenser and monitoring device"); U.S. Pat. No. 6,687,544 ("System and method for determining safety alert conditions for implantable medical devices"); U.S. Pat. No. 6,646,556 ("Apparatus and method for reducing the risk of decubitus ulcers"); U.S. Pat. No. 6,454,705 ("Medical wellness parameters management system, apparatus and method"); U.S. Pat. No. 6,383,137 ("Labor alerting device"); U.S. Pat. No. 6,305,377 ("System and method for improving compliance of a medical regimen").

Figure 96:
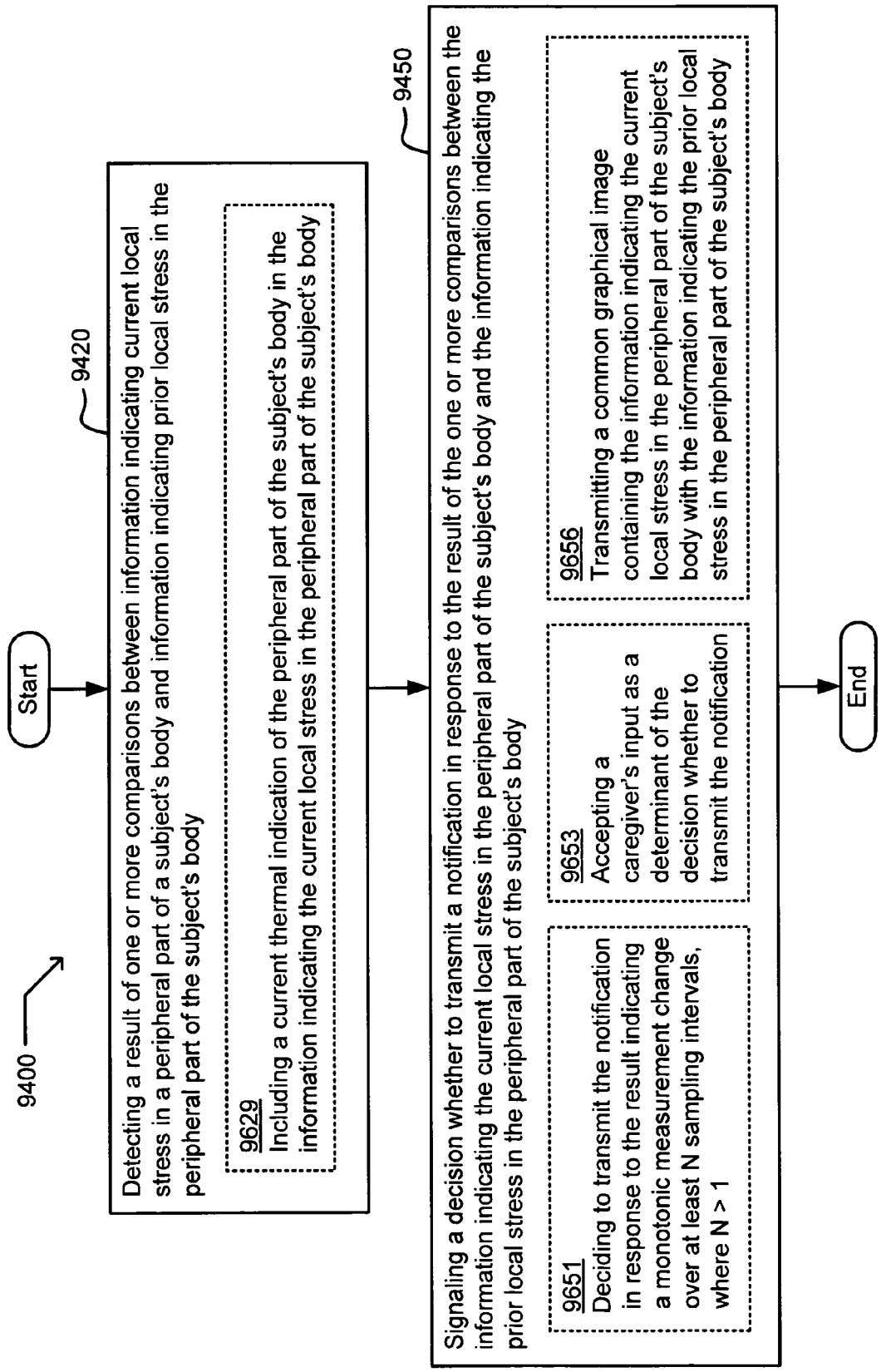

With reference now to FIG. 96, there are shown several variants of the flow 9400 of FIG. 94 or 95. Operation 9420—detecting a result of one or more comparisons between information indicating current local stress in a peripheral part of a subject's body and information indicating prior local stress in the peripheral part of the subject's body—may (optionally) include operation 9629. In some embodiments, variants of operation 9420 may be performed by one or more instances of utility devices 325 or other devices in networks 590, 1380, 1490, 1590, 2215, 2995, 3545, 5280, 5290, 5580, 5840, 6295, 6390, 6400, 7490, 7580, 7890 containing sensors or otherwise configured to handle sensory data. Operation 9450—signaling a decision whether to transmit a notification in response to the result of the one or more comparisons between the information indicating the current local stress in the peripheral part of the subject's body and the information indicating the prior local stress in the peripheral part of the subject's body—may include one or more of the following operations: 9651, 9653 or 9656. In some embodiments, variants of operation 9450 may be performed by one or more instances of decision logic 275, 1460, 2250, 2975, 3230, 5750, 6130, 6395, 7415; subtraction logic; pattern recognition logic; or other circuitry or software implementing comparators or otherwise configured to handle data derived from comparison. Alternatively or additionally, flow 9400 may be performed in a context as described above with reference to any of FIGS. 1-80 and/or in conjunction with other flow variants as described below.

Operation 9629 describes including a current thermal indication of the peripheral part of the subject's body in the information indicating the current local stress in the peripheral part of the subject's body (e.g. external device 7491 and/or other sensor-containing modules 7493 configuring communication 7485 to include one or more thermal images 7471, thermal input 7472 from subject 7495 or other users, or other such indications 7480 of recent physical phenomena relating to region 7496). This can occur, for example, in a context in which one or more components of server 7410 and/or network 7490 each performs operation 9420 and in which communication 7485 also bears tension-indicative data 7473, timing data 7474, blood pressure data 7475, historical data 7476, or other data 7477 facilitating current comparisons or other analysis. In some contexts in which an expert or expert system may monitor a large number of subjects' weight-bearing sites programmatically ranked, for example, according to which have recent images exhibiting the largest colorimetric, areal, thermal, or other detectable trends. Statistics like these rankings may be used at a given subject's site or at an expert's site for triage, for triggering treatment or other testing, or for other resource allocation functions. Alternatively or additionally, a current thermal indication may warrant a higher or lower priority for a subject exhibiting a measurable abnormality in local stress.

In light of teachings herein, numerous existing techniques may be applied for obtaining and expressing temporal or spatial topographies of stress, temperature, or other physical properties as described herein without undue experimentation. See, e.g., U.S. Pat. No. 7,339,587 ("Method for medical imaging and image processing, computed tomography machine, workstation and computer program product"); U.S. Pat. No. 7,303,555 ("Imaging and therapeutic procedure for carpal tunnel syndrome"); U.S. Pat. No. 7,162,068 ("Medical image displaying device, image obtaining and displaying device, method for displaying image in displaying device, and program for selecting display format"); U.S. Pat. No. 6,975,898 ("Medical imaging, diagnosis, and therapy using a scanning single optical fiber system"); U.S. Pat. No. 6,793, 625 ("Method and apparatus for concurrently displaying respective images representing real-time data and non real-time data"); U.S. Pat. No. 6,776,756 ("Applanation tonometer"); U.S. Pat. No. 6,757,412 ("System and method for helping to determine the condition of tissue"); U.S. Pat. No. 6,631,287 ("Infrared thermometer"); U.S. Pat. No. 6,551,306 ("Refractive laser ablation through topography"); U.S. Pat. No. 5,987,345 ("Method and system for displaying medical images").

Operation 9651 describes deciding to transmit the notification in response to the result indicating a monotonic measurement change over at least N sampling intervals, where N>1 (e.g. module 7412 of decision logic 7415 generating one or more notification transmission decisions 7414 responsive to a succession 7420 of N or more measurement change indications 7421, 7422, 7423 each signifying a respective increase). This can occur, for example, in a context in which notification logic 7460 performs at least one instance of operation 9450 and in which an abnormal succession 7430 of measurements 7431, 7432, 7433 manifest a constantly increasing or other monotonic deviation from a baseline value 7442, and in which a therapeutic treatment is more likely to be effective at an early stage of a subject's pathology. Such a trend may, in many therapeutic contexts, signify a progression toward a worsening patient state over a period of several minutes, hours, days, months, or other sampling periods. Under these circumstances, one or more such notifications 7451, 7452 can occur in response to exceeding a defined event count 7441 or other time-indicative threshold. In some variants, for example, a notification 7452 may be sent for a subject 7495 being monitored remotely via one or more external devices 7491 or other sensor-containing modules 7492, 7493 when a blood pressure increase or other apparent trend persists for more than 1-10 hours.

In light of teachings herein, numerous existing techniques may be applied for using condition duration or other trend-related indicators as determinants in notification decisions as described herein without undue experimentation. See, e.g., U.S. Pat. No. 7,319,400 ("Method and apparatus for monitoring a restraint device"); U.S. Pat. No. 7,117,036 ("Using activity-based rest disturbance as a metric of sleep apnea"); U.S. Pat. No. 7,030,764 ("Apparatus and method for reducing the risk of decubitus ulcers"); U.S. Pat. No. 6,671,529 ("System and method for closed loop controlled inspired oxygen concentration"); U.S. Pat. No. 6,305,377 ("System and method for improving compliance of a medical regimen"); U.S. Pat. No. 6,014,346 ("Medical timer/monitor and method of monitoring patient status").

Operation 9653 describes accepting a caregiver's input as a determinant of the decision whether to transmit the notification (e.g. module 2245 using instructions or other parameters 2249 received via medium 2225 to specify one or more conditions under which each type of notification 2241, 2242 will be sent to interface 2210). This can occur, for example, in a context in which decision logic 2250 performs operation 9450 and in which a clinician 2205 indicates via interface 2210 that one or more prior notifications 2201, 2202 warranted no therapeutic response. In some variants, for example, notifications of subject interactions such as administration of medicine and/or other therapeutic actions are logged locally and/or a notification 2242 is transmitted to a remote server 2220. Alternatively or additionally, other such log entries and/or notifications may be generated from caregiver observations of a subject's status.

In light of teachings herein, numerous existing techniques may be applied for the generation of one or more notifications based upon input received from one or more external interfaces as described herein without undue experimentation. See, e.g., U.S. Pat. No. 7,340,240 ("Monitoring device"); U.S. Pat. No. 7,269,484 ("Vehicular touch switches with adaptive tactile and audible feedback"); U.S. Pat. No. 7,133,661 ("Emergency information notifying system, and apparatus, method and moving object utilizing the emergency information notifying system"); U.S. Pat. No. 7,047,083 ("Method and apparatus for identifying lead-related conditions using lead impedance measurements"); U.S. Pat. No. 7,035,684 ("Method and apparatus for monitoring heart function in a subcutaneously implanted device"); U.S. Pat. No. 6,559,769 ("Early warning real-time security system"); U.S. Pat. No. 6,525,712 ("Method and device for manual recording of various events or states"); U.S. Pat. No. 6,014,346 ("Medical timer/monitor and method of monitoring patient status").

Operation 9656 describes transmitting a common graphical image containing the information indicating the current local stress in the peripheral part of the subject's body with the information indicating the prior local stress in the peripheral part of the subject's body (e.g. module 2972 of decision logic 2975 invoking transmitter 2980 to cause one or more composite images or other such successive indications 7530 relating to a subject's limb or back to output 2953). This can occur, for example, in a context in which local system 7570 uploads such images or other measurement data to an implementation of response logic 2970 in network 7580, for example, responsive to a request that remote users may generate after notifications as described herein. Alternatively or additionally, one or more such users may respond by modifying one or more standards 7675, 7685, 7695 or configurations of buffers 7652-7654, in some variants, so that subsequent sense data may result in other patterns of data capture and/or notification as described herein.

In light of teachings herein, numerous existing techniques may be applied for the transmission of graphical images of subject body parts for display and storage as described herein without undue experimentation. See, e.g., U.S. Pat. No. 7,310,564 ("Arrangement and method for producing therapeutic insoles"); U.S. Pat. No. 7,289,883 ("Apparatus and method for patient rounding with a remote controlled robot"); U.S. Pat. No. 7,286,877 ("Device programmer with enclosed imaging capability"); U.S. Pat. No. 7,158,861 ("Tele-robotic system used to provide remote consultation services"); U.S. Pat. No. 7,016,467 ("Mobile digital radiography x-ray apparatus and system"); U.S. Pat. No. 6,625,252 ("Emergency vehicle with medical image scanner and teleradiology system"); U.S. Pat. No. 6,621,918 ("Teleradiology systems for rendering and visualizing remotely-located volume data sets"); U.S. Pat. No. 6,612,982 ("Fully-swallowable endoscopic system"); U.S. Pat. No. 6,529,757 ("Picture archiving and communication system and method for multi-level image data processing"); U.S. Pat. No. 6,490,490 ("Remote operation support system and method"); U.S. Pat. No. 6,137,527 ("System and method for prompt-radiology image screening service via satellite").

With reference now to FIG. 97, shown is a system 9700 in which one or more technologies may be implemented in relation to respective portions 9703, 9704, 9705 of a subject's body 9710, one or more of which may exhibit an inflammation or other abnormality 9709. An adaptable support 9750 comprises several oblong actuators 9752, 9753, 9754, 9755 supported on a common frame or other suitable substrate 9760. Support 9750 further includes or otherwise supports one or more sensor modules 9713, 9714, 9715 (including or in proximity to a respective one or more actuators 9753, 9754, 9755) operable for transmitting or otherwise detecting quantitative or other values 9723, 9724, 9725 of measurement data 9729 for circuitry 9790. Circuitry 9790 may further include one or more processors 9744 and/or modules 9781, 9782, 9783 of support control logic 9780, such as may be configured to provide one or more control signals 9785, 9786 selectively to one or more actuators 9752, 9753, 9754, 9755 as shown.

With reference now to FIG. 98, shown is a flow 9800 comprising operation 9840—causing an artificial support to modify a force upon a first external portion of a subject's body as a programmatic response to locally-abnormal-stress-indicative information obtained from a second external portion of the subject's body (e.g. at least support control logic 9780 causing one or more actuators 9753 to increase a force at least upon external portion 9703 in response to measurement data 9729 containing an indication from sensor module 9715 of an unusual swelling or other local manifestation of pressure within external portion 9705 of body 9710). This can occur, for example, in a context in which one or more other sensor modules 9714 indicate a lower pressure nearby and/or in which the locally-abnormal-stress-indicative information has persisted for about a minute or more.

With reference now to FIG. 99, shown is a flow 9900 comprising operation 9950—obtaining locally-abnormal thermal information about a first external portion of a subject's limb (e.g. one or more modules 9781, 9782, 9783 of support control logic 9780 and/or processor 9744 receiving and/or computing measurement data 9729 indicating a local abnormality 9709 relating to the temperatures of one or more portions 9703, 9704, 9705 in a subject's arm or other limb). This can occur, for example, in a context in which substrate 9760 comprises a bed, a seat, a cast or other fitted article, or other such support structures as described herein.

Operation 9970 describes causing an artificial support to exert an increasing force upon a second external portion of the subject's limb at least partly in response to locally-abnormal thermal information about the first external portion of the subject's limb (e.g. support control logic 9780 causing at least actuator 9753 to exert an increasing force upon portion 9703 in response to abnormality 9709 comprising a locally warm or cool part of a limb of body 9710). This can occur, for example, in an embodiment in which such actuators form part of a feedback system responsive to thermal, force-indicative, circulation-indicative, or other such values as described herein.

With reference now to FIG. 100, there are shown several variants of the flow 9800 of FIG. 98. Operation 9840—causing an artificial support to modify a force upon a first external portion of a subject's body as a programmatic response to locally-abnormal-stress-indicative information obtained from a second external portion of the subject's body—may include one or more of the following operations: 10043, 10044, or 10049. In some embodiments, variants of operation 9840 may (optionally) be performed by one or more instances of configuration logic 1050, 5235; 7755 or other configuration or control logic as described herein. Flow 9800 may likewise include one or more of operations 10085 or 10088, for example. In some contexts, for example, flow 9800 may be performed in a context as described above with reference to any of FIGS. 1-80 and/or in conjunction with other flow variants as described below.

Operation 10043 describes configuring a valve of the artificial support to modify the force upon the first external portion of the subject's body (e.g. one or more modules 783 urging cell 740 laterally toward or away from adjacent cell 710 by causing one or more elements 743 to expand or contract). See FIG. 7. This can occur, for example, in a context in which support control logic 780 performs operation 9840 and in which module 783 selectively opens one or more valves 746, 747 in fluid communication with higher- or lower-pressure reservoirs (not shown) so that element 743 controllably expands or contracts. In some variants, for example, one or more other elements 741 may (optionally) undergo an offsetting transition so that the net motion of cell 740 is primarily lateral. Alternatively or additionally, such other elements may undergo a transition like that of element 743 so that the net motion of cell 740 is primarily orthogonal to structure 765.

Operation 10044 describes configuring a motor of the artificial support to modify the force upon the first external portion of the subject's body (e.g. module 1152 causing one or more piezomotors or other motor-containing actuators 1120 to retract, reducing or removing forces exerted at one or more external portions 1111, 1112). This can occur, for example, in a context in which control logic 1160 of FIG. 11 performs operation 9840 such as by selectively engaging one or more motors to extend and/or contract one or more elements 1121, 1122 of actuators in adjustment to a programmatic operating mode, such as for massage, and/or in response to one or more indications of local phenomena as described herein. In some variants, for example, control module 9780 adjusts actuator elements to maintain a consistent pressure or a programmatically cycled pressure at external portions 9703-9705 to treat poor circulation, cramps, or other pathologies aggravated by immobility. Alternatively or additionally, such motors may be configured as shown in FIG. 7 in which the engagement of one or more motors 715 may selectively constrict or expand selected ones of cells 710-750, effectuating a local profile increasing or decreasing the pressure selectively applied to portions of subjects as described herein.

In light of teachings herein, numerous existing techniques may be applied for the use of motors to adjust the pressure and/or force applied to a structure as described herein without undue experimentation. See, e.g., U.S. Pat. No. 7,273,053 ("Monitoring and control for a laryngeal mask airway device"); U.S. Pat. No. 7,270,374 ("Structure for anatomical support with frame and convex cushioned plate for back, headrest and seat, for seating in general, especially seats in motor vehicles, with manual and motor-driven adaption of cushioned plate covexity and position"); U.S. Pat. No. 7,134,157 ("Motor-adjustable head rest"); U.S. Pat. No. 6,961,971 ("Motor adjustable support device for the upholstery of a seat and/or reclining furniture"); U.S. Pat. No. 6,810,876 ("Assisted ventilation to match patient respiratory need"); U.S. Pat. No. 6,689,974 ("Pressure switch for motorized chairs"); U.S. Pat. No. 6,547,749 ("Body pulsating method and apparatus").

Operation 10049 describes configuring the programmatic response partly based on thermal data obtained from the second external portion of the subject's body (e.g. module 1052 of FIG. 10 selecting one or more control profiles 1071, 1072 or other operating parameters 1075, 1076 configured to update at least a force exerted upon portion 1011 in response to module 1091 indicating that portion 1012 has apparently remained beyond thermal threshold 1086 for longer than time threshold 1087). This can occur, for example, in a context in which configuration logic 1050 performs operation 9840, in which thermal threshold 1086 is within an order of magnitude of 0.5° C. or 5° C. of a nominally normal temperature, in which time threshold 1087 is within an order of magnitude of 1 hour or 1 day, in which pattern recognition module 1092 is configured to determine whether thermal data 1081 from one or more sensors 1002 adjacent portion 1012 indicates such an abnormality, and in which the programmatic response comprises updating one or more control signals 1031, 1032 to respective ones of actuators 1021, 1022 supporting respective zones of the subject's skin 1010. In some contexts, for example, an external portion of a subject's limb remaining at 1° C. or more lower than a standard value for a period of hours may trigger an automatic therapy (such as massage), a timely-scheduled examination by a caregiver, and/or other such programmatic responses. Alternatively or additionally, the programmatic response(s) may be tailored according to locally-abnormal-stress-indicative information, such as by including an urgency indicator, notifying additional parties, or otherwise responding to such information in one or more notifications as described herein. One or more such response may be adapted in some contexts, moreover, in response to whether other data 1082 from any such sensors 1001, 1002 indicates a systemic or local abnormality as described herein.

In light of teachings herein, numerous existing techniques may be applied for recognizing patterns in thermal, pressure, and/or other measurement data as described herein without undue experimentation. See, e.g., U.S. Pat. No. 7,331,667 ("Iris pattern recognition and alignment"); U.S. Pat. No. 7,324,661 ("Computer-implemented system and method for automated and highly accurate plaque analysis, reporting, and visualization"); U.S. Pat. No. 7,252,640 ("Detection of disordered breathing"); U.S. Pat. No. 7,248,733 ("Color-image processing apparatus and method, and storage medium"); U.S. Pat. No. 7,190,996 ("Monitor for early detection of ischemic heart disease"); U.S. Pat. No. 7,162,061 ("Abnormal pattern detection processing method and system"); U.S. Pat. No. 6,675,040 ("Optical object tracking system"); U.S. Pat. No. 6,647,093 ("Method and device for the processing of X-ray images"); U.S. Pat. No. 6,606,579 ("Method of combining spectral data with non-spectral data in a produce recognition system"); U.S. Pat. No. 6,196,973 ("Flow estimation using an ultrasonically modulated contrast agent"); U.S. Pat. No. 6,069,696 ("Object recognition system and method").

Operation 10085 describes comparing the locally-abnormal-stress-indicative information with other locally-abnormal-stress-indicative information from the second external portion of the subject's body (e.g. one or more modules 1181, 1182 of processing logic 1180 triggering or otherwise performing comparisons between swelling-indicative data 1162 received in signal 1125 and prior data 1161 from the same or similar site. This can occur, for example, in a context in which module 1183 is configured either (a) to process one or more changes in measurement data 1163 from portion 1111 in relation to at least some measurement information from portion 1111 to determine whether differences are apparently localized or systemic or (b) to aggregate such data or otherwise permit at least some such processing at a common facility as described herein. In some variants, for example, changes in such information localized to one observation region (e.g. from portion 1112) may be used as an indication of healing or deterioration progress for a pressure wound or other abnormality thereof.

In light of teachings herein, numerous existing techniques may be applied for using comparisons of information acquired from two or more observation sites as described herein without undue experimentation. See, e.g., U.S. Pat. No. 7,340,951 ("Distributed impedance sensor"); U.S. Pat. No. 7,340,337 ("Vehicle control system for detecting a short-circuit condition between redundant position sensors"); U.S. Pat. No. 7,337,677 ("Differential pressure flowmeter, flow controller, and apparatus for processing substrate"); U.S. Pat. No. 7,225,013 ("Adaptive prediction of changes of physiological/pathological states using processing of biomedical signals"); U.S. Pat. No. 6,898,457 ("Method for determining temperature, radiation thermometer with several infrared sensor elements"); U.S. Pat. No. 6,584,345 ("Apparatus and method for measuring a plurality of electrical signals from the body of a patient"); U.S. Pat. No. 6,413,233 ("Perfusion hyperthermia treatment system and method"); U.S. Pat. No. 6,304,775 ("Seizure warning and prediction"); U.S. Pat. No. 5,755,571 ("Differential measurement periodontal structures mapping system").

Operation 10088 describes causing a data recordation responsive to the locally-abnormal-stress-indicative information (e.g. module 1351 of decision logic 1350 requesting one or more storage devices 1340 to record locally-abnormal-stress-indicative information 1341 from a vehicle or other remote source 1385). This can occur, for example, in a context in which remote source 1385 comprises a system configured to receive such information in some form via one or more sensors in a vicinity of the subject's body—such as by responsive logic 260 or decision logic 275 receiving information 221-224 via sensor(s) 215 in real time—and in which a conventional structure may aggravate a seat occupant's pressure ulcer or other such pathology. In some contexts, module 1351 may then (or later) receive and store at least a sample of such information as the locally-abnormal-stress-indicative information 1341, optionally in a form that is selected or otherwise distilled from information 221-224 as described herein. Alternatively or additionally, module 1351 may likewise cause a recordation of subject or site identifiers 1345, time or place indications 1346, other measurement data 1343 from one or more sensors in the subject's vicinity, and/or other related, diagnostically useful information 1342 as described herein that may potentially relate to one or more pathologies as indicated in information 1341.

In light of teachings herein, numerous existing techniques may be applied for the recording of subject information resulting from sensor measurements as described herein without undue experimentation. See, e.g., U.S. Pat. No. 7,338,443 ("Secure patient data recorder for recording monitored vital sign data"); U.S. Pat. No. 7,294,108 ("Cardiac event microrecorder and method for implanting same"); U.S. Pat. No. 7,277,903 ("Method and apparatus for distributed data archiving"); U.S. Pat. No. 7,142,632 ("Radiation image recording device"); U.S. Pat. No. 7,104,955 ("System and method for collection and analysis of regularly retrieved patient information for automated remote patient care"); U.S. Pat. No. 6,966,650 ("Method and apparatus for an automated procedure to detect and monitor early-stage glaucoma"); U.S. Pat. No. 6,668,188 ("Determination of long-term condition of cardiac patients"); U.S. Pat. No. 6,468,242 ("Medical apparatus with patient data recording"); U.S. Pat. No. 5,879,292 ("Bandage including data acquisition components").

Figure 101:
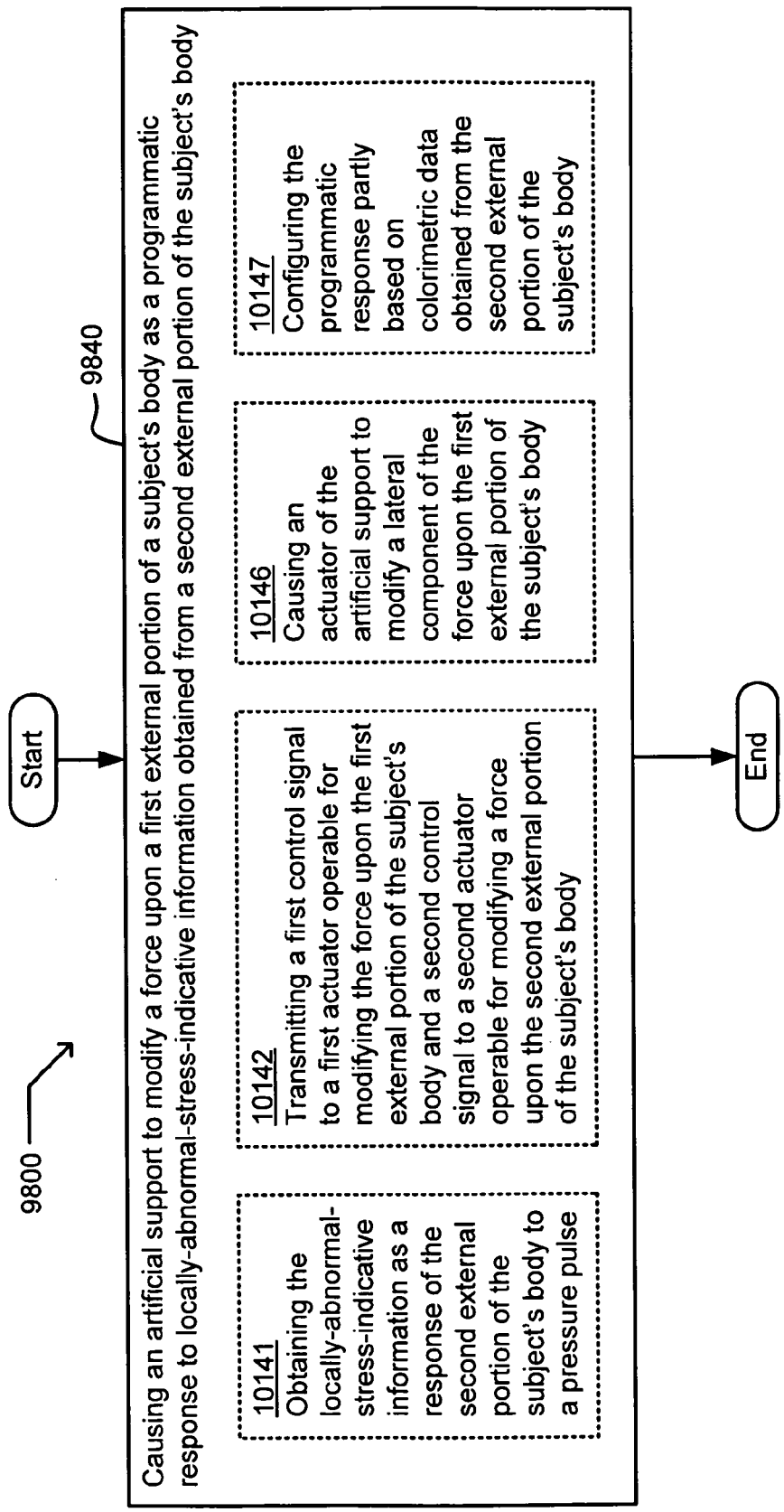

With reference now to FIG. 101, there are shown several variants of the flow 9800 of FIG. 98 or 100. Operation 9840—causing an artificial support to modify a force upon a first external portion of a subject's body as a programmatic response to locally-abnormal-stress-indicative information obtained from a second external portion of the subject's body—may include one or more of the following operations: 10141, 10142, 10146 or 10147. Variants of operation 9840 may be performed by one or more instances of controller 775, support control logic 9780, or other configuration or control logic, for example, implemented in a bed, vehicle, or other primary and/or local module described herein. Alternatively or additionally, flow 9800 may be performed in a context as described above with reference to any of FIGS. 1-80 and/or in conjunction with other flow variants as described below.

Operation 10141 describes obtaining the locally-abnormal-stress-indicative information as a response of the second external portion of the subject's body to a pressure pulse (e.g. a special-purpose tonometer 925 or other components of sensor-containing instrument 900 deriving one or more images 931, signals 932, 933, or other data 935 indicative of a locally abnormal tension or pressure in a subject's skin or other body surface). This can occur, for example, in a context in which a pulse element 905 exerts the pressure pulse upon skin 910, in which one or more sensors 902 convert a physical response to the pulse into a digital or other signal 932, and in which module 943 of evaluation logic 950 applies one or more thresholds 941 or other criteria 942 configured to evaluate whether such signals 932 or other data 935 are abnormal. In some variants, for example, such a threshold 941 may be derived from nearby tissue, from a prior signal of the "second" external portion, and/or from one or more other subjects. Alternatively or additionally, such data 935 may likewise include colorimetric or other abnormality-indicative signals 933 signifying a status of the external body portion.

In light of teachings herein, numerous existing techniques may be applied for using tissue response to external perturbations as a probe for detecting abnormalities, features, and/or other physiological information as described herein without undue experimentation. See, e.g., U.S. Pat. No. 7,260,440 ("Method and apparatus for measurement of pressure at a device/body interface"); U.S. Pat. No. 7,232,415 ("System and method for noninvasively evaluating a limb suspected of compartment syndrome"); U.S. Pat. No. 7,211,063 ("Pressure sensor for therapeutic delivery device and method"); U.S. Pat. No. 6,845,146 ("Mammography apparatus and method"); U.S. Pat. No. 6,733,461 ("Methods and apparatus for measuring arterial compliance, improving pressure calibration, and computing flow from pressure data"); U.S. Pat. No. 6,706,001 ("Dual tonometer pressure measurement device"); U.S. Pat. No. 6,547,746 ("Method and apparatus for determining response thresholds"); U.S. Pat. No. 6,507,663 ("Method and apparatus for detecting very small breast anomalies"); U.S. Pat. No. 6,425,875 ("Method and device for detection of a tooth root apex"); U.S. Pat. No. 6,361,495 ("Hand-held non-contact tonometer"); U.S. Pat. No. 6,186,962 ("Method and device for detecting edema"); U.S. Pat. No. 6,139,499 ("Ultrasonic medical system and associated method"); U.S. Pat. No. 6,063,044 ("Apparatus for measuring muscle tone").

Operation 10142 describes transmitting a first control signal to a first actuator operable for modifying the force upon the first external portion of the subject's body and a second control signal to a second actuator operable for modifying a force upon the second external portion of the subject's body (e.g. module 9782 of support control logic 9780 transmitting signals 9785, 9786 or other control data selectively to two or more actuators 9752, 9753, 9754, 9755 in an array configured to reduce one or more shear stress measurements or otherwise to respond to information from one or more sensor modules 9713, 9714, 9715 near an inflammation or other externally detected abnormality 9709). This can occur, for example, in a context in which support control logic 9780 performs operation 9840 and in which respective states of the actuators change simultaneously or in respective cycles, for example, with or without closed-loop control (via sensors of modules 9713-9715, e.g.) configured to respond to tissue stress indications in a vicinity of the actuator(s). In some variants, for example, module 1156 of control logic 1160 implements a vector grid 1165, profile 1167, transfer function, or other such control data 1170 to respective instances of actuators 1122 each configured to alleviate at least one worst-case shear in skin 1110 by exerting forces upon respective portions of skin 1110 within a vicinity of which a stress-indicative signal 1125 is obtained. Alternatively or additionally, module 784 of support control logic 780 may be configured with one or more parameters 793, 794 defining a model that increases a normal incident force at one or more actuator cells (e.g. at cell 730) in a vicinity of a detected anomaly (e.g. at cell 740). Such a model may be implemented for coarse positioning, for example, in response to one or more motion sensors 2472 or other elements of local modules 2320, 2450, 2510, or 2690 detecting the subject's limb being repositioned.

In light of teachings herein, numerous existing techniques may be applied for configuring a system for implementing a programmatic response to local sensor observations as described herein without undue experimentation. See, e.g., U.S. Pat. No. 7,164,948 ("Cardiac output measurement using dual oxygen sensors in right and left ventricles"); U.S. Pat. No. 6,947,780 ("Auditory alarms for physiological data monitoring"); U.S. Pat. No. 6,892,405 ("Therapeutic bed and related apparatus and methods"); U.S. Pat. No. 6,671,547 ("Adaptive analysis method for an electrotherapy device and apparatus"); U.S. Pat. No. 6,658,292 ("Detection of patient's position and activity status using 3D accelerometer-based position sensor"); U.S. Pat. No. 6,604,650 ("Bottle-cap medication reminder and overdose safeguard"); U.S. Pat. No. 6,440,090 ("Spinal cord simulation systems with patient activity monitoring and therapy adjustments"); U.S. Pat. No. 6,413,233 ("Perfusion hyperthermia treatment system and method"); U.S. Pat. No. 5,963,997 ("Low air loss patient support system providing active feedback pressure sensing and correction capabilities for use as a bed mattress and a wheelchair seating system").

Operation 10146 describes causing an actuator of the artificial support to modify a lateral component of the force upon the first external portion of the subject's body (e.g. module 1155 of control logic 1160 executing a command sequence 1157 causing a transmission of one or more control signals 1131, 1132 to respective elements 1121, 1122 each configured to exert a primarily-tangential force across the subject's skin 1110). This can occur, for example, in a context in which command sequence 1157 is configured to control one or more actuator elements 741, 742, 743 configured to push and/or pull one or more cells 740 supporting the "first" external body portion. In some variants, for example, one or more such actuator cells may include (a) a seat 211, 814, bed, or other support element operable for engaging or otherwise supporting a subject's leg and (b) two or more respectively selectable non-coaxial actuator elements 741, 742 operable to guide at least one cell of the support element each according to a respective state thereof. Alternatively or additionally, one or more such actuators may be configured to exert a primarily-lateral force at least upon cell 740, such as for measurably reducing a shear force between cell 740 and the body portion.

In light of teachings herein, numerous existing techniques may be applied for electronically or otherwise controlling or otherwise configuring microelectromechanical, fluidic, or other actuator systems as described herein without undue experimentation. See, e.g., U.S. Pat. No. 7,339,299 ("Electric actuator and motor used therein"); U.S. Pat. No. 7,336,018 ("Circuit configuration for charging and discharging a plurality of capacitive actuators"); U.S. Pat. No. 7,327,637 ("Acoustic pulse actuator"); U.S. Pat. No. 7,301,256 ("Method and circuit configuration for operating a piezoelectric actuator"); U.S. Pat. No. 7,199,494 ("Electric linear actuator"); U.S. Pat. No. 7,172,493 ("Fine force actuator assembly for chemical mechanical polishing apparatuses"); U.S. Pat. No. 7,144,099 ("Liquid drop emitter with split thermo-mechanical actuator"); U.S. Pat. No. 7,124,837 ("Pneumatic motor trigger actuator"); U.S. Pat. No. 7,100,491 ("Fluid-powered mechanical actuator and method for controlling"); U.S. Pat. No. 7,052,427 ("Electric screw actuator system"); U.S. Pat. No. 6,955,113 ("Electro-hydraulic actuator with mechanical servo position feedback"); U.S. Pat. No. 6,748,929 ("Electronic circuit configuration and corresponding method for controlling actuators such as valves or injectors"); U.S. Pat. No. 6,717,337 ("Piezoelectric acoustic actuator"); U.S. Pat. No. 6,715,402 ("Hydraulic control circuit for operating a split actuator mechanical mechanism"); U.S. Pat. No. 6,685,303 ("Thermal actuator with reduced temperature extreme and method of operating same"); U.S. Pat. No. 6,497,222 ("Actuator configuration and method in particular for actuating an injection valve of an internal combustion engine"); U.S. Pat. No. 6,271,618 ("Method and configuration for driving a capacitive actuator").

Operation 10147 describes configuring the programmatic response partly based on colorimetric data obtained from the second external portion of the subject's body (e.g. configuration module 777 selecting one or more control profiles 796 and/or other parameters 795 configured to reduce a force upon the second external portion by a greater degree in response to one or more indications of bruising or inflammation thereof). This can occur, for example, in a context in which controller 775 includes one or more local modules as described herein, in which optical sensor 2525 detects one or more indications of discoloration within or overlapping the "second" external portion, in which the "first" or other external portions extend within a few millimeters thereof, and in which reflectance sensor 2511 or other optical sensors described herein are sensitive to visible frequency phenomena or other such symptoms. In some variants, for example, shape recognition, thermal, pathological, or other analysis as described herein may likewise be used for selecting profile 796 or other parameters 795 of the programmatic response. Alternatively or additionally, some such responses may include other notifications, evaluations, therapies, aggregations, or other protocols as described herein.

In light of teachings herein, numerous existing techniques may be applied for analyzing, treating, or otherwise responding in contexts in which optically detectable symptoms can occur as described herein without undue experimentation. See, e.g., U.S. Pat. No. 7,297,154 ("Optical apparatus for detecting and treating vulnerable plaque"); U.S. Pat. No. 7,275,829 ("Ophthalmic laser irradiation apparatus"); U.S. Pat. No. 7,244,122 ("Methods for determining optical characteristics of dental objects"); U.S. Pat. No. 7,155,273 ("Blanching response pressure sore detector apparatus, and method"); U.S. Pat. No. 6,950,692 ("Optical coherence tomography apparatus optical fiber lateral scanner and a method for studying biological tissues in vivo"); U.S. Pat. No. 6,663,242 ("Simultaneous, wavelength multiplexed vision screener"); U.S. Pat. No. 6,507,747 ("Method and apparatus for concomitant structural and biochemical characterization of tissue"); U.S. Pat. No. 5,892,570 ("Method and apparatus for measuring and correcting metamorphopsia").

Figure 102:
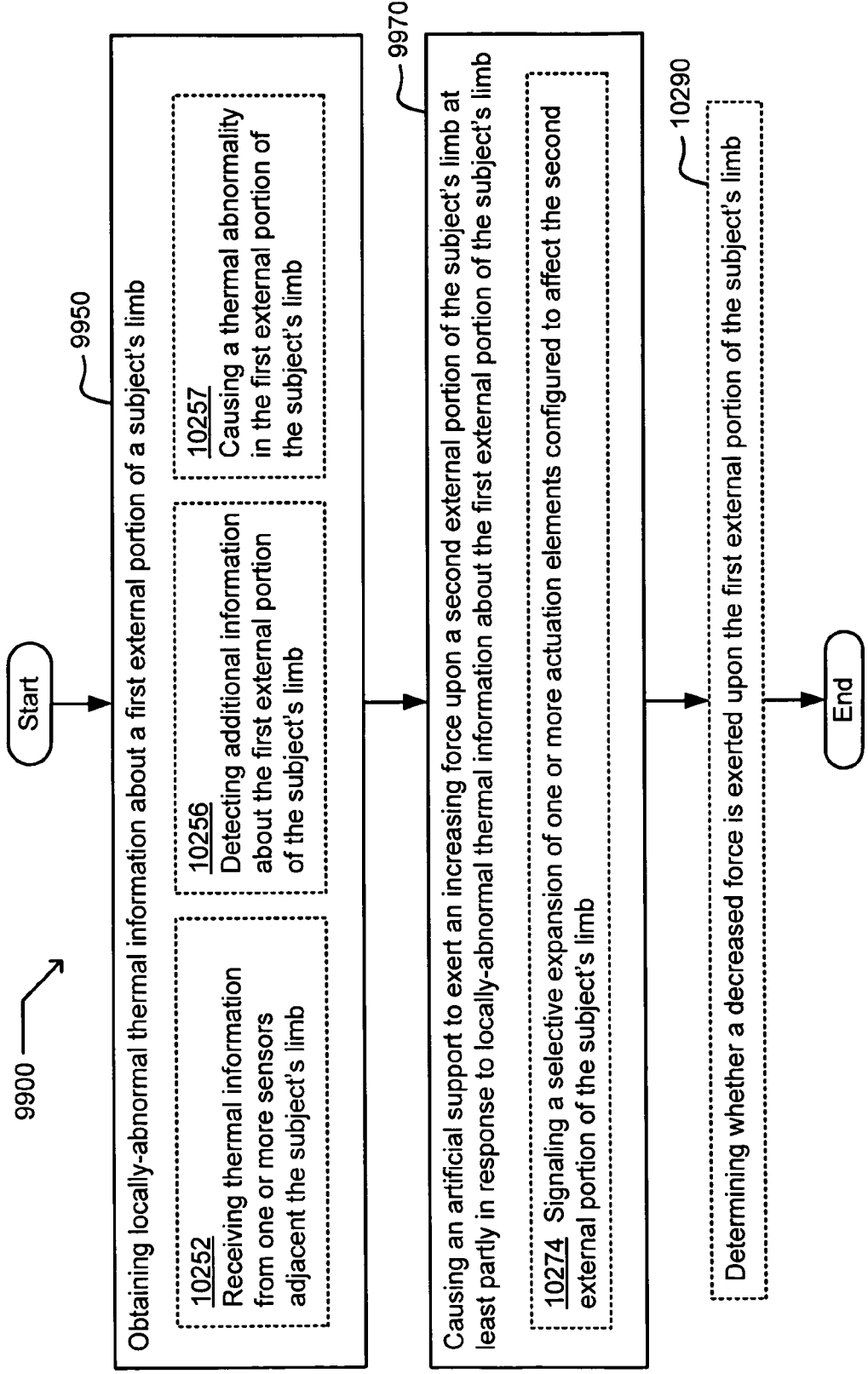
FIGS. 102-103 depict variants of the flow of FIG. 99.

With reference now to FIG. 102, there are shown several variants of the flow 9900 of FIG. 99. Operation 9950—obtaining locally-abnormal thermal information about a first external portion of a subject's limb—may (optionally) include one or more of the following operations: 10252, 10256 or 10257. In some embodiments, variants of operation 9950 may be performed by one or more instances of detection logic 180, 640, 1275, 3285, 3550, 5135, 5670, 6110, 6720, 7940 and/or local modules 2320, 2450, 2510, 2690, 5730 (in a vicinity of one or more subjects 310, 320, 1720, 1910, 2270, 2920, 3270, 3360, 5220, 6090, e.g.) configured to handle infrared images, temperature readings, or other such sensor data of potential diagnostic utility. Operation 9970—causing an artificial support to exert an increasing force upon a second external portion of the subject's limb at least partly in response to locally-abnormal thermal information about the first external portion of the subject's limb—may include operation 10274. In some embodiments, variants of operation 9970 may be performed by one or more instances of decision logic 275, 2250, 2730, 3230, 5750, 5930, 6130, 6395, 7415; support control logic 780, 9780; or other configuration or control logic described herein. Alternatively or additionally, flow 9900 may be performed in a context as described above with reference to any of FIGS. 1-80 or in conjunction with other flow variants as described below.

Operation 10252 describes receiving thermal information from one or more sensors adjacent the subject's limb (e.g. interface 5265 receiving temperature-indicative data 5252 from one or more sensors 5203 relating to a subject's arm or leg). This can occur, for example, in a context in which one or more instances of interface 5265 and/or configuration logic 5235 each perform operation 9950 and in which one or more such sensors are implanted into, affixed to, or arranged around a subject site and configured to send thermal and/or other status indicative information to system module 5250. In some variants, for example, communication between the sensor(s) and the system module will be accomplished through a continuous conduit 5208. Alternatively or additionally, other such linkages among sensors or other modules as described herein may incorporate one or more wireless linkages such as Bluetooth, wireless USB, RF telemetry, cellular, 802.11 (B, G, N), far field telemetry, or other such existing technologies.

Operation 10256 describes detecting additional information about the first external portion of the subject's limb (e.g. module 1272 of detection logic 1275 receiving auditory data 1244, optical data 1247, subject-provided data 1246, pressure-indicative data 1245, or other additional data 1248 relating to an upper portion 1201 of a subject's limb). This can occur, for example, in a context in which detection logic 1275 performs operation 9950 and in which module 1273 is configured to receive the locally-abnormal thermal information 1251 from one or more other sensors of array 1221 before or after module 1272 receives such "additional" data. In some variants, for example, optical sensors 2525 implanted into, affixed onto or arranged near upper portion 1201 may be configured to provide other thermal information 1241, chemical composition information 1242, and/or other physiological information 1243. Other such sensors or related logic described above with reference to FIGS. 23-26 may likewise be included in the monitoring, evaluation, or other detection modules of this document, for example, many of which may be configured to record or otherwise respond to status-indicative information 1260 selectively as described herein.

In light of teachings herein, numerous existing techniques may be applied for using one or more sensor types to detect and/or derive suitable types of status information as described herein without undue experimentation. See, e.g., U.S. Pat. No. 7,292,719 ("System and method for imaging"); U.S. Pat. No. 7,254,430 ("Measuring apparatus for measuring a metabolic characteristic in a human body"); U.S. Pat. No. 7,226,426 ("Apparatus and method for the detection and quantification of joint and tissue inflammation"); U.S. Pat. No. 7,205,991 ("Graphical user interface widgets viewable and readable from multiple viewpoints in a volumetric display"); U.S. Pat. No. 7,187,960 ("Apparatus and method for measuring biologic parameters"); U.S. Pat. No. 6,733,447 ("Method and system for remotely monitoring multiple medical parameters"); U.S. Pat. No. 6,679,830 ("Infant incubator with non-contact sensing and monitoring"); U.S. Pat. No. 6,454,718 ("Intra aural integrated vital signs monitor").

Operation 10257 describes causing a thermal abnormality in the first external portion of the subject's limb (e.g. module 5210 applying thermal energy to a target region 5225). This can occur, for example, in a context in which the region is heated or cooled to produce a thermal perturbation, such as by dispensing a suitable reactive material or actuating a heating element. In some variants, for example, the duration and/or shape of such perturbations may be used as an indication of circulation and/or other thermal transfer properties of local tissues in the target region 5225. Alternatively or additionally, one or more modules 5232 of configuration logic 5235 may selectively or otherwise record one or more thermal images 5241, timing data 5242, or other attributes of response 5245 of the region to such thermal deviations may be used to characterize local tissue for diagnostic purposes.

In light of teachings herein, numerous existing techniques may be applied for the use of thermal manipulation and/or detection to probe subject status information and/or pathological indicators as described herein without undue experimentation. See, e.g., U.S. Pat. No. 7,300,453 ("System and method for inducing hypothermia with control and determination of catheter pressure"); U.S. Pat. No. 7,254,430 ("Measuring apparatus for measuring a metabolic characteristic in a human body"); U.S. Pat. No. 7,226,426 ("Apparatus and method for the detection and quantification of joint and tissue inflammation"); U.S. Pat. No. 7,214,094 ("Twist mount wiring receiver"); U.S. Pat. No. 7,167,734 ("Method for optical measurements of tissue to determine disease state or concentration of an analyte"); U.S. Pat. No. 6,974,463 ("System and method for patient temperature control employing temperature projection algorithm"); U.S. Pat. No. 6,950,693 ("Device recording a thermo-optical image of the female breast"); U.S. Pat. No. 6,660,028 ("Method for determining the effective thermal mass of a body or organ using a cooling catheter"); U.S. Pat. No. 6,464,646 ("Instrument and method for locating and marking a hot spot in a person's body tissue"); U.S. Pat. No. 6,458,150 ("Method and apparatus for patient temperature control"); U.S. Pat. No. 6,086,247 ("Differential temperature sensor device for use in the detection of breast cancer and breast disease").

Operation 10274 describes signaling a selective expansion of one or more actuation elements configured to affect the second external portion of the subject's limb (e.g. one or more modules 9781 of support control logic 9780 triggering one or more actuators 9752, 9753, 9754, 9755 to either advance or retract thereby increasing or reducing a force applied to subject body part 9710). This can occur, for example, in a context in which one or more instances of circuitry 9790 locally perform operation 9840, in which a local tissue abnormality 9709 is detected, and in which one or more adjacent actuators 9752, 9753, 9754 are advanced and local actuator 9755 is retracted to reduce the pressure and/or force exerted upon portion 9705. In some variants, for example, support 9750 is incorporated into a bed in which one or more actuators 9752, 9753, 9754, 9755 are selectively advanced or retracted automatically based upon detected tissue abnormalities 9709. Alternatively or additionally, actuators 9752, 9753, 9754, 9755 may be cycled in one or more selected patterns or randomly by support control logic 9780 to avoid the formation of pressure wounds or other adverse effects.

In light of teachings herein, numerous existing techniques may be applied for the adjustment of support pressure on one or more body parts to treat and/or prevent pressure wounds, circulatory disruptions, or other adverse physiological phenomena as described herein without undue experimentation. See, e.g., U.S. Pat. No. 7,330,127 ("Force optimization surface apparatus and method"); U.S. Pat. No. 7,278,179 ("Inflatable decubitis mat with vent structures controlled by heat sensors"); U.S. Pat. No. 7,146,664 ("Pneumatic surgical prone head support and system"); U.S. Pat. No. 6,721,980 ("Force optimization surface apparatus and method"); U.S. Pat. No. 6,584,628 ("Hospital bed having a rotational therapy device"); U.S. Pat. No. 6,560,804 ("System and methods for mattress control in relation to patient distance"); U.S. Pat. No. 6,034,526 ("Apparatus for controlling the inflation pressure of a mattress in response to deformation of the mattress using impedance measurement"); U.S. Pat. No. 5,983,429 ("Method and apparatus for supporting and for supplying therapy to a patient").

Operation 10290 describes determining whether a decreased force is exerted upon the first external portion of the subject's limb (e.g. one or more sensor modules 9713, 9714, 9715 placed in one or more subject contact regions detecting localized pressure and/or force-change-indicative values 9723, 9724, 9725 in some or all of these regions). This can occur, for example, in a context in which a portion of the subject body 9710 rests on support 9750 as shown and in which a symptom is effectively detectable only by monitoring such force-indicative, shape-indicative, size-indicative, or other stress-indicative data in relation that portion over a period of several seconds or more. (Motion from the subject may affect the pressure and/or force observed exerted on the subject body 9710 by the support 9750 for shorter periods.) In some variants, for example, brief subject movements may be tracked by monitoring one or more pressure values recorded by sensor modules 9713, 9714, 9715. Alternatively or additionally, pressure changes in respective portions 9703, 9704, 9705 may be used to adjust actuator positions to maintain the force exerted on the subject body part 9710 within a desired range.

In light of teachings herein, numerous existing techniques may be applied for monitoring the pressure exerted on a body part by a support as described herein without undue experimentation. See, e.g., U.S. Pat. No. 7,337,680 ("System and method for measuring plantar foot pressure"); U.S. Pat. No. 7,234,359 ("Semiconductor force sensor"); U.S. Pat. No. 6,822,571 ("Patient movement detection system for a bed including a load cell mounting assembly"); U.S. Pat. No. 6,791,460 ("Patient position detection apparatus for a bed"); U.S. Pat. No. 6,770,045 ("Orthosis knee joint"); U.S. Pat. No. 6,721,980 ("Force optimization surface apparatus and method"); U.S. Pat. No. 6,585,328 ("Customized mattress evaluation system"); U.S. Pat. No. 6,133,837 ("Patient position system and method for a support surface"); U.S. Pat. No. 5,993,400 ("Apparatus and method for monitoring contact pressure between body parts and contact surfaces").

Figure 103:
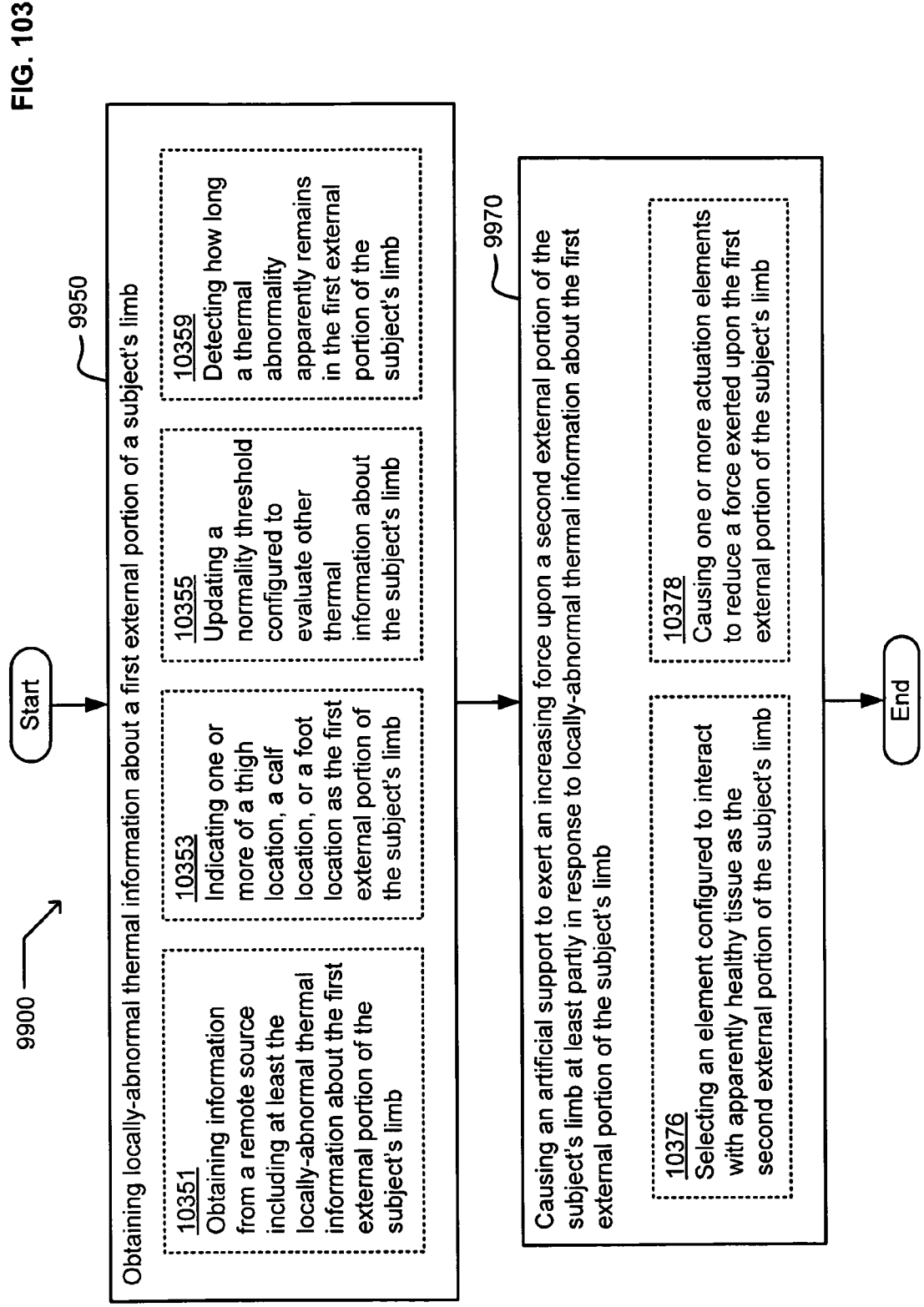

With reference now to FIG. 103, there are shown several variants of the flow 9900 of FIG. 99 or 102. Operation 9950—obtaining locally-abnormal thermal information about a first external portion of a subject's limb—may (optionally) include one or more of the following operations: 10351, 10353, 10355 or 10359. In some embodiments, variants of operation 9950 may be performed by one or more instances of sensors and/or interfaces configured to handle thermal information of potential diagnostic utility. Operation 9970—causing an artificial support to exert an increasing force upon a second external portion of the subject's limb at least partly in response to locally-abnormal thermal information about the first external portion of the subject's limb—may include one or more of the following operations 10376 or 10378. In some embodiments, variants of operation 9970 may be performed by one or more instances of actuators, control circuitry, and/or other responsive elements as described herein. Alternatively or additionally, flow 9900 may be performed in a context as described with reference to any of FIGS. 1-80 or in conjunction with other flow variants as described below.

Operation 10351 describes obtaining information from a remote source including at least the locally-abnormal thermal information about the first external portion of the subject's limb (e.g. aggregation module 5281 remotely receiving information 5260 including at least some local-abnormality-indicative data 5253 about region 5225). This can occur, for example, in a context in which port 5261 and network 5290 each performs operation 9950 by receiving such data from one or more sensors 5203 local to region 5225, with or without comparative information 5276. Alternatively or additionally, system module 5250 may implement one or more controllers 775, notification logic 7875, and/or other such structures in this document suitable for acting upon comparative information 5276 or other such information 5260 after retrieving it or otherwise receiving distributions of update data 5255 from aggregation module 5281 or other resources.

In light of teachings herein, numerous existing techniques may be applied for connecting to and retrieving subject status information from a remote data source and/or processing system as described herein without undue experimentation. See, e.g., U.S. Pat. No. 7,269,476 ("Smart medicine container"); U.S. Pat. No. 7,250,855 ("False alarm mitigation using a sensor network"); U.S. Pat. No. 7,248,917 ("Self treatment device"); U.S. Pat. No. 7,226,426 ("Apparatus and method for the detection and quantification of joint and tissue inflammation"); U.S. Pat. No. 7,147,600 ("System and method for determining a reference baseline of patient information"); U.S. Pat. No. 7,027,871 ("Aggregation of data from external data sources within an implantable medical device"); U.S. Pat. No. 6,922,592 ("Implantable medical device controlled by a non-invasive physiological data measurement device"); U.S. Pat. No. 6,824,512 ("Communications system for an implantable device and a drug dispenser"); U.S. Pat. No. 6,801,137 ("Bidirectional communication between a sensor unit and a monitor unit in patient monitoring"); U.S. Pat. No. 6,463,310 ("Method and circuit for storing and providing historical physiological data"); U.S. Pat. No. 6,440,067 ("System and method for remotely monitoring functional activities").

Operation 10353 describes indicating one or more of a thigh location, a calf location, or a foot location as the first external portion of the subject's limb (e.g. module 2973 of decision logic 2975 receiving communication 2935 or other data 2955 activating one or more sensors identified with or otherwise identifying a subject body portion). This can occur, for example, in a context in which decision logic 2975 performs operation 9950 and in which one or more sensors 2927 are placed on or near the subject limb, optionally in one or more arrays 1221, 1222 as shown in FIG. 12. In some contexts, for example, one or more such portions 1201, 1202 may be selected as a primary sensor location for limb monitoring. Alternatively or additionally, one or more other sensors as described with reference to FIGS. 23-26 may be positioned to monitor such subject portions 1201 and/or other contemporaneous attributes of the subject as described herein.

In light of teachings herein, numerous existing techniques may be applied for the selective inclusion and/or activation of one or more sensors from a sensor set as a primary sensor location without undue experimentation. See, e.g., U.S. Pat. No. 7,332,743 ("Thin film transistor array panel and liquid crystal display"); U.S. Pat. No. 7,208,983 ("Image-sensor signal processing circuit"); U.S. Pat. No. 7,190,987 ("Neonatal bootie wrap"); U.S. Pat. No. 7,155,281 ("Complimentary activity sensor network for disease monitoring and therapy modulation in an implantable device"); U.S. Pat. No. 7,149,645 ("Method and apparatus for accurate on-die temperature measurement"); U.S. Pat. No. 6,275,733 ("Dual sensor rate response pacemaker"); U.S. Pat. No. 6,271,766 ("Distributed selectable latent fiber optic sensors").

Operation 10355 describes updating a normality threshold configured to evaluate other thermal information about the subject's limb (e.g. module 5233 of configuration logic 5235 changing or otherwise updating one or more thermal thresholds 5271). This can occur, for example, in a context in which a symptom is effectively detectable only by monitoring such thermal indicia in relation to the limb and in which new operating parameters 5275 or other comparative information 5276 are received from a sensor as described above, for example, in relation to FIGS. 23-26. In some variants, for example, information from an ambient sensor 5201 and/or a core body sensor 5202 may be used to generate and/or adjust thresholds applied to sensor data 5251 from one or more other sensors extending into, in contact with, or otherwise arranged around the subject. Alternatively or additionally, historic and/or processed information from a remote storage and/or processing device 5291 or from other resources 5292 may be used to provide and/or adjust thresholds or other filtering information applied to the sensor data 5251 or other portions of information 5260 obtained from the subject limb.

In light of teachings herein, numerous existing techniques may be applied for requesting, receiving, or otherwise interacting with numerical thresholds as described herein without undue experimentation. See, e.g., U.S. Pat. No. 7,250,855 ("False alarm mitigation using a sensor network"); U.S. Pat. No. 7,079,035 ("Method and apparatus for controlling an alarm while monitoring"); U.S. Pat. No. 7,037,273 ("Core body temperature monitoring in heart failure patients"); U.S. Pat. No. 6,942,626 ("Apparatus and method for identifying sleep disordered breathing"); U.S. Pat. No. 6,569,095 ("Adaptive selection of a warning limit in patient monitoring"); U.S. Pat. No. 6,552,531 ("Method and circuit for processing signals for a motion sensor"); U.S. Pat. No. 6,263,243 ("Rate adaptive pacemaker").

Operation 10359 describes detecting how long a thermal abnormality apparently remains in the first external portion of the subject's limb (e.g. counter 5173 or other timing logic 5175 generating one or more values 5181 indicating how long a limb portion remains below a temperature-change-rate or other thermal threshold 5112). This can occur, for example, in a context in which detection logic 5135 performs operation 9950, in which module 5133 signals counter 5173 to stop responsive to one or more values 5181 satisfying a normality-indicative condition 5125, in which module 5131 of detection logic 5135 is configured to reset and/or enable one or more counters 5173 in response to module 5132 detecting that sensor data 5184 violates data filter 5121, and in which one or modules 5131, 5132, 5133 of detection logic 5135 are configured to halt and/or read counter 5173 in response to a reset of filter violation status 5183. Alternatively or additionally, one or more such modules of detection logic 5135 may trigger a recording device to store one or more event records 5160 containing, for example, one or more of a timestamp 5161, filter configuration data 5167, sensor data 5168, or other information relating to a condition in which a filter status is engaged or removed.

In light of teachings herein, numerous existing techniques may be applied for using experimental data for measuring or otherwise estimating intervals as described herein without undue experimentation. See, e.g., U.S. Pat. No. 7,319,400 ("Method and apparatus for monitoring a restraint device"); U.S. Pat. No. 7,151,957 ("Method and device for analyzing a periodic or semi-periodic signal"); U.S. Pat. No. 7,029,447 ("Measuring blood pressure"); U.S. Pat. No. 6,720,875 ("Self-adjusting alarm device with low energy consumption"); U.S. Pat. No. 6,691,979 ("Adaptive object-sensing system for automatic flusher"); U.S. Pat. No. 6,600,425 ("Method and apparatus for detecting and recording episodic overloads in a circuit"); U.S. Pat. No. 6,580,994 ("Driving force controlling apparatus and method for four-wheel drive vehicle"); U.S. Pat. No. 6,200,270 ("Sensor for non-invasive and continuous determination of the duration of arterial pulse waves"); U.S. Pat. No. 6,047,201 ("Infant blood oxygen monitor and SIDS warning device"); U.S. Pat. No. 6,014,346 ("Medical timer/monitor and method of monitoring patient status").

Operation 10376 describes selecting an element configured to interact with apparently healthy tissue as the second external portion of the subject's limb (e.g. one or more modules 782 of support control logic 780 selecting one or more cells 740 or one or more of their actuation elements 741, 742, 743 in response to a determination that no anomalies have been detected in tissue adjacent cell 740). This can occur, for example, in a context in which support control logic 780 performs operation 9970, in which support 420 of FIG. 4 implements array 705 of FIG. 7, in which component 414 contains cell 740, in which one or more sensors 424 as described herein are positioned in or near cell 740 for detecting one or more tissue attributes of external portion 404 of body 410, in which one or more such cells 740, 750 are positioned so that a movement of cell 740 may directly result in an increasing lateral and/or normal force upon external portion 404, and in which a selection of cell 740 may thereby effectively result in a determination of the "second" external portion. In some variants, for example, an expansion of one or more elements 742, 743 may cause such an increasing force, a direction of which may be modified by one or more other elements 741. Alternatively or additionally, module 782 may may control such movement of component 414 with closed-loop control so that component 414 is positioned to minimize a shear force or otherwise favorably influence an attribute of abnormality 409 detected, for example, via sensor 425.

In light of teachings herein, numerous existing techniques may be applied for detecting or characterizing injuries or other localized structures and/or phenomena as described herein without undue experimentation. See, e.g., U.S. Pat. No. 7,303,555 ("Imaging and therapeutic procedure for carpal tunnel syndrome"); U.S. Pat. No. 7,226,426 ("Apparatus and method for the detection and quantification of joint and tissue inflammation"); U.S. Pat. No. 7,155,273 ("Blanching response pressure sore detector apparatus and method"); U.S. Pat. No. 7,006,676 ("Method and apparatus for detecting an abnormality within a host medium utilizing frequency-swept modulation diffusion tomography"); U.S. Pat. No. 6,993,167 ("System and method for examining, recording and analyzing dermatological conditions"); U.S. Pat. No. 6,880,387 ("Acoustic micro imaging method providing improved information derivation and visualization"); U.S. Pat. No. 6,544,186 ("System and method for diagnostic imaging"); U.S. Pat. No. 6,464,646 ("Instrument and method for locating and marking a hot spot in a person's body tissue"); U.S. Pat. No. 6,258,046 ("Method and device for assessing perfusion failure in a patient by measurement of blood flow"); U.S. Pat. No. 6,233,479 ("Microwave hematoma detector"); U.S. Pat. No. 6,192,143 ("Apparatus for detecting very small breast anomalies"); U.S. Pat. No. 6,056,692 ("Apparatus and method for locating and marking blood vessels"); U.S. Pat. No. 5,999,836 ("Enhanced high resolution breast imaging device and method utilizing non-ionizing radiation of narrow spectral bandwidth"); U.S. Pat. No. 5,989,194 ("Method and apparatus for detecting ocular disease and abnormalities").

Operation 10378 describes causing one or more actuation elements to reduce a force exerted upon the first external portion of the subject's limb (e.g. module 781 of support control logic 780 causing a contraction of one or more elements 753 so that cell 750 exerts a decreasing shear or other force upon a subject's leg wound). This can occur, for example, in a context in which one or more arrangements of actuation and/or sensor elements are distributed over a region of concern in a subject limb, in which system module 1230 configures a suitable actuation controller as described herein, and in which conventional modes of observation may fail to reveal an abnormality in time. In some variants, for example, array 705 may expand or contract to maintain a pressure within a detection range as the body part expands or contracts due to increased or decreased tissue swelling. Alternatively or additionally, one or more modules 783, 784 of support control logic 780 may be configured to actuate one or more arrays 1221, 1222 or other configurations of actuators cyclically or otherwise in patterns selected by specifying one or more parameters 793-795, such as to prevent circulatory disruptions or other adverse effects.

In light of teachings herein, numerous existing techniques may be applied for the adjustment of pressure and/or force applied to one or more body parts by a surface contact element to treat and/or prevent circulatory disruptions or other adverse physiological phenomena as described herein without undue experimentation. See, e.g., U.S. Pat. No. 7,338,482 ("External catheter access to vacuum bandage"); U.S. Pat. No. 7,314,478 ("High efficiency external counterpulsation apparatus and method for controlling same"); U.S. Pat. No. 7,214,202 ("Therapeutic apparatus for treating ulcers"); U.S. Pat. No. 7,135,032 ("Femoral compression device with support"); U.S. Pat. No. 7,135,007 ("Compression garments and related methods"); U.S. Pat. No. 7,037,256 ("Method, system and kit for treatment of Peyronie's disease"); U.S. Pat. No. 6,988,499 ("Mechanical resuscitator"); U.S. Pat. No. 6,945,944 ("Therapeutic limb covering using hydrostatic pressure"); U.S. Pat. No. 6,786,879 ("Gradient sequential compression system for preventing deep vein thrombosis"); U.S. Pat. No. 6,752,771 ("Cardiac assist method using an inflatable vest"); U.S. Pat. No. 6,645,165 ("Lymphedema treatment system"); U.S. Pat. No. 6,620,146 ("Adult incontinence article with body-shaping elastics").

Figure 104:
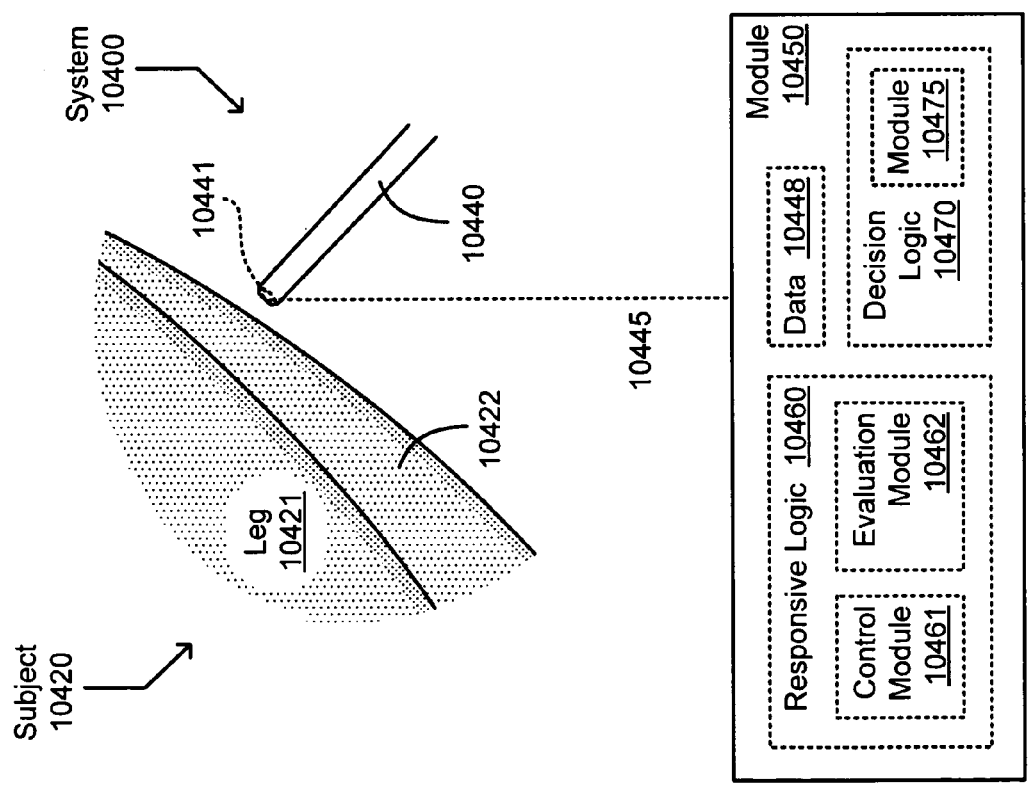
FIG. 104 depicts an exemplary environment in which one or more technologies may be implemented.

With reference now to FIG. 104, shown is a system 10400 in which one or more technologies may be implemented in relation to an instrument 10440 configured to interact with one or more legs 10421, 10422 of subject 10420. As shown, instrument 10440 may (optionally) include one or more sensors 10441 configured at least to provide data 10448 to module 10450 via channel 10445. Module 10450 may include one or more instances of responsive logic 10460 and/or modules 10475 of decision logic 10470 configured to act upon data 10448. Responsive logic 10460, for example, may include one or more instances of control modules 10461 and/or evaluation modules 10462 as described herein.

Figure 105:
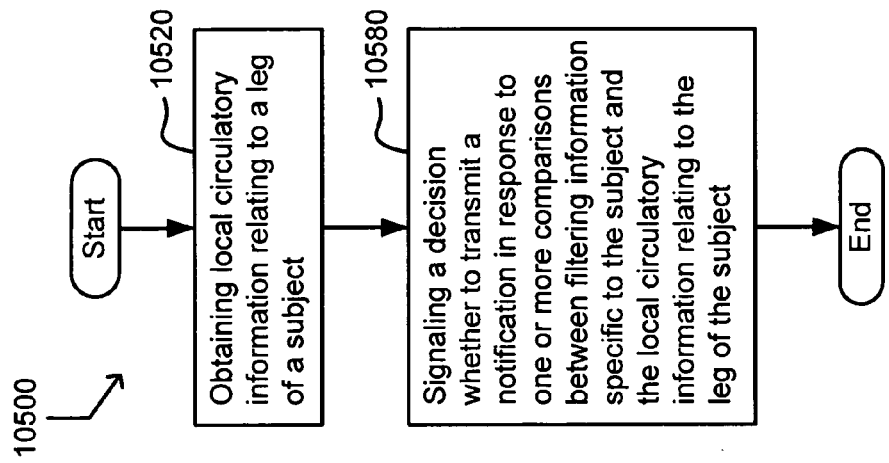
FIG. 105 depicts a high-level logic flow of an operational process.

With reference now to FIG. 105, shown is a flow 10500 comprising operation 10520—obtaining local circulatory information relating to a leg of a subject (e.g. responsive logic 10460 receiving local flow rate or other data 10448 describing circulation within one or more legs 10421 of subject 10420). This can occur, for example, in a context in which instrument 10440 detects physical conditions within leg 10421 directly or via sensors in clothing or otherwise supported near leg 10421 as described herein. Alternatively or additionally, the local circulatory information may include a history of such measurements of leg 10421 over a period of hours, days, or months.

Operation 10580 describes signaling a decision whether to transmit a notification in response to one or more comparisons between filtering information specific to the subject and the local circulatory information relating to the leg of the subject (e.g. decision logic 10470 sounding an alarm or otherwise transmitting a notification if module 10475 detects unusually slow flow or other evidence of poor circulation locally within leg 10421). This can occur, for example, in a context in which module 10475 is configured to perform a normalcy comparison operation and in which module 10450 is implemented in or otherwise operable for interacting with a portable instrument 10440, a utility device, or some other suitable hardware at least sometimes accessible to subjects as described herein.

Figure 106:
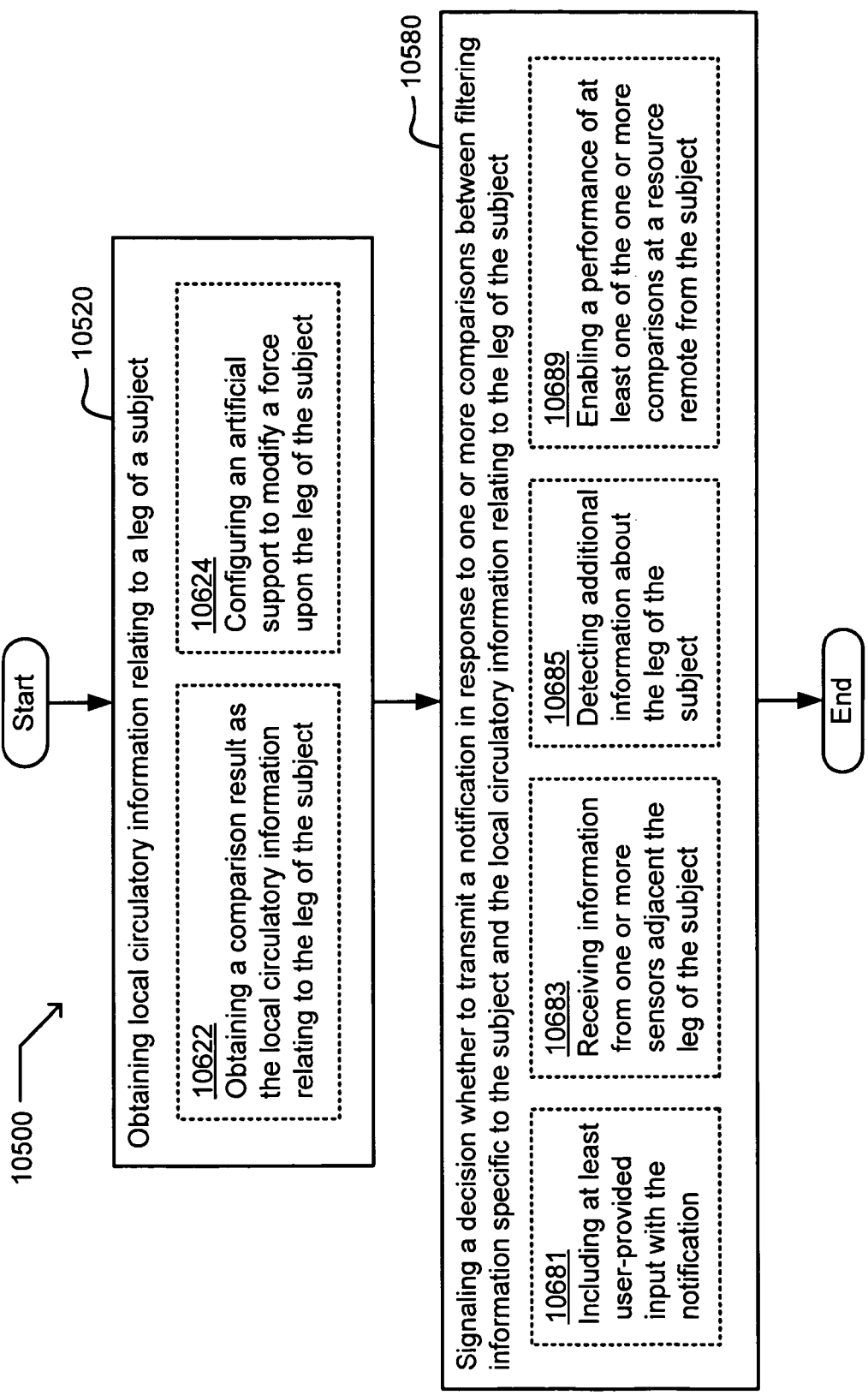
FIGS. 106-107 depict variants of the flow of FIG. 105.

With reference now to FIG. 106, there are shown several variants of the flow 10500 of FIG. 105. Operation 10520—obtaining local circulatory information relating to a leg of a subject—may (optionally) include one or more of the following operations: 10622 or 10624. In some embodiments, variants of operation 10520 may be performed by one or more instances of support control logic 780, invocation logic 3140, or other such sensor-containing or other responsive elements as described herein. Operation 10580—signaling a decision whether to transmit a notification in response to one or more comparisons between filtering information specific to the subject and the local circulatory information relating to the leg of the subject—may include one or more of the following operations 10681, 10683, 10685 or 10689. In some embodiments, variants of operation 10580 may be performed by one or more instances of notification logic 1290, 3535, 3991, 6180, 7460, 7875; evaluation logic 150, 250, 950, 1530, 7565; remote resources, or other components responsive to a measurement, user input, and/or other indication of circulatory status. Alternatively or additionally, flow 10500 may be performed in a context as described above with reference to any of FIGS. 1-80 and/or in conjunction with other flow variants as described below.

Operation 10622 describes obtaining a comparison result as the local circulatory information relating to the leg of the subject (e.g. module 3143 obtaining one or more results 3136 of one or more comparisons between earlier indications 3115, 3183 and later indications 3125, 3184 of flow in the subject). This can occur, for example, in a context in which one or more such indications 3183-3185 are extracted from measurements or other event-indicative records 3110, 3120, in which invocation logic 3140 performs operation 10520 by invoking evaluation logic 3197 (remotely) or other data filters 3151 that perform such comparisons. Such filtering information 3170 may (optionally) be partly based upon contemporaneous local circulatory information obtained from other body parts of the subject, for example, to ascertain whether a detected change is apparently vascular, as described herein. See, e.g., the description of operation 10788 below.

Operation 10624 describes configuring an artificial support to modify a force upon the leg of the subject (e.g. one or more modules 783 of support control logic 780 urging cell 740 laterally toward or away from adjacent cell 710 by causing one or more elements 741, 742, 743 to expand or contract). This can occur, for example, in a context in which a support layer or other suitable structure 765 adhesively or otherwise holds array 705 in a vicinity of leg 10421, in which control module 10461 implements controller 775, in which support control logic 780 performs operation 10520, and in which module 783 selectively opens one or more valves 746, 747 in fluid communication with higher- or lower-pressure reservoirs (not shown) so that element 743 controllably expands or contracts. In some variants, for example, one or more other elements 741, 742 may undergo an offsetting transition so that the net motion of cell 740 is primarily across the subject's skin. Alternatively or additionally, such other elements may undergo a like transition as that of element 743 so that the net motion of cell 740 is primarily orthogonal to structure 765, toward or away from the subject's skin.

In light of teachings herein, numerous existing techniques may be applied for configuring expanding, contracting, and/or other actuator elements as described herein without undue experimentation. See, e.g., U.S. Pat. No. 7,328,472 ("Configurable inflatable support devices"); U.S. Pat. No. 6,893,089 ("Method and apparatus for lumbar support with integrated actuator housing"); U.S. Pat. No. 6,886,200 ("Hydraulic actuator apparatus for a surgical table"); U.S. Pat. No. 6,837,351 ("Electromagnetic clutch assembly having enhanced torque throughput"); U.S. Pat. No. 6,240,582 ("Apparatus for positioning a patient-support deck"); U.S. Pat. No. 6,098,908 ("Configuration of an actuation mechanism which controls operation of a sub-drag mechanism in a fishing reel").

Operation 10681 describes including at least user-provided input with the notification (e.g. module 7752 of configuration logic 7755 including a category 7731, response 7732, verification 7733, distribution 7734, or other user input 7738 within or otherwise with notification content 7771). This can occur, for example, in a context in which various subjects 7710, caregivers, or other parties provide such input as described herein and in which these or other inputs 7738, 7739 may affect what the notification includes and/or whether or where the notification is transmitted. In some variants, for example, module 7752 may respond to an indication 7780 of a resource availability change, such as by rerouting, rescheduling, or otherwise reconfiguring a potential or partial notification's content or delivery parameters. Alternatively or additionally, an indication of a lack of timely input (from a first user, e.g.) may be included in a notification to another user, in some variants.

In light of teachings herein, numerous existing techniques may be applied for configuring a notification to include or otherwise indicate user preferences, status, or other such input as described herein without undue experimentation. See, e.g., U.S. Pat. No. 7,325,054 ("System for notifying destination user when status of consumable products of printing devices meets user selected notification condition"); U.S. Pat. No. 7,209,955 ("Notification system and method for a mobile data communication device"); U.S. Pat. No. 6,968,294 ("Automatic system for monitoring person requiring care and his/her caretaker"); U.S. Pat. No. 6,907,375 ("Method and apparatus for dynamic checking and reporting system health"); U.S. Pat. No. 6,878,111 ("System for measuring subjective well being"); U.S. Pat. No. 6,277,071 ("Chronic disease monitor"); U.S. Pat. No. 6,190,313 ("Interactive health care system and method").

Operation 10683 describes receiving information from one or more sensors adjacent the leg of the subject (e.g. module 10475 of decision logic 10470 receiving images or other data 10448 via one or more sensors 10441 adjacent leg 10421). This can occur, for example, in a context in which decision module 10470 performs operation 10580, in which a symptom is effectively detectable only by monitoring a subject's leg(s) over a period of a few hours or more, and in which the sensor(s) are configured to send circulatory and/or other status indicative information to module 10450. In some variants, for example, one or more channels 10445 between the sensor(s) and the system module may be accomplished through a continuous conduit. Alternatively or additionally, other such linkages among sensors or other circuitry as described herein may incorporate one or more wireless linkages such as Bluetooth, wireless USB, RF telemetry, cellular, 802.11 (B, G, N), far field telemetry, or other such existing technologies.

In light of teachings herein, numerous existing techniques may be applied for using wired and/or wireless technology for the communication between one or more sensor modules and the acquisition system as described herein without undue experimentation. See, e.g., U.S. Pat. No. 7,299,085 ("Remote monitoring of implanted medical device and surface ECG signals"); U.S. Pat. No. 7,289,253 ("System and methods for shearless hologram acquisition"); U.S. Pat. No. 7,198,603 ("Apparatus and methods using acoustic telemetry for intrabody communications"); U.S. Pat. No. 7,069,086 ("Method and system for improved spectral efficiency of far field telemetry in a medical device"); U.S. Pat. No. 6,970,737 ("Portable ECG device with wireless communication interface to remotely monitor patients and method of use"); U.S. Pat. No. 6,816,744 ("Device and system for remote for in-clinic transabdominal/vaginal/cervical acquisition, and detection, analysis, and communication of maternal uterine and maternal and fetal cardiac and fetal brain activity from electrical signals"); U.S. Pat. No. 6,597,948 ("Defibrillator with wireless communications"); U.S. Pat. No. 6,577,901 ("Network compatible RF wireless link for medical device data management"); U.S. Pat. No. 6,485,416 ("Remote monitoring apparatus for medical conditions").

Operation 10685 describes detecting additional information about the leg of the subject (e.g. module 1272 of detection logic 1275 receiving auditory data 1244, optical data 1247, subject-provided data 1246, pressure-indicative data 1245, or other additional data 1248 relating to one or more portions of the leg). This can occur, for example, in a context in which detection logic 1275 performs operation 10580, in which a subject is at home or at some other site at which maintaining adequate vigilance may be difficult, and in which module 1273 is configured to receive (locally-abnormal) thermal information 1251 or other information from one or more other sensors of array 1221 before or after module 1272 receives such "additional" data. In some variants, for example, optical sensors 2525 implanted into, affixed onto or arranged near the leg may be configured to provide other thermal information 1241, chemical composition information 1242, and/or other physiological information 1243. Other such sensors or related logic described above with reference to FIGS. 23-26 may likewise be included in the monitoring, evaluation, or other detection modules of this document, for example, many of which may be configured to record or otherwise respond to status-indicative information 1260 selectively as described herein.

Operation 10689 describes enabling a performance of at least one of the one or more comparisons at a resource remote from the subject (e.g. interface 7563 transmitting force estimates or other stress-indicative information 7533 with corresponding locality information 7531, timing information 7532, patient-specific information 7534, or other such comparative parameters). This can occur, for example, in a context in which evaluation logic 7565 performs operation 10580 and in which comparative information and/or other data as described herein is transmitted to or otherwise affects a configuration of one or more standards 7588, logic modules 7562, or other such comparison mode determinants 7535 configured to be applied remotely. In some variants, for example, one or more signal channels 7575 may be implemented in one or more aggregators or other such adjunct services 7590 operable remotely from an external module 9320 or other structures described herein for interacting with subjects. Alternatively or additionally, one or more comparisons or other evaluations as described herein may initially be performed locally to the subject's body.

In light of teachings herein, numerous existing techniques may be applied for comparing measurements, images, pathologies, profiles, or other such patterns as described herein without undue experimentation. See, e.g., U.S. Pat. No. 7,258,670 ("System and method for diagnosing and monitoring respiratory insufficiency for automated remote patient care"); U.S. Pat. No. 7,252,637 ("Method for continuous monitoring of patients to detect the potential onset of sepsis"); U.S. Pat. No. 6,926,668 ("System and method for analyzing normalized patient voice feedback in an automated collection and analysis patient care system"); U.S. Pat. No. 6,921,365 ("Remote non-invasive biofeedback diagnostic system based on patient image"); U.S. Pat. No. 6,908,437 ("System and method for diagnosing and monitoring congestive heart failure for automated remote patient care"); U.S. Pat. No. 6,616,613 ("Physiological signal monitoring system"); U.S. Pat. No. 6,501,849 ("System and method for performing image-based diagnosis over a network"); U.S. Pat. No. 6,454,705 ("Medical wellness parameters management system, apparatus and method"); U.S. Pat. No. 6,416,471 ("Portable remote patient telemonitoring system"); U.S. Pat. No. 5,793,969 ("Network review and analysis of computer encoded slides"); U.S. Pat. No. 6,210,301 ("Patient monitoring system").

Figure 107:
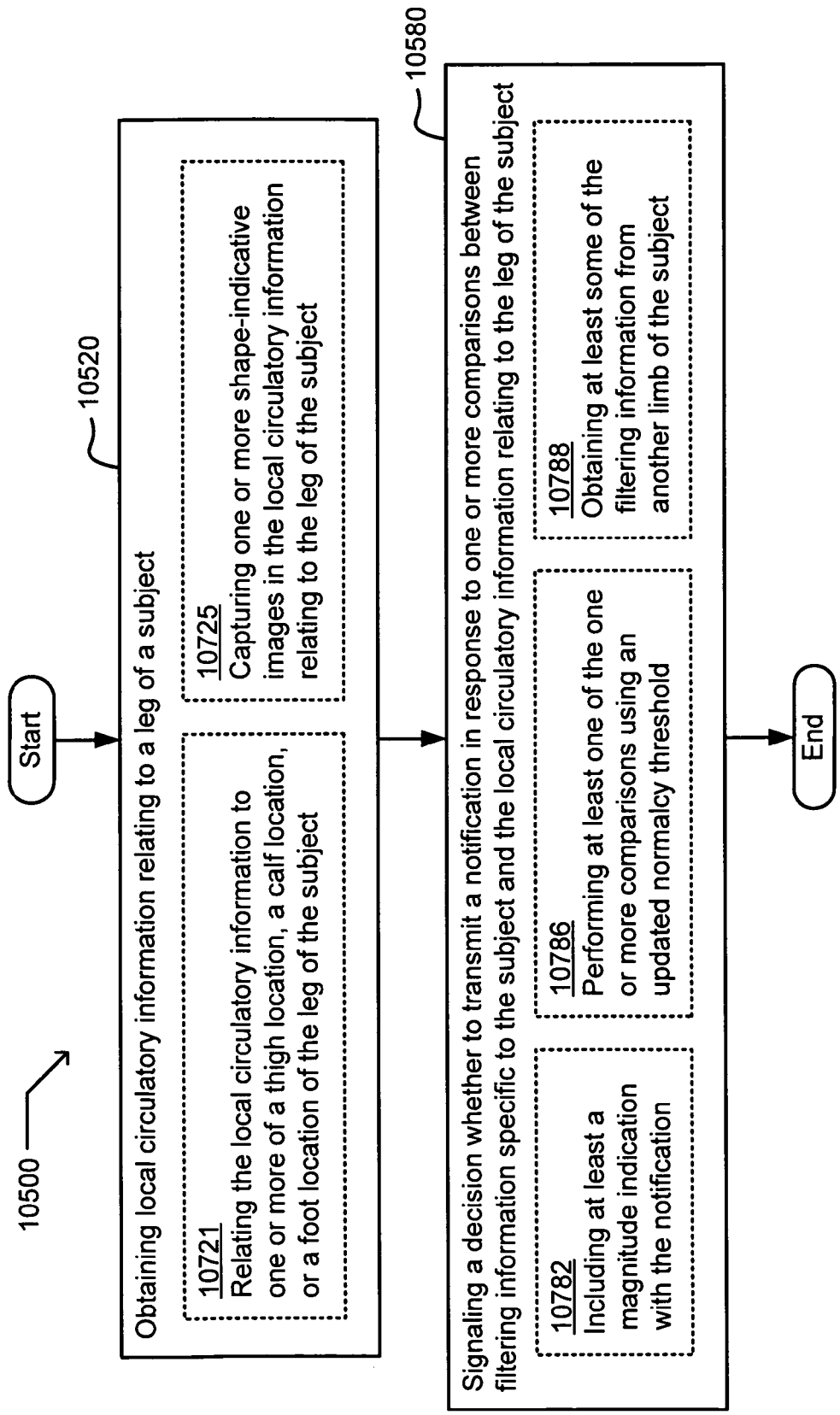

With reference now to FIG. 107, there are shown several variants of the flow 10500 of FIG. 105 or 106. Operation 10520—obtaining local circulatory information relating to a leg of a subject—may (optionally) include one or more of the following operations: 10721 or 10725. In some embodiments, variants of operation 10520 may be performed by one or more instances of decision logic 2975 or other response logic as described herein. Operation 10580—signaling a decision whether to transmit a notification in response to one or more comparisons between filtering information specific to the subject and the local circulatory information relating to the leg of the subject—may include one or more of the following operations 10782, 10786 or 10788. In some embodiments, variants of operation 10580 may be performed by one or more instances of control logic, configuration logic 5235, 7755, notification logic 1290, 3535, 3991, 6180, 7460, 7875; evaluation logic 150, 250, 950, 1530, 7565; or other components suitable for generating content for use in such a decision or notification. Alternatively or additionally, flow 10500 may be performed in a context as described above with reference to any of FIGS. 1-80 and/or in conjunction with other flow variants as described herein.

Operation 10721 describes relating the local circulatory information to one or more of a thigh location, a calf location, or a foot location of the leg of the subject (e.g. module 2973 of decision logic 2975 receiving communication 2935 or other data causing an activation of one or more sensors identified with or otherwise identifying such a body portion within subject 2920). This can occur, for example, in a context in which decision logic 2975 performs operation 10520 and in which one or more sensors 2927 are placed on or near the subject portion, optionally in one or more arrays 1221, 1222 as shown in FIG. 12). In some contexts, for example, one or more such portions 1201, 1202 may be selected as a primary sensor location for limb monitoring. Alternatively or additionally, one or more other sensors as described with reference to FIG. 23-26 may be positioned to monitor such subject portions 1201 and/or other contemporaneous attributes of the subject as described herein.

In light of teachings herein, numerous existing techniques may be applied for the selective inclusion and/or activation of one or more sensors from a sensor set as a primary sensor location without undue experimentation. See, e.g., U.S. Pat. No. 7,332,743 ("Thin film transistor array panel and liquid crystal display"); U.S. Pat. No. 7,208,983 ("Image-sensor signal processing circuit"); U.S. Pat. No. 7,190,987 ("Neonatal bootie wrap"); U.S. Pat. No. 7,155,281 ("Complimentary activity sensor network for disease monitoring and therapy modulation in an implantable device"); U.S. Pat. No. 7,149,645 ("Method and apparatus for accurate on-die temperature measurement"); U.S. Pat. No. 6,275,733 ("Dual sensor rate response pacemaker"); U.S. Pat. No. 6,271,766 ("Distributed selectable latent fiber optic sensors").

Operation 10725 describes capturing one or more shape-indicative images in the local circulatory information relating to the leg of the subject (e.g. module 1621 causing a recordation of one or more images 1697 from an array or other configuration of sensors 7717 into memory 7765 or other media 1695). This can occur, for example, in embodiments in which response module performs operation 10520 and in which primary module 7790 may communicate in one or both directions with one or more active sets of ultrasound sensors 1981 or other shape-indicative sensors configured to apply one or more respective-set-specific intensity thresholds 1653 and/or frequency thresholds 1654. Such an embodiment may be used, for example, to estimate an areal expansion or other gradient relating to a region of abnormal circulation. Alternatively or additionally, such data may be used to derive an aspect ratio, a shape type, or other such shape-indicative attributes 1699 of such detectable abnormalities.

In light of teachings herein, numerous existing techniques may be applied for pattern recognition or other such techniques suitable for use in monitoring pathologies as described herein without undue experimentation. See, e.g., U.S. Pat. No. 7,336,804 ("Method and apparatus for detection of drowsiness and quantitative control of biological processes"); U.S. Pat. No. 7,317,821 ("Automatic abnormal tissue detection in MRI images"); U.S. Pat. No. 7,214,195 ("Method of and apparatus for detecting diseased tissue by sensing two bands of infrared radiation"); U.S. Pat. No. 7,214,194 ("Method for thermal diagnosis of pathology of a bioobject and device for carrying out said method"); U.S. Pat. No. 7,171,680 ("Method and apparatus for electro-biometric identity recognition"); U.S. Pat. No. 7,162,061 ("Abnormal pattern detection processing method and system"); U.S. Pat. No. 6,963,772 ("User-retainable temperature and impedance monitoring methods and devices"); U.S. Pat. No. 6,440,084 ("Thermal scanning system and method").

Operation 10782 describes including at least a magnitude indication with the notification (e.g. module 781 of support control logic 780 causing a contraction of one or more elements 753 so that cell 750 exerts a decreasing shear or other force upon a subject's leg wound). This can occur, for example, in a context in which one or more arrays 1221, 1222 of FIG. 12 implement array 705 of FIG. 7, in which at least control logic 1280 performs operation 10580, in which one or more arrangements of actuation and/or sensor elements are distributed over a region of concern in a subject limb and in which system module 1230 configures a suitable actuation controller as described herein. In some variants, for example, array 705 may expand or contract to maintain a pressure within a detection range as the body part expands or contracts due to increased or decreased tissue swelling. Alternatively or additionally, one or more modules 783, 784 of support control logic 780 may be configured to actuate one or more arrays or other configurations of actuators cyclically or otherwise in patterns selected by specifying one or more parameters 793-795, such as to prevent circulatory disruptions or other adverse effects.

Operation 10786 describes performing at least one of the one or more comparisons using an updated normalcy threshold (e.g. module 7751 of configuration logic 7755 changing or otherwise updating one or more optical or other normalcy thresholds 7762). This can occur, for example, in a context in which configuration logic 7755 performs operation 10580, in which such comparative information is derived from sensor data described herein, and in which one or more users or devices have indicated an availability to receive such notifications with one or more such parametric updates. In some variants, for example, information from one or more sensors 7717 on or near a subject 7710 may be used to generate and/or adjust thresholds applied to sensor data 7741 from one or more other sensors extending into, in contact with, or otherwise arranged around the subject. Alternatively or additionally, historic and/or processed information from a remote storage and/or processing device may be used to provide and/or adjust thresholds or other filtering information applied to the sensor data 7741 or other types of information 7745 obtained about the subject limb.

In light of teachings herein, numerous existing techniques may be applied for requesting, receiving, or otherwise interacting with numerical thresholds as described herein without undue experimentation. See, e.g., U.S. Pat. No. 7,250,855 ("False alarm mitigation using a sensor network"); U.S. Pat. No. 7,079,035 ("Method and apparatus for controlling an alarm while monitoring"); U.S. Pat. No. 7,037,273 ("Core body temperature monitoring in heart failure patients"); U.S. Pat. No. 6,942,626 ("Apparatus and method for identifying sleep disordered breathing"); U.S. Pat. No. 6,569,095 ("Adaptive selection of a warning limit in patient monitoring"); U.S. Pat. No. 6,552,531 ("Method and circuit for processing signals for a motion sensor"); U.S. Pat. No. 6,263,243 ("Rate adaptive pacemaker").

Operation 10788 describes obtaining at least some of the filtering information from another limb of the subject (e.g. one or more modules 782 of support control logic 780 selecting one or more cells 740 or one or more of their actuation elements 741, 742, 743 in response to a determination that no anomalies have been detected in tissue adjacent cell 740). This can occur, for example, in a context in which support control logic 780 performs operation 10580, in which component 414 contains cell 740, in which one or more sensors 424 as described herein are positioned in or near cell 740 for detecting one or more tissue attributes of external portion 404 of body 410, in which one or more such cells 740, 750 are positioned so that a movement of cell 740 may directly result in an increasing lateral and/or normal force upon external portion 404, and in which a selection of cell 740 may thereby effectively implement a determination of the "second" external portion. In some variants, for example, an expansion of one or more elements 742, 743 may cause such an increasing force, a direction of which may be modified by one or more other elements 741. Alternatively or additionally, module 782 may may control such movement of component 414 with closed-loop control so that component 414 is positioned to minimize a shear force or otherwise favorably influence an attribute of abnormality 409 detected, for example, via sensor 425.

In light of teachings herein, numerous existing techniques may be applied for detecting or characterizing injuries or other localized structures and/or phenomena as described herein without undue experimentation. See, e.g., U.S. Pat. No. 7,303,555 ("Imaging and therapeutic procedure for carpal tunnel syndrome"); U.S. Pat. No. 7,226,426 ("Apparatus and method for the detection and quantification of joint and tissue inflammation"); U.S. Pat. No. 7,155,273 ("Blanching response pressure sore detector apparatus and method"); U.S. Pat. No. 7,006,676 ("Method and apparatus for detecting an abnormality within a host medium utilizing frequency-swept modulation diffusion tomography"); U.S. Pat. No. 6,993,167 ("System and method for examining, recording and analyzing dermatological conditions"); U.S. Pat. No. 6,880,387 ("Acoustic micro imaging method providing improved information derivation and visualization"); U.S. Pat. No. 6,544, 186 ("System and method for diagnostic imaging"); U.S. Pat. No. 6,464,646 ("Instrument and method for locating and marking a hot spot in a person's body tissue"); U.S. Pat. No. 6,258,046 ("Method and device for assessing perfusion failure in a patient by measurement of blood flow"); U.S. Pat. No. 6,233,479 ("Microwave hematoma detector"); U.S. Pat. No. 6,192,143 ("Apparatus for detecting very small breast anomalies"); U.S. Pat. No. 6,056,692 ("Apparatus and method for locating and marking blood vessels"); U.S. Pat. No. 5,999, 836 ("Enhanced high resolution breast imaging device and method utilizing non-ionizing radiation of narrow spectral bandwidth"); U.S. Pat. No. 5,989,194 ("Method and apparatus for detecting ocular disease and abnormalities").

With reference now to FIG. 108, shown is an example of a system 10800 that may serve as a context for introducing one or more processes and/or devices described herein, comprising one or more instances of module 10830 operable for interacting with module 10890. As shown, module 10830 may include one or more modules 10811 of dispensing logic 10810 operable for controlling statin dispenser 10818 or (other) therapeutic dispenser 10819; memory 10821 operable for handling software-implemented or other regimens; or one or more sensors 10822 as described herein. Also shown is a kidney or other organ 10860 having one or more (therapeutic-agent-) suffused portions 10861 and one or more other portions 10862, at least one of the suffused portions 10861 comprising a vicinity 10865 of (converging venules 10864 of) lumen 10895

Next downstream as shown, module 10890 comprises one or more modules 10831, 10832 of response logic 10835; (transvascular or other) extraction modules 10845; sensors 10881; dispensers 10882; or clamps 10855. As shown, extraction module 10845 comprises one or more ports 10841 to be formed through vessel wall 10846, operable for extracting a portion 10844 of lytic-material-infused blood 10842, for example, into one or more absorbent elements 10847, dialysis extractors, and/or to other such disposal vessels. As shown, one or more clamps 10855 are configured to limit outflow 10899 from module 10890 by expanding one or more actuators 10857, thereby levering lumen 10895 to occlude it temporarily as shown. Alternatively or additionally, vicinity 10885 of lumen 10895 may include one or more conduits 10867 operable for selectively removing a portion of outflow 10899 by redirecting it to one or more artificial disposal vessels 10870 as shown.

Concerning the opening of port 10841 or other timing of capture logic 2880 (of FIG. 28) or similar responsive circuitry described herein, a delay time between a capture site and an upstream site can be readily estimated. A blood cell typically travels about ⅓ of a millimeter per second in human capillaries, for example. In some contexts, an accurate model may best be developed by measuring a specific interpositional delay empirically using, for example, a fluorescent material or other detectable measurement technique. Such a delay can readily be implemented in a digital or other timing feature of modules as described herein, for example, initiating a later operation at a programmed interval following a triggering event as described herein. In situations where a more reliable model is needed, a pulse-dependent, local-pressure-dependent, or other adaptive model may be appropriate, and well within the capabilities of skilled practitioners without undue experimentation in light of teachings herein.

An embodiment provides a module 10890 comprising a clamp 10855 and/or other artificial structure(s) operable to impede most of outflow 10899 from vascular lumen 10895 and a dispenser 10819 or other structure operable to administer a lytic or other therapeutic material locally to the lumen 10895. (Other such embodiments are described, for example, with reference to FIG. 36.) Such dispensers can be positioned upstream from some or all of organ 10860, for example, in an artery or arteriole. Such artificial structures can likewise include one or more disposals 2889, pumps 2887, extraction modules 10845, sensors, a housing or other support structure (as indicated in system 2800), communication conduits, or other components described herein.

With reference now to FIG. 109, shown is a flow 10900 comprising operation 10910—obtaining one or more indications of a lytic material in a vicinity of one or more body lumens (e.g. module 10831 of response logic 10835 responding to a signal from one or more sensors 10822, 10881 or some other indication that an anticoagulant or other lytic material will apparently be present in a vicinity 10865 of lumen 10895). In some variants, this exemplifies circuitry or other means for obtaining one or more indications of a lytic material in a vicinity of one or more body lumens. This can occur, for example, in a context in which response logic 10835 receives a notification that one or more lytic-material-containing dispensers 10819 have been activated. Alternatively or additionally, such indications can result from one or more sensors 10881 detecting one or more natural chemical markers resulting from injury, for example. Alternatively or additionally, such indications can result from dispenser 10882 administering a lytic compound by backflow into organ portion 10861—injecting the compound at a somewhat higher pressure than that of blood in venules 10864.

Flow 10900 further comprises operation 10970—accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens (e.g. port 10841 or conduit 10867 opening shortly after a dispensation of fibrinolytic material in upstream vicinity). In some variants, this exemplifies circuitry or other means for accelerating a decrease in a local concentration of the lytic material in the vicinity of one or more body lumens by causing one or more elements to extract at least a portion of the lytic material in the vicinity of the one or more body lumens in response to the one or more indications of the lytic material in the vicinity of one or more body lumens. This can occur, for example, in embodiments in which such ports or conduits are configured to allow higher-than-nominal concentrations of the lytic material to drain out of the vascular system, optionally by a timely exposure to an absorbent element 10847 or other disposal vessel 10870. Alternatively or additionally, such extraction may be performed actively, such as by microfluidic or other pumps as described herein.

Figure 110:
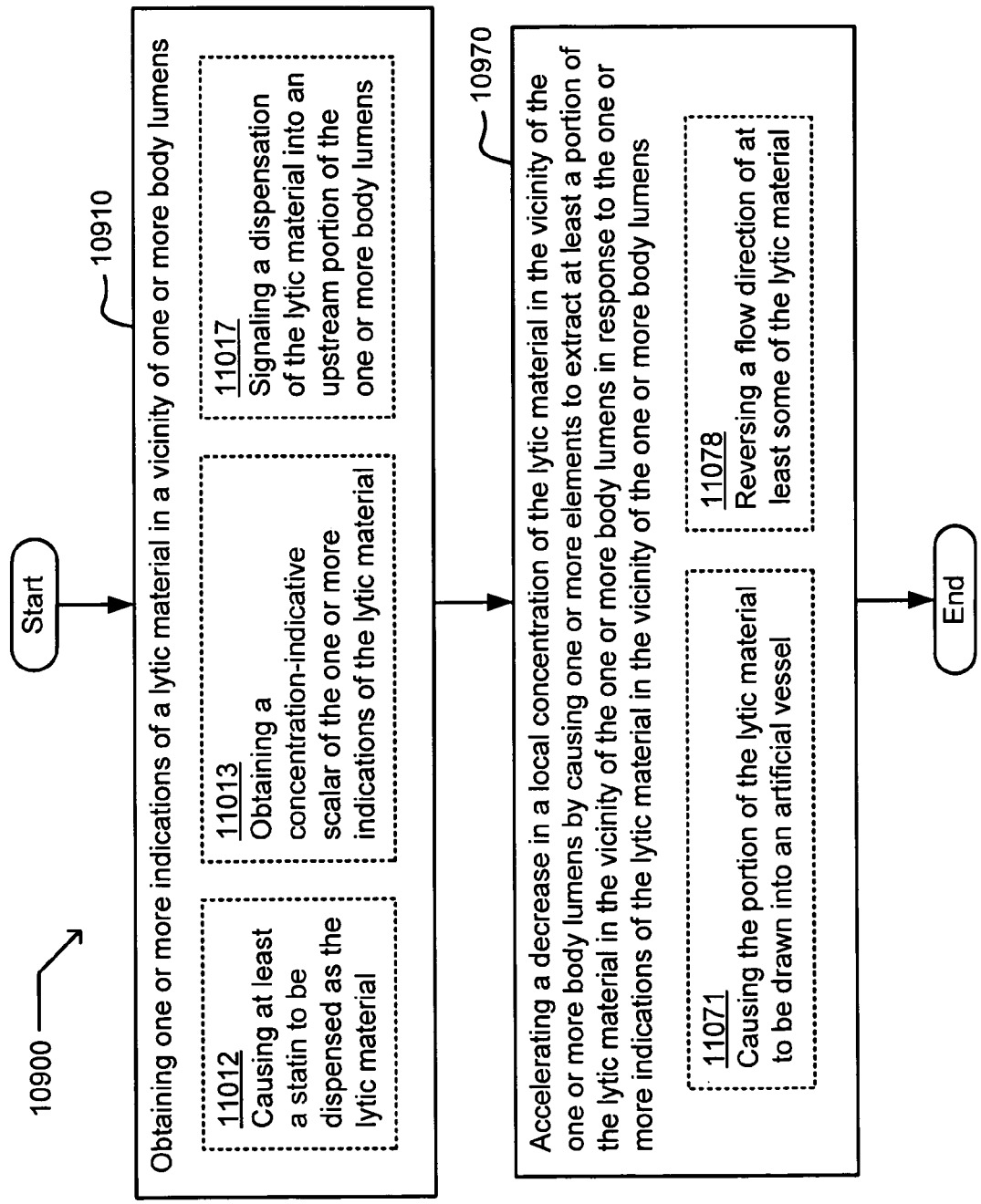

With reference now to FIG. 110, there are shown several variants of the flow 10900 of FIG. 109. Operation 10910—obtaining one or more indications of a lytic material in a vicinity of one or more body lumens—may (optionally) include one or more of the following operations: 11012,

11013, or 11017. In some embodiments, variants of operation 10910 may be performed by one or more instances of sensors 4510, 10822, response logic 4555, 10835, or the like as exemplified herein. Operation 10970—accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens—may include one or more of the following operations: 11071 or 11078. In some embodiments, variants of operation 10970 may be performed by one or more instances of extraction device 4580 or the like as described herein.

Operation 11012 describes causing at least a statin to be dispensed as the lytic material (e.g. dispensing logic 10810 invoking module 10811 or other circuitry for actuating statin dispenser 10818 or other lytic-material-containing dispenser 10819 according to one or more dosage profiles in memory 10821). In some variants, this exemplifies circuitry or other means for obtaining one or more indications of a lytic material in a vicinity of one or more body lumens comprising means for causing at least a statin to be dispensed as the lytic material. This can occur, for example, in embodiments in which one or more instances of modules 10830 are positioned (locally) upstream from a lung or other organ 10860 and in which at least a portion 10861 of organ 10860 has been perfused with an abnormally high concentration of lytic material (relative to a time-averaged systemic normal range, for example). Alternatively or additionally, in some variants, module 10890 may be configured in a context in which one or more hemorrhage-risk determinants have been established in relation to one or more other organs in a downstream vicinity 10885 of lumen 10895 relative to outflow 10899.

Operation 11013 describes obtaining a concentration-indicative scalar of the one or more indications of the lytic material (e.g. one or more modules 6732 of detection logic 6720 receiving a scalar value 6723 indicative of a concentration gradient or other concentration-indicative data 6724 from an optical sensor 2525 or other concentration-indicative sensor 2560 nearby or downstream from a dispensation). In some variants, this exemplifies circuitry or other means for obtaining one or more indications of a lytic material in a vicinity of one or more body lumens comprising means for obtaining a concentration-indicative scalar of the one or more indications of the lytic material. This can occur, for example, in a context in which detection logic 6720 is configured to perform operation 10910, and in which configuration system 6710 overlaps or otherwise interacts with one or more local systems having sensors in a vicinity of the dispensation, in which the lytic material dispensed includes an optically or other detectable marker material that does not interfere significantly with the desired action of the lytic material. In some variants, for example, a quantitative expression of lytic material concentration can be generated directly, such as by measuring a concentration of a marker material covalently bonded or otherwise linked to the lytic material. Alternatively or additionally, some such expressions can by generated by inference, such as by detecting a marker material commingled with the lytic material or by interpolating a concentration between two measurement locations.

Operation 11017 describes signaling a dispensation of the lytic material into an upstream portion of the one or more body lumens (e.g. module 7261 of control logic 7270 triggering actuator 7281 to inject or release tissue plasminogen activator 7283 or other lytic materials 7284 locally into a common carotid artery 7350 responsive to data 7213 signifying a sudden volumetric decrease in one or more flows 7321, 7331 exiting a segment downstream). In some variants, this exemplifies circuitry or other means for obtaining one or more indications of a lytic material in a vicinity of one or more body lumens comprising means for dispensing the lytic material into an upstream portion of the one or more body lumens. This can occur, for example, in a context in which a clot has lodged itself downstream (in the anterior or middle cerebral arteries, for example) and/or in which one or more systemic determinants 7212 indicate an absence of detectable hemorrhaging in subject 7310, and in which a care provider has defined a programmatic regimen 7263 by which such material(s) are to be administered immediately in these contingencies. In some variants, regimen 7263 may further depend upon one or more complementary determinants 7211 or other data 7214: whether one or more complementary arteries exhibit a substantially increased local blood pressure or flow. Alternatively or additionally, regimen 7263 may define a (therapeutic contraindication or other) response to other systemic determinants 7212 such as a substantial increase in (resting) heart rate or substantial decreases in blood pressure over a course of minutes or hours. (In some embodiments, such "substantial" changes as described herein may include changes of about 10% or more, except as noted.)

Operation 11071 describes causing the portion of the lytic material to be drawn into an artificial vessel (e.g. actuator 2881 allowing one or more ports 2882 to draw out at least some of outflow 2899 through one or more vessel walls 2883, 2884 into vessel 2885). In some variants, this exemplifies circuitry or other means for accelerating a decrease in a local concentration of the lytic material in the vicinity of one or more body lumens by causing one or more elements to extract at least a portion of the lytic material in the vicinity of the one or more body lumens in response to the one or more indications of the lytic material in the vicinity of one or more body lumens comprising means for causing the portion of the lytic material to be drawn into an artificial vessel. This can occur, for example, in a context in which a dispenser has been dispensing one or more therapeutic agents 2841 containing one or more carcinogens or other ingredients having potentially undesirable side effects in outflow 2899. Alternatively or additionally, a conduit 2886 and/or pump 2887 may be used for accelerating a decrease of the local concentration of such materials (near port 2882, e.g.).

Operation 11078 describes reversing a flow direction of at least some of the lytic material (e.g. pump 7282 withdrawing some of a dispensed lytic-agent-containing material from one or more arteries responsive to one or more sensors 7345 indicating a local diastolic blood pressure decrease). In some variants, this exemplifies circuitry or other means for accelerating a decrease in a local concentration of the lytic material in the vicinity of one or more body lumens by causing one or more elements to extract at least a portion of the lytic material in the vicinity of the one or more body lumens in response to the one or more indications of the lytic material in the vicinity of one or more body lumens comprising means for reversing a flow direction of at least some of the lytic material. This can occur, for example, in a context in which a flow is apparently restored or in a context of hemorrhage, either of which may warrant a such a prompt withdrawal pursuant to regimen 7263. Alternatively or additionally, in some contexts, a reverse flow direction may be used for perfusing an organ with a lytic-agent-containing material via one or more venules. See, e.g., descriptions above relating to FIGS. 33 & 34.

With reference now to FIG. 111, there are shown several variants of the flow 10900 of FIG. 109 or 110. Operation 10910—obtaining one or more indications of a lytic material in a vicinity of one or more body lumens—may include one or more of the following operations: 11111, 11114, 11116, 11118, or 11119. In some embodiments, variants of operation 10910 may be performed by one or more instances of response logic 4555, 10835 or the like as exemplified herein. Operation 10970—accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens—may include one or more of the following operations: 11175 or 11177. In some embodiments, variants of operation 10970 may be performed by one or more instances of extraction device 4580 or the like as described herein.

Operation 11111 describes permitting the lytic material to perfuse one or more organs in the vicinity of the one or more body lumens (e.g. dispensing logic 10810 invoking one or more dispensers 10819 to inject a lytic compound or other lytic material into a renal artery or otherwise to perfuse organ 10860). In some variants, this exemplifies circuitry or other means for obtaining one or more indications of a lytic material in a vicinity of one or more body lumens comprising means for permitting the lytic material to perfuse one or more organs in the vicinity of the one or more body lumens. This can occur, for example, in an embodiment in which dispensing logic 10810 can invoke other logic modules and in which system 10800 implements one or more devices like those disclosed in U.S. Pat. No. 6,592,567 ("Kidney perfusion catheter") or U.S. Pat. No. 6,514,226 ("Method and apparatus for treatment of congestive heart failure by improving perfusion of the kidney"). Alternatively or additionally, such a perfusion may reasonably be inferred at some time after a sufficiently large systemic administration of the lytic material. In some contexts this may be desirable, for example, even for a cancer patient for whom a lytic treatment in outflow 10899 presents a danger. In a case in which a majority of blood flowing through module 10890 is removed from a patient's vasculature into one or more conduits 10867, for example, a transfusion or other blood replacement at module 10890 may be provided to supplement outflow 10899 (optionally with a concomitant decrease in the local concentration of the lytic material).

Operation 11114 describes signaling at least one of the one or more indications of the lytic material via a wireless signal (e.g. module 7122 of control logic 7120 activating one or more modules of communication logic 7140 resulting in the transmission of measurement data 7133 and/or lytic-material-indicative data 7131 to one or more remote modules through telemetry or other wireless signals 7132). In some variants, this exemplifies circuitry or other means for obtaining one or more indications of a lytic material in a vicinity of one or more body lumens comprising means for signaling at least one of the one or more indications of the lytic material via a wireless signal. This can occur, for example, in a context in which sensor data indicating the presence and/or concentration of lytic material at one or more target regions in a subject are sent to a display module to facilitate monitoring by a subject and/or caregiver. Alternatively or additionally, module 7121 can perform operation 11114 by transmitting such output to remote resources 7161, 7162 in network 7160 for storage, correlation analysis, and/or monitoring of a subject by remote personnel.

Operation 11116 describes detecting a marker material indicative of the lytic material in the vicinity of the one or more body lumens (e.g. module 6731 of detection logic 6720 detecting one or more attributes of a marker material using one or more fluorescence sensors 2322, radioactivity sensors 2462, electrochemical sensors 2548, or other suitable sensors implemented in device 6790). In some variants, this exemplifies circuitry or other means for obtaining one or more indications of a lytic material in a vicinity of one or more body lumens comprising means for detecting a marker material indicative of the lytic material in the vicinity of the one or more body lumens. This can occur, for example, in a context in which detection logic 6720 performs operation 10910; in which device 6790 is positioned on, in, or near a target vessel; and in which such a device is configured to indicate one or more categorical attributes 6725 and/or quantitative attributes 6726 of an artificial marker material via wireless communication linkage 6752. In some embodiments, device 6790 may be configured to perform or facilitate such modes of detection continuously, intermittently, upon request, conditionally, or otherwise. Alternatively or additionally, one or more such local modules 2320, 2450, 2510 can be implemented on a subject's skin or in a hand-held instrument as described herein, especially in a context in which a subject has varicose veins or other large-enough body lumens of interest near the subject's skin.

Operation 11118 describes causing the lytic material to be urged into the one or more body lumens (e.g. module 7123 of control logic 7120 transmitting an activation signal 7171 to a pump 7184, iontophoretic module 7183, or other delivery unit 7180 causing one or more lytic components to flow into one or more target vessel sites). In some variants, this exemplifies circuitry or other means for obtaining one or more indications of a lytic material in a vicinity of one or more body lumens comprising means for causing the lytic material to be urged into the one or more body lumens. This can occur, for example, in a context in which activation of one or more delivery modules triggers an actuator 7182 in such units to exert an increasing pressure upon one or more lytic-material-containing reservoirs 7181. The increase in pressure forces a lytic-component-containing material through a needle or other conduit into a target region. Alternatively or additionally, electrical, acoustic, or other energy systems can be used to drive the delivery of the lytic material into a target tissue.

Operation 11119 describes accelerating a dispensation of the lytic material transluminally into the one or more body lumens as a programmed response to one or more pathology-indicative signals (e.g. a command sequence or other module 6774 of control logic 6770 signaling an injection of a bolus of an antiplatelet drug or other antiaggregant transluminally responsive to one or more imaging and/or pressure sensors indicating an apparent blockage). In some variants, this exemplifies circuitry or other means for obtaining one or more indications of a lytic material in a vicinity of one or more body lumens comprising means for accelerating a dispensation of the lytic material transluminally into the one or more body lumens as a programmed response to one or more pathology-indicative signals. This can occur, for example, in a context in which control logic 6770 performs operation 10910, in which one or more implantable devices 6790 indicate a vessel blockage or other pathology treatable with an available lytic compound, and in which such a dispensation can be signaled (a) directly to dispenser 6780 or (b) via an interface 6740 to a person with a syringe. In some variants, for example, one or more sensors and dispensers 6780 of a local module 2320, 2450, 2510 may be implanted or otherwise positioned near a common vascular blockage site and configured to respond to an apparent blockage with a targeted release of lytic material locally to alleviate the blockage. Alternatively or additionally, decision logic 2250 can be configures so that detection of a local blockage or dispensation will cause a notification 2241 of such local conditions and/or a notification 2242 of a systemic dispensation of a lytic material. In some crises, for example, an informed subject might elect to self-administer a treatment promptly in light of such information, even before reaching a hospital and completing a diagnostic protocol sufficient to avoid hospital liability. Alternatively or additionally, one or more interfaces may ask or otherwise monitor a (conscious) subject for an indication of whether such action is being taken and provide such parameters 2249 to emergency caregivers who later encounter the subject. In some variants, moreover, one or more modules 2245 of decision logic 2250 may inquire of an authorized caregiver, a central medical history database, or some other such resource 7161 whether a recent surgery or other contraindications of an immediate lytic therapy may exist.

Operation 11175 describes causing the lytic material to be exposed to a lytic-material-absorbent element (e.g. module 7033 of control logic 7092 signaling one or more actuators 7055 to guide flow from inlet 7005 toward extraction unit 7080 so that lytic-material-containing fluid comes into contact with one or more foams 7071, fibers 7072, or other such materials 7073 suitable for binding to or otherwise absorbing at least some of the lytic material). In some variants, this exemplifies circuitry or other means for accelerating a decrease in a local concentration of the lytic material in the vicinity of one or more body lumens by causing one or more elements to extract at least a portion of the lytic material in the vicinity of the one or more body lumens in response to the one or more indications of the lytic material in the vicinity of one or more body lumens comprising means for causing the lytic material to be exposed to a lytic-material-absorbent element. This can occur, for example, in a context in which such actuators 7045, 7055 comprise one or more valves 7050 and/or pumps 7060 selectively operable to divert at least some lytic-material-containing fluid from a normal flow (toward extraction unit 7080 or into an alternate outlet 7092, for example, rather than to a primary return 7091). Once the fluid has been in contact with the lytic-material-absorbent element(s) for a suitable interval (one the order of seconds or minutes, e.g.) it may then be returned to transfer unit 7010. In some variants, for example, one or more pumps 7060 or other actuators 7055 may be configured to regulate a fraction of an inflow (via inlet 7005, e.g.) that is routed to contact absorbent materials. Alternatively or additionally, one or more modules 7032 may perform operation 11175 by routing a primary flow (containing an artificial lytic material, for example, and flowing from inlet 7005 to return 7091, e.g.) along one or more preferentially absorbent structures. In some variants, moreover, such structures (a) may include one or more such units in an implant and/or (b) may include one or more dispensers 7020 as described herein.

Operation 11177 describes causing a lytic activity inhibitor dispensation into the one or more body lumens (e.g. module 3981 of control logic 3980 causing one or more dispensers 3831 to release an amount of protease nexin or other such plasminogen activator inhibitors sufficient to inhibit a lytic activity of at least about 0.1% to 1% of an amount of a plasminogen activator currently dispensed in vasculature 3805). In some variants, this exemplifies circuitry or other means for accelerating a decrease in a local concentration of the lytic material in the vicinity of one or more body lumens by causing one or more elements to extract at least a portion of the lytic material in the vicinity of the one or more body lumens in response to the one or more indications of the lytic material in the vicinity of one or more body lumens comprising means for causing a lytic activity inhibitor dispensation into the one or more body lumens. This can occur, for example, in a context in which one or more other dispensers 3831 has released the plasminogen activator(s) earlier and/or upstream, in which two or more such dispensers 3821, 3831 for different materials are configured in a common body 3830, in which control module 3820 implements control logic 3980 configured to perform operation 10970, and in which such inhibitors directly or indirectly cause at least one lytic activity of the lytic material to be inhibited in vasculature 3805. In some variants, the inhibitor(s) may be release in sufficient quantities to inhibit a lytic activity of up to about 5% to 50% of the dispensed plasminogen activator(s). Alternatively or additionally, module 3982 may perform operation 11177 in response to one or more of a hemorrhage indication 3973 or blockage removal indication 3974 indicating a vessel 3840 near or downstream from dispenser 3821. Alternatively or additionally, module 3982 may likewise perform operation 11177 in response to one or more of a continuing lytic material dispensation indication 3971 or an indication 3972 that vessel 3840 is an appropriate (low risk, e.g.) location in which to dispense the inhibitor(s) for a systemic effect upon the subject.

Figure 112:
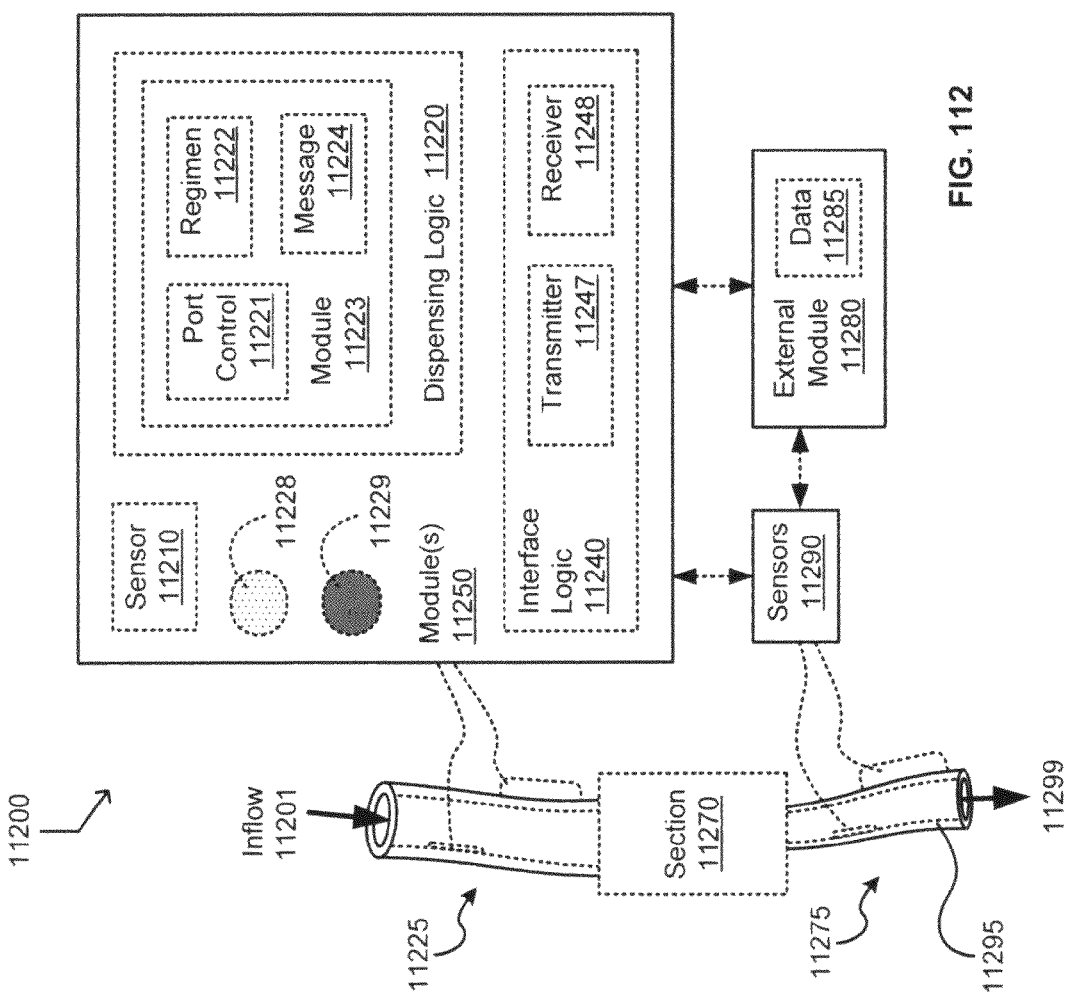
FIG. 112 depicts an exemplary environment in which one or more technologies may be implemented.

With reference now to FIG. 112, shown is an example of a system that may serve as a context for introducing one or more processes and/or devices described herein. As shown system 11200 may affect or otherwise relate to vicinity 11225, section 11270, and vicinity 11275 of a vascular lumen 11295 through which one or more blood components may flow. One or more inflows 11201 of blood enter respective portions of lumen 11295 as shown, pass through section 11270, and exit as one or more outflows 11299. In respective variants, arteries, veins, or smaller vessels of lumen 11295 may traverse vicinities 11225, 11275 as shown. Section 11270 may likewise comprise one or more capillary beds as well as vital organs and other tissues served by lumen 11295.

In some variants, one or more intravascular or other modules 11250 in vicinity 11225 may (optionally) include one or more instances of sensors 11210; modules 11223 or other dispensing logic 11220; dispensers 11228, 11229; or transmitters 11247, receivers 11248, or other interface logic 11240. (Some such modules 11250 may be operable for penetrating a vascular structure with ultrasonic or other energy, for example, or may comprise an implanted cannula or other transvascular structure.) Module 11223 may, as shown, comprise one or more instances of port controls 11221, regimens 11222 or other programmatic dispensing information (optionally embodied in software or other instruction sequences, for example), or requests or other messages 11224.

Alternatively or additionally, system 11200 may comprise one or more intravascular or other sensors 11290 that may be configured to communicate (in one or both directions) with module 11250, such as by a signal-bearing conduit or radio-frequency signal. (Some such sensors 11290 may be operable for monitoring one or more physical phenomena within vascular structures, for example, from within or in a vicinity of the structures.) Systems 11200 may likewise be configured to include or otherwise interact with one or more instances of external modules 11280 operable, for example, for obtaining and providing data 11285 as described herein. In some variants, for example, the one or more sensors 11290 are only operable for communicating sensed analog or digital values to module 11250. In others, one or more of the sensor(s) 11290 are able to receive updates or other information from one or more external modules 11280 or other transmitters 11247 as described herein.

Figure 113:
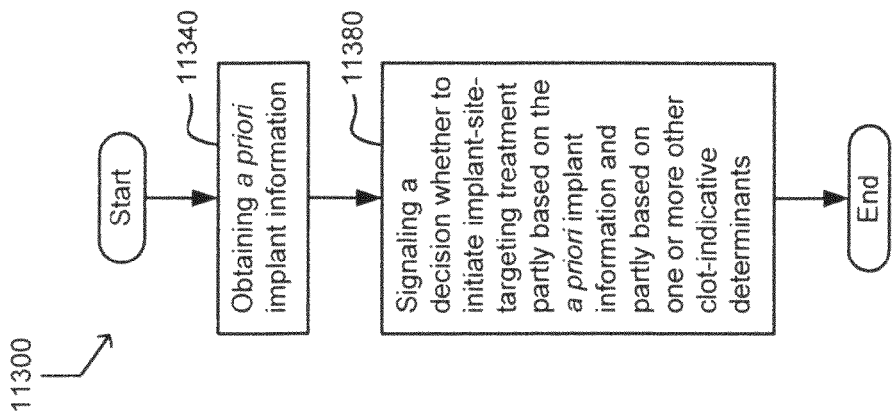
FIG. 113 depicts a high-level logic flow of an operational process.

With reference now to FIG. 113, shown is a flow 11300 comprising operation 11340—obtaining a priori implant information (e.g. receiver 11248 receiving user-provided or other data 11285 describing one or more sensors 11290 or other implants downstream from one or more modules 11250 in a vicinity 11275 of lumen 11295). This can occur, for example, in a context in which module 11250 comprises a cannula or other implantable structure positioned upstream from an outflow 11299 local to the implant(s) to which the apriori information pertains. Alternatively or additionally, receiver 11248 may obtain sensor data or other determinants relating to such implants, as described herein.

Flow 11300 further comprises operation 11380—signaling a decision whether to initiate implant-site-targeting treatment partly based on the a priori implant information and partly based on one or more other clot-indicative determinants (e.g. interface logic 11240 invoking one or more modules 11223 of dispensing logic 11220 operable for activating one or more dispensers 11228 containing one or more thrombolytic agents or other locally-administered therapeutic materials selectively when apparently needed in a vicinity 11275 of lumen 11295). This can occur, for example, in a context in which the a priori implant information indicates a drug-eluting stent or other potentially thrombogenic implant at outflow 11299.

Figure 114:
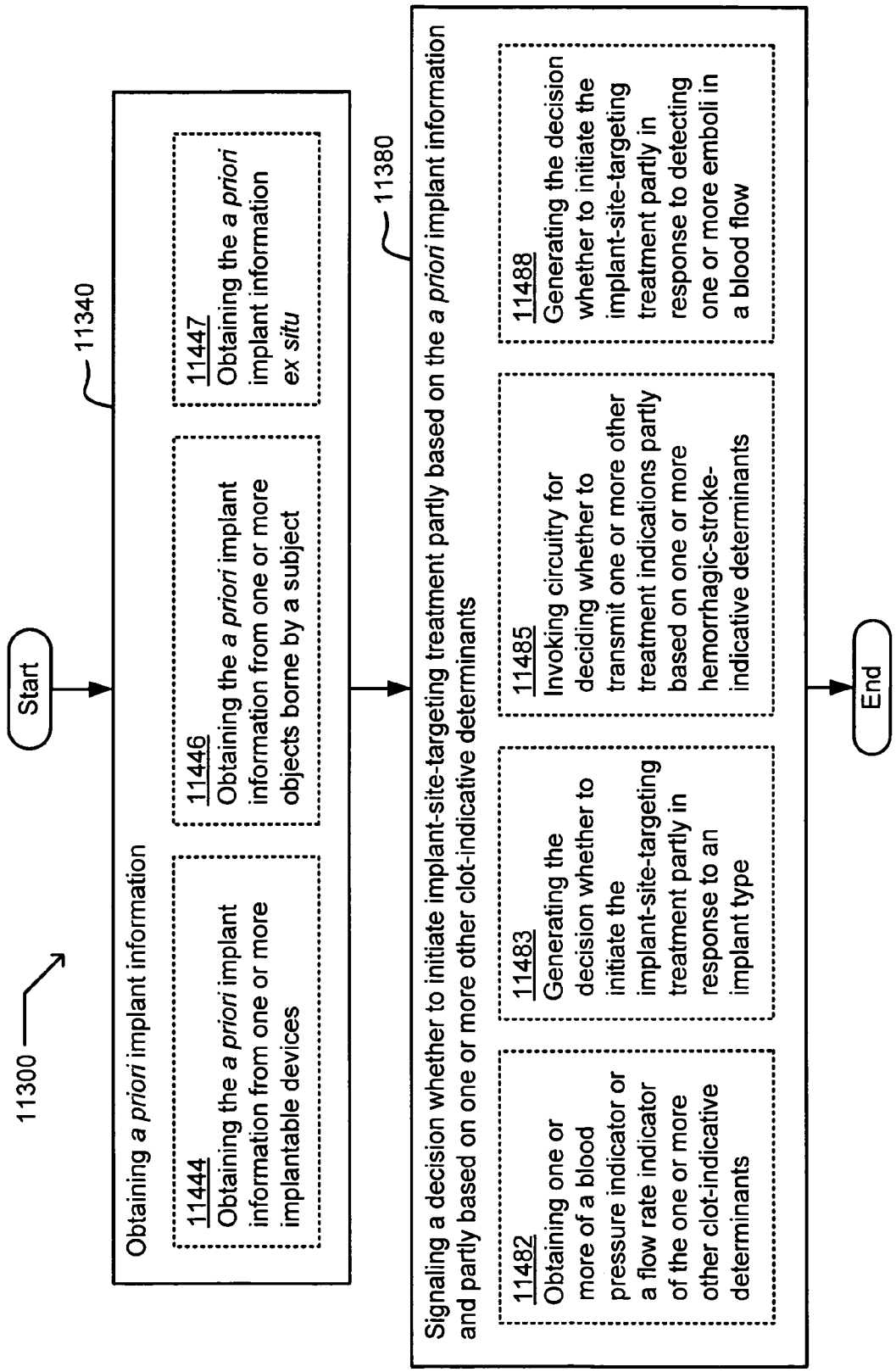
FIGS. 114-115 depict variants of the flow of FIG. 113.

With reference now to FIG. 114, there are shown several variants of the flow 11300 of FIG. 113. Operation 11340—obtaining a priori implant information—may include one or more of the following operations: 11444, 11446, or 11447. In some embodiments, variants of operation 11340 may be performed by one or more instances of dispensing logic 4515, 11220, receivers 4548, 11248, or the like as exemplified herein. Operation 11380—signaling a decision whether to initiate implant-site-targeting treatment partly based on the a priori implant information and partly based on one or more other clot-indicative determinants—may include one or more of the following operations: 11482, 11483, 11485, or 11488. In some embodiments, variants of operation 11380 may be performed by one or more instances of dispensers 4519, 11229, transmitters 4547, 11247, or the like as described herein.

Operation 11444 describes obtaining the a priori implant information from one or more implantable devices (e.g. external module 11280 receiving specifications or other data 11285 about module 11250 from a wireless or other transmitter 11247 thereof). This can occur, for example, in a context in which external module 11280 notifies locally-available caregivers of the existence of module 11250 and/or of dispensations or dosages from it. Such information may be used to expedite care or avoid redundant dispensations, for example.

Operation 11446 describes obtaining the a priori implant information from one or more objects borne by a subject (e.g. one or more modules 5561 of receiver 5565 accepting a type 5511, a date 5512, a status 5513, a location 5514, or other such implant data 5510 from at least one of the implant(s) 5597, from a wristwatch or other information-bearing article worn by a subject, or from a cell phone or other such carried article). This can occur, for example, in a context in which such items are configured to provide such information as a component of a subject's medical history. Alternatively or additionally, configuration module 5570 or an external device may be configured to poll such objects for such information during a crisis, for example, in a context in which system 5500 is implemented in a mobile or emergency-room unit.

Operation 11447 describes obtaining the a priori implant information ex situ (e.g. receiver 5340 externally accepting one or more messages 5341, 5342 containing contextual information 5345 pertaining to patient and/or device status from device 5310). This can occur, for example, in a context in which external device 7491 of FIG. 74 implements primary system 5380, and in which identification, history, location, monitoring type, and/or other such configuration information 5345, 5355 is available via one or more devices 5310, 5320 implanted, attached or otherwise associated with a subject area to be monitored. In some variants, for example, a receiver 5350 is configured to deliver subject or implant information 5355 suitable to guide follow-up care, for example, via a hand-held projection device or other user interface 5370. Alternatively or additionally, primary system 5380 or other such logic can be implemented in a computer module 5360 configured for use, for example, in a rescue unit.

In some embodiments, a "device state" may comprise "available" or some other such state-descriptive labels, an event count or other such memory values, a partial depletion or other such physical property of a supply device, a voltage, or any other such conditions or attributes that may change between two or more possible values irrespective of device location. Such device states may be received directly as a measurement or other detection, in some variants, and/or may be inferred from a module's behavior over time. A distributed or other composite system may comprise vector-valued device states, moreover, which may affect dispensations or departures in various ways as exemplified herein.

Concerning variants of operation 11380 presented in FIG. 114, these or other operations may (optionally) be performed in a preparatory sub-operation—before or during one or more instances or variants of operation 11340 as described above, for example—or may be performed at other times or omitted. Operation 11482, for example, describes obtaining one or more of a blood pressure indicator or a flow rate indicator of the one or more other clot-indicative determinants (e.g. one or more modules 5661 of receiver 5665 accepting blood pressure measurement 5651, flow rate measurement 5652, and/or other such clot-indicative determinants 5655). This can occur, for example, in a context in which decision logic 5635 and detection logic 5670 jointly perform operation 11380 and in which the determinants indicate a large clot at or downstream from an implanted dispenser or other suitable injection site of a subject. See, e.g., dispenser configurations of FIGS. 35 through 46. In some variants, for example, a speaker or other local output device 5694 may announce an apparent need for a lytic material (a fibrinolytic-enzyme-containing syringe carried by a patient, e.g.) to be injected into a left femoral or popliteal vein responsive to a large pressure drop just downstream. Alternatively or additionally, in some variants, operation 11380 may include signaling implanted dispensers as described herein.

Operation 11483 describes generating the decision whether to initiate the implant-site-targeting treatment partly in response to an implant type (e.g. module 5741 of decision logic 5750, 5760 signaling a selection of a suitable lytic material indicator 5743 and/or quantity indicator 5744 partly based on a thrombosis symptom or other such symptom indicator 5774 and partly based upon a model number 5761, material indicator 5762, or other type indication 5770 of a stent or other implant just downstream from a dispensation site). This can occur, for example, in a context in which such indications signal a venerable patient, a recent surgery, a side effect from a current dispensation regimen, a controllable material removal or other partial containment structure, a measurement 5771 indicative of local blockage, or other such contraindications of indiscriminate (non-targeted) dispensations as described herein. In some variants, for example, module 5741 may indicate an affirmative decision 5745 for any evaluation context exceeding a threshold of 3 to 5 points, with each such factor counting 1 to 2 points. Such local blockage may be indicated by an unusual pressure drop, a change in D-dimer score or other such chemical marker indications, a flow rate change, or others as described herein. Alternatively or additionally, a recent lytic material dispensation, an apparent loss of cognitive function, presence at a hospital, or other such factors may each count −1 or −2 points on a similar scale. Alternatively or additionally, a blockage size indicator may count one or more points on a similar scale, for example, so that larger and/or more recent occlusions generally bear toward larger targeted dispensations. In some variants, for example, a targeted dispensation may comprise 20% or more of a recommended systemic dosage of an identified material, and may optionally exceed such a dosage. Alternatively or additionally, antibiotics or other appropriate medicinal components may be dispensed in a manner that similarly targets regions of detected local infection or related pathologies.

Operation 11485 describes invoking circuitry for deciding whether to transmit one or more other treatment indications partly based on one or more hemorrhagic-stroke-indicative determinants (e.g. module 5892 of invocation logic 5895 activating one or more comparators 5842, 5893 configured for comparing current data from sensors 5851, 5852, 5853 with historic, concurrent, threshold, and/or other pertinent information in deciding whether to transmit one or more treatment indications 5841, 5890). This can occur, for example, in a context in which sensors 5852, 5853 configured to observe a vicinity of a major blood vessel 5809 are monitored for changes in blood pressure, flow, and/or other status-indicative information 5896 to determine if one or more treatment indication messages 5825, 5898 are to be transmitted. In some variants, for example, an implanted or other detection module 5860 configured to monitor a region 5810 near vessel 5809 will trigger one or more messages 5815, 5825 to a bedside monitor 5830 and/or nurse station 5820 warning of an apparent (actual or imminent) vessel rupture. Alternatively or additionally, transdermal sensors employed in external monitors can be employed for such detection and notification.

Operation 11488 describes generating the decision whether to initiate the implant-site-targeting treatment partly in response to detecting one or more emboli in a blood flow (e.g. module 5742 of decision logic 5750 transmitting an activation signal to a transvascular or other dispenser directly in response to one or more signals 5725 from sensors 5701, 5702 or other such elements directly or indirectly indicating the presence of emboli 5708 in detection region 5710). This can occur, for example, in a context in which one or more sensors 11210, 11290 outside a blood vessel indicate one or more (apparent) emboli manifesting ultrasonic signatures 5772, impedance changes 5773, and/or other such data 5780, 5790 are configured to trigger decision logic 5760 to enable a dispensing module. Alternatively or additionally, transdermal detection and/or delivery systems can be employed in subjects where surgical intervention is dangerous or is otherwise undesirable. In some variants, for example, an extravascular or other implanted sensor 5701, 5702 can be inserted relative to a surgical site to detect emboli released as a result of the surgical trauma triggering the release of medicinal components to aid in the elimination of the emboli.

Figure 115:
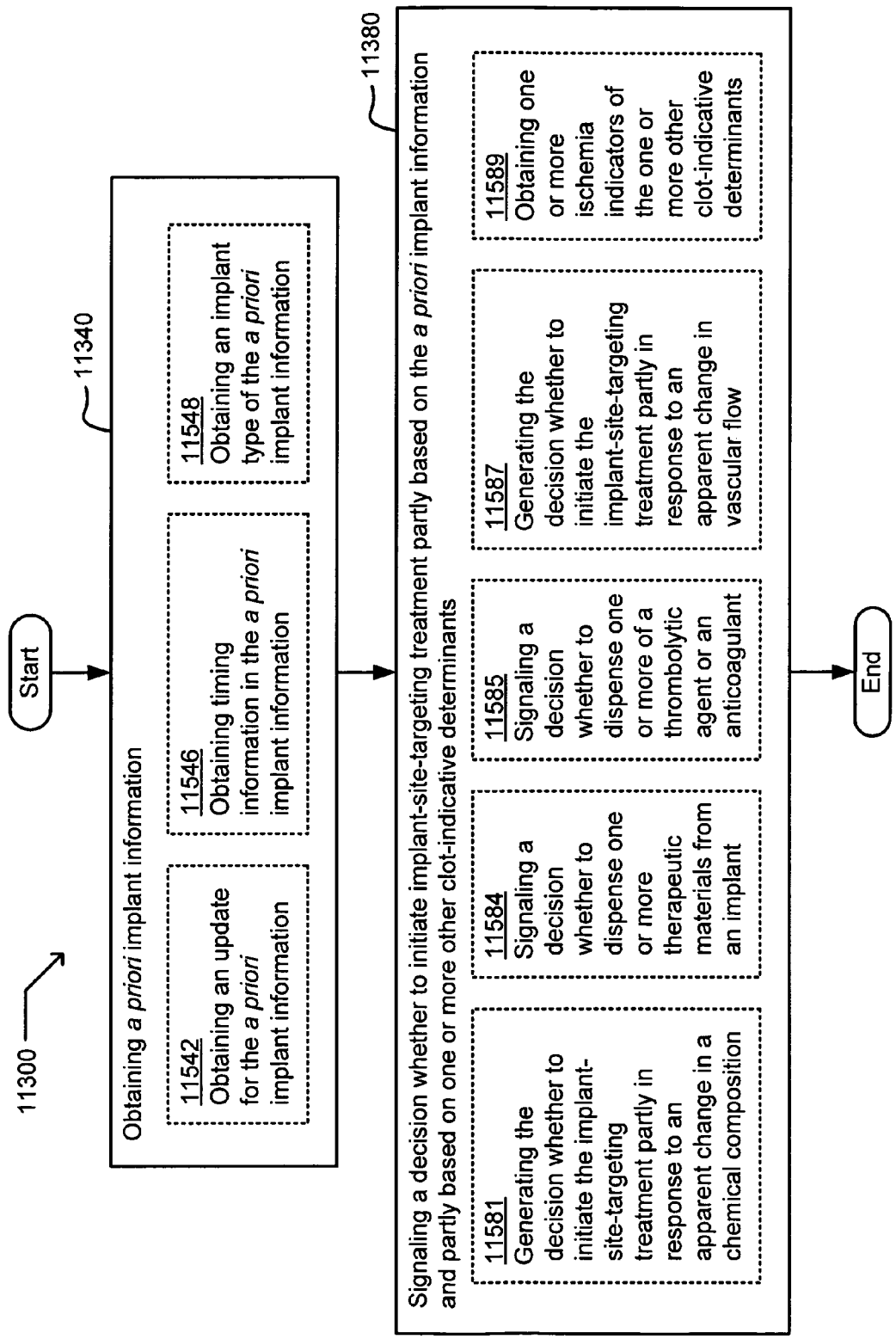

With reference now to FIG. 115, there are shown several variants of the flow 11300 of FIG. 113 or 114. Operation 11340—obtaining a priori implant information—may include one or more of the following operations: 11542, 11546, or 11548. In some embodiments, variants of operation 11340 may be performed by one or more instances of dispensing logic 4515, 11220, receivers 4548, 11248, or the like as exemplified herein. Operation 11380—signaling a decision whether to initiate implant-site-targeting treatment partly based on the a priori implant information and partly based on one or more other clot-indicative determinants—may include one or more of the following operations: 11581, 11584, 11585, 11587, or 11589. In some embodiments, variants of operation 11380 may be performed by one or more instances of dispensers 4519, 11229, transmitters 4547, 11247, or the like as described herein.

Operation 11542 describes obtaining an update for the a priori implant information (e.g. module 5562 of receiver 5565 accepting one or more modifications of implant data 5510 in storage 5542 as a result of status or other changes in an implant, an implanted subject, a pathology, or other such internal or external information about implant 5597). This can occur, for example, in a context in which comparison data 5531 and/or therapeutic delivery parameters 5532 are modified based upon one or more status indications 5534 of a progression in a subject's pathology or health. In some variants, for example, progression through post surgical healing can lead to adjustments of therapeutic component delivery parameters 5521, subject location indices 5522, sensor types 5523, or other such mode identifiers 5524, 5525 operable for describing and/or implementing modes of monitoring. Alternatively or additionally, module 5552 may be configured to respond to one or more indicators of a disease state progression by conditionally implementing (a) an appropriate change in dosage or other delivery parameters 5521, (b) an invocation of instruction sequence 5551 or other such modules responsive in scenarios previously excluded, or (c) other such operational adjustments as described herein.

Operation 11546 describes obtaining timing information in the a priori implant information (e.g. module 5425 of receiver 5430 accepting one or more records 5450 associating a measurement or other parametric data 5451 with data 5452 indicative of one or more device update times 5464, implant times 5465, dispensation times 5466, measurement times, or other such timing information 5470 of potential diagnostic relevance). This can occur, for example, in a context in which implant, therapeutic delivery, decision logic trigger, and/or notification message date and time is stored in memory 5440 or other storage units 5445 for later retrieval. In some variants, for example, one or more records indicating at least one recent delivery of a therapeutic component is made available for retrieval by a remote or other external module, configured to indicate a potential current need, or lack of need, for additional delivery. Alternatively or additionally, record 5450 may contain data indicative of one or more results of subject and/or device diagnostics.

Operation 11548 describes obtaining an implant type of the a priori implant information (e.g. module 5563 of receiver 5565 receiving an implant type 5511 or other such distinguishing data usable to retrieve or otherwise determine one or more capacities of an implant). This can occur, for example, in a context in which implant 5597 is configurable to monitor and conditionally record, to monitor and conditionally notify, to monitor and conditionally deliver therapy, or otherwise to invoke appropriate responsive circuitry as described herein. In some variants, for example, configuration module 5570 may request and/or receive determinants 5540 indicating a current category, protocol, or state relating to an implant and/or subject from a network 5580. In some contexts, for example, one or more modules 5561, 5563 of receiver 5565 may obtain one or more mode identifiers 5525 indicating that implant 5597 is in "notification mode" and/or that one or more notification events have occurred. Alternatively or additionally, configuration module 5570 can likewise obtain a mode identifier 5524 indicating an apparent type of dispensation, monitoring, or other responsive protocol—"arterial rupture," "emboli detection," "swelling," or other such modes as described herein. Any of these variants of operation 11340 may be omitted or performed before, after, or interleaved with one or more instances or variants of operation 11380 as described herein, in some embodiments.

Operation 11581 describes generating the decision whether to initiate the implant-site-targeting treatment partly in response to an apparent change in a chemical composition (e.g. module 11223 of dispensing logic 11220 causing transmitter 11247 to transmit a message 11224 indicating one or more diagnostic or therapeutic material dispensers 11228, 11229 and/or a dispensation site local to section 11270 as a programmatic response to an apparently severe hypoxic condition or other circumstance detected via one or more sensors 11210, 11290 operable for detecting chemical concentrations). This can occur, for example, in a context in which a caregiver can validate and/or administer the dispensation of such a treatment material via an intravenous catheter. Alternatively or additionally, the decision to administer an already-implanted material may be performed according to a programmatic crisis-response regimen 11222 specified in advance by a caregiver in response to an abnormally high platelet concentration detected locally, for example, by sensor 11210.

Operation 11584 describes signaling a decision whether to dispense one or more therapeutic materials from an implant (e.g. module 5644 of control logic 5640 transmitting one or more commands 5625, 5626 configured to cause a dispensation at implant 5690 wirelessly via antenna 5628). This can occur, for example, in a context in which an external support device 5610 implements a dosage and timing by triggering one or more communication components 5620 or other such logic to transmit timing, dispensation, detection, evaluation, notification, or other such commands to implant 5690. In some variants, for example, sensor information and/or a subject request can serve as a trigger for such communications and dispensations. Alternatively or additionally, such a transmission can implement a periodic or responsive treatment profile 5622 specified by a physician.

Operation 11585 describes signaling a decision whether to dispense one or more of a thrombolytic agent or an anticoagulant (e.g. module 5645 of control logic 5640 signaling such a dispensation from implant 5690 only if module 5634 detects an apparent need for one or more such materials). This can occur, for example, in a context in which implant 5690 includes one or more dispensers 11228, 11229 and/or sensors 11290 in close proximity, in which support device 5610 comprises external module 11280, and in which module 5668 signals an apparent blockage in lumen 11295 warranting an activation of one or more dispensers 11228. In many treatment contexts for healthy human adults, for example, a 50% reduction in blood flow through an artery provides a sufficient indication of blockage to call for dispensing a 100,000 I.U. of streptokinase over a 10 to 30 minute period starting within a few minutes or hours of such detection.

Operation 11587 describes generating the decision whether to initiate the implant-site-targeting treatment partly in response to an apparent change in vascular flow (e.g. module 5923 of decision logic 5930 generating an affirmative decision 5925 only if indicators 5954, 5955 of change in flow through a vessel violates one or more given criteria 5908, 5909). This can occur, for example, in a context in which criterion 5909 includes a requirement that the flow change be local, which module 5923 may determine by invoking comparator 5921 or other other such modules for comparing measurements or other sensor transmissions 5950 of the the subject region each with corresponding indicators 5952, 5953 of one or more other sites of the same subject. Alternatively or additionally, module 5923 may likewise invoke circuitry or other modules 5923 for comparing a succession 5951 of transmissions from a common sensor, such as for determining whether a shape of a specific vessel of of interest is changing too fast. In some variants, for example, module 5923 can effectively detect a rupture in a vessel wall as either of a rapid increase of flow into the vessel or a large-enough, rapid-enough, non-reversing change in the vessel's shape. Alternatively or additionally, module 5923 may likewise invoke circuitry 5922 for detecting an apparent obstruction of the vessel manifesting as a large-enough, rapid-enough local decrease in vascular flow (as criterion 5907, e.g.).

In some embodiments, decision logic 5940 may contraindicate dispensing (a) a lytic agent into a target region within which a vessel has apparently ruptured or (b) a coagulant into a target region within which a vessel has apparently not ruptured. Such contraindications may manifest as a negative recommendation, a requirement for a confirmation by a user, or other such appropriate output 5983. In a more aggressive variant, one or more modules of decision logic 5940 may be configured to perform a dispensation of (a) a lytic agent into a target region within which a vessel has apparently not ruptured or (b) a coagulant into a target region within which a vessel has apparently ruptured.

Operation 11589 obtaining one or more ischemia indicators of the one or more other clot-indicative determinants (e.g. module 5891 of invocation logic 5895 receiving a significant D-dimer score increase indication 5879 from one or more detection modules 5860, 5870). This can occur, for example, in a context in which a "significant" score increase is ascertained by a fractional score increase (with an existing point-of-care assay, e.g.) on the order of 5% or 50% within a time span on the order of an hour or a day. In some contexts, for example, such a recent transition can be indicative of ischemia. Alternatively or additionally, such clot-indicative determinants 5875 may include a complaint of sudden and severe local leg pain or other such subject-provided input 5872; symptom interpretations or other such secondary user input 5873 (via network 5840, e.g.); an ultrasound image 5861, computed tomography image 5862, or other such shape-indicative data 5865; contraindications of hemorrhage or other indications 5879 relating to alternative hypotheses, or other such ischemia indicators 5880.

With reference now to FIG. 116, shown is an example of a system that may serve as a context for introducing one or more processes and/or devices described herein. As shown system 11600 may affect or otherwise relate to vicinity 11605, section 11630, and vicinity 11635 of a subject's lumen 11695 through which one or more blood components may flow. One or more inflows 11601 of blood enter respective portions of lumen 11695 as shown, pass through section 11630, and exit as one or more outflows 11699. In respective variants, arteries, veins, or smaller vessels of lumen 11695 may traverse vicinities 11605, 11635 as shown. Section 11630 may likewise comprise one or more capillary beds as well as vital organs and other tissues served by lumen 11695.

In some variants, module 11660 may (optionally) include one or more instances of modules 11613, 11614 of dispensing logic 11615; dispensers 11617, 11618, 11619; modules 11621, 11622 of evaluation logic 11620; interface logic 11640; modules 11651 or other response logic 11655; or intravascular or other sensors 11650. (Some such sensors 11650 may be operable for monitoring radiant or other physical phenomena within a lumen 11695, for example, from within or in a detection vicinity 11605 of lumen 11695.) Interface logic 11640 may, as shown, comprise one or more instances of transmitters 11647, receivers 11648, or other modules 11642 operable for communicating (in one or both directions) with one or more sensors 11610 in (upstream) vicinity 11605 of lumen 11695.

In some variants, system components described herein may be configured to trigger or otherwise facilitate dispensation of therapeutic materials. Other such embodiments are described above, for example, with reference to FIGS. 28 and 35-45. In some embodiments, a material is "therapeutic" if it contains one or more medications or other components having a primary effect or purpose of relieving symptoms, reducing health risks, or otherwise promoting the subject's health. Some treatment regimens may comprise one or more conditional or other "therapeutic material dispensations" and/or other aspects of treatment. In some contexts, such a therapy may be administered "locally" by positioning a significant portion of a material or other physical component thereof at a treatment site, even if some of the component is then extracted or permitted to metabolize systemically.

With reference now to FIG. 117, shown is a flow 11700 comprising operation 11730—obtaining a flow-change-indicative measurement (e.g. one or more modules 11621 of evaluation logic 11620 detecting abnormally frequent blood pressure fluctuations for days consecutively). This can occur, for example, in a context in which a blood pressure fluctuation distribution for a specific pressure sensor is empirically determined and in which module 11621 implements a threshold or other baseline derived by a reasonable statistical model. In some variants, for example, an appropriate normality threshold may be selected so that a frequency of occurrence or other measurable variable will be expected only to exceed the threshold once per decade (or similar duration within 1-2 orders of magnitude. Alternatively or additionally, a triggering condition may be selected in relation to one or more of optical, force, auditory, or other measurable criteria or to a combination of such criteria. Numerous reasonable triggering conditions will readily be apparent to those skilled in the art without undue experimentation, many of which are a mere matter of design choice in light of teachings herein.

Flow 11700 further comprises operation 11790—signaling a decision whether to administer one or more clot-reducing agents at least partly based on the flow-change-indicative measurement (e.g. one or more modules 11613, 11614 of dispensing logic 11615 causing one or more dispensers 11617, 11618 to administer an antiplatelet-drug-containing or other therapeutic agent in response to the one or more modules 11621, 11622 of evaluation logic 11620). This can occur, for example, in a context in which module 11614 specifically selects such a therapeutic material by selecting the dispenser 11618 containing the material in lieu of another dispenser. Alternatively or additionally, one or more modules 11642 may be configured to signal the decision in some other way, such as by a speaker or other transmitter 11647 conveying medication instructions to the (implanted) subject, or otherwise by sending such a message to a party who is able to implement the decision.

Figure 118:
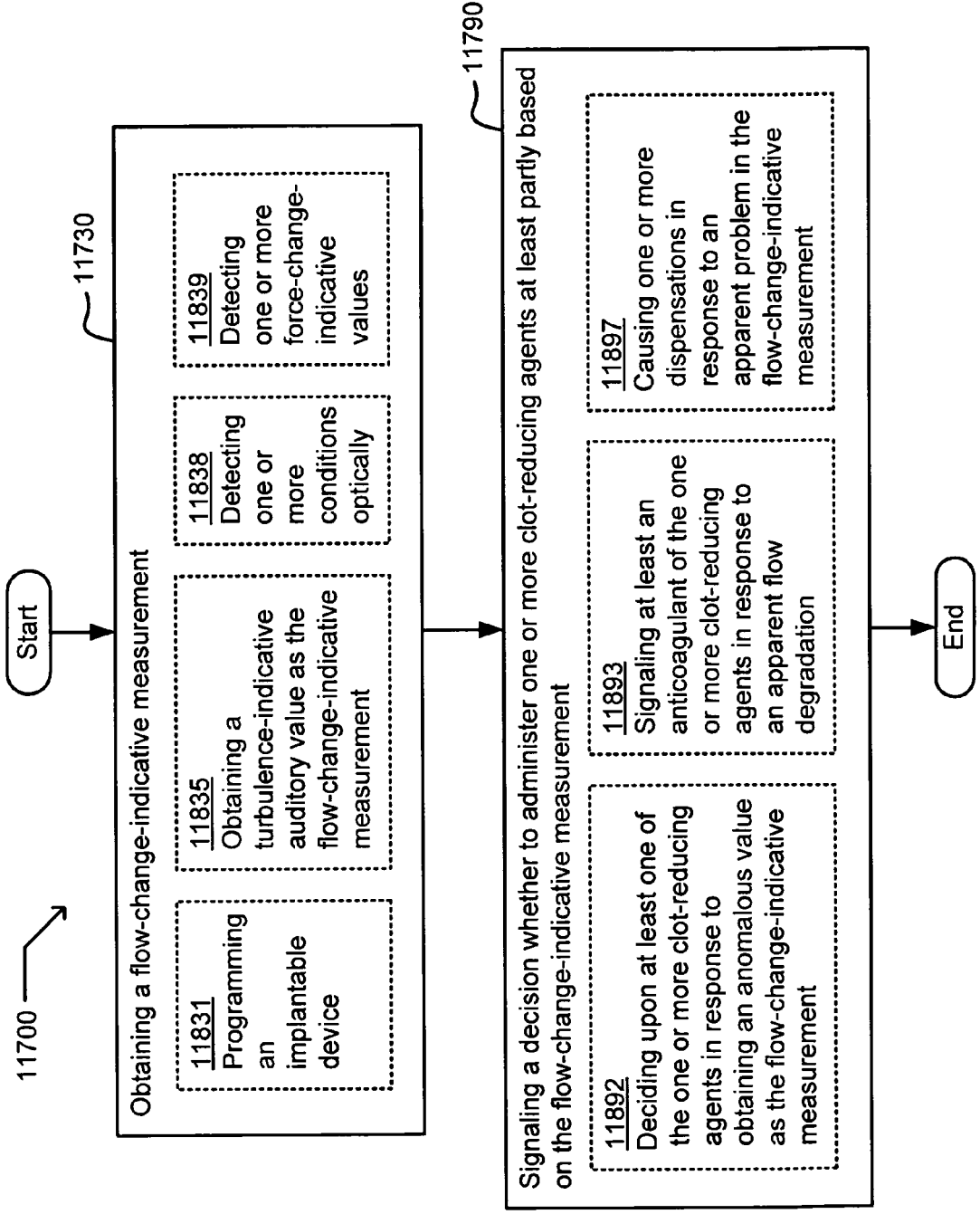

With reference now to FIG. 118, there are shown several variants of the flow 11700 of FIG. 117. Operation 11730—obtaining a flow-change-indicative measurement—may (optionally) include one or more of the following operations: 11831, 11835, 11838, or 11839. In some embodiments, variants of operation 11730 may be performed by one or more instances of sensors 4579, 11650, evaluation logic 4520, 11620, or the like as exemplified herein. Operation 11790—signaling a decision whether to administer one or more clot-reducing agents at least partly based on the flow-change-indicative measurement—may include one or more of the following operations: 11892, 11893, or 11897. In some embodiments, variants of operation 11790 may be performed by one or more instances of output devices 4526, dispensing logic 4515, 11615, or the like as described herein.

As FIG. 118 indicates, (optional) operation 11831 describes programming an implantable device (e.g. module 6772 of control logic 6770 transferring one or more device settings 6771 or command sequences 6761, 6762 into an intravascular dispenser 6780 or other implantable device). This can occur, for example, in a context in which dispenser 6780 is operably coupled via a wireless communication linkage 6752 and/or docking port 6751, in which such controls affect one or more operating modes of the implanted or other device, and in which control logic 6770 performs operation 11730. In some variants, for example, wireless communication linkage 6751 may implement an 802.11b/g/n, Bluetooth, far field telemetry, near field telemetry, wireless USB, or other such protocol for communicating with one or more implantable devices automatically or in response to requests by a subject and/or caregiver. In various configurations and contexts, such devices can be enabled, disabled, and/or adjusted by one or more modules 6773 performing operation 11730. Alternatively or additionally, an initial set of device settings 6771 or other such parameters can be programmed into such devices prior to implantation to establish a baseline of device operation in the subject.

Operation 11835 describes obtaining a turbulence-indicative auditory value as the flow-change-indicative measurement (e.g. module 6332 of processing logic 6330 accepting one or more decibel measurements 6351, 6352 high enough to indicate past or present turbulence in a blood vessel). This can occur, for example, in a context in which module 6333 associates an earlier laminar-flow-indicative value 6371 or a later laminar-flow-indicative value 6372 (a Reynolds number or other such measurement below a turbulence-indicative threshold 6331, e.g.) with timing data 6361 signifying an appearance or disappearance of detectable turbulence in the blood vessel. In some variants, for example, such transition-indicative timing data may signify a growing thrombosis, a thrombosis breakage, a therapeutic success, or other such flow-change-indicative phenomena. Alternatively or additionally, invocation logic 6320 may trigger one or more remote evaluation modules 6396 to evaluate whether such timing data sufficiently coincides with timing data 6362 of a dispensation, timing data 6363 of a pressure-indicative or other confirmatory measurement 6353, or other such therapeutically relevant and detectable events.

Operation 11838 describes detecting one or more conditions optically (e.g module 6662 of processing logic 6660 detecting an apparent blockage manifested in an image 6664 of one or more regions 6691, 6692 of a subject vessel 6696). This can occur, for example, in a context in which network 6295 includes detection system 6650 and in which there are one or more differences 6251, 6252 between spectral and/or temporal absorbance distributions 6211, 6212 and the corresponding baseline distribution(s) 6221, 6222 indicative of a blockage. In some variants, for example, the heterogeneous nature of blood can cause an absorbance distribution that fluctuates rapidly over time (at a primary or mean frequency F, e.g.) so that a reduced flow can manifest as a measurably more stable signal (at a primary or mean frequency lower than F, e.g., by at least a threshold of 5% to 50% in some contexts). Alternatively or additionally, a change rate 6255 or other such indicator 6256 of color or intensity change in a signal 6232 from an optical sensor 2525 can likewise trigger module 6201 to generate a Boolean alarm indicator 6257 (signifying an apparent blockage, e.g.) and optionally provide positional information 6253 and/or timing information 6254 relating to objects in a subject region.

Operation 11839 describes detecting one or more force-change-indicative values (e.g module 6661 of processing logic 6660 detecting a fractional force change indication 6663 from a subject region indicative of an apparent blockage, aneurism, or other such flow-modifying phenomenon). This can occur, for example, in a context in which one or more distortion sensors or other force-change-indicative sensors 6682 detect a sudden, substantial change in one or more mechanical properties internal tissue in a body part 6690 of subject 6670. In some contexts, for example, a complete or partial blockage of a subject vessel 6696 (in region 6692, e.g.) can measurably increase such rigidity in a vicinity of such blockages. Alternatively or additionally, such blockages in blood vessels can manifest as a measurably increased rigidity and/or pressure in tissue adjacent to the blockage (at region 6692, e.g.) and/or as a contemporaneous change several millimeters away from the blockage. Such changes can manifest as changes in vascular pressure in an upstream region 6691 and/or a downstream region 6693, for example, detectable by one or more other sensors 6681, 6683 of module 6680.

Operation 11892 describes deciding upon at least one of the one or more clot-reducing agents in response to obtaining an anomalous value as the flow-change-indicative measurement (e.g. module 6041 of decision logic 6050 selecting one or more injectable therapeutic components from a set of locally available therapeutic components 6073 for use in response to one or more comparator results 6031, 6033 corresponding thereto, of which at least one indicates abnormally poor circulation in a subject 6090 under observation). This can occur, for example, in a context in which a blood thinner or other such therapeutic component is selected programmatically based upon the comparator result(s) 6033. Alternatively or additionally, one or more such results may depend upon a body part identifier 6061 (identifying a measurement or dispensation site of subject 6090, e.g.), an elevation, or other such location indicators 6060 (such as by deciding against an automatic administration to a prone and unresponsive subject, as determined via a programmatic triage or other such interaction protocol 6043). In some variants, moreover, a complete blockage of a subject vessel or a partial blockage in a primary location may warrant a selection of a faster-acting therapeutic agent than a partial blockage or a blockage in a secondary location. Alternatively or additionally, module 6042 may display an ingestible clot-reducing agent indication 6025 (via output 6024, e.g.) or may indicate other medically appropriate responses (being seated or calling an ambulance, e.g.).

Operation 11893 describes signaling at least an anticoagulant of the one or more clot-reducing agents in response to an apparent flow degradation (e.g. module 6322 of invocation logic 6320 receiving and relaying the decision 6391 to administer one or more therapeutic components to a nurse or other party cable of administering such agents via port 6321). This can occur, for example, in a context in which invocation logic 6320 and decision logic 6395 jointly or iteratively perform operation 11730, in which mediation module 6310 interacts with a local module as described herein via port 6321, and in which such flow degradation manifests as one or more of a complaint or other severe limb pain indication 6344, a swelling indication 6346, a local discoloration indication 6348, other such detectable phenomena local to a portion of subject's body, or as a confirmatory measurement 6353 (in combination with such indications, e.g.). In some variants, moreover, another module 6323 may signal a caregiver to check one or more potential effects of the clot-reducing or other therapeutic agents or to provide other appropriate follow-up. Alternatively or additionally, module 6322 may invoke recorder 6311 to capture a distillation of one or more dispensation indications 6347, symptom indications 6349, and/or related timing data 6363 selectively for future evaluation.

Operation 11897 describes causing one or more dispensations in response to an apparent problem in the flow-change-indicative measurement (e.g. module 6122 of invocation logic 6120 enabling or otherwise facilitating an activation of one or more dispensers 6075 containing one or more local dispensations of a vasodilator 6071, a lytic agent 6072, or other such therapeutic components 6073 effective for modifying circulatory flow). This can occur, for example, in a context in which system 6100 includes or otherwise interacts with administration unit 6010, in which one or more location sensors 6101 or flow attribute sensors 6102 are implemented in or can otherwise detect vessel properties in relation to hand-held unit 6080, and in which module 6104 of detection logic 6110 detects a sharply decreased volume, speed, or other flow attribute (of 5% to 50% or more, e.g., such as may manifest an apparent obstruction) in a vessel segment near or downstream from an injection or implant site. In some variants including an injection dispenser, for example, a physician or veterinarian may configure one or more modules 6122, 6123 to trigger such a dispenser to inject an anticoagulant or other such component locally and promptly upstream from a clot-prone site. Alternatively or additionally, module 6182 can be configured to respond similarly by transmitting a (human) subject or other such care provider a notification 6170 including one or more of a dispensation indication 6172 or an indication 6173 of detected conditions that warrant the dispensation.

Operation 11932 describes receiving the flow-change-indicative measurement from a user (e.g. record 3110 accepting one or more parameters 3168 indicative of flow change from a user via remote module 3190). This can occur, for example, in a context in which remote module 3190 includes one or more user interface elements 6291 accessible to a subject or other user, in which invocation logic 3140 prompts a user for such information, and in which the measurement(s) are accepted as input 6292. Such measurements can include one or more local measurements of blood pressure, pulse, or other such flow change indicators, some of which may be programmatically measured or confirmed using devices not configured to communicate directly with administration system 6200. Alternatively or additionally, some such parameters can be used for guiding an intake protocol, even without recordation.

Operation 11934 describes detecting one or more impedance-change-indicative values (e.g module 6733 of detection logic 6720 detecting a sustained, small-enough change rate 6721 to indicate an apparent blood vessel obstruction or some other impedance change indication 6722 reflecting a circulatory phenomenon of interest). This can occur, for example, in a context in which configuration system 6710 includes or otherwise interacts with one or more local modules 2320, 2450 and in which impedance sensor 2323 or other sensors are positioned to detect a change in a conductivity or other electrical property of fluid and/or tissue in a subject region. In some variants, for example, such modes of detection can confirm or otherwise facilitate an identification of plaque or other such affixed structures in a vessel as described herein.

Operation 11937 describes comparing an earlier-flow-indicative value with a later-flow-indicative value (e.g. module 6202 of evaluation logic 6210 comparing current flow-indicative data 6233 with historic data 6234 provided to or measured by a sensor-containing device). This can occur, for example, in a context in which one or more ankle images 6272, size measurements 6271, or other such indications 822 are held locally in a data-handling medium 885 and later used by one or more comparators 882 or other entities as a baseline value or other historic indication for comparison with one or more similar (subsequent or current) images 6272, 6263 or other values 6274, 6275. In some variants, for example, such values may include one or more representative values, averages, and/or other appropriate arithmetic combinations thereof. Alternatively or additionally, such historic flow indicative information can be loaded into an implanted device for use in future data filtering as described herein.

Operation 11939 describes confirming a flow-change indication with a confirmatory evaluation (e.g. module 6132 of decision logic 6130 performing, guiding, or otherwise causing one or more measurements, comparisons, or other such operations configured to confirm or refute a pathological hypothesis, a course of action, a normalcy determination, or other such apparent circumstance). This can occur, for example, in a context in which mediation module 6310 is operably coupled with system 6100 of FIG. 61 and in which discrimination against false indications is important enough to warrant two or more modes of evaluation. In some variants, for example, such confirmatory measurements 6353 may comprise additional data 6340 of the same and/or orthogonal types in the subject region can be employed as additional information in the evaluation. In some variants in which an in situ or other convenient sensor initially generates one or more cooling indications 6345 or swelling indications 6346 relating to a subject region, such indications may be corroborated or otherwise selectively confirmed by more accurate instrumentation. Alternatively or additionally, similar data 6340 obtained from one or more alternate subject sites (using a sensor array or manipulable sensor instrument, e.g.) can effectively differentiate between localized and systemic variations.

Operation 11991 describes indicating one or more options by which a user can override the decision whether to administer the one or more clot-reducing agents (e.g. module 6245 of decision logic 6240 causing a user interface element 6291 to present a subject and/or caregiver an option to initiate, select, approve, and/or refuse one or more of a set 6244 of two or more therapy regimens 6241, 6242, 6243). This can occur, for example, in a context in which one or more implants 1730, 1940, 5690 detect an apparent pathological state indication 6296 (via network 6295, e.g.) triggering a request 6276 to administration system 6200 to query user 6290 for approval and/or selection of one or more therapy regimens 6242, 6243. In some variants, for example, one or more expert system modules 6294 of administration system 6200 will present such a set of regimens pursuant to one or more identifiers of values 6274, 6275 or other current input 6292 from user 6290. Alternatively or additionally, a subject or other user 6290 may obtain other regimens, options, prognoses, or other information or advice from expert system module 6294 or other resources on network 6295.

Operation 11994 describes communicating a notification partly based on a risk indicator and partly based on the flow-change-indicative measurement to a user interface (e.g. module 6423 of notification logic 6420 transmitting one or more notifications 6440, 6450 configured by module 6422 to include one or more risk indicators 6431, 6432 and two or more sequential samples 6441, 6442, 6443 of signal 6445). This can occur, for example, in a context in which module 6454 invokes one or more such modules of notification logic 6420 in response to a sustained trend or other symptom-indicative event sequence in signal 6446. In some variants, for example, one or more modules 6461 of evaluation logic 6460 compute a marginal probability 6462 or other such risk indicator 6431 periodically (each 5 to 50 sample periods, e.g.). Alternatively or additionally, one or more such notifications may be deferred or otherwise made dependent upon a low-enough-risk (below threshold 6463, e.g.). Alternatively or additionally, one or more such notifications 6440, 6450 may include computed differences or other composite indicators 6491 derived from signal 6445, pictographic data, measurements, timing data 6494, current personnel availability or other resource availability data 6493, or other such information.

Operation 11995 describes signaling a response protocol reflecting the decision via a user interface (e.g. module 6181 of notification logic 6180 transmitting notification 6160 to a telephonic or other interface articulating an initiation 6151 or update 6152 of one or more clot-reducing protocols). This can occur, for example, in a context in which notification logic 6180 and one or more interfaces described herein iteratively perform operation 11790. Alternatively or additionally, one or more attributes of the decision(s) 6133 and/or regimen(s) 6134 may, in some variants, be implemented after receiving an approval 6103 or similar decision indicator via the user interface (from a subject and/or caregiver, e.g.).

Operation 11998 describes communicating the flow-change-indicative measurement to a remote user (e.g. module 6538 of notification logic 6540 transmitting one or more notifications 6544 to one or more remote client systems as a result of one or more comparators 6521 signaling the violation of one or more evaluation criteria 6523). This can occur, for example, in a context in which server system 6490 implements interface 6500. In some variants, for example, a nurses' station or other aggregation destination 6402 is configured to receive remote notifications of patient blood flow changes such as those described below with reference to FIG. 66. Alternatively or additionally, notifications can be sent to off-site caregivers and/or emergency health professionals to trigger appropriate telephonic or other follow-up.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

In light of teachings herein, and referring again to FIG. 45, those skilled in the art will recognize that any of these systems may include a variant in which receiver 4546 obtains a priori implant information by receiving configuration information to describe or otherwise accommodate a lower module 4590 that has been or will be implanted. This can occur, for example, in a context in which one or more instances of upper module 4550 is (or will be) well situated to administer one or more lytic materials or other therapies that may be needed at one or more instances of lower module 4590. Alternatively or additionally, the a priori implant information may include implant status, material reservoir status, or other such indications of modules as described herein.

Any of the above-described embodiments can likewise comprise a variant in which interface logic 4540 invokes circuitry for performing operation 11380 (of FIG. 113) such as one or more modules 4513 of dispensing logic 4515 operable for activating one or more dispensers 4518, 4519 when an apparent clot is detected. This can occur, for example, in a context in which the a priori implant information is embedded in circuitry or other structure of such dispensing logic 4515.

Any of the above-described embodiments can likewise comprise a variant in which timing module 4552 or another module 4551 of response logic 4555 performs operation 10910 by responding to a signal from sensor 4510 or some other indication that a lytic material will apparently be present in or near section 4530 of lumen 4595. This can occur, for example, in a context in which response logic 4555 receives a notification that dispenser 4519 has been activated. Alternatively or additionally, such indications may be received from one or more sensors 4510 operable for detecting the lytic material directly or by detecting other such conditions as described herein. Alternatively or additionally, any of these modules or other components may likewise include a delay or other timing module 4552 responsive to at least one of the one or more dispensation components. Alternatively or additionally, any of these modules or other components may likewise include one or more semi-permeable membranes 4581.

Referring again to FIGS. 108-116, those skilled in the art will recognize that any of the herein-described modules or other components may likewise include one or more thrombolytic-agent-containing dispensers 11228 and/or may include one or more (artificial) disposal vessels 10870 and/or other features described herein. Referring again to FIG. 28, for example, those skilled in the art will recognize that any such components may likewise include one or more disposals 2888, optionally transluminal ones like disposal 2889 in which one or more conduits 2886 are configured to bear a blood-containing material into a body lumen. Any may likewise include one or more radiotherapy treatment modules or other such therapeutic structures 2842.

Referring again to FIG. 46, alternatively or additionally, any of these modules or systems herein may likewise include an implantable, dispenser-containing valve 4610. Any may likewise include one or more instances of wireless communication modules 4644 for sending data to or receiving data from an outside network or other entity. Any may likewise include one or more optical sensors 4675, auditory sensors 4676, pressure sensors, pressure-limiting valves, strain gauges, or other such flow-force-responsive elements 4678. In some variants, one or more such elements exemplify circuitry or other means for obtaining one or more indications of a lytic material in a vicinity of one or more body lumens comprising a flow-force-responsive element. Alternatively or additionally, any of these extraction modules or other material movement components may likewise comprise a lower-than-ambient pressure, at least initially. Alternatively or additionally, any of the above-described modules or other components may (optionally) include one or more implant-site-targeting dispensers, positioned for dispensing (a) above an implant of interest or (b) from an upstream or intermediate portion of the implant of interest.

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP)

entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A therapeutic administration system comprising:
    means for obtaining one or more indications of a lytic material in a vicinity of one or more body lumens; and
    means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens;
    in which the means for obtaining one or more indications of a lytic material in a vicinity of one or more body lumens comprises means for obtaining a concentration-indicative scalar of the one or more indications of the lytic material.

2. The therapeutic administration system of claim 1 in which the means for obtaining one or more indications of a lytic material in a vicinity of one or more body lumens comprises:
    circuitry for detecting a marker material indicative of the lytic material in the vicinity of the one or more body lumens.

3. The therapeutic administration system of claim 1 in which the means for obtaining one or more indications of a lytic material in a vicinity of one or more body lumens comprises:
    means for causing at least a statin to be dispensed as the lytic material.

4. The therapeutic administration system of claim 1 in which the means for obtaining one or more indications of a lytic material in a vicinity of one or more body lumens comprises:
    means for dispensing the lytic material into an upstream portion of the one or more body lumens.

5. The therapeutic administration system of claim 1 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:
    means for causing the portion of the lytic material to be drawn into an artificial vessel.

6. The therapeutic administration system of claim 1 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:
    means for reversing a flow direction of at least some of the lytic material.

7. The therapeutic administration system of claim 1 in which the means for obtaining one or more indications of a lytic material in a vicinity of one or more body lumens comprises:
    means for signaling at least one of the one or more indications of the lytic material via a wireless signal.

8. The therapeutic administration system of claim 1 in which the means for obtaining one or more indications of a lytic material in a vicinity of one or more body lumens comprises:
    means for causing the lytic material to be urged into the one or more body lumens.

9. The therapeutic administration system of claim 1 in which the means for obtaining one or more indications of a lytic material in a vicinity of one or more body lumens comprises:
    means for accelerating a dispensation of the lytic material transluminally into the one or more body lumens as a programmed response to one or more pathology-indicative signals.

10. The therapeutic administration system of claim 1 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:
    means for causing a lytic activity inhibitor dispensation into the one or more body lumens.

11. The therapeutic administration system of claim 1, further comprising:
    a thrombolytic-agent-containing dispenser operable for dispensing at least the lytic material.

12. The therapeutic administration system of claim 1, further comprising:
    an implant-site-targeting dispenser operable for dispensing at least the lytic material.

13. The therapeutic administration system of claim 1, further comprising:
    a first dispenser operable for dispensing at least the lytic material;
    a second dispenser operable for targeting an implant site by dispensing at least the lytic material; and
    a wireless-communication device operable for communicating a selection of one or more of the first dispenser or the second dispenser.

14. A therapeutic administration system comprising:
    means for obtaining one or more indications of a lytic material in a vicinity of one or more body lumens; and
    means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens;

in which the means for obtaining one or more indications of a lytic material in a vicinity of one or more body lumens comprises means for detecting a marker material indicative of the lytic material in the vicinity of the one or more body lumens.

15. The therapeutic administration system of claim 14 in which the means for obtaining one or more indications of a lytic material in a vicinity of one or more body lumens comprises:

circuitry for obtaining a concentration-indicative scalar of the one or more indications of the lytic material.

16. The therapeutic administration system of claim 14 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:

circuitry for causing the portion of the lytic material to be drawn into an artificial vessel.

17. The therapeutic administration system of claim 14 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:

circuitry for causing a lytic activity inhibitor dispensation into the one or more body lumens.

18. The therapeutic administration system of claim 14, further comprising:

an implant-site-targeting dispenser operable for dispensing at least the lytic material.

19. The therapeutic administration system of claim 14 in which the means for obtaining one or more indications of a lytic material in a vicinity of one or more body lumens comprises:

circuitry for causing at least a statin to be dispensed as the lytic material;

circuitry for obtaining a concentration-indicative scalar of the one or more indications of the lytic material;

circuitry for dispensing the lytic material into an upstream portion of the one or more body lumens;

circuitry for permitting the lytic material to perfuse one or more organs in the vicinity of the one or more body lumens;

circuitry for signaling at least one of the one or more indications of the lytic material via a wireless signal;

circuitry for causing the lytic material to be urged into the one or more body lumens;

circuitry for accelerating a dispensation of the lytic material transluminally into the one or more body lumens as a programmed response to one or more pathology-indicative signals;

a flow-force-responsive element; and one or more of a sonic sensor or an ion sensor.

20. The therapeutic administration system of claim 14, further comprising:

a first dispenser operable for dispensing at least the lytic material;

a second dispenser operable for targeting an implant site by dispensing at least the lytic material; and a wireless-communication device operable for communicating a selection of one or more of the first dispenser or the second dispenser.

21. The therapeutic administration system of claim 14 in which the means for obtaining one or more indications of a lytic material in a vicinity of one or more body lumens comprises:

means for permitting the lytic material to perfuse one or more organs in the vicinity of the one or more body lumens.

22. The therapeutic administration system of claim 14 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:

means for causing the lytic material to be exposed to a lytic-material-absorbent element.

23. The therapeutic administration system of claim 14 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:

means for reversing a flow direction of at least some of the lytic material.

24. The therapeutic administration system of claim 14 in which the means for obtaining one or more indications of a lytic material in a vicinity of one or more body lumens comprises:

means for causing the lytic material to be urged into the one or more body lumens.

25. The therapeutic administration system of claim 14 in which the means for obtaining one or more indications of a lytic material in a vicinity of one or more body lumens comprises:

means for accelerating a dispensation of the lytic material transluminally into the one or more body lumens as a programmed response to one or more pathology-indicative signals.

26. The therapeutic administration system of claim 14 in which the means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens comprises:

means for causing a lytic activity inhibitor dispensation into the one or more body lumens.

27. The therapeutic administration system of claim 14, further comprising:
   a thrombolytic-agent-containing dispenser operable for dispensing at least the lytic material.

28. A therapeutic administration method comprising:
   invoking means for obtaining one or more indications of a lytic material in a vicinity of one or more body lumens; and
   invoking means for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens;
   in which the invoking means for obtaining one or more indications of the lytic material in the vicinity of one or more body lumens comprises detecting a marker material indicative of the lytic material in the vicinity of the one or more body lumens.

29. The therapeutic administration method of claim 28 in which the invoking means for obtaining one or more indications of a lytic material in a vicinity of one or more body lumens comprises:
   invoking circuitry for causing at least a statin to be dispensed as the lytic material.

30. The therapeutic administration method of claim 28 in which the invoking means for obtaining one or more indications of a lytic material in a vicinity of one or more body lumens comprises:
   invoking circuitry for obtaining a concentration-indicative scalar of the one or more indications of the lytic material.

31. The therapeutic administration method of claim 28 in which the invoking means for obtaining one or more indications of a lytic material in a vicinity of one or more body lumens comprises:
   invoking circuitry for accelerating a dispensation of the lytic material transluminally into the one or more body lumens as a programmed response to one or more pathology-indicative signals.

* * * * *

UNITED STATES PATENT AND TRADEMARK OFFICE
CERTIFICATE OF CORRECTION

PATENT NO. : 8,317,776 B2  
APPLICATION NO. : 12/154162  
DATED : November 27, 2012  
INVENTOR(S) : Ferren et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this  
Twelfth Day of March, 2013

Teresa Stanek Rea  
*Acting Director of the United States Patent and Trademark Office*